(12) United States Patent
Hanaki et al.

(10) Patent No.: US 8,039,532 B2
(45) Date of Patent: Oct. 18, 2011

(54) HETEROCYCLIC COMPOUND, ULTRAVIOLET ABSORBENT AND COMPOSITION CONTAINING THE SAME

(75) Inventors: Naoyuki Hanaki, Minami-ashigara (JP); Masuji Motoki, Minami-ashigara (JP); Toshihiko Yawata, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 0 days.

(21) Appl. No.: 12/669,611

(22) PCT Filed: Aug. 15, 2008

(86) PCT No.: PCT/JP2008/064625
§ 371 (c)(1),
(2), (4) Date: Jan. 19, 2010

(87) PCT Pub. No.: WO2009/022736
PCT Pub. Date: Feb. 19, 2009

(65) Prior Publication Data
US 2010/0210762 A1    Aug. 19, 2010

(30) Foreign Application Priority Data

Aug. 16, 2007 (JP) .................. 2007-212318
Aug. 16, 2007 (JP) .................. 2007-212319
Sep. 28, 2007 (JP) .................. 2007-255732
Feb. 7, 2008 (JP) .................. 2008-028229
Feb. 7, 2008 (JP) .................. 2008-028230

(51) Int. Cl.
C08K 5/45 (2006.01)
C07D 495/04 (2006.01)

(52) U.S. Cl. ............... 524/83; 524/84; 524/89; 549/31; 546/187; 546/281.1; 546/270.1; 546/86; 544/79; 548/302.1

(58) Field of Classification Search .................. 524/83, 524/84, 89; 549/31; 546/187, 281.1, 270.1, 546/86; 544/79; 548/302.1
See application file for complete search history.

(56) References Cited

U.S. PATENT DOCUMENTS

| | | | |
|---|---|---|---|
| 3,694,211 A | 9/1972 | Sato et al. | |
| 5,380,807 A | 1/1995 | Havinga et al. | |
| 5,599,522 A | 2/1997 | Jorgensen et al. | |
| 2006/0022177 A1 | 2/2006 | Kownemann | |

FOREIGN PATENT DOCUMENTS

| DE | 3728452 A1 | 3/1989 |
|---|---|---|
| FR | 96.399 A1 | 6/1972 |
| JP | 46-6716 A | 12/1971 |
| JP | 49-11155 B1 | 3/1974 |
| JP | 63-150273 A | 6/1988 |
| JP | 63-150274 A | 6/1988 |
| JP | 4-85547 A | 3/1992 |
| JP | 5-506428 A | 9/1993 |
| JP | 5-339033 A | 12/1993 |
| JP | 5-345639 A | 12/1993 |
| JP | 6-56466 A | 3/1994 |
| JP | 6-145387 A | 5/1994 |
| JP | 7-252350 A | 10/1995 |
| JP | 7-285927 A | 10/1995 |
| JP | 2000-251958 A | 9/2000 |
| JP | 2003-177235 A | 6/2003 |
| JP | 2005-517787 A | 6/2005 |
| JP | 2005-526881 A | 9/2005 |
| WO | WO 2005/106868 A1 | 11/2005 |
| WO | WO 2008/105301 A1 | 9/2008 |

OTHER PUBLICATIONS

Frenzel et al., Synthetic Metals 80 (1996) 172-182.*
International Search Report for PCT/JP2008/064625 completed Sep. 30, 2008.
Xike Gao et al., Linear benzene-fused bis(tetrathiafulvalene) compounds for solution processed organic field-effect transistors, Journal of Materials Chemistry, 2007, pp. 736-743, vol. 17, No. 8, RSC Publishing.

(Continued)

Primary Examiner — Robert D. Harlan
(74) Attorney, Agent, or Firm — Buchanan Ingersoll & Rooney PC

(57) ABSTRACT

A compound represented by formula (I-1):

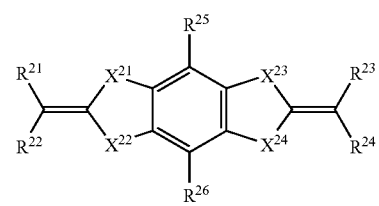

Formula (I-1)

wherein $R^{21}$, $R^{22}$, $R^{23}$ and $R^{24}$ each independently represent a hydrogen atom or a monovalent substituent, with the proviso that compounds, in which $R^{21}$, $R^{22}$, $R^{23}$ and $R^{24}$ each are an alkylthio group, are excluded; $R^{21}$ and $R^{22}$ and/or $R^{23}$ and $R^{24}$ each may bond to each other to form a ring, with the proviso that compounds, in which the formed ring is a dithiol ring or a dithiolane ring, are excluded;
$R^{25}$ and $R^{26}$ each independently represent a hydrogen atom or a monovalent substituent;
$X^{21}$, $X^{22}$, $X^{23}$ and $X^{24}$ each independently represent a hetero atom;
compounds, wherein $R^{21}$, $R^{22}$, $R^{23}$ and $R^{24}$ each represent a cyan group; $X^{21}$, $X^{22}$, $X^{23}$ and $X^{24}$ each represent a sulfur atom; and $R^{25}$ and $R^{26}$ each represent a hydroxyl group or a hydrogen atom, are excluded; and
compounds, wherein $R^{21}$ and $R^{23}$ each represent a hydrogen atom; $R^{22}$ and $R^{24}$ each represent an arylcarbonyl group; $X^{21}$, $X^{22}$, $X^{23}$ and $X^{24}$ each represent a sulfur atom; and $R^{25}$ and $R^{26}$ each represent a hydroxyl group, are excluded; and an ultraviolet absorbent, which has molecular weight of 10,000 or less and molar extinction coefficient at the maximum absorption wavelength of the ultraviolet absorbent of 80,000 or more.

14 Claims, 1 Drawing Sheet

OTHER PUBLICATIONS

Stephen F. Nelsen et al., Estimation of Electron Transfer Distances from AM1 Calculations, Journal of Physical Chemistry A., 2000, pp. 10023-10031, vol. 104, No. 44, American Chemical Society.

D.R. Greve et al., Molecules with multi-directional charge-transfer (MDCT) transitions as promising chromophores for third order non-linear optics, Synthetic Metals, 1999, pp. 1533-1534, vol. 102, No. 1-3, Elsevier Science S.A.

Jun Peng et al., Synthesis, electrical properties and crystal structure of a new radical-ion salt based on π-extended bis(TTF) and a Keggin heteropolymolybdate, Journal of the Chemical Society, Dalton Transaction, 1998, pp. 3865-3869, No. 22.

Stefan Franzel et al., A tetrathiafulvalene-based conjugated donor-acceptor-donor system, Synthetic Metals, 1996, pp. 175-182, vol. 80, No. 2, Elsevier Science S.A.

Stefan Frenzel et al., Synthesis of Tetrathiafulvalene Polymers, Journal of Materials Chemistry, 1995, pp. 1529-1537, vol. 5, No. 10.

Khalid Lahlil et al., Intervalence Transitions in Mixed Valence Bis(tetrathiafulvalene) Compounds, Journal of the American Chemical Society, 1995, pp. 9995-10002, vol. 117, No. 40, American Chemical Society.

P. Cassoux et al., 1,1'-Dithiolenes: The Good, The Not Bad, and The Ugly, Acta Physica Polonica A, 1995, pp. 743-748, vol. 87, No. 4-5.

K. Pokhodnia et al., Spectroscopic Investigation of the Symmetry Breakdown in Bis-TTF Compounds, Synthetic Metals, 1997, pp. 1999-2000, vol. 86, No. 1-3, Elsevier Science S.A.

Martin Adam et al., Conjugated tris-tetrathiafulvalenes, Synthetic Metals, 1994, vol. 66, No. 3, pp. 275-283, Elsevier Science S.A.

M. Adam, Extended Donors based on Tetrathiafulvalene, Synthetic Metals, 1993, vol. 56, No. 1, pp. 2108-2112, Elsevier Sequoia.

William H. Watson et al., Tetrathiafulvalene Quinones, Hydroquinones and Esters, Tetrahedron, 1993, vol. 49, No. 15, pp. 3035-3042.

Ute Scherer et al., Extended homologues of tetrathioalkyl-Tetrathiafulvalenes, Advanced Materials, 1993, vol. 5, No. 2, pp. 109-112.

Bobby Wegner et al., Novel oligomeric TTF systems with extended conjugation, Synthetic Metals, 1993, vol. 53, No. 3, pp. 353-363, Elsevier Sequoia.

M. Adam et al., Oligomeric Tetrathiafulvalenes, Synthetic Metals, 1991, vol. 41-43, No. 1-2, pp. 1623-1626, Elsevier Sequoia.

Salem E. Zayed et al., Keten-S,S-gem, Dithiols. Interaction with Heterogeneous Radicals and Study the Effect of Products as Antimicrobiol Agents, Egyptian Journal of Chemistry, 1990, vol. Date 1988, No. 1, pp. 29-40.

Martin Adam et al., Conjugated 'Tris'-tetrathiafulvalenes, Journal of the Chemical Society, Chemical Communications, 1990, No. 22, pp. 1624-1625.

Yves Gimbert et al., Regiochemical Effects Associated with Nucleophilic Aromatic Substitutions by Bidentate Sulfur Nucleophiles, Journal of Organic Chemistry, 1990, vol. 55, pp. 5347-5350, No. 19, American Chemical Society.

Kiprianov, A.I. et al., Cyanine dyes with two conjugated chromophores. IX, Zhurnal Organicheskoi Khimii, 1968, vol. 4, No. 12, pp. 2222-2225.

Mushkalo, I.L., Anhydro bases of p-hydroxystyryl derivatives of benzobisthiazoles, Ukrainskii Khimicheskii Zhurnal (Russian Edition), 1974, vol. 40, No. 11, pp. 1217-1220.

N.G. Demetriadis et al., Design and Synthesis of Poly(substituted) Tetrathiafulvalene Precursors, Tetrahedron Letters, 1997, No. 26, pp. 2223-2226, Pergamon Press, Great Britain.

* cited by examiner

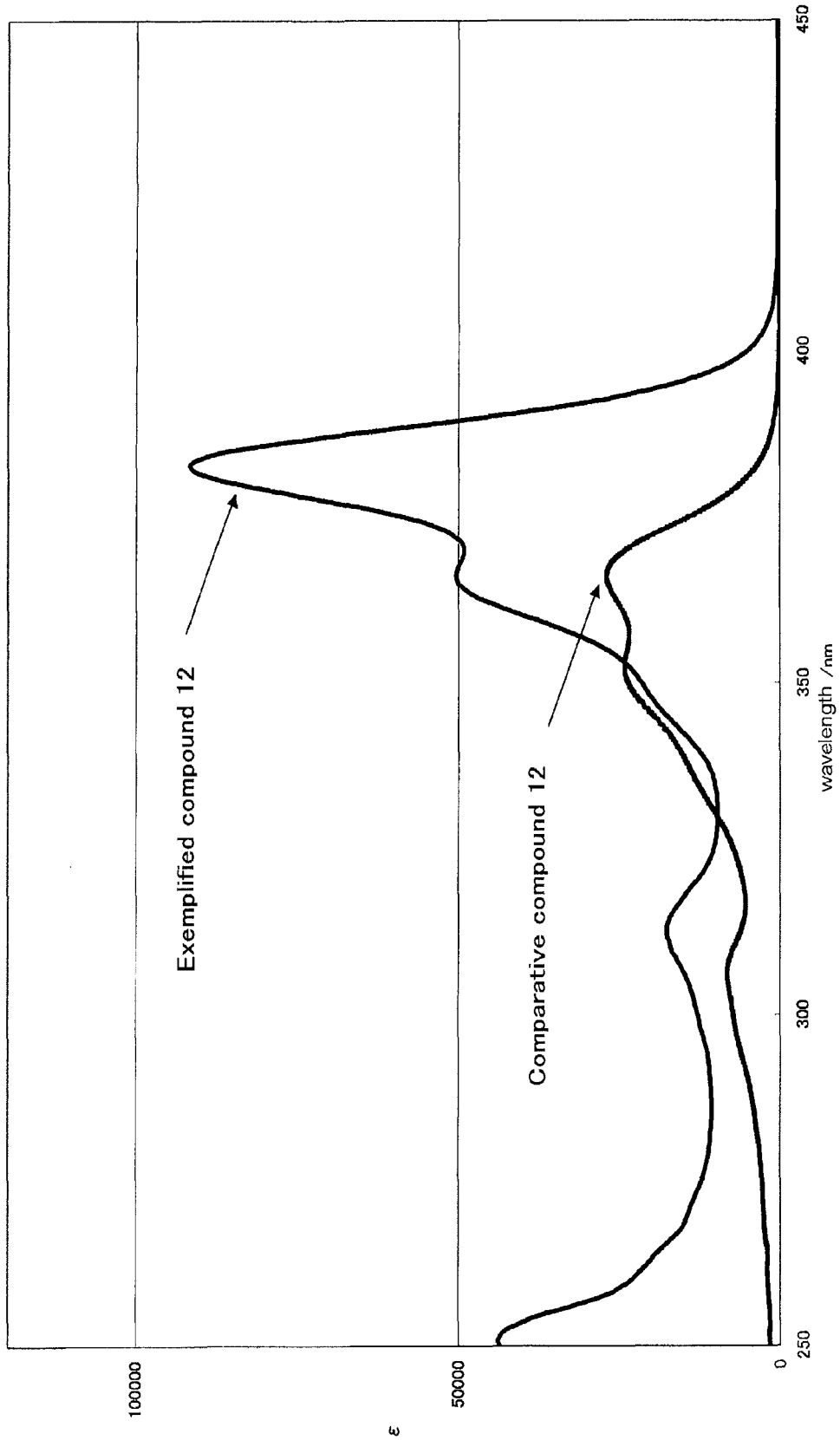

HETEROCYCLIC COMPOUND, ULTRAVIOLET ABSORBENT AND COMPOSITION CONTAINING THE SAME

TECHNICAL FIELD

The present invention relates to a novel heterocyclic compound, an ultraviolet absorbent and a composition including the same.

BACKGROUND ART

As for heterocyclic compounds, compounds in which two heterocycles are condensed to a benzene ring are hitherto known (see, for example, JP-A-63-150273 ("JP-A" means unexamined published Japanese patent application), JP-A-4-85547, JP-T-5-506428 ("JP-T" means published Japanese translation of PCT application), and Journal of the American Chemical Society, 1995, Vol. 117, pages 9995 to 10002). In these publications, there are disclosures relating to tetrathiafulvalene analogs probably because these heterocyclic compounds interested mainly in a charge-transfer complex. Therefore, a majority of the condensed heterocycles disclosed therein is dithiol rings. More specifically, most of the dithiol rings are those having a structure wherein an alkylmercapto group or a dithiol ring is substituted via exomethylene at 2-position of the dithiol ring.

Further, with respect to the use of these compounds having such a structure for various kinds of functional materials, there are one case where these compounds are used as a charge-transfer complex for use in an organic electrophotographic material (see, for example, JP-A-4-85547), and another case where these compounds are used as an inert carbon free radical partial structure (see, for example, JP-T-5-506428). However, these structures are limited to a narrow scope whereby desirable properties can be provided. Since then, new compounds have not been found, probably because studies on other applications of the dithiol rings have not been tried.

Ultraviolet absorbents have been used in combination with various resins for providing the resins with ultraviolet-absorptivity. Both inorganic and organic ultraviolet absorbents are used as the ultraviolet absorbent. The inorganic ultraviolet absorbents (see, for example, JP-A-5-339033, JP-A-5-345639 and JP-A-6-56466) are superior in durability properties such as weather resistance and heat resistance. However, the freedom in selecting the compound is limited, because the absorption wavelength is determined by the band gap of the compound. In addition, there is no inorganic absorbent that absorbs the light in a long-wavelength ultraviolet (UV-A) range of around 400 nm. And any such absorbent that absorbs long-wavelength ultraviolet would have color because it would have absorption also in the visible range.

In contrast, the freedom in designing the absorbent structure is much wider for organic ultraviolet absorbents, and thus, it is possible to obtain absorbents having various absorption wavelengths by designing the absorbent chemical structure properly.

Various organic ultraviolet absorbent systems have been studied, and for absorption in the long-wavelength ultraviolet range, it is conceivable either to use an absorbent having the wavelength of maximal absorption in the long-wavelength ultraviolet range or to use a high concentration of absorbent. However, the absorbents described in, for example, JP-A-6-145387 and JP-A-2003-177235 having the wavelength of maximal absorption in the long-wavelength ultraviolet range are inferior in light stability, and their absorption capacity declines over time.

In contrast, benzophenone- and benzotriazole-based ultraviolet absorbents are relatively higher in light stability, and increase in concentration or film thickness leads to relatively clean blocking of the light in the longer-wavelength range (see, for example, JP-T-2005-517787 and JP-A-7-285927). However, when such an ultraviolet absorbent is applied as mixed with a resin or the like, the film thickness is limited to several tens of μm at the most. For utilizing the film thickness to block the light in the longer-wavelength range, it is necessary to add the ultraviolet absorbent to a considerably high concentration. However, simple increase in concentration only results in a problem of precipitation and bleed-out of the ultraviolet absorbent during long-term use. In addition, among benzophenone-based and benzotriazole-based ultraviolet absorbents, there are some ultraviolet absorbents that may cause concern about skin irritation and accumulation in body. Therefore, intensive care should have been given to these compounds during use.

Meanwhile, as for the heterocyclic compound, compounds represented by any one of the following Formulae (S-1) to (S-5) are known (see, for example, JP-A-63-150273, Tetrahedron Letters, 1977, Vol. 26, page 2223). These compounds interested only in a charge-transfer complex component and an intermediate thereof. In fact, these compounds absorb little visible light in solution. Therefore, they have never been considered the use for a coloring agent.

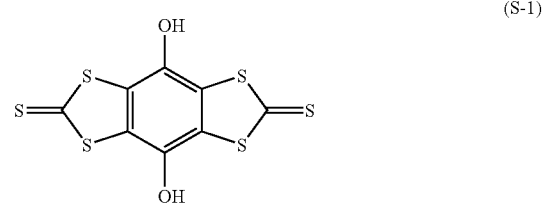

(S-1)

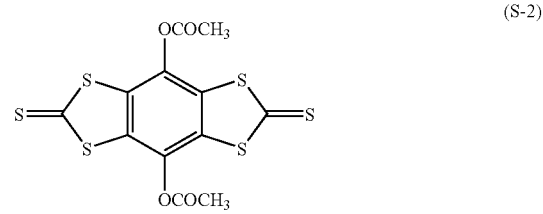

(S-2)

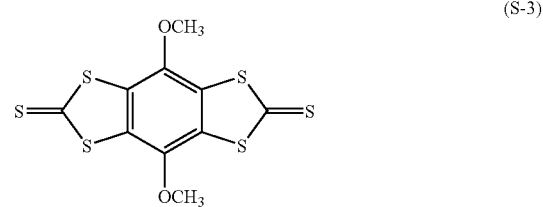

(S-3)

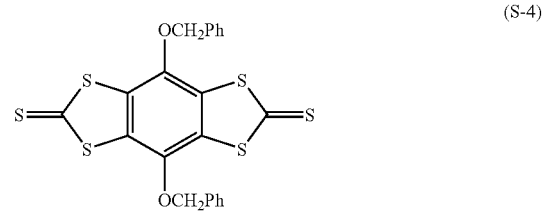

(S-4)

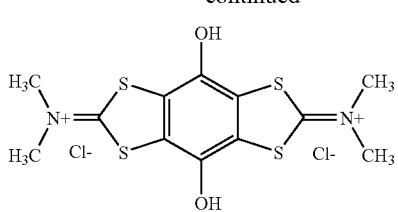

(S-5)

DISCLOSURE OF INVENTION

According to the present invention, there can be provided a novel heterocyclic compound useful for functional materials such as medicines, agricultural chemicals, dyes, pigments, ultraviolet absorbents or liquid crystals, and synthetic intermediates thereof.

Further, according to the present invention, it is possible to dissolve the aforementioned problems, and there can be provided an ultraviolet absorbent sustaining a long-wavelength ultraviolet absorbing capacity for a long time with causing neither deposition nor bleed-out, and moreover enabling not only to improve ultraviolet resistance of a polymer material that is used together with the ultraviolet absorbent, but also to prevent other unstable compounds from decomposition by employing the polymer material as an ultraviolet filter.

The present inventors have intensively made studies on synthesis of the heterocyclic compound in which two heterocycles are condensed to a benzene ring. As a result, it has been found a heterocyclic compound having a particular structure that is never known. Further, taking notice of heterocyclic compounds in development of new ultraviolet absorbents, the present inventors have repeated syntheses of various heterocyclic compounds and evaluation of the synthesized compounds in detail. As a result of investigation, it has been found that the aforementioned problems can be dissolved by using a monomolecular ultraviolet absorbent that does not have a plurality of ultraviolet absorbing structures, but has a large molar extinction coefficient. More specifically, it has been found that novel heterocyclic compounds having a particular structure having both a high fastness to light and a considerably excellent long-wavelength ultraviolet absorbing capacity each of which satisfies the aforementioned physical properties. The present invention was completed based on the above described findings.

The present invention provides the following means:
[1] A compound represented by formula (I-1):

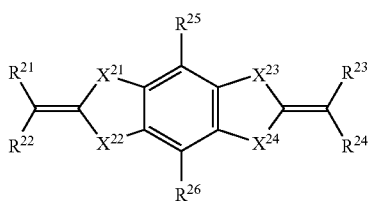

Formula (I-1)

wherein $R^{21}$, $R^{22}$, $R^{23}$ and $R^{24}$ each independently represent a hydrogen atom or a monovalent substituent, with the proviso that compounds, in which $R^{21}$, $R^{22}$, $R^{23}$ and $R^{24}$ each are an alkylthio group, are excluded; $R^{21}$ and $R^{22}$ and/or $R^{23}$ and $R^{24}$ may bond to each other to form a ring, with the proviso that compounds, in which the formed ring is a dithiol ring or a dithiolane ring, are excluded;

$R^{25}$ and $R^{26}$ each independently represent a hydrogen atom or a monovalent substituent;

$X^{21}$, $X^{22}$, $X^{23}$ and $X^{24}$ each independently represent a hetero atom;

compounds, wherein $R^{21}$, $R^{22}$, $R^{23}$ and $R^{24}$ each represent a cyan group; $X^{21}$, $X^{22}$, $X^{23}$ and $X^{24}$ each represent a sulfur atom; and $R^{25}$ and $R^{26}$ each represent a hydroxyl group or a hydrogen atom, are excluded; and compounds, wherein $R^{21}$ and $R^{23}$ each represent a hydrogen atom; $R^{22}$ and $R^{24}$ each represent an arylcarbonyl group; $X^{21}$, $X^{22}$, $X^{23}$ and $X^{24}$ each represent a sulfur atom; and $R^{25}$ and $R^{26}$ each represent a hydroxyl group, are excluded.

[2] The compound described in the above item [1], wherein, in formula (I-1), $R^{25}$ and $R^{26}$ each independently represent an alkoxy group, an aryloxy group, an acyloxy group, an alkoxycarbonyloxy group, an aryloxycarbonyloxy group, an acylamino group, a carbamoyloxy group, or a carbamoylamino group.

[3] The compound described in the above item [1] or [2], wherein, in formula (I-1), $X^{21}$, $X^{22}$, $X^{23}$ and $X^{24}$ each are a sulfur atom.

[4] The compound described in any one of the above items [1] to [3], wherein, in formula (I-1), at least one of $R^{21}$, $R^{22}$, $R^{23}$ and $R^{24}$ represents —CN, —COOR$^{28}$, —CONR$^{29}$R$^{30}$, —COR$^{31}$ or —SO$_2$R$^{32}$ (in which $R^{28}$, $R^{29}$, $R^{30}$, $R^{31}$ and $R^{32}$ each represent a hydrogen atom or a monovalent substituent).

[5] The compound described in the above item [1], wherein at lest one of the pair of $R^{21}$ and $R^{22}$ and the pair of $R^{23}$ and $R^{24}$ in formula (I-1) bonds to each other to form a ring.

[6] The compound described in the above item [1], wherein, in formula (I-1), $R^{21}$, $R^{22}$, $R^{23}$ and $R^{24}$ each independently represent a group selected from the group consisting of an aryl group, a heterocyclic group, an acyl group, a nitro group, a cyano group, an alkoxycarbonyl group, a carbamoyl group and an arylcarbamoyl group.

[7] The compound described in the above item [1] or [5], wherein the compound represented by formula (I-1) is a compound represented by formula (II-1):

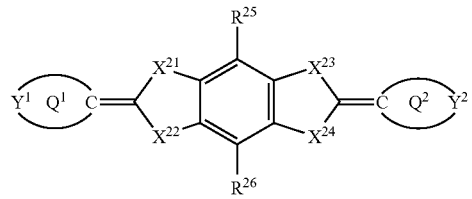

Formula (II-1)

wherein $R^{25}$ and $R^{26}$ each independently represent a hydrogen atom or a monovalent substituent; $X^{21}$, $X^{22}$, $X^{23}$ and $X^{24}$ each independently represent a hetero atom which may have a substituent; and $Y^1$ and $Y^2$ each represent a group of atoms necessary to form a 4- to 7-membered ring $Q^1$ or $Q^2$ together with the carbon atom to which $Y^1$ or $Y^2$ bonds.

[8] The compound described in the above item [7], wherein, in formula (II-1), the rings $Q^1$ and $Q^2$ each independently represent a heterocycle.

[9] The compound described in the above item [7] or [8], wherein, in formula (II-1), the rings $Q^1$ and $Q^2$ each independently represent a nitrogen-containing heterocycle.

[10] The compound described in any one of the above items [7] to [9], wherein, in formula (II-1), the rings $Q^1$ and $Q^2$ each independently represent a 5-membered or 6-membered heterocycle.

[11] An ultraviolet absorbent, which has molecular weight of 1,000 or less and molar extinction coefficient at the maximum absorption wavelength of the ultraviolet absorbent of 75,000 or more.
[12] The ultraviolet absorbent described in the above item [11], which has the molecular weight of 350 or more and 950 or less, and the molar extinction coefficient at the maximum absorption wavelength of 78,000 or more and 120,000 or less.
[13] The ultraviolet absorbent described in the above item [11] or [12], which has the maximum absorption wavelength of 350 nm or more, and the half width of 60 nm or less.
[14] The ultraviolet absorbent described in any one of the above items [11] to [13], which has the maximum absorption wavelength of 370 nm or more, and the half width of 10 nm or more and 45 nm or less.
[15] The ultraviolet absorbent described in any one of the above items [11] to [14], comprising a compound, in which two heterocycles are fused to one benzene ring.
[16] The ultraviolet absorbent described in the above item [15], comprising a compound represented by formula (I):

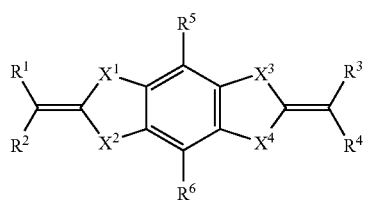

Formula (I)

wherein $R^1$, $R^2$, $R^3$ and $R^4$ each independently represent a hydrogen atom or a monovalent substituent; $R^5$ and $R^6$ each independently represent a hydrogen atom or a monovalent substituent; and $X^1$, $X^2$, $X^3$ and $X^4$ each independently represent a hetero atom.
[17] The ultraviolet absorbent described in the above item [16], wherein, in formula (I), $R^5$ and $R^6$ each independently represent an alkoxy group, an aryloxy group, an acyloxy group, an alkoxycarbonyloxy group, an aryloxycarbonyloxy group, a carbamoyloxy group, an amino group, an acylamino group, or a carbamoylamino group.
[18] The ultraviolet absorbent described in the above item [16] or [17], wherein, in formula (I), at least one of $R^1$, $R^2$, $R^3$ and $R^4$ represents a substituent having a Hammett substituent constant σp of 0.2 or more.
[19] The ultraviolet absorbent described in any one of the above items [16] to [18], wherein, in formula (I), at least one of $R^1$, $R^2$, $R^3$ and $R^4$ represents a cyano group, an alkoxycarbonyl group, an aryloxycarbonyl group, a carbamoyl group, an alkylcarbonyl group, an arylcarbonyl group, an alkylsulfonyl group, or an arylsulfonyl group.
[20] The ultraviolet absorbent described in any one of the above items [16] to [19], wherein, in formula (I), $X^1$, $X^2$, $X^3$ and $X^4$ each are a sulfur atom.
[21] The ultraviolet absorbent described in any one of the above items [16] to [20], wherein at least one of the pair of $R^1$ and $R^2$ and the pair of $R^3$ and $R^4$ does not form any ring.
[22] The ultraviolet absorbent described in any one of the above items [16] to [21], wherein the pair of $R^1$ and $R^2$ and the pair of $R^3$ and $R^4$ do not form any ring.
[23] The ultraviolet absorbent described in any one of the above items [16] to [22], wherein, in formula (I), at least one of $R^1$, $R^2$, $R^3$ and $R^4$ is an alkoxycarbonyl group having 6 or more carbon atoms.
[24] The ultraviolet absorbent described in any one of the above items [16] to [23], wherein, in formula (I), $R^5$ and $R^6$ are an alkoxy group having 2 or more carbon atoms.
[25] A composition, comprising the ultraviolet absorbent described in any one of the above items [11] to [24].
[26] A polymer composition, comprising the ultraviolet absorbent described in any one of the above items [11] to [25] and a polymer substance.

Please note that compounds having structures similar to the structure of the ultraviolet absorbent according to the present invention (for example, compounds wherein each of $R^1$, $R^2$, $R^3$ and $R^4$ in the aforementioned formula (I) is an alkylthio group) are known from a long ago as the structure of a charge-transfer complex. However, utility of these compounds as an ultraviolet absorbent has not been reported. Further, the compound represented by the aforementioned formula (I) in which two heterocycles are condensed to a benzene ring exhibits the molar extinction coefficient ε as much as two or more times than the molar extinction coefficient of the similar compound in which one heterocycle is condensed to a benzene ring (such as the compound described in JP-B-49-11155 ("JP-B" means examined Japanese patent publication)). Enhancement of molar extinction coefficient of the compound in which two heterocycles are condensed exceeds an ordinary expectation that a double ultraviolet absorbing effect would be obtained by forming a double heterocycles. Therefore, it has never been expected that the compound represented by the aforementioned formula (I) exhibits such excellent ultraviolet absorbing performance.

Hereinafter, a first embodiment of the present invention means to include the novel heterocyclic compounds described in the items [1] to [10].

A second embodiment of the present invention means to include the ultraviolet absorbents described in the items [11] to [24], the composition described in the item [25], and the polymer composition described in the item [26].

Herein, the present invention means to include all of the above first and second embodiments, unless otherwise specified.

Other and further features and advantages of the invention will appear more fully from the following description, taking the accompanying drawing into consideration.

BRIEF DESCRIPTION OF DRAWINGS

FIG. 1 shows spectra of the exemplified compound (12) and the comparative compound 12 in Example 38.

BEST MODE FOR CARRYING OUT INVENTION

Hereinafter, the present invention will be described in detail.

First, the first embodiment of the present invention is described in detail.

In formula (I-1), $R^{21}$, $R^{22}$, $R^{23}$ and $R^{24}$ each independently represent a hydrogen atom or a monovalent substituent. Examples of the monovalent substituent include a halogen atom (e.g., a fluorine atom, a chlorine atom, a bromine atom, an iodine atom), a straight chain or branched alkyl group having 1 to 20 (preferably 1 to 10) carbon atoms (e.g., methyl, ethyl), an aryl group having 6 to 20 (preferably 6 to 10) carbon atoms (e.g., phenyl, naphthyl), a cyano group, a carboxyl group, an alkoxycarbonyl group having 1 to 20 (preferably 1 to 10) carbon atoms (e.g., methoxycarbonyl), an aryloxycarbonyl group having 6 to 20 (preferably 6 to 10) carbon atoms (e.g., phenoxycarbonyl), a substituted or unsubstituted carbamoyl group having 0 to 20 (preferably 0 to 10) carbon atoms (e.g., carbamoyl, N-phenylcarbamoyl, N,N-dimethylcarbamoyl), an alkylcarbonyl group having 1 to 20 (preferably 1 to 10) carbon atoms (e.g., acetyl), an arylcarbonyl group having 6 to 20 (preferably 6 to 10) carbon atoms (e.g., benzoyl), a nitro group, a substituted or unsubstituted amino group having 0 to 20 (preferably 0 to 10) carbon atoms (e.g., amino, dimethylamino, anilino), an acylamino group having 1 to 20 (preferably 1 to 10) carbon atoms (e.g., acetamino, ethoxycarbonylamino), a sulfonamido group having 0 to 20 (preferably 0 to 10) carbon atoms (e.g., methanesulfonamido), an imido group having 2 to 20 (preferably 2 to 10) carbon atoms (e.g., succinimido, phthalimido), an imino group having 1 to 20 (preferably 1 to 10) carbon atoms (e.g., benzylideneimino), a hydroxyl group, an alkoxy group having 1 to 20 (preferably 1 to 10) carbon atoms (e.g., methoxy), an aryloxy group having 6 to 20 (preferably 6 to 10) carbon atoms (e.g., phenoxy), an acyloxy group having 1 to 20 (preferably 1 to 10) carbon atoms (e.g., acetoxy), an alkylsulfonyloxy group having 1 to 20 (preferably 1 to 10) carbon atoms (e.g., methanesulfonyloxy), an arylsulfonyloxy group having 6 to 20 (preferably 6 to 10) carbon atoms (e.g., benzenesulfonyloxy), a sulfo group, a substituted or unsubstituted sulfamoyl group having 0 to 20 (preferably 0 to 10) carbon atoms (e.g., sulfamoyl, N-phenylsulfamoyl), an alkylthio group having 1 to 20 (preferably 1 to 10) carbon atoms (e.g., methylthio), an arylthio group having 6 to 20 (preferably 6 to 10) carbon atoms (e.g., phenylthio), an alkylsulfonyl group having 1 to 20 (preferably 1 to 10) carbon atoms (e.g., methanesulfonyl), an arylsulfonyl group having 6 to 20 (preferably 6 to 10) carbon atoms (e.g., benzenesulfonyl), and a 4- to 7-membered (preferably 5- to 6-membered) heterocyclic group (e.g., pyridyl, morpholino). The substituent may be further substituted. In the case where there are a plurality of substituents, they may be the same as or different from. Alternatively, they may bond together to form a ring.

However, in the first embodiment of the present invention, the case is excluded that each of $R^{21}$, $R^{22}$, $R^{23}$ and $R^{24}$ is an alkylthio group.

It is preferable that at least one of $R^{21}$, $R^{22}$, $R^{23}$ and $R^{24}$ represents a substituent having a Hammett substituent constant σp value of 0.2 or more.

The expression "Hammett substituent constant σ value" used herein will be briefly described. Hammett's rule is a rule of thumb advocated by L. P. Hammett in 1935 for quantitatively considering the effect of substituents on the reaction or equilibrium of benzene derivatives, and the appropriateness thereof is now widely recognized. The substituent constant determined in the Hammett's rule involves $\sigma_p$ value and $\sigma_m$ value. These values can be found in a multiplicity of general publications, and are detailed in, for example, "Lange's Handbook of Chemistry" 12th edition by J. A. Dean, 1979 (McGraw-Hill), "Kagaku no Ryoiki" special issue, No. 122, pp. 96 to 103, 1979 (Nankodo) and Chem. Rev., vol. 91, pp. 165 to 195, 1991. The substituent having a Hammett substituent constant σp of 0.2 or more in the present invention is an electron-withdrawing group. The σp value is preferably 0.25 or more, more preferably 0.3 or more, and particularly preferably 0.35 or more. The upper limit of the σp value is not particularly limited, but it is preferable 1.20 or less, more preferable 1.00 or less.

Examples of the substituent having a Hammett substituent constant σp of 0.2 or more include a cyano group (0.66), a carboxyl group (—COOH: 0.45), an alkoxycarbonyl group (e.g. —COOMe: 0.45), an aryloxycarbonyl group (e.g. —COOPh: 0.44), a carbamoyl group (—CONH$_2$: 0.36), an alkylcarbonyl group (e.g. —COMe: 0.50), an arylcarbonyl group (e.g. —COPh: 0.43), an alkylsulfonyl group (e.g. —SO$_2$Me: 0.72), an arylsulfonyl group (e.g. —SO$_2$Ph: 0.68) and the like. In the present specification, "Me" represents a methyl group and "Ph" represents a phenyl group. The values in parenthesis are the σp values of typical substituents, as extracted from Chem. Rev., 1991, vol. 91, p. 165 to 195.

$R^{21}$ and $R^{22}$ and/or $R^{23}$ and $R^{24}$ may bond to each other to form a ring. The σp values of $R^{21}$ and $R^{22}$ may not be specified when, for example, a ring is formed by $R^{21}$ and $R^{22}$. However, the σp values thereof when a ring is formed are defined, assuming that partial ring structures are substituted respectively as $R^{21}$ and $R^{22}$, in the first embodiment of the present invention. For example, when a 1,3-indandione ring is formed, benzoyl groups are considered to be substituted respectively as $R^{21}$ and $R^{22}$. Where a ring is formed by $R^{23}$ and $R^{24}$, the σp value is also defined in the same manner as described above.

At least one of $R^{21}$, $R^{22}$, $R^{23}$ and $R^{24}$ preferably represents a substituent having a Hammett substituent constant σp of 0.2 or more. The groups in at least one of the combination of $R^{21}$ and $R^{22}$ and the combination of $R^{23}$ and $R^{24}$ are preferably the substituent above. More preferably, three groups of $R^{21}$, $R^{22}$, $R^{23}$ and $R^{24}$ are the substituent. Particularly preferably, all of $R^{21}$, $R^{22}$, $R^{23}$ and $R^{24}$ are the substituent.

At least one of $R^{21}$, $R^{22}$, $R^{23}$ and $R^{24}$ is more preferably —CN, —COOR$^{28}$, —CONR$^{29}$R$^{30}$, —COR$^{31}$ or —SO$_2$R$^{32}$ (wherein, $R^{28}$, $R^{29}$, $R^{30}$, $R^{31}$ and $R^{32}$ each represent a hydrogen atom or a monovalent substituent); more preferably, —CN, —COOR$^{28}$, —COR$^{31}$ or —SO$_2$R$^{32}$; still more preferably —CN or —COOR$^{28}$; and particularly preferably —CN.

The combination of $R^{21}$ and $R^{22}$ and the combination $R^{23}$ and $R^{24}$ may be arbitrary as long as the conditions described above are satisfied, but the combination of $R^{21}$ and $R^{22}$ and that of $R^{23}$ and $R^{24}$ are preferably the same as each other.

$R^{21}$ and $R^{22}$ and/or $R^{23}$ and $R^{24}$ may bind to each other to form a ring. The ring formed may be a saturated or unsaturated, hydrocarbon ring or heterocycle. However, the ring formed is not a dithiol or dithiolane ring. Examples of the carbon-atom-containing ring formed by $R^{21}$ and $R^{22}$ defined in formula (I-1) include a cyclopropane ring, a cyclobutane ring, a cyclopentane ring, a cyclohexane ring, a cycloheptane ring, a pyrrolidine ring, a tetrahydrofuran ring, a tetrahydrothiophene ring, an oxazoline ring, a thiazoline ring, a pyrroline ring, a pyrazolidine ring, a pyrazoline ring, an imidazolidine ring, an imidazoline ring, a piperidine ring, a piperazine ring, and a pyran ring. Each of the rings may be substituted at any positions additionally. The substituent is, for example, the monovalent substituent described above. Examples of a bivalent substituent include a carbonyl group and an imino group. Multiple substituents, when present, may be the same as or different from each other. The substituents may bind to each other, forming a fused ring or a spiro ring.

Favorable examples of the combination of $R^{21}$ and $R^{22}$ or $R^{23}$ and $R^{24}$ are shown in the following Table 1, but the present invention is not restricted thereby. "Et" represents an ethyl group and "Bu" represents a butyl group in the present specification. "Me" represents a methyl group, "Ph" represents a phenyl group, and "Ac" represents an acetyl group. The wavy line in the Table indicates the binding site on the heterocycle shown in formula (I-1).

TABLE 1
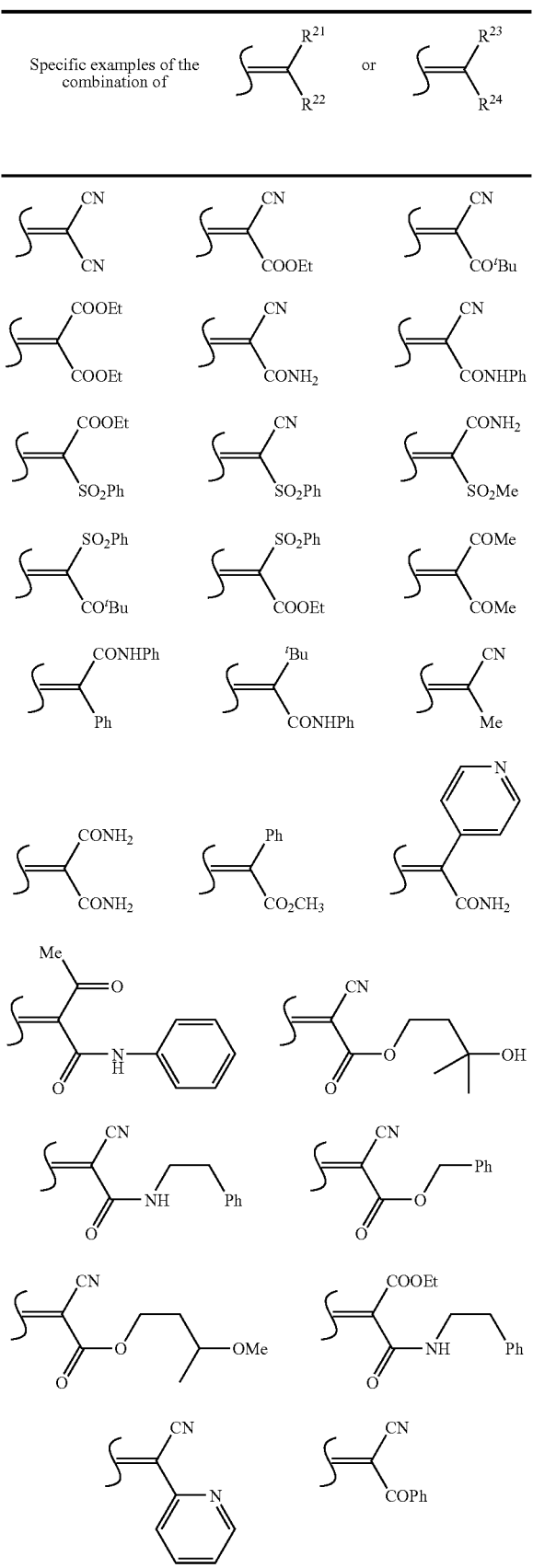
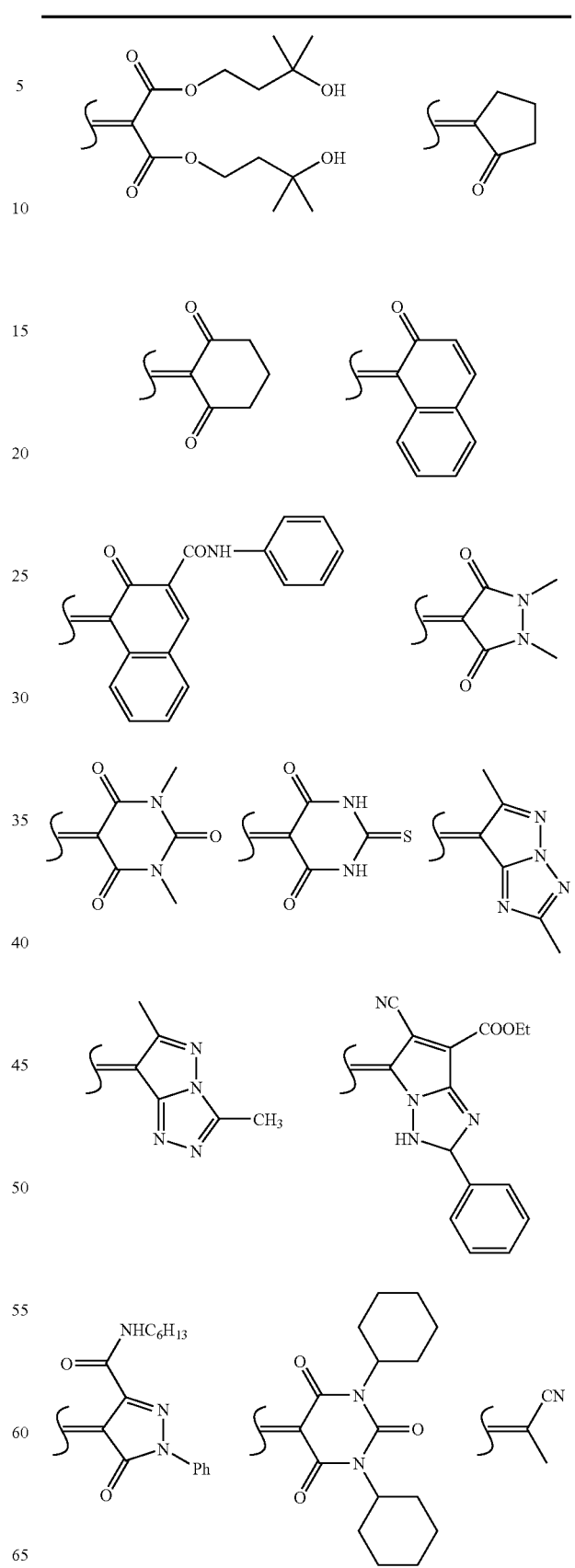

TABLE 1-continued
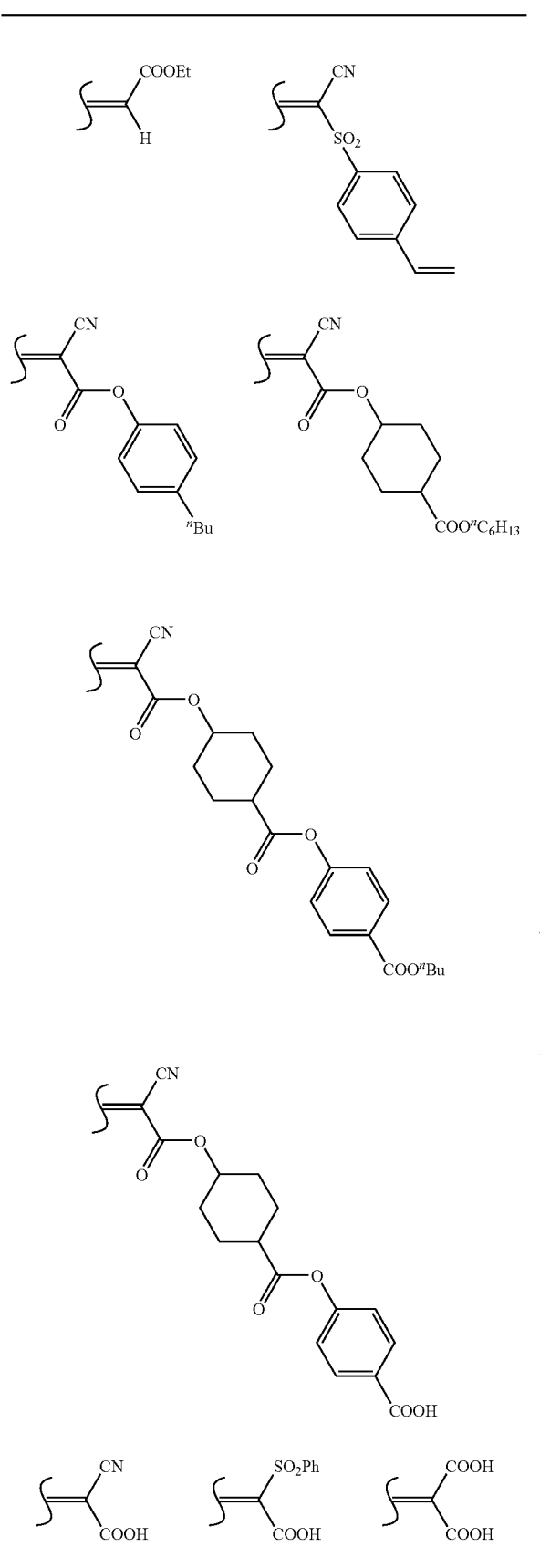
TABLE 1-continued

TABLE 1-continued
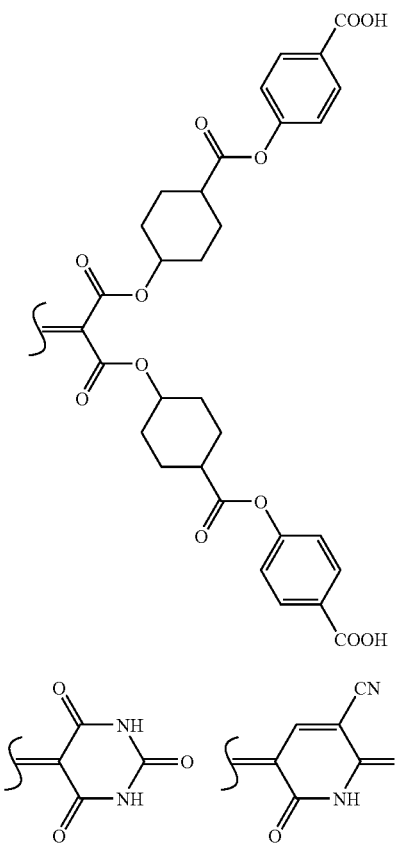
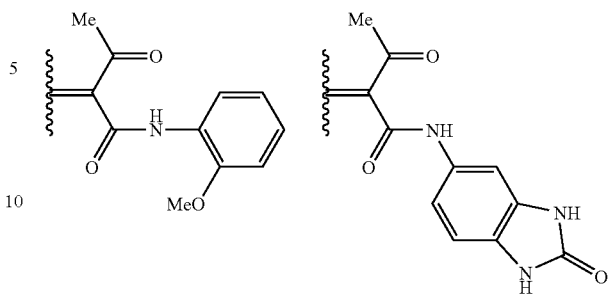
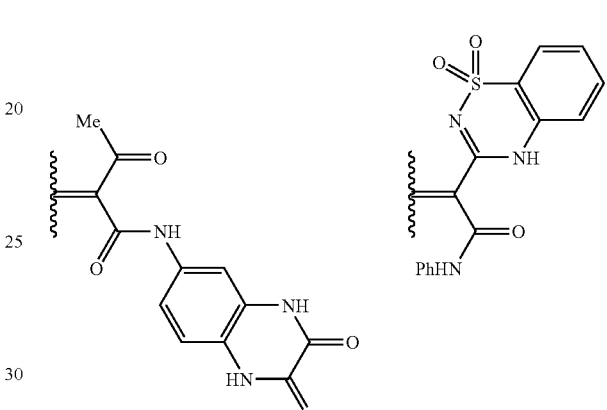
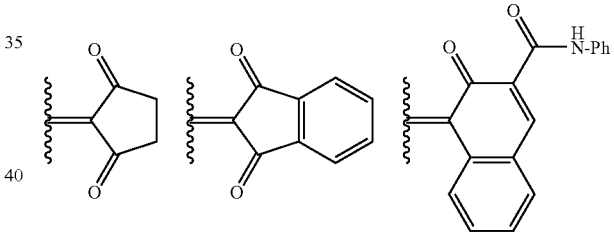
| Specific examples of the combination of | 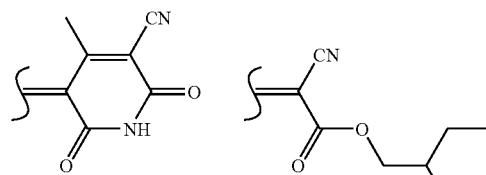 |
|---|---|
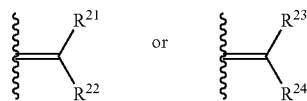
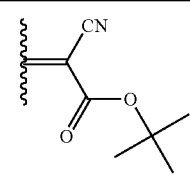
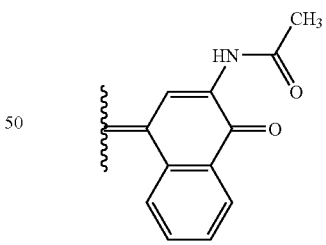 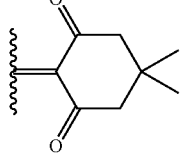
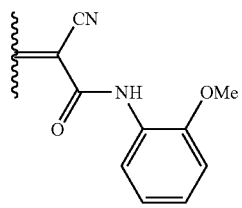
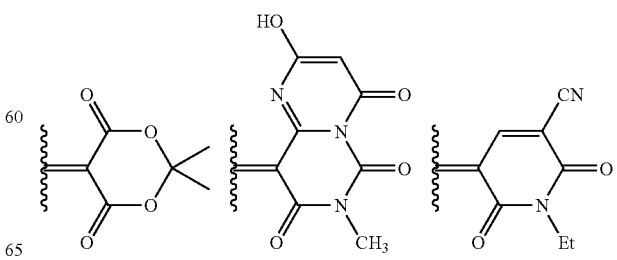

TABLE 1-continued
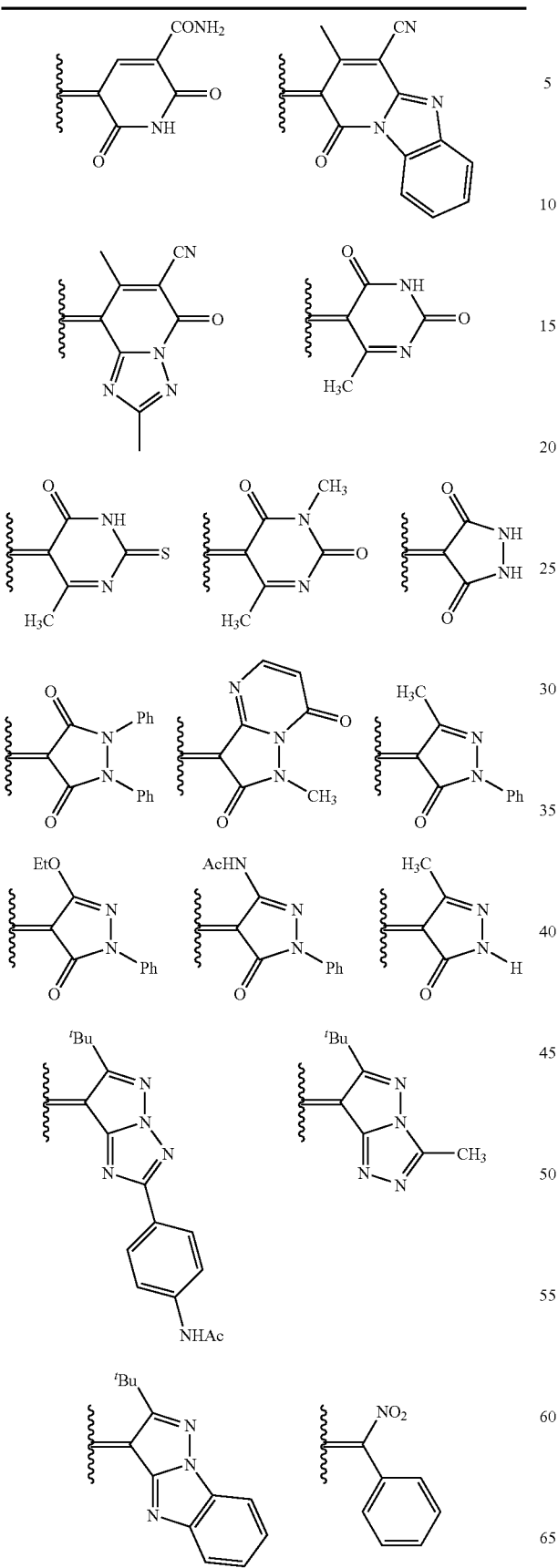
TABLE 1-continued
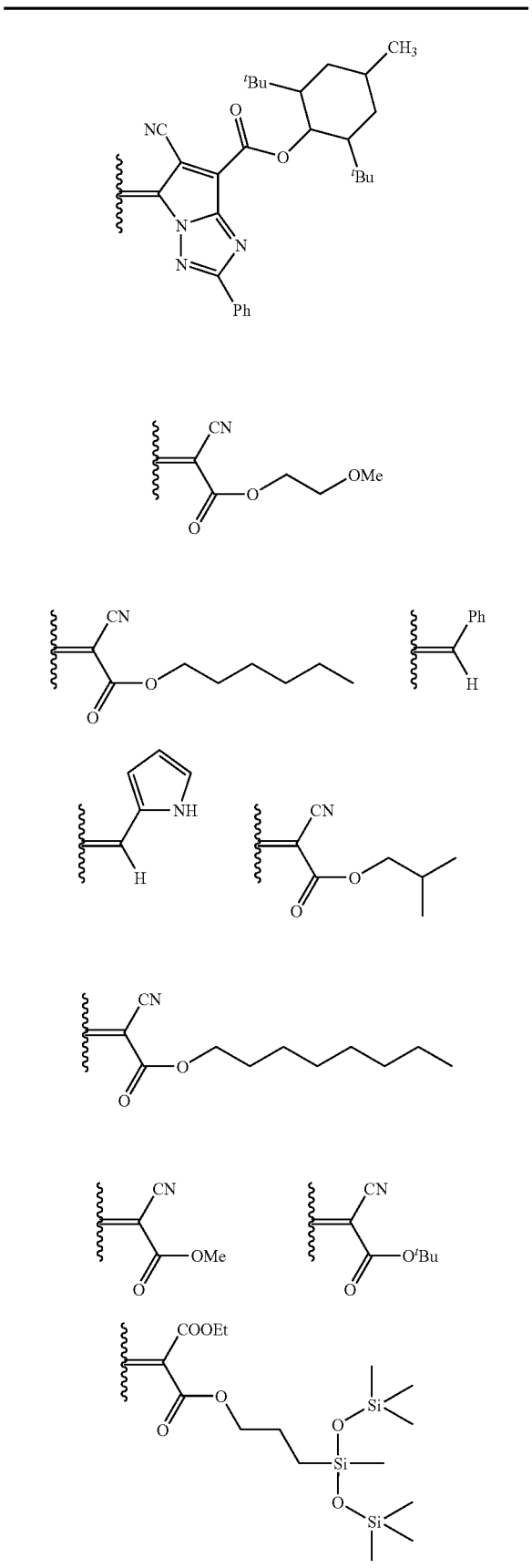

TABLE 1-continued
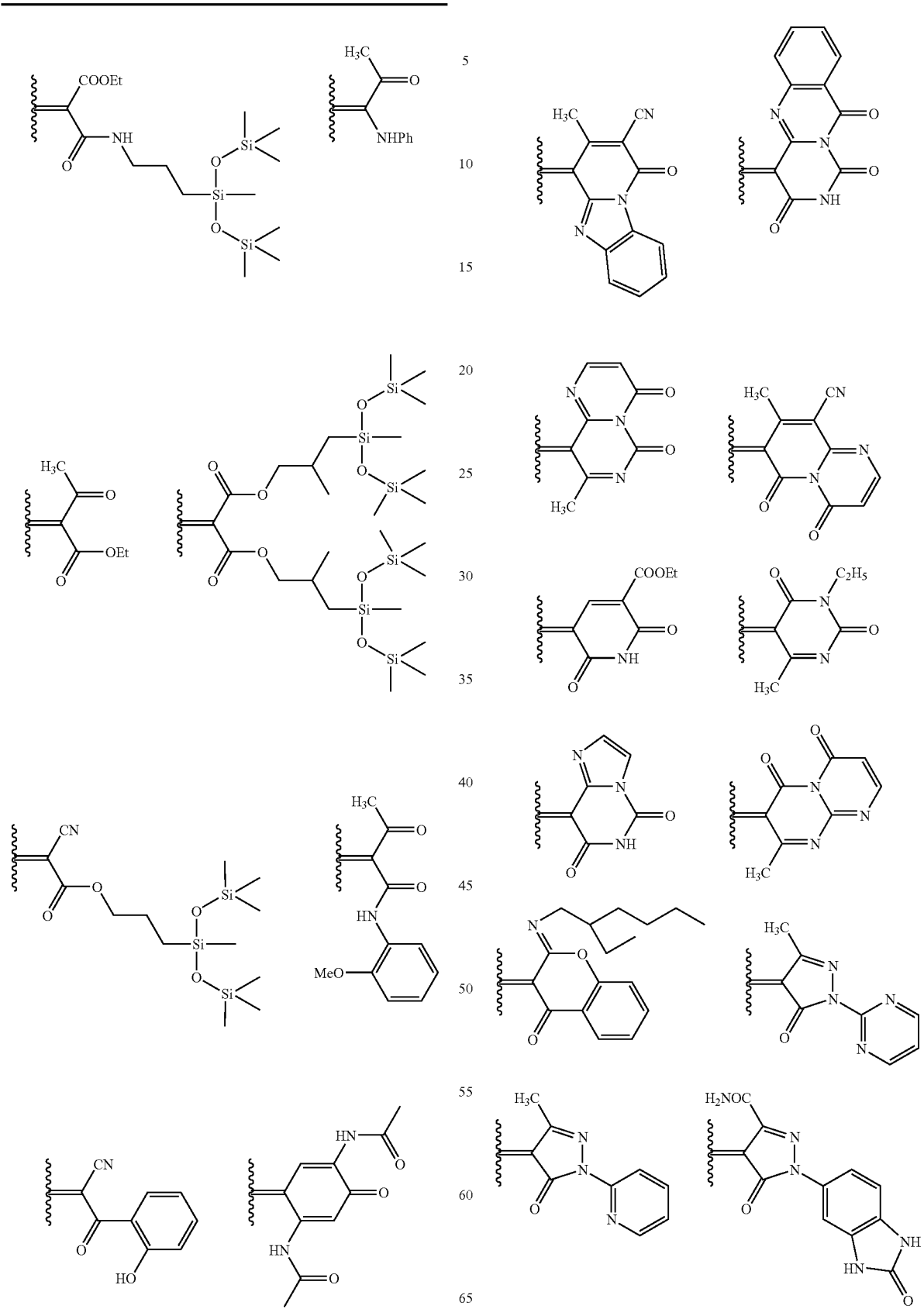

TABLE 1-continued
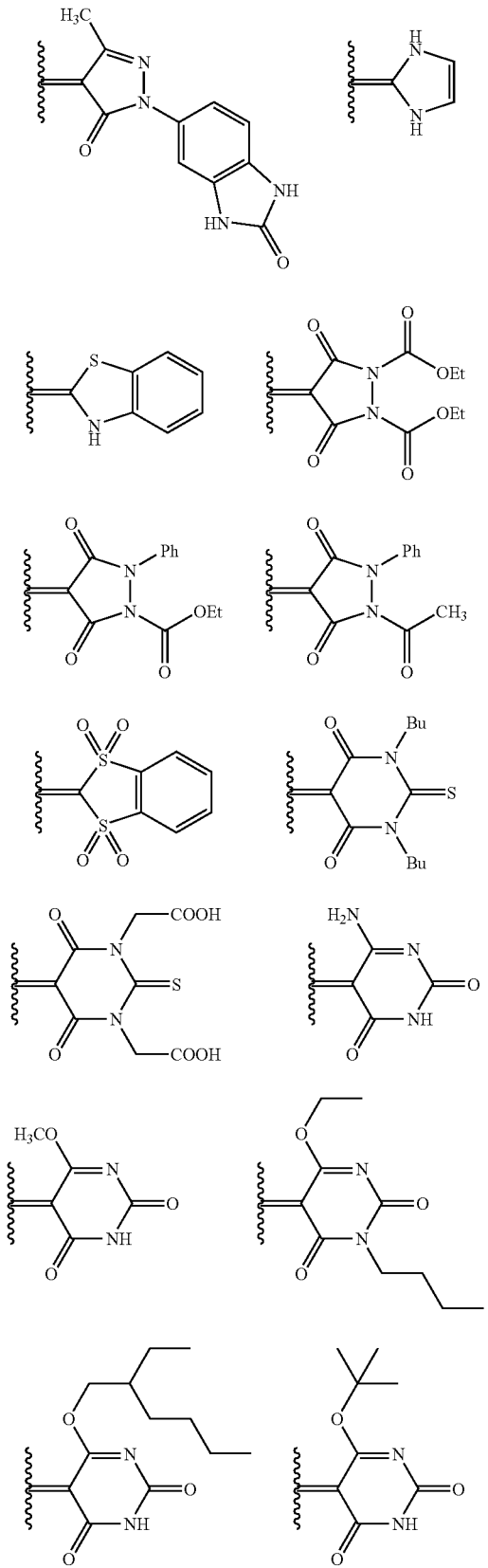
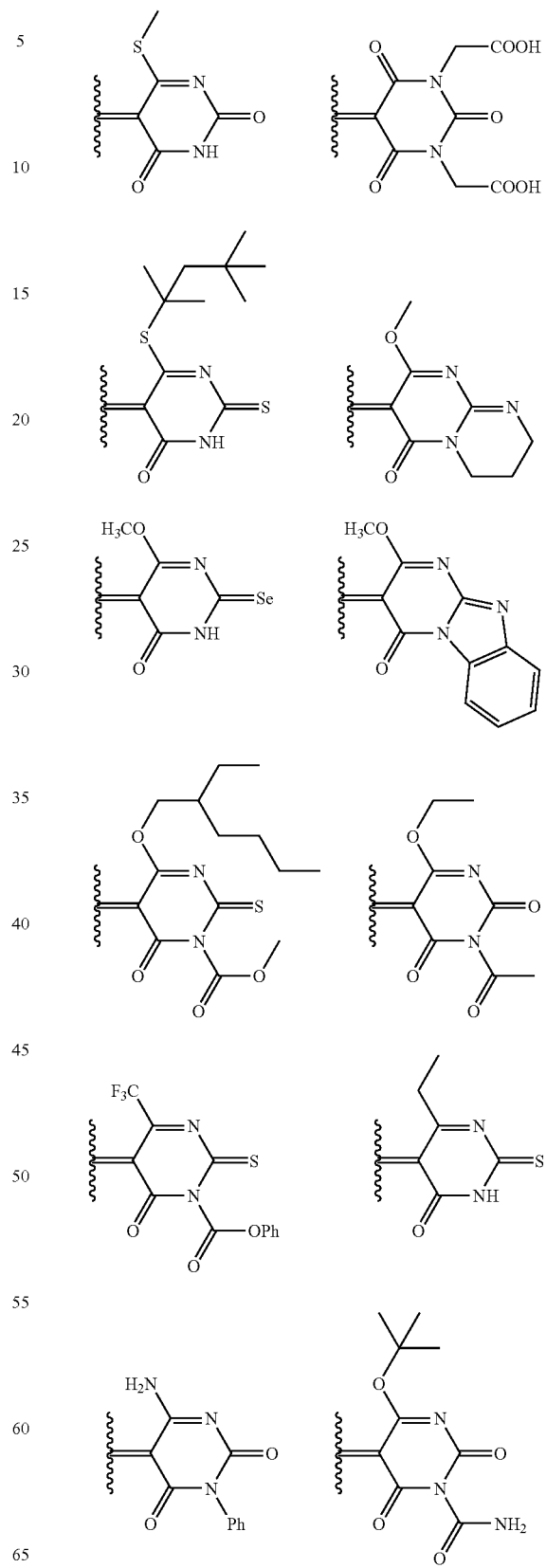

TABLE 1-continued
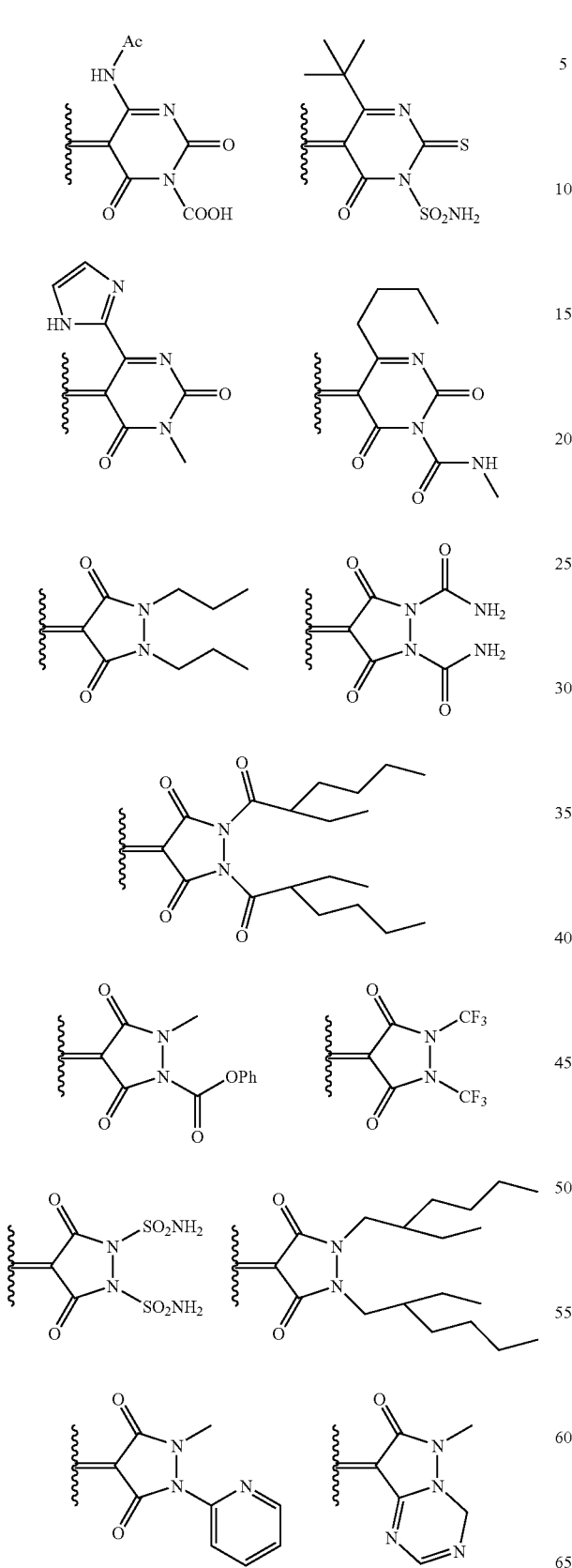
TABLE 1-continued
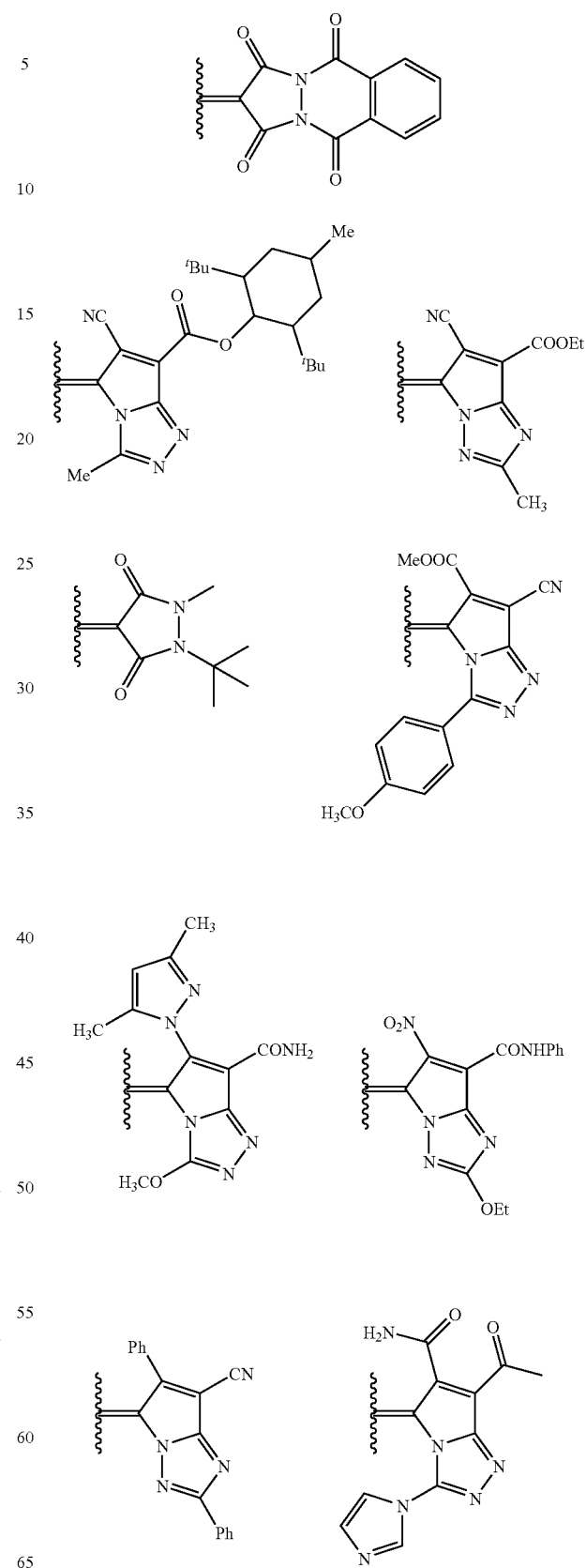

TABLE 1-continued

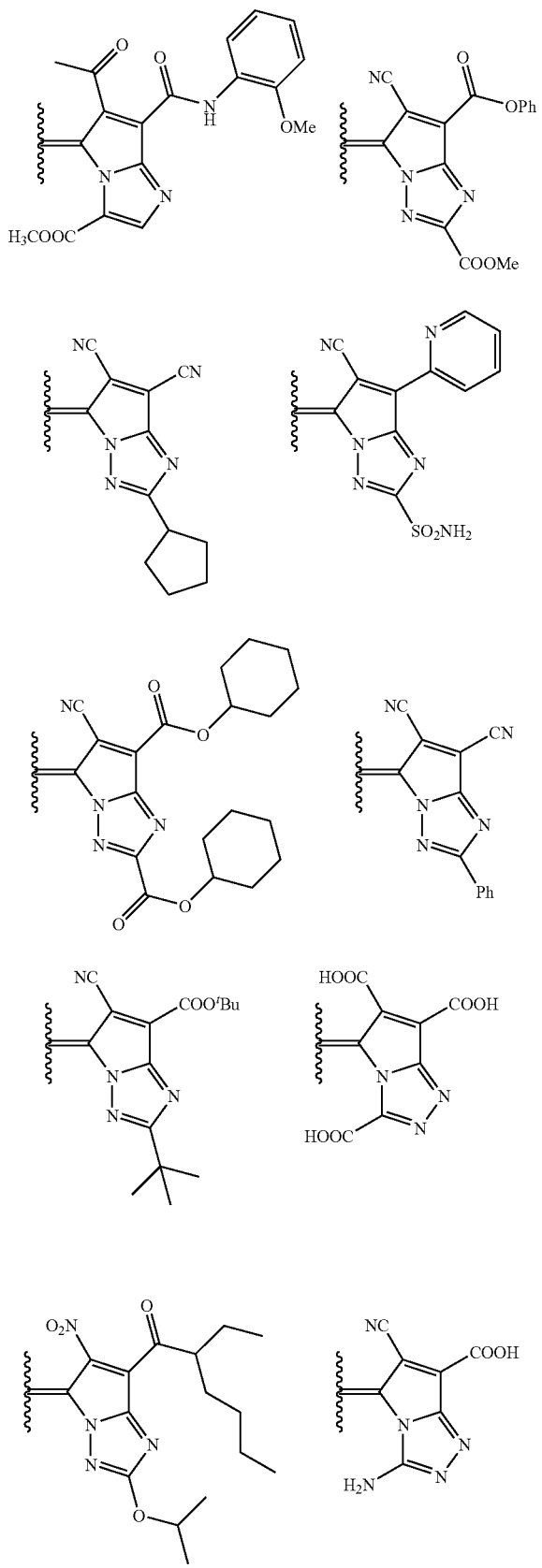
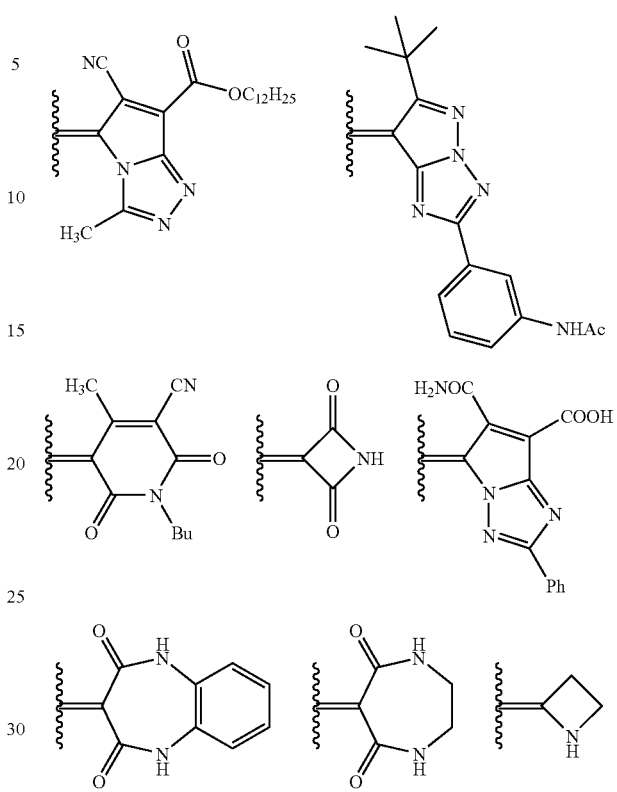

In formula (I-1), $R^{25}$ and $R^{26}$ each independently represent a hydrogen atom or a monovalent substituent. The monovalent substituent is, for example, a monovalent substituent described above.

In particular, $R^{25}$ and $R^{26}$ are preferably a hydrogen atom, a halogen atom, an alkyl group, an aryl group, a cyano group, a carboxyl group, an alkoxycarbonyl group, an aryloxycarbonyl group, a carbamoyl group, an alkylcarbonyl group, an arylcarbonyl group, a nitro group, an amino group, an acylamino group, a sulfonamido group, a hydroxy group, an alkoxy group, an aryloxy group, an acyloxy group, an alkylsulfonyloxy group, an arylsulfonyloxy group, a sulfo group, an alkylthio group, or an arylthio group; more preferably a hydrogen atom, a halogen atom, an amino group, an acylamino group, a hydroxy group, an alkoxy group, an aryloxy group, an acyloxy group, an alkylthio group or an arylthio group; further preferably an alkoxy group, an aryloxy group, an acyloxy group, an alkoxycarbonyloxy group, an aryloxycarbonyloxy group, an acylamino group, a carbamoyloxy group, or a carbamoylamino group; particularly preferably an alkoxy group, an aryloxy group or an acyloxy group; and still more preferably an alkoxy group.

The alkyl group in the alkoxy group is preferably an alkyl group having 1 to 20 carbon atoms, such as a methyl group, an ethyl group, a propyl group, a hexyl group, and an octyl group. The alkyl group may be substituted with one or more monovalent substituents at any positions. The monovalent substituent is, for example, a monovalent substituent described above. Any of the substituents may bond to each other to form a ring. The alkyl group in the alkoxy group is preferably an alkyl group having 3 to 20 carbon atoms, more preferably an alkyl group having 5 to 18 carbon atoms, and particularly preferably an alkyl group having 6 to 12 carbon atoms.

The aryl group in the aryloxy group is preferably an aryl group having 6 to 20 carbon atoms, such as a phenyl group, and a naphthyl group. The aryl group may be substituted with one or more monovalent substituents at any position. The monovalent substituent is, for example, a monovalent substituent described above. Any of the substituents may bond to each other to form a ring. The aryl group in the aryloxy group is preferably an aryl group having 6 to 14 carbon atoms, more preferably an aryl group having 6 to 10 carbon atoms, and particularly preferably a phenyl group.

The acyl group in the acyloxy group is preferably an acyl group having 1 to 20 carbon atoms, such as an acetyl group, a propionyl group, a butanoyl group, a hexanoyl group, an octanoyl group, a benzoyl group, and a naphthoyl group. The acyl group may be substituted with one or more monovalent substituents at any position. The monovalent substituent is, for example, a monovalent substituent described above. Any of the substituents may bond to each other to form a ring. The acyl group in the acyloxy group is preferably an acyl group having 1 to 15 carbon atoms, more preferably an acyl group having 1 to 10 carbon atoms, and particularly preferably an acyl group having 4 to 8 carbon atoms.

The alkyl group in the alkoxycarbonyloxy group is preferably an alkyl group having 1 to 20 carbon atoms, such as a methyl group, an ethyl group, a propyl group, a hexyl group, and an octyl group. The alkyl group may be substituted with one or more monovalent substituents at any positions. The monovalent substituent is, for example, a monovalent substituent described above. Any of the substituents may bond to each other to form a ring. The alkyl group in the alkoxycarbonyloxy group is preferably an alkyl group having 3 to 20 carbon atoms, more preferably an alkyl group having 5 to 18 carbon atoms, and particularly preferably an alkyl group having 6 to 12 carbon atoms.

The aryl group in the aryloxycarbonyloxy group is preferably an aryl group having 6 to 20 carbon atoms, such as a phenyl group, and a naphthyl group. The aryl group may be substituted with one or more monovalent substituents at any position. The monovalent substituent is, for example, a monovalent substituent described above. Any of the substituents may bond to each other to form a ring. The aryl group in the aryloxycarbonyloxy group is preferably an aryl group having 6 to 14 carbon atoms, more preferably an aryl group having 6 to 10 carbon atoms, and particularly preferably a phenyl group.

The acyl group in the acylamino group is preferably an acyl group having 1 to 20 carbon atoms, such as an acetyl group, a propionyl group, a butanoyl group, a hexanoyl group, an octanoyl group, a benzoyl group, and a naphthoyl group. The acyl group may be substituted with one or more monovalent substituents at any position. The monovalent substituent is, for example, a monovalent substituent described above. Any of the substituents may bond to each other to form a ring. The acyl group in the acylamino group is preferably an acyl group having 1 to 15 carbon atoms, more preferably an acyl group having 1 to 10 carbon atoms, and particularly preferably an acyl group having 4 to 8 carbon atoms.

The substituent on the nitrogen atom in the case of a carbamoyloxy group is preferably a hydrogen atom, an alkyl group having 1 to 20 carbon atoms, or an aryl group having 6 to 20 carbon atoms. Examples thereof include a hydrogen atom, a methyl group, an ethyl group, a propyl group, a hexyl group, an octyl group, a phenyl group, and a naphthyl group. The alkyl group and the aryl group may be substituted with one or more monovalent substituents at any position. The monovalent substituent is, for example, a monovalent substituent described above. The alkyl group and the aryl group in the carbamoyloxy group is preferably an alkyl group having 3 to 20 carbon atoms or an aryl group having 6 to 14 carbon atoms, and more preferably an alkyl group having 6 to 12 carbon atoms or an aryl group having 6 to 10 carbon atoms.

The substituent on the nitrogen atom in the case of a carbamoylamino group is preferably a hydrogen atom, an alkyl group having 1 to 20 carbon atoms, or an aryl group having 6 to 20 carbon atoms. Examples thereof include a hydrogen atom, a methyl group, an ethyl group, a propyl group, a hexyl group, an octyl group, a phenyl group, and a naphthyl group. The alkyl group and the aryl group may be substituted with one or more monovalent substituents at any position. The monovalent substituent is, for example, a monovalent substituent described above. The alkyl group and the aryl group in the carbamoylamino group is preferably an alkyl group having 3 to 20 carbon atoms or an aryl group having 6 to 14 carbon atoms, and more preferably an alkyl group having 6 to 12 carbon atoms or an aryl group having 6 to 10 carbon atoms.

$R^{25}$ and $R^{26}$ may be different from each other, but are preferably the same as each other.

Favorable examples of $R^{25}$ or $R^{26}$ are shown in the following Table 2, but the present invention is not restricted thereby. The wavy line in the Table indicates the binding site on the benzene ring shown in formula (I-1).

TABLE 2

Specific examples of the combination of $R^{25}$ or $R^{26}$

H, Cl, F, NO$_2$, COOEt (structures with OH, OMe, O-alkyl groups)

$^nC_8H_{17}$, $^nC_{12}H_{25}$ $^nC_{16}H_{33}$, $C_{18}H_{37}$ (allyl ether, COOEt ether, Ph ether)

(Ph ketone ether, diether)

(diether-OH), CN

TABLE 2-continued
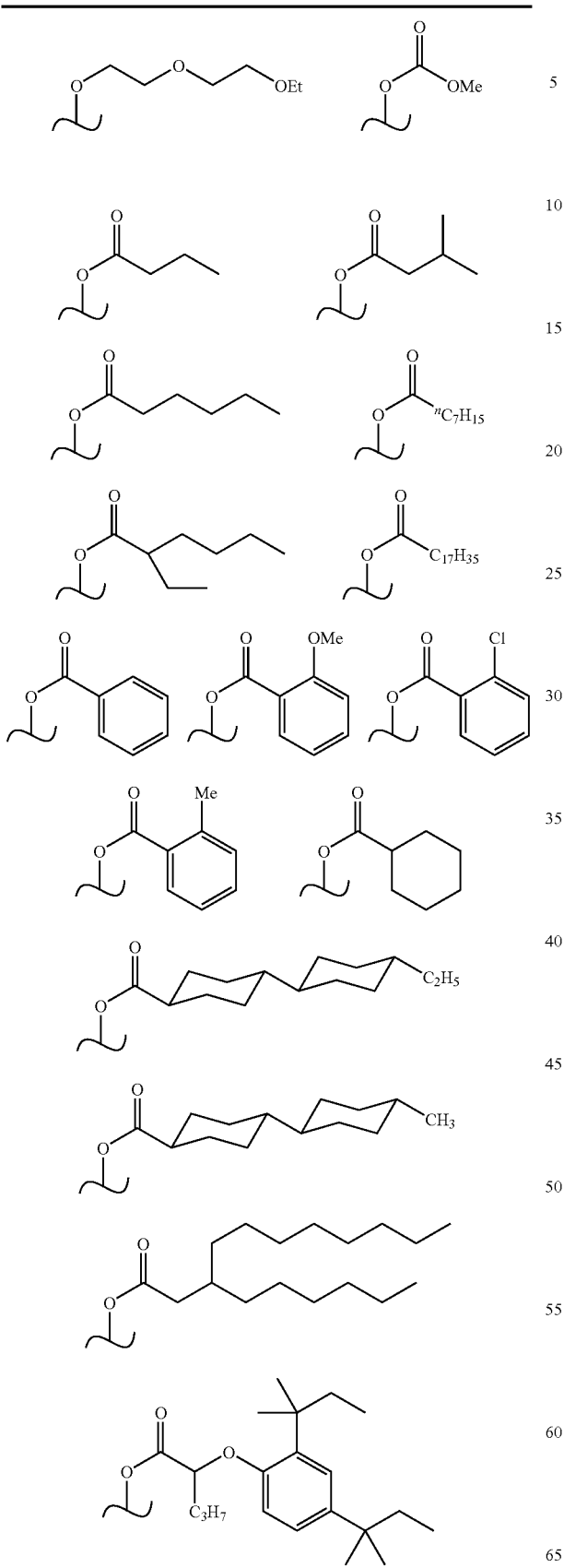
TABLE 2-continued
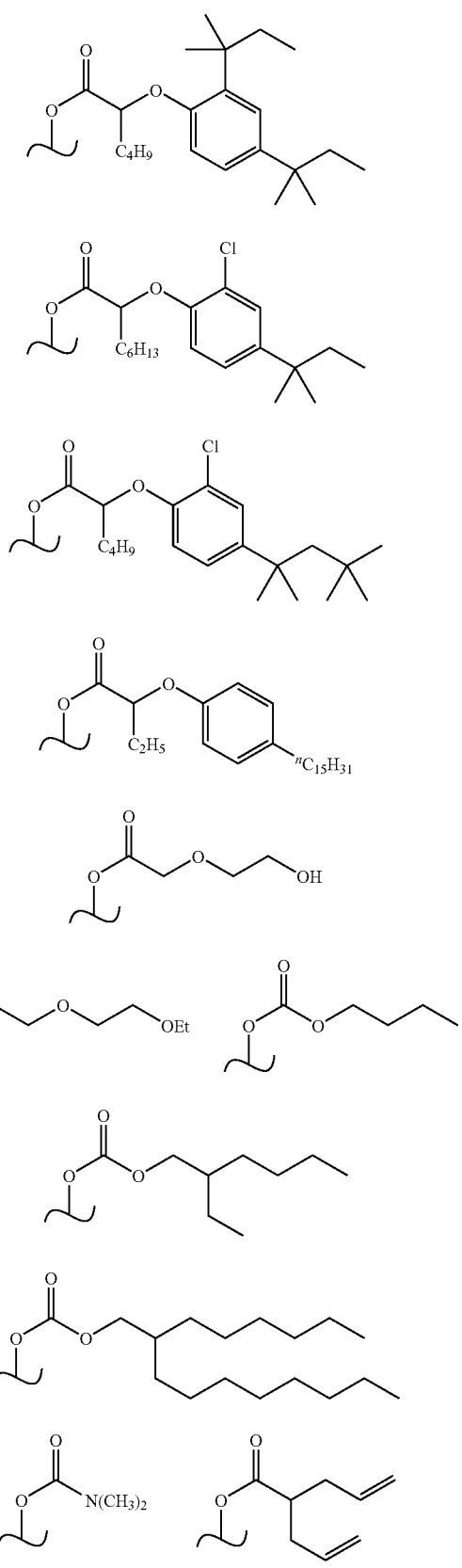

TABLE 2-continued
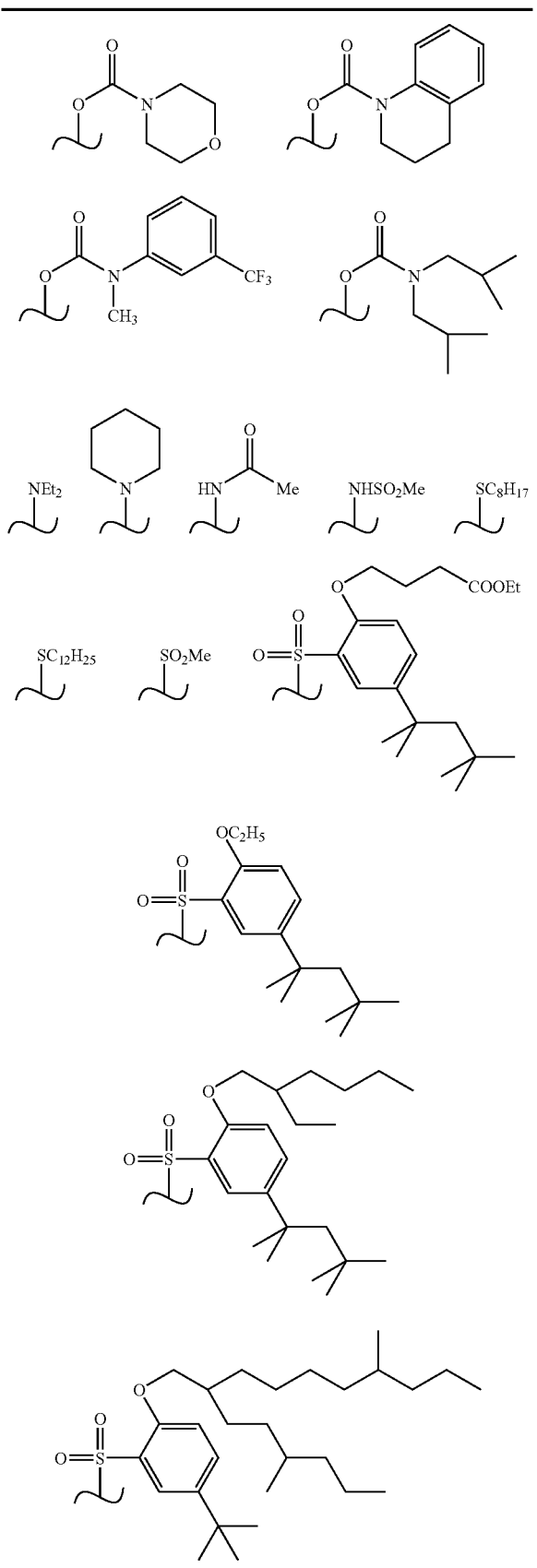
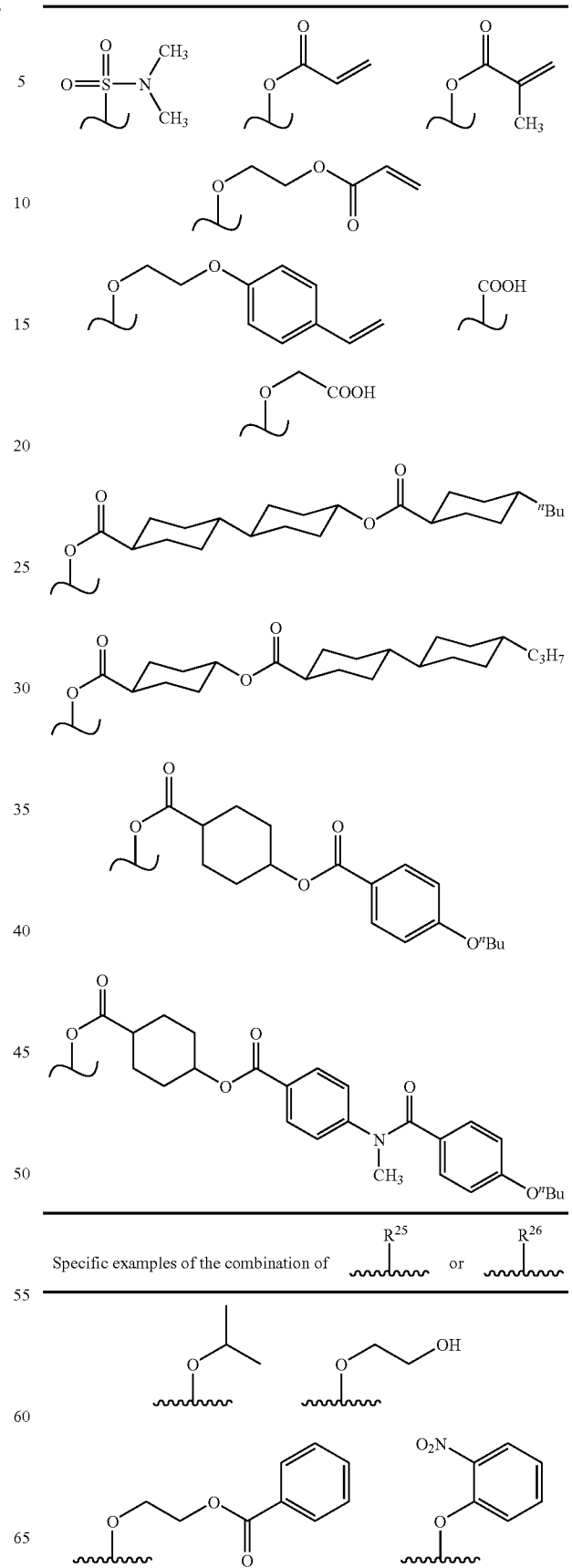

TABLE 2-continued

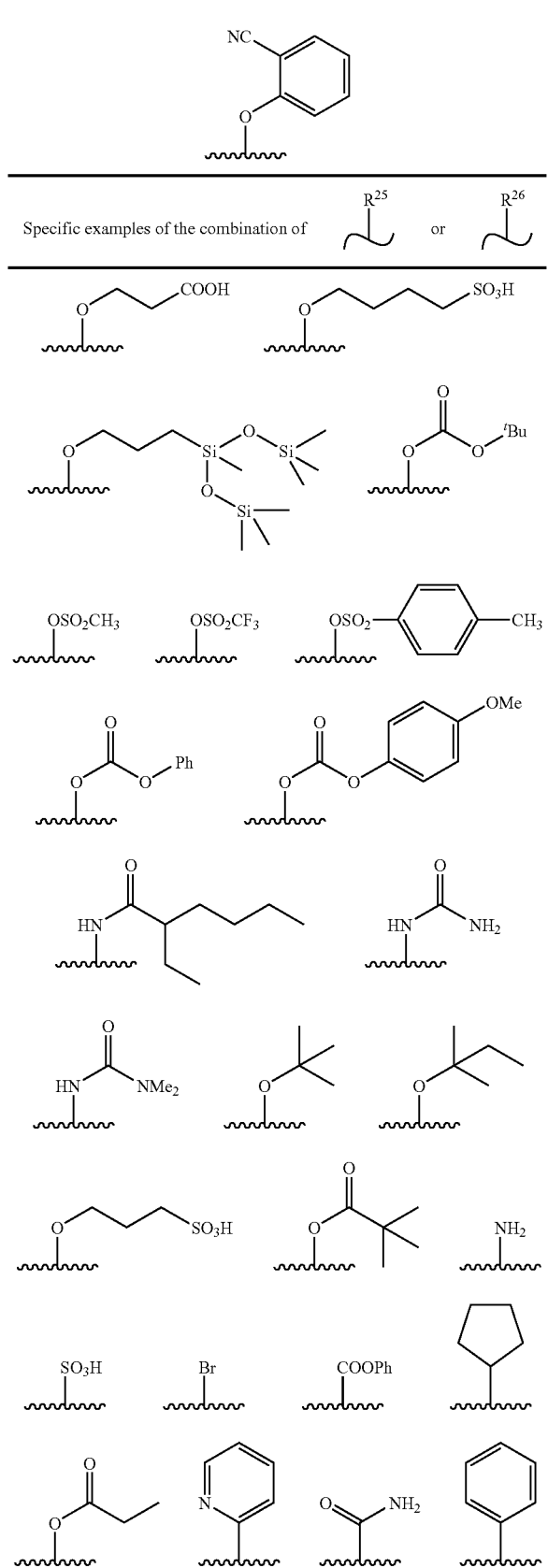

TABLE 2-continued

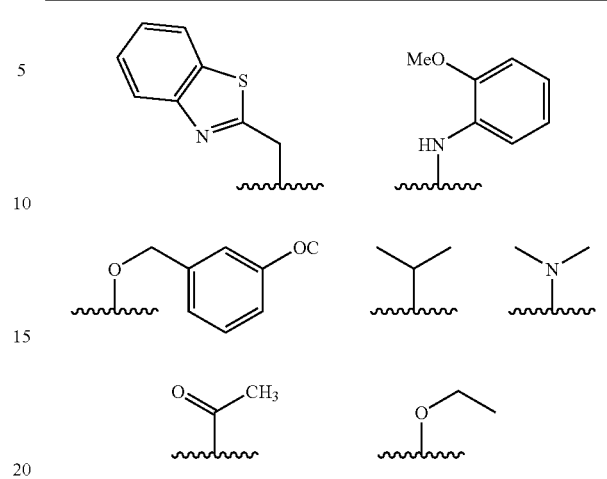

$X^{21}$, $X^{22}$, $X^{23}$ and $X^{24}$ each independently represent a hetero atom. Examples of the hetero atom include a boron atom, a nitrogen atom, an oxygen atom, a silicon atom, a phosphorus atom, a sulfur atom, a selenium atom, and a tellurium atom. $X^{21}$, $X^{22}$, $X^{23}$ and $X^{24}$ each are preferably a nitrogen atom, an oxygen atom or a sulfur atom; more preferably a nitrogen atom or a sulfur atom; and particularly preferably a sulfur atom.

$X^{21}$, $X^{22}$, $X^{23}$ and $X^{24}$ may be different from each other, but the combination of $X^{21}$ and $X^{22}$ and the combination of $X^{23}$ and $X^{24}$ are preferably the same as each other. Particularly preferably, all groups are the same; and most preferably, all groups each represent a sulfur atom.

Favorable examples of the combination of $X^{21}$ and $X^{22}$ or the combination of $X^{23}$ and $X^{24}$ are shown in the following Table 3, but the present invention is not restricted thereby. Ac represents an acetyl group in the present specification. The wavy line in the Table indicates the binding site on the carbon atoms in formula (I-1) to which $R^{21}$ and $R^{22}$ or $R^{23}$ and $R^{24}$ bound.

TABLE 3

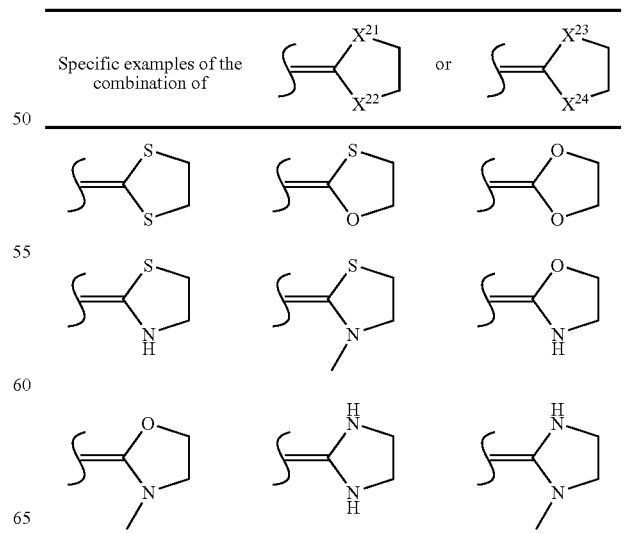

TABLE 3-continued

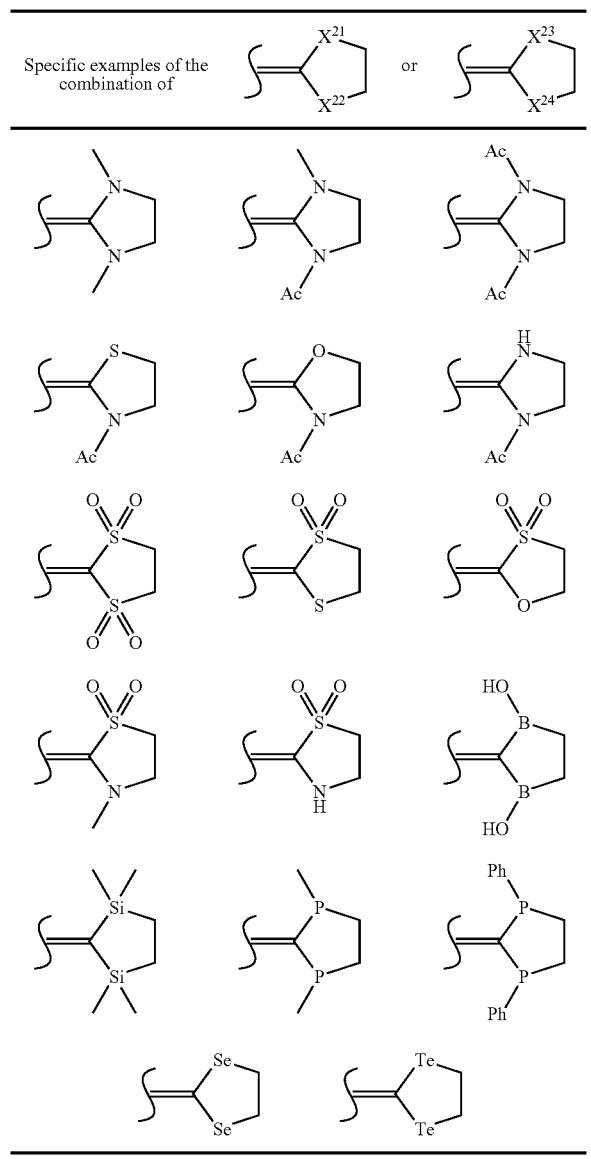

When the compound represented by formula (I-1) is used as an ultraviolet absorbent, the compound represented by formula (I-1) is preferably a compound represented by formula (Ia-1).

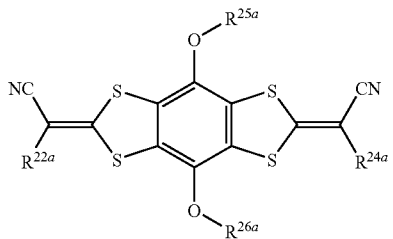

Formula (Ia-1)

In formula (Ia-1), $R^{22a}$ and $R^{24a}$ each have the same meaning as those of $R^{22a}$ and $R^{24a}$ in formula (I-1), respectively, and preferable ranges thereof are also the same. $R^{25a}$ and $R^{26a}$ each represent a monovalent substituent. $R^{25a}$ and $R^{26a}$ each are preferably an alkyl group having 1 to 20 carbon atoms (preferably 1 to 10 carbon atoms), an aryl group having 6 to 20 carbon atoms (preferably 6 to 10 carbon atoms), or a 4- to 7-membered (preferably 5- or 6-membered) heterocyclic group. These may be substituted with a substituent. The substituent is, for example, the monovalent substituent described above. Examples of a bivalent substituent include a carbonyl group and an imino group. Multiple substituents, when present, may be the same as or different from each other. The substituents may bind to each other, forming a fused ring or a spiro ring.

However, among compounds represented by Formula (I-1), the compounds, wherein $R^{21}$, $R^{22}$, $R^{23}$ and $R^{24}$ each represent a cyan group; $X^{21}$, $X^{22}$, $X^{23}$ and $X^{24}$ each represent a sulfur atom; and $R^{25}$ and $R^{26}$ each represent a hydroxyl group or a hydrogen atom, are excluded from the first embodiment of the present invention. Further, among compounds represented by Formula (I-1), the compounds, wherein $R^{21}$ and $R^{23}$ each represent a hydrogen atom; $R^{22}$ and $R^{24}$ each represent an arylcarbonyl group; $X^{21}$, $X^{22}$, $X^{23}$ and $X^{24}$ each represent a sulfur atom; and $R^{25}$ and $R^{26}$ each represent a hydroxyl group, are excluded from the first embodiment of the present invention.

Next, the use of the compound represented by Formula (I-1) for an ultraviolet absorbent compound is described below.

In the first embodiment of the present invention, where the compound represented by Formula (I-1) is used as an ultraviolet absorbent compound, it is preferable that $R^{25}$ and $R^{26}$ each have 5 or less carbon atoms, or they are a substituent having high flatness from the viewpoints of providing resistance to solvent and resistance to water by enhancing an intramolecular interaction and an intermolecular interaction. Specifically, $R^{25}$ and $R^{26}$ each are preferably a hydrogen atom, an alkyl group having 1 to 5 carbon atoms, a cycloalkyl group having 3 to 5 carbon atoms, an aryl group, a heterocyclic group, an acyl group having 2 to 5 carbon atoms, an alkoxy group having 1 to 5 carbon atoms, an aryloxy group, a heterocyclic oxy group, an acyloxy group having 2 to 5 carbon atoms, a hydroxyl group, a halogen atom, a nitro group, a cyano group, an amino group, a mono/dialkylamino group having 1 to 5 carbon atoms, an arylamino group, a heterocyclic amino group, an alkoxycarbonyl group having 1 to 5 carbon atoms, an aryloxycarbonyl group, a carbamoyl group, or a sulfamoyl group; and more preferably a hydrogen atom, an alkoxy group having 1 to 5 carbon atoms, an acyloxy group having 2 to 5 carbon atoms, a cyano group, or a halogen atom. From a viewpoint of ease of production, it is especially preferable that $R^{25}$ and $R^{26}$ each are a hydrogen atom, a methoxy group, an ethoxy group, an acetoxy group or a chlorine atom. An absorption maximum wavelength of the compound represented by Formula (I-1) can be controlled by electronic effects (electron-donating property or electron-attracting property) of $R^{25}$ and $R^{26}$. Therefore, it is possible to select a suitable substituent in accordance with an intended hue.

In the first embodiment of the present invention, where the compound represented by Formula (I-1) is used as an ultraviolet absorbent compound, it is preferable that $R^{25}$ and $R^{26}$ each have 6 to 36 carbon atoms, or they are a bulky substituent or a substituent having high hydrophilicity, from the viewpoints of suppressing interaction between molecules and providing a compatibility with respect to a medium. Specifically, $R^{25}$ and $R^{26}$ each are preferably a hydrogen atom, an alkyl group, a cycloalkyl group, aryl group, a heterocyclic group, an acyl group, an alkoxy group, an aryloxy group, a heterocyclic oxy group, an acyloxy group, a hydroxyl group, an amino group, a mono/dialkylamino group, an arylamino group, a heterocyclic amino group, an alkoxycarbonyl group having 1 to 5 carbon atoms, an aryloxycarbonyl group, a carboxyl group, a sulfo group, or a phosphonic acid group; and more preferably a hydrogen atom, an isopropyl group, a t-butyl group, a t-amyl group, a 2-ethylhexyl group, an isopropyloxy group, a t-butyloxy group, a t-amyloxy group, a 2-ethylhexyloxy group, a pivaloyloxy group, a 2-ethylhexanoyloxy group, a hydroxyl group, an amino group, a carboxyl group, or a sulfo group. From a viewpoint of ease of production, it is especially preferable that $R^{25}$ and $R^{26}$ each are a hydrogen atom, a t-butyloxy group, a 2-ethylhexyloxy group, or a 2-ethylhexanoyloxy group. An absorption maximum wavelength of the compound represented by Formula (I-1) can be controlled by electronic effects (electron-donating property or electron-attracting property) of $R^{25}$ and $R^{26}$. Therefore, it is possible to select a suitable substituent in accordance with an intended hue.

In the first embodiment of the present invention, where the compound represented by Formula (I-1) is used as an ultraviolet absorbent compound, it is preferable that $R^{21}$, $R^{22}$, $R^{23}$ and $R^{24}$ each have 5 or less carbon atoms, or they are a substituent having high flatness, from the viewpoints of providing resistance to solvent and resistance to water by enhancing an intramolecular interaction and an intermolecular interaction. Further, it is preferable that $R^{21}$, $R^{22}$, $R^{23}$ and $R^{24}$ each are an electron-accepting substituent necessary for forming a so-called donor/acceptor type chromophore with the hetero atoms $X^{21}$ to $X^{24}$, to provide the compound with a favorable optical property for absorbing visible light. Specifically, $R^{21}$, $R^{22}$, $R^{23}$ and $R^{24}$ are each preferably a substituent selected from the group consisting of an aryl group, a heterocyclic group, an acyl group having 2 to 5 carbon atoms, a nitro group, a cyano group, an alkoxycarbonyl group having 2 to 5 carbon atoms, an aryloxycarbonyl group, a carbamoyl group and an arylcarbamoyl group; more preferably a substituent selected from the group consisting of an acyl group having 2 to 5 carbon atoms, a cyano group, an alkoxycarbonyl group having 2 to 5 carbon atoms, a carbamoyl group and an arylcarbamoyl group; and especially preferably an acetyl group, a cyano group, a methoxycarbonyl group, an ethoxycarbonyl group, a N-phenylcarbamoyl group, or a N-(2-methoxyphenyl)carbamoyl group.

In the first embodiment of the present invention, where the compound represented by Formula (I-1) is used as an ultraviolet absorbent compound, it is preferable that $R^{21}$, $R^{22}$, $R^{23}$ and $R^{24}$ each have 6 to 36 carbon atoms, or they are a bulky substituent or a substituent having high hydrophilicity, from the viewpoints of suppressing interaction between molecules and providing a compatibility with respect to a medium. Further, it is preferable that $R^{21}$, $R^{22}$, $R^{23}$ and $R^{24}$ each are an electron-accepting substituent necessary for forming a so-called donor/acceptor type chromophore with the hetero atoms $X^{21}$ to $X^{24}$, to provide the compound with a favorable optical property for absorbing visible light. Specifically, $R^{21}$, $R^{22}$, $R^{23}$ and $R^{24}$ each are preferably an acyl group, a cyano group, an alkoxycarbonyl group, a carbamoyl group, an arylcarbamoyl group, a carboxyl group, a sulfo group, or a phosphonic acid group; more preferably a pivaloyl group, a cyano group, a t-butyloxycarbonyl group, a 2-ethylhexyloxycarbonyl group, a carbamoyl group, a N-(4-sulfophenyl)carbamoyl group, a mesitylcarbamoyl group, a carboxyl group, or a sulfo group; and especially preferably a t-butyloxycarbonyl group, a 2-ethylhexyloxycarbonyl group, or a carboxyl group.

In the first embodiment of the present invention, it is assumed that at least one of a pair of $R^{21}$ and $R^{22}$, and a pair of $R^{23}$ and $R^{24}$ in the aforementioned Formula (I-1) bonds to each other to form a ring whereby conjugation in the molecule increases in length which results in the absorption maximum being shifted to a long-wavelength side as long as a visible range. For this reason, it is preferable that at least one of these pairs bonds to each other to form a ring. Another ring may be condensed to this ring. Meanwhile, further this ring may have a substituent. Examples of the substituent include the same examples as the aforementioned "(monovalent) substituent in the present invention", and preferable examples are also the same as those listed above.

In the case where at least one of a pair of $R^{21}$ and $R^{22}$, and a pair of $R^{23}$ and $R^{24}$ in the aforementioned Formula (I-1) bonds to each other to form a ring, the formed ring may be an aliphatic or aromatic, hydrocarbon ring or heterocycle. However, from the viewpoints of optical properties and various fastness of the dye compound represented by Formula (I-1), the formed ring is preferably a heterocycle, more preferably a nitrogen-containing heterocycle. Further, in view of thermodynamic stability of the dye compound, the formed ring is more preferably a 5- or 6-membered ring.

In the first embodiment of the present invention, from the viewpoints of optical properties and various fastness of the compound, it is preferable that the dye compound represented by the aforementioned Formula (I-1), when used as an ultraviolet absorbent compound, is represented by the following Formula (II-1).

Formula (II-1)

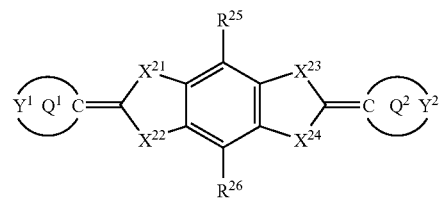

In formula (II-1), $R^{25}$ and $R^{26}$ each independently represent a hydrogen atom or a monovalent substituent. $X^{21}$, $X^{22}$, $X^{23}$ and $X^{24}$ each represent a hetero atom which may have a substituent. $Y^1$ and $Y^2$ each represent a group of atoms necessary to form a 4- to 7-membered ring $Q^1$ or $Q^2$ together with the carbon atom to which $Y^1$ or $Y^2$ bonds.

In the first embodiment of the present invention, where the compound represented by Formula (II-1) is used as an ultraviolet absorbent compound, it is preferable that $R^{25}$ and $R^{26}$ each have 5 or less carbon atoms, or they are a substituent having high flatness, from the viewpoints of providing resistance to solvent and resistance to water by enhancing an intramolecular interaction and an intermolecular interaction. Specifically, $R^{25}$ and $R^{26}$ each are preferably a hydrogen atom, an alkyl group having 1 to 5 carbon atoms, a cycloalkyl group having 3 to 5 carbon atoms, an aryl group, a heterocyclic group, an acyl group having 2 to 5 carbon atoms, an alkoxy group having 1 to 5 carbon atoms, an aryloxy group, a heterocyclic oxy group, an acyloxy group having 2 to 5 carbon atoms, a hydroxyl group, a halogen atom, a nitro group, a cyano group, an amino group, a mono/dialkylamino group having 1 to 5 carbon atoms, an arylamino group, a heterocyclic amino group, an alkoxycarbonyl group having 1 to 5 carbon atoms, an aryloxycarbonyl group, a carbamoyl group, or a sulfamoyl group; and more preferably a hydrogen atom, an alkoxy group having 1 to 5 carbon atoms, an acyloxy group having 2 to 5 carbon atoms, a cyano group, or a halogen atom. From a viewpoint of ease of production, it is especially preferable that $R^{25}$ and $R^{26}$ are each a hydrogen atom, a methoxy group, an ethoxy group, an acetoxy group or a chlorine atom.

An absorption maximum wavelength of the compound represented by Formula (II-1) can be controlled by electronic effects (electron-donating property or electron-attracting property) of $R^{25}$ and $R^{26}$. Therefore, it is possible to select a suitable substituent in accordance with an intended hue.

In the first embodiment of the present invention, where the compound represented by Formula (II-1) is used as an ultraviolet absorbent compound, it is preferable that $R^{25}$ and $R^{26}$ each have 6 to 36 carbon atoms, or they are a bulky substituent or a substituent having high hydrophilicity, from the viewpoints of suppressing interaction between molecules and providing a compatibility with respect to a medium. Specifically, $R^{25}$ and $R^{26}$ each are preferably a hydrogen atom, an alkyl group, a cycloalkyl group, an aryl group, a heterocyclic group, an acyl group, an alkoxy group, an aryloxy group, a heterocyclic oxy group, an acyloxy group, a hydroxyl group, an amino group, a mono/dialkylamino group, an arylamino group, a heterocyclic amino group, an alkoxycarbonyl group having 1 to 5 carbon atoms, an aryloxycarbonyl group, a carboxyl group, a sulfo group, or a phosphonic acid group; and more preferably a hydrogen atom, an isopropyl group, a t-butyl group, a t-amyl group, a 2-ethylhexyl group, an isopropyloxy group, a t-butyloxy group, a t-amyloxy group, a 2-ethylhexyloxy group, a pivaloyloxy group, a 2-ethylhexanoyloxy group, a hydroxyl group, an amino group, a carboxyl group, or a sulfo group. From a viewpoint of ease of production, it is especially preferable that $R^{25}$ and $R^{26}$ are each a hydrogen atom, a t-butyloxy group, a 2-ethylhexyloxy group, or a 2-ethylhexanoyloxy group. An absorption maximum wavelength of the compound represented by Formula (II-1) can be controlled by electronic effects (electron-donating property or electron-attracting property) of $R^{25}$ and $R^{26}$. Therefore, it is possible to select a suitable substituent in accordance with an intended hue.

In Formula (II-1) according to the first embodiment of the present invention, $X^{21}$, $X^{22}$, $X^{23}$ and $X^{24}$ each represent a hetero atom which may have a substituent. Examples of such a hetero atom include a boron atom, a nitrogen atom, an oxygen atom, a silicon atom, a phosphor atom, a sulfur atom and a selenium atom. From the viewpoints of optical properties and various fastness of the compound, a nitrogen atom, an oxygen atom or a sulfur atom is preferable. Among these atoms, a sulfur atom is particularly preferable. In the case where these hetero atoms are those capable of forming three or more covalent bonds (e.g., a boron atom, a nitrogen atom, a silicon atom, a phosphor atom), the hetero atom may have a substituent.

In the first embodiment of the present invention, where the compound represented by Formula (II-1) is used as an ultraviolet absorbent compound, it is preferable that the substituent on the hetero atom has 5 or less carbon atoms, or it is a substituent having high flatness, from the viewpoints of providing resistance to solvent and resistance to water by enhancing an intramolecular interaction and an intermolecular interaction. Specifically, it is preferably an alkyl group having 1 to 5 carbon atoms or an aryl group; more preferably a methyl group, an ethyl group, a propyl group or a phenyl group; and particularly preferably a methyl group.

In the first embodiment of the present invention, where the compound represented by Formula (II-1) is used as an ultraviolet absorbent compound, it is preferable that the substituent on the hetero atom has 6 to 36 carbon atoms, or they are a bulky substituent or a substituent having high hydrophilicity, from the viewpoints of suppressing interaction between molecules and providing a compatibility with respect to a medium. Specifically, it is preferably an alkyl group or an aryl group; more preferably a t-butyl group, a t-amyl group, a 2-ethylhexyl group or a mesityl group; and particularly preferably a t-butyl group or a 2-ethylhexyl group.

In Formula (II-1) according to the first embodiment of the present invention, $Y^1$ and $Y^2$ each represent a group of atoms necessary to form a 4- to 7-membered ring $Q^1$ or $Q^2$ together with the carbon atom to which $Y^1$ or $Y^2$ bonds. It is preferable that $Y^1$ and $Y^2$ each represent a group of non-metallic atoms necessary to form a 4- to 7-membered ring $Q^1$ or $Q^2$.

The ring $Q^1$ or $Q^2$ in the first embodiment of the present invention is a 4- to 7-membered aliphatic or aromatic, hydrocarbon ring or heterocycle. Further, another ring may be fused to these rings.

Preferable substituents for $R^{21}$ to $R^{26}$ and $Q^1$ or $Q^2$ in the first embodiment of the present invention are those generally hitherto-known as a substituent capable of enhancing an interaction between molecules and increasing characteristic properties of the ultraviolet absorbent. Specifically, for example, substituents having an amide bond are preferable, and those having a benzimidazolone or quinoxalinedione structure in particular are also preferable.

It is assumed that where the ring $Q^1$ or $Q^2$ in the first embodiment of the present invention forms a heterocycle, particularly an electron-deficient heterocycle, absorption maximum of the compound represented by Formula (II-1) is shifted to a long-wavelength side whereby more preferable optical properties for an ultraviolet absorbent are provided. For this reason, the ring $Q^1$ or $Q^2$ in the first embodiment of the present invention is preferably a heterocycle, and more preferably a nitrogen-containing heterocycle. Further, in view of thermodynamic stability of the compound, it is more preferable that the ring $Q^1$ or $Q^2$ is a 5- or 6-membered ring.

Hereinafter, specific examples of the compound represented by formula (I-1) or (Ia-1) will be shown, but the present invention should not be considered to be limited thereto. In the present description, "Pr" represents a propyl group, and "Hex" represents a hexyl group.

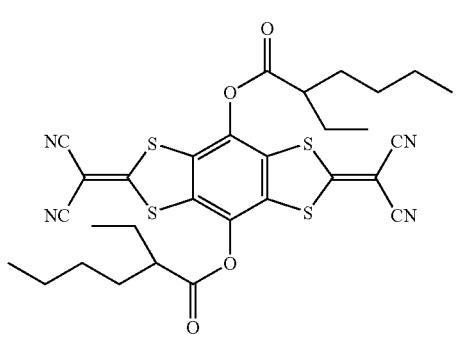

(1)

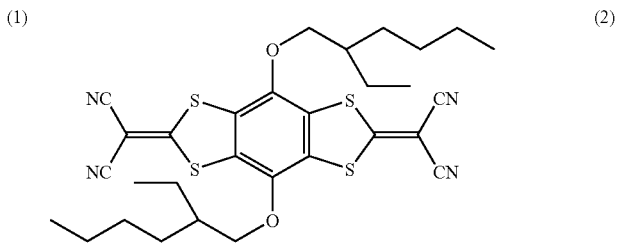

(2)

-continued
(3)
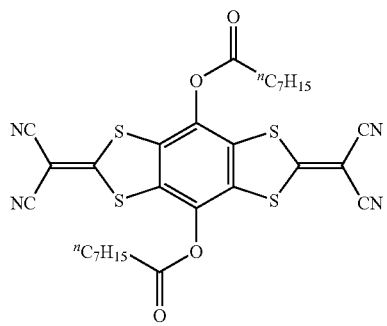
(4)
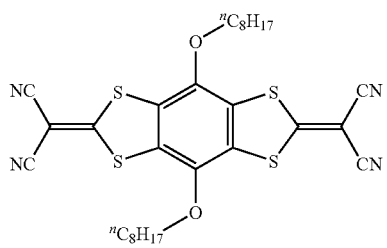
(5)
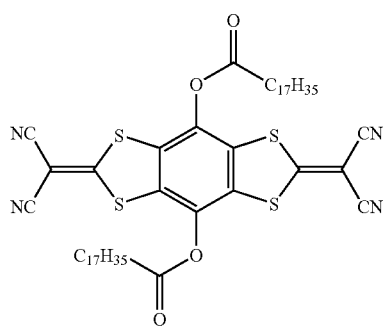
(6)
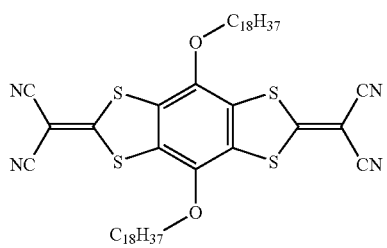
(7)
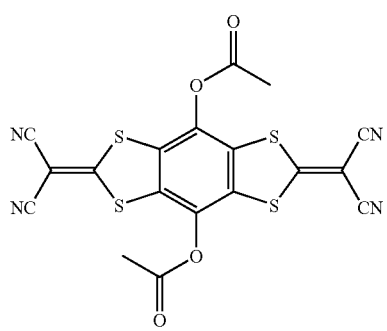
(8)
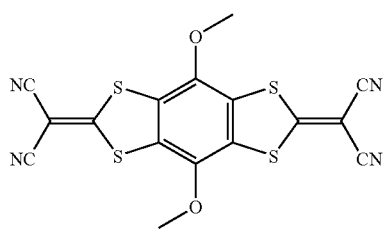
(9)
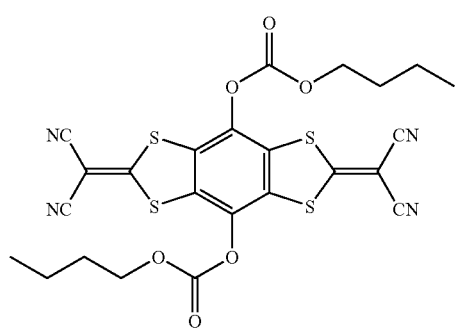
(10)
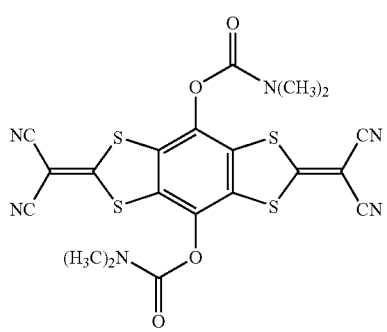
(11)
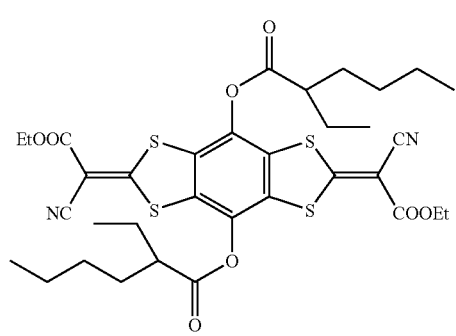
(12)
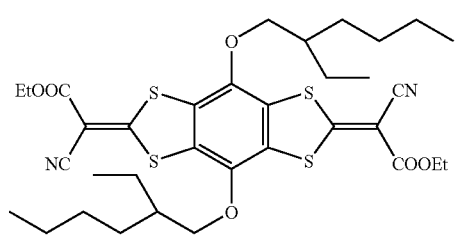

-continued
(13)
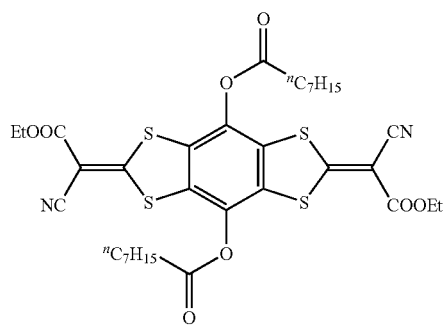
(14)
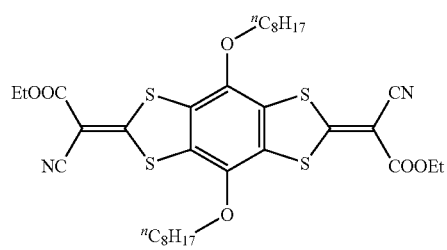
(15)
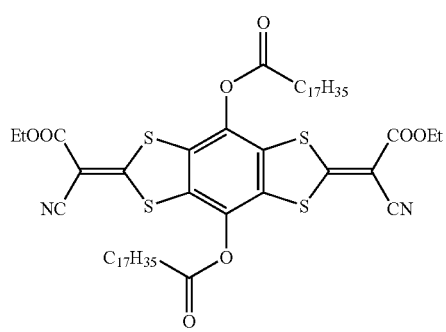
(16)
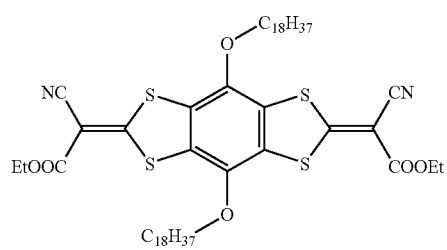
(17)
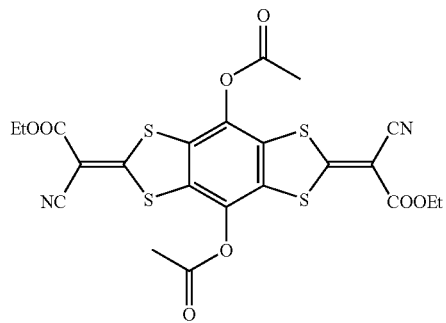
(18)
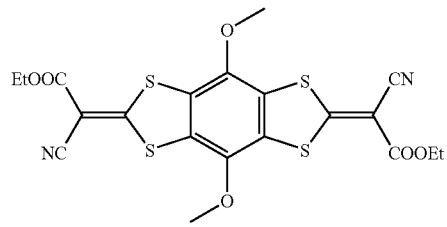
(19)
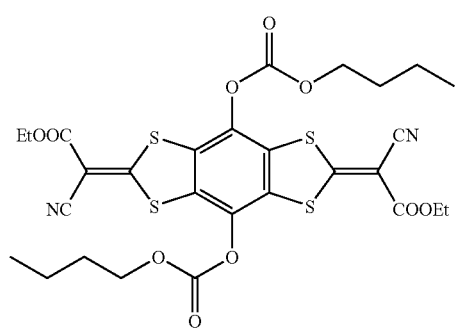
(20)
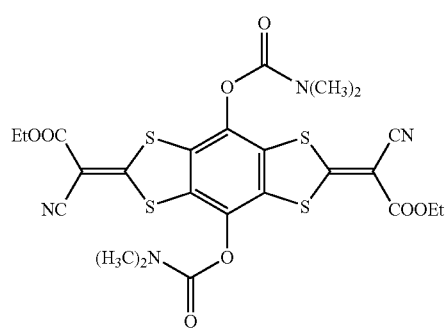
(21)
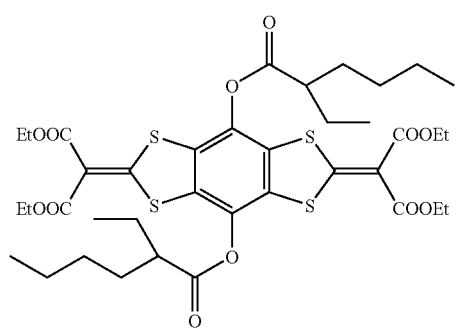
(22)
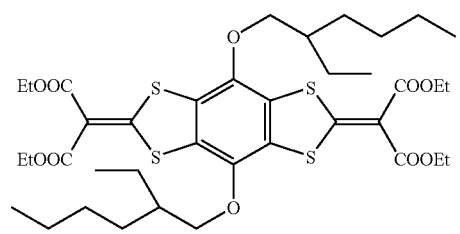

-continued
(23)
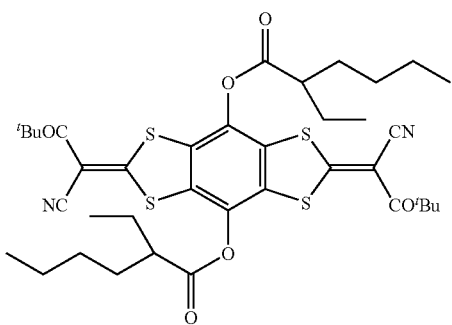
(24)
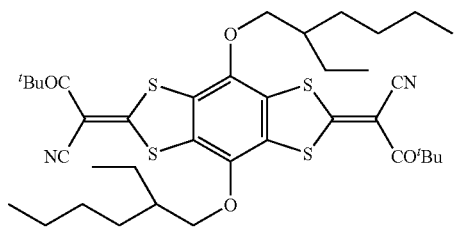
(25)
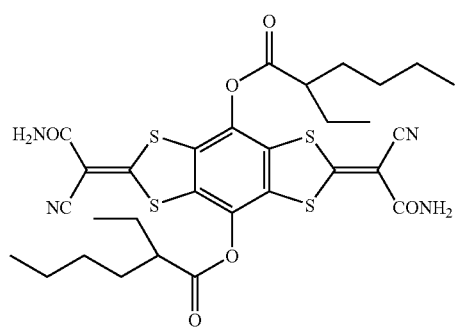
(26)
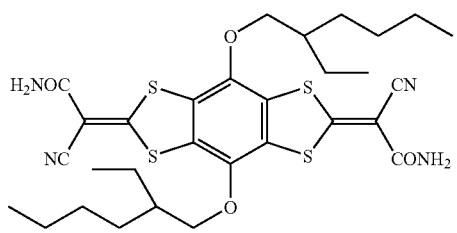
(27)
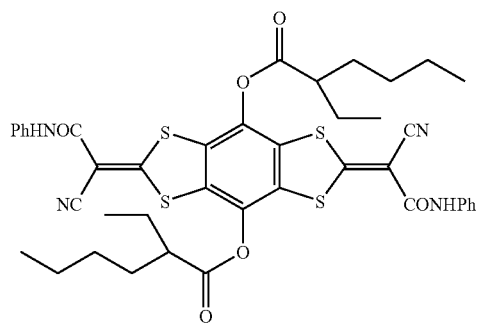
(28)
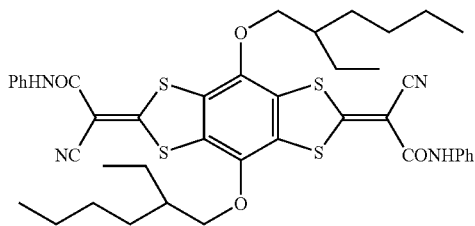
(29)
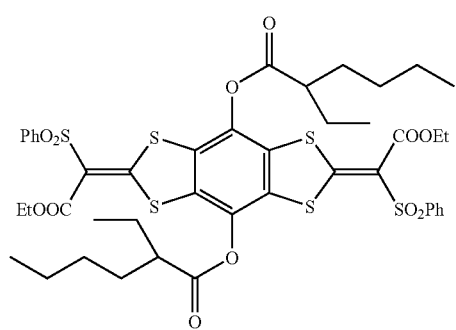
(30)
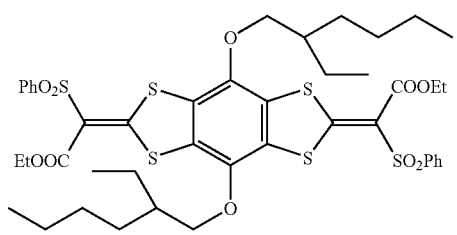
(31)
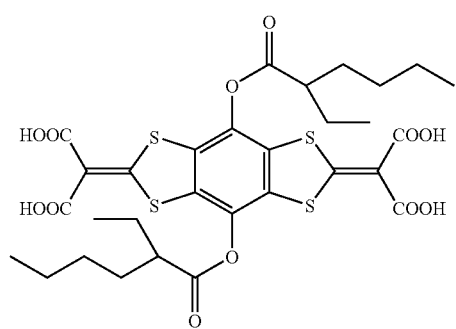
(32)
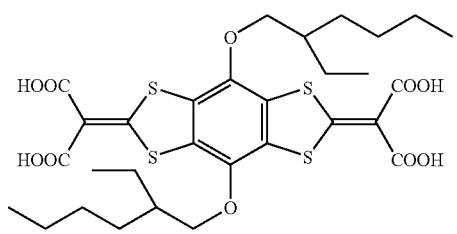

-continued
(33) 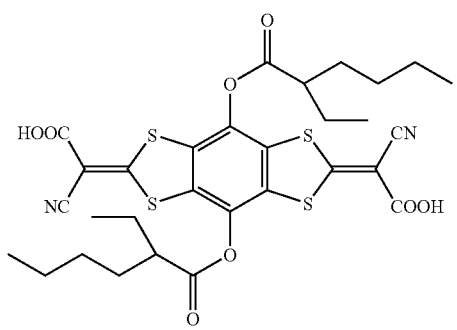
(34) 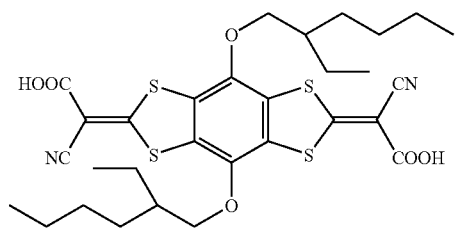
(35) 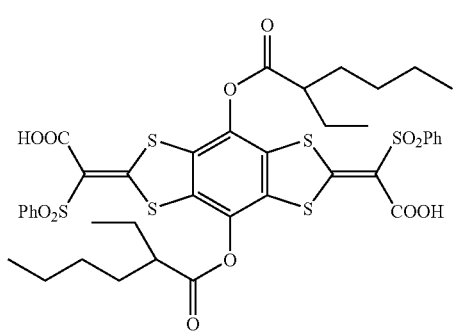
(36) 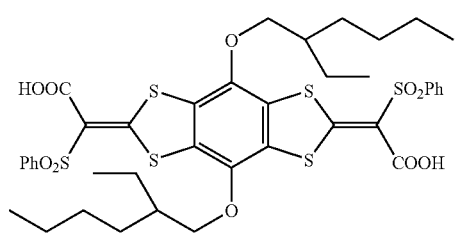
(37) 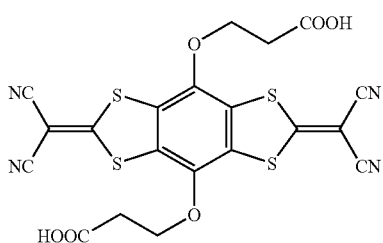
(38) 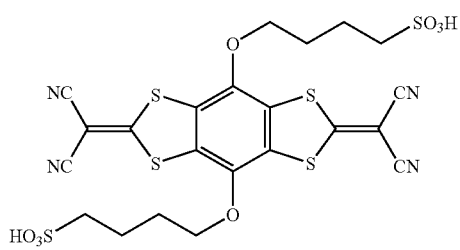
(39) 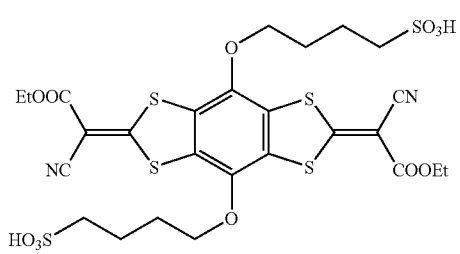
(40) 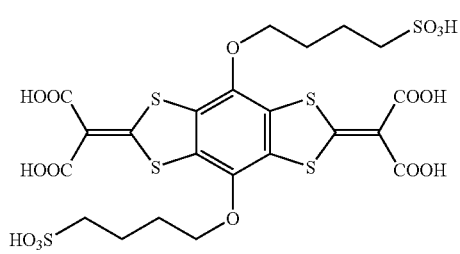
(41) 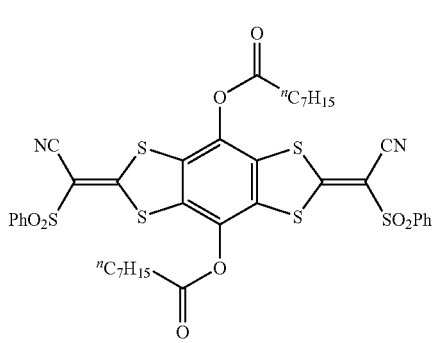
(42) 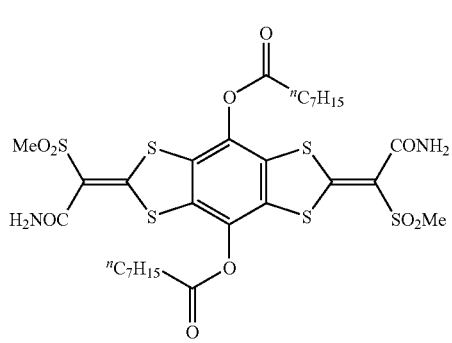

-continued
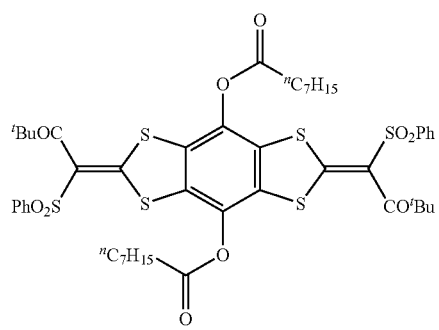
(43)
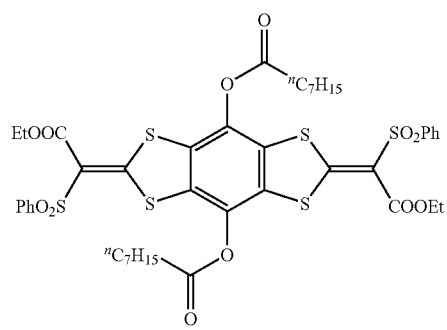
(44)
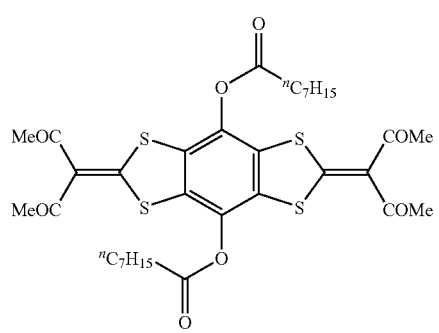
(45)
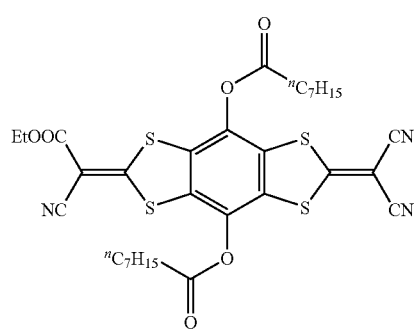
(46)
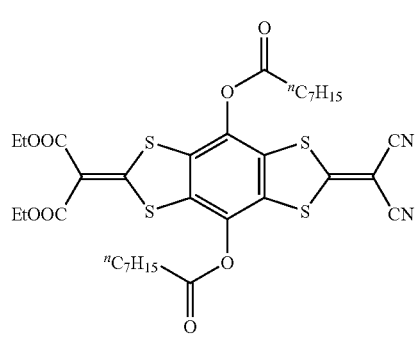
(47)
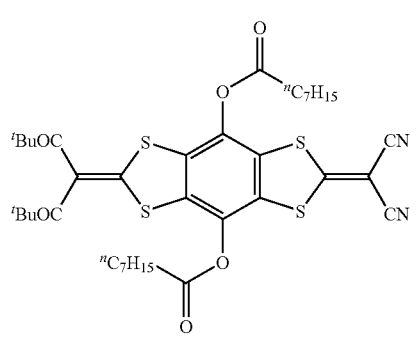
(48)
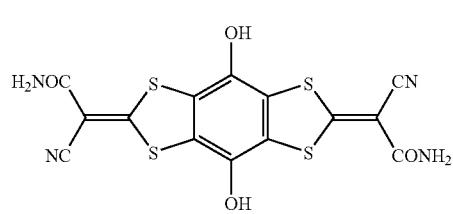
(49)
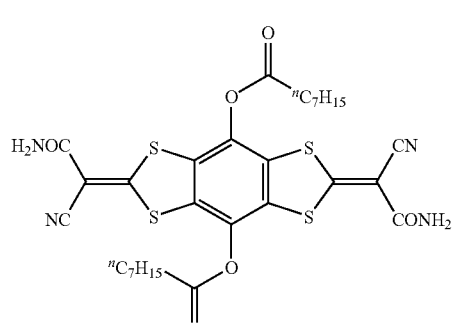
(50)
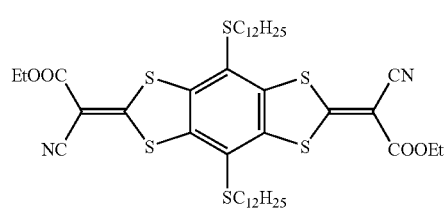
(51)
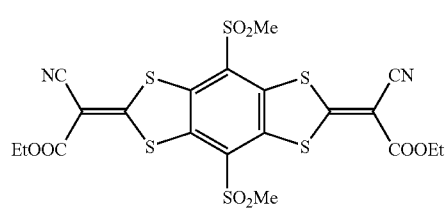
(52)

-continued
(53)
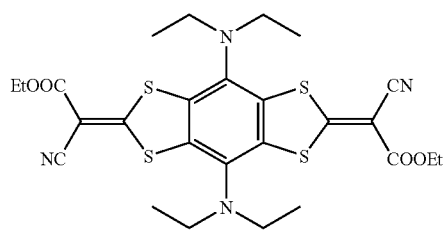
(54)
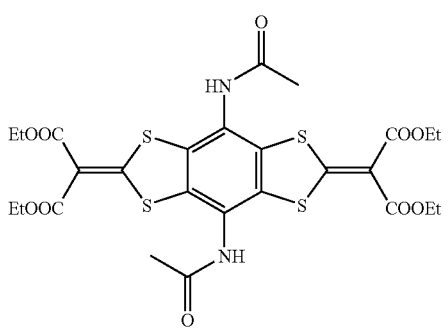
(55)
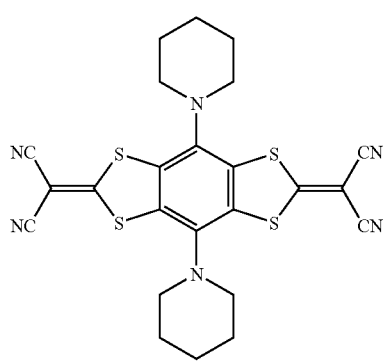
(56)
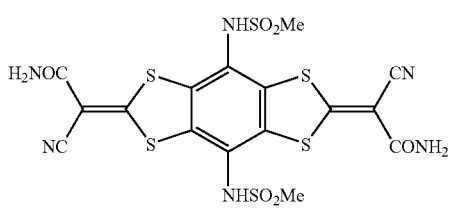
(57)
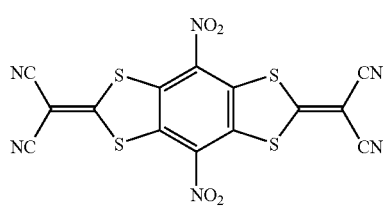
(58)
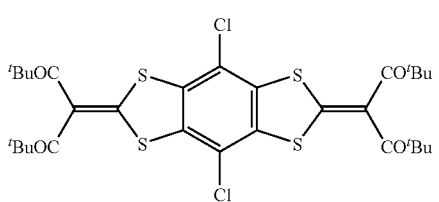
(59)
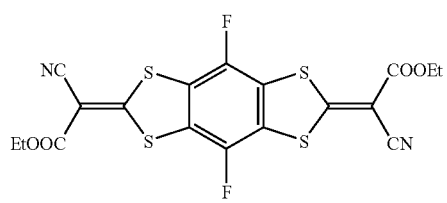
(60)
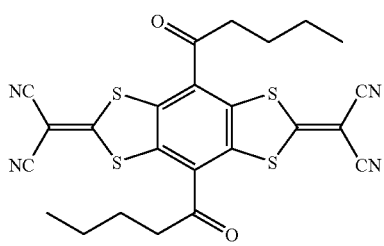
(61)
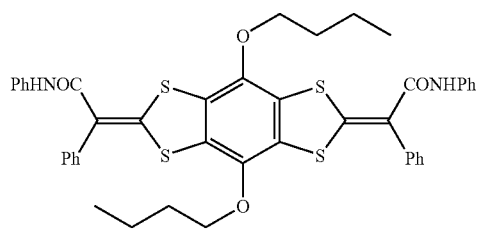
(62)
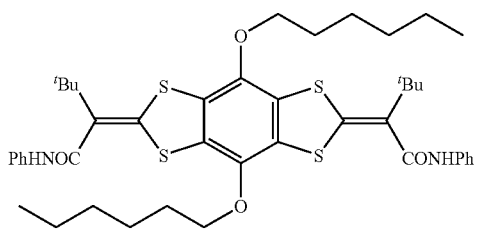

-continued
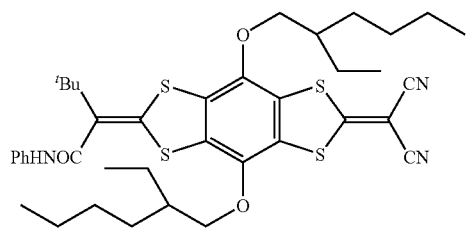 (63)
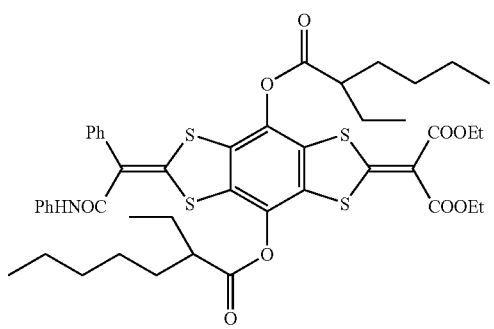 (64)
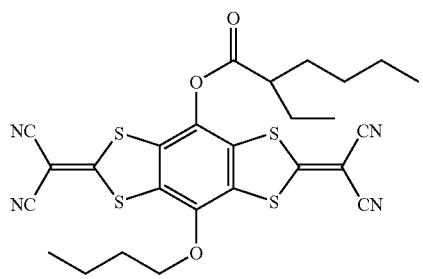 (65)
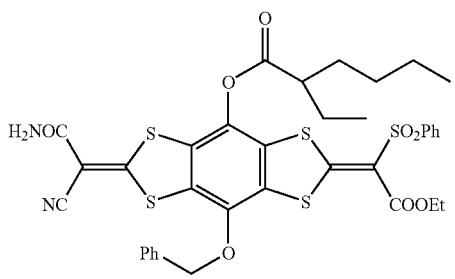 (66)
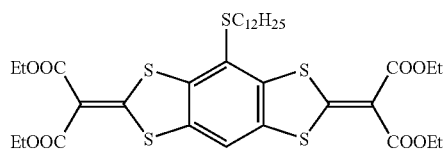 (67)
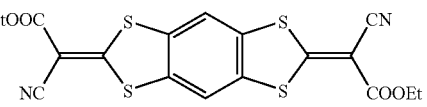 (68)
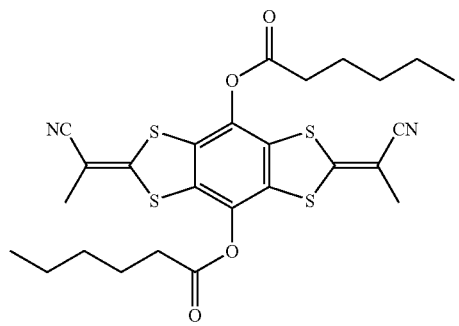 (69)
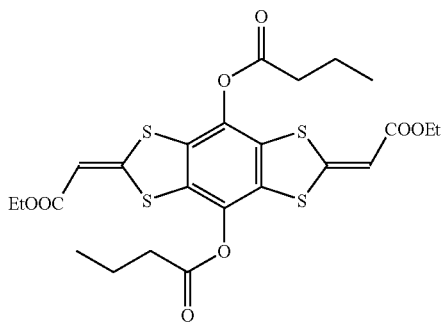 (70)
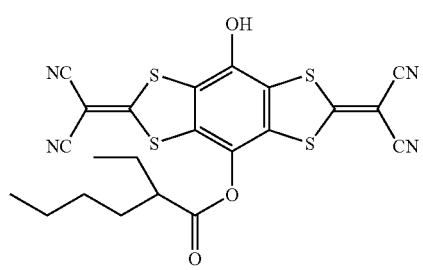 (71)
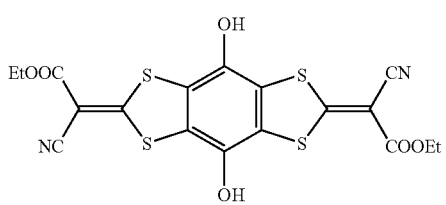 (72)

-continued
(73) 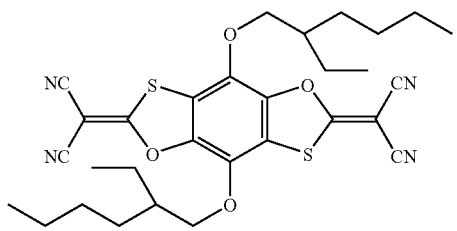
(74) 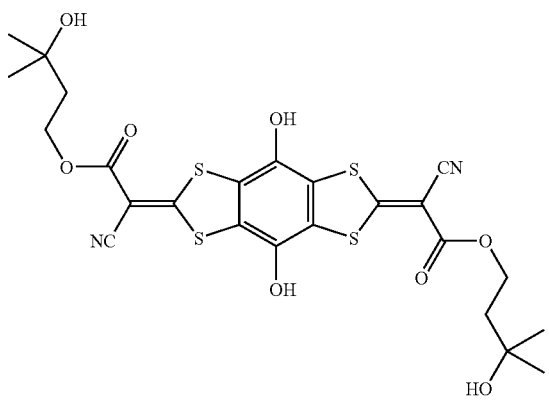
(75) 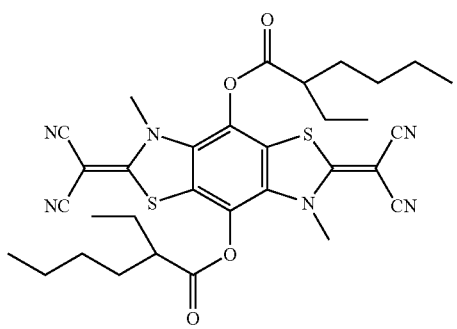
(76) 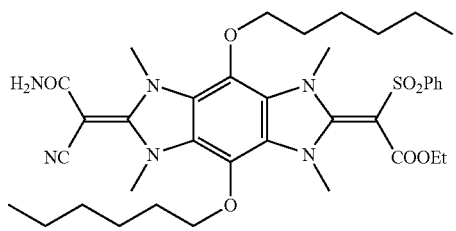
(77) 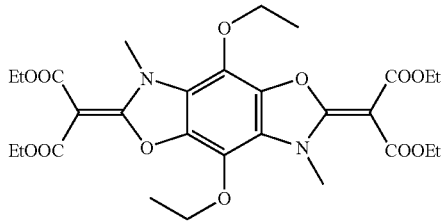
(78) 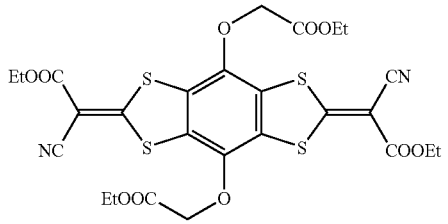
(79) 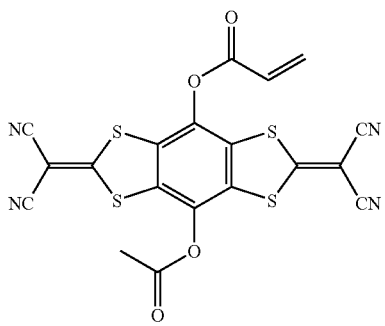
(80) 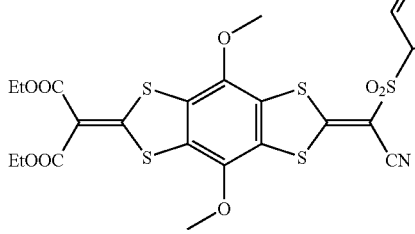
(81) 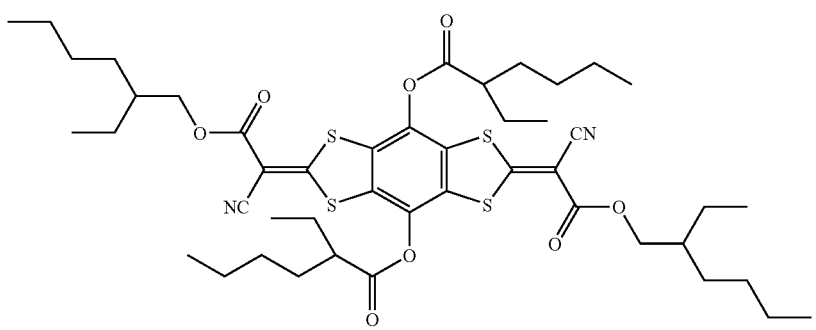

-continued
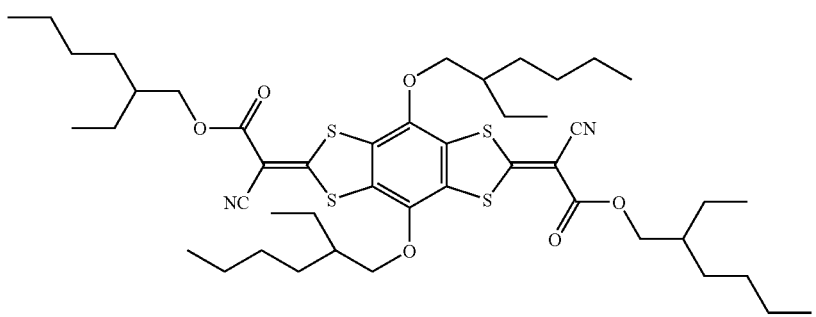
(82)
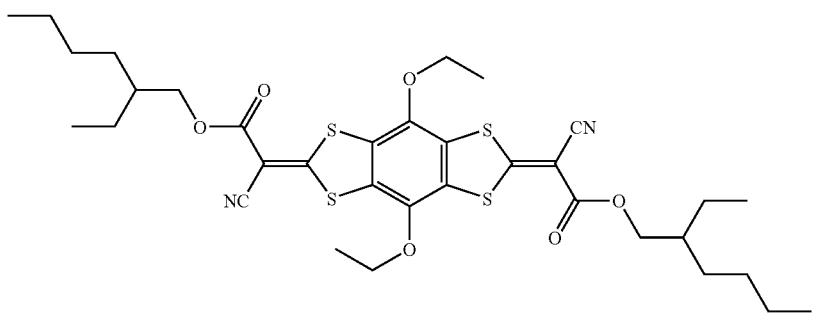
(83)
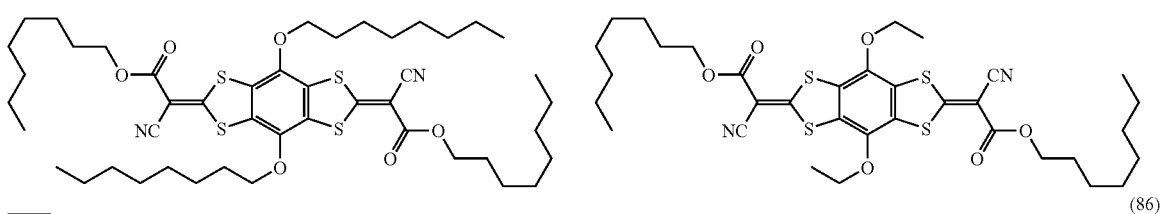
(84)     (85)
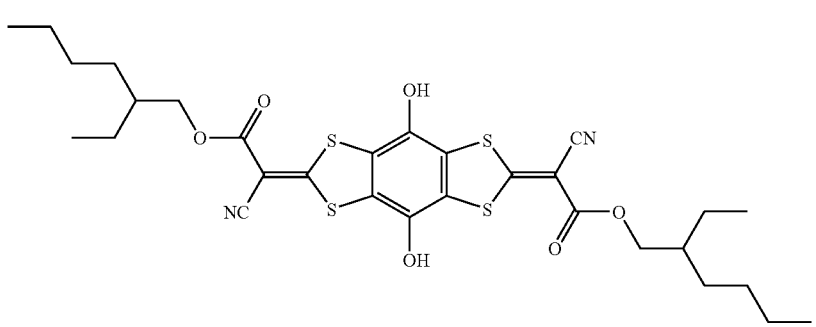
(86)
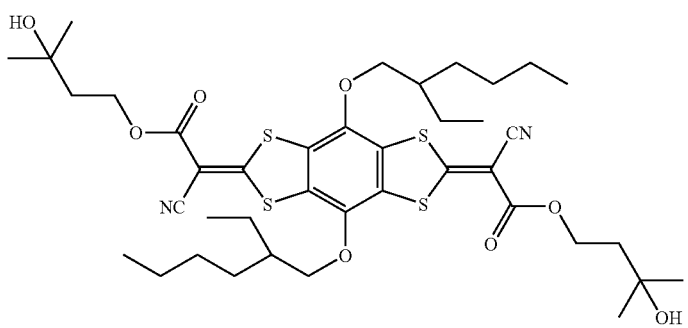
(87)

(88)
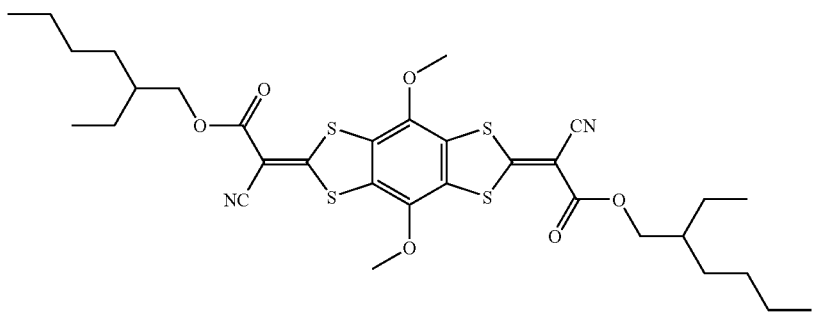
(89)
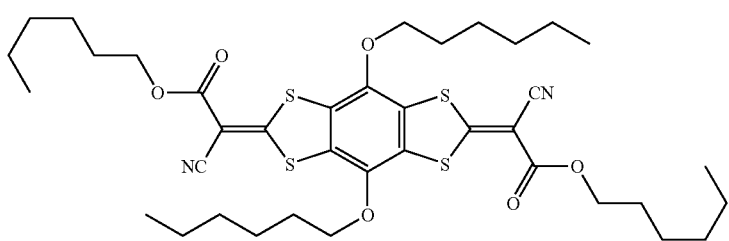
(90)
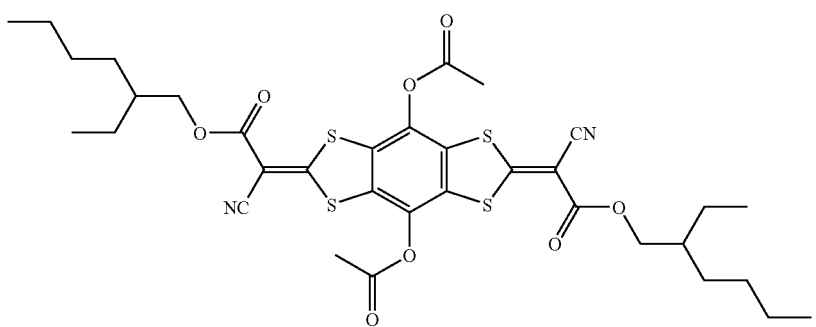
(91)
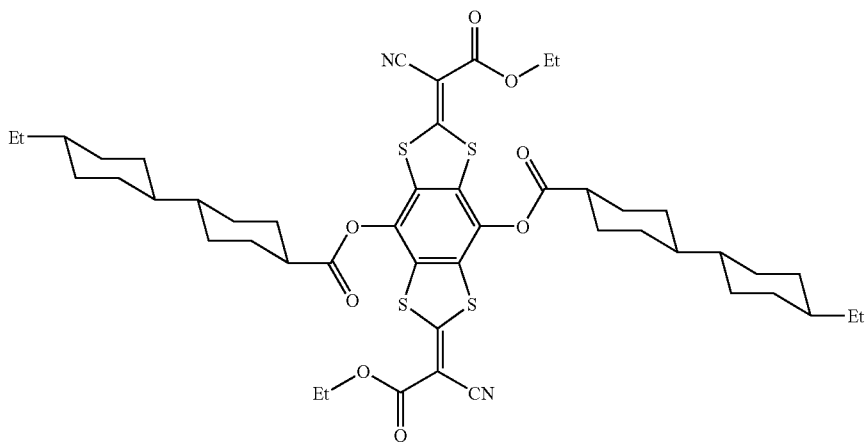

-continued
(92)
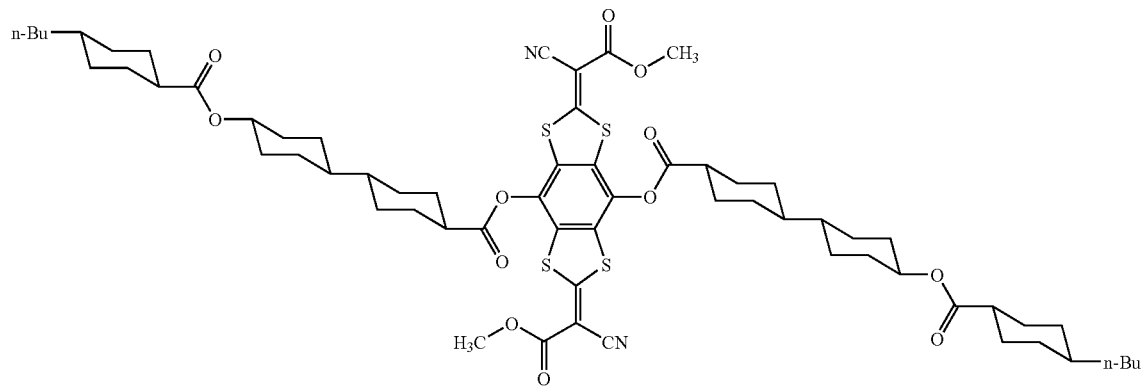
(93)
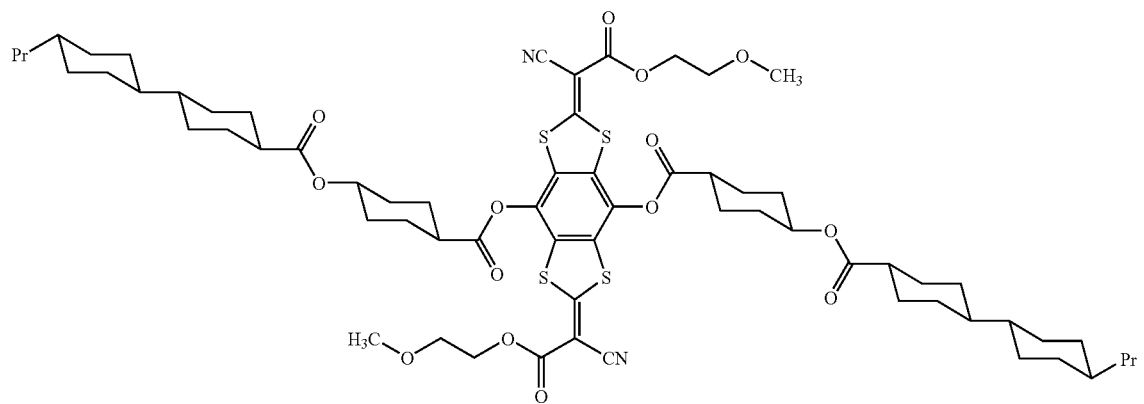
(94)
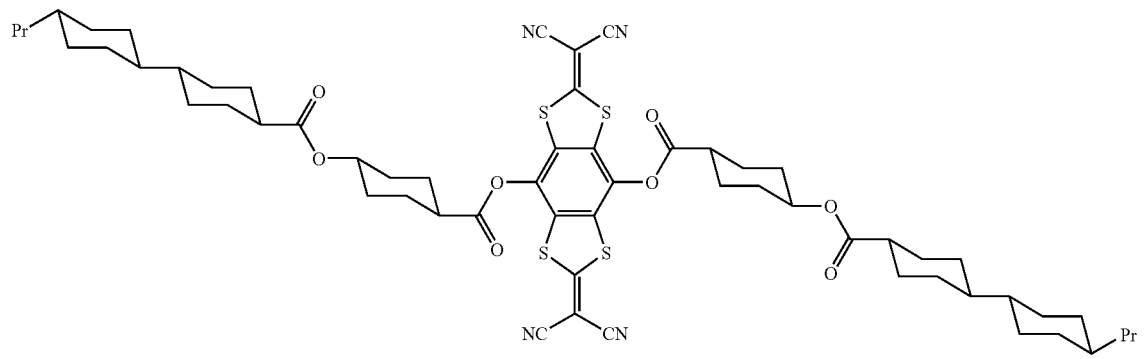

-continued
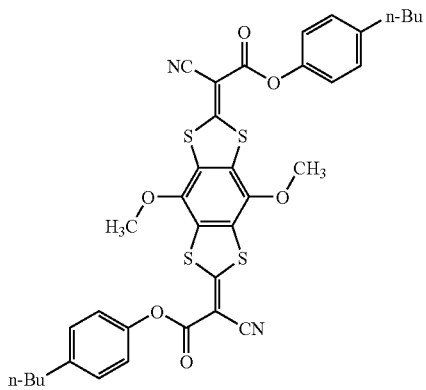
(95)
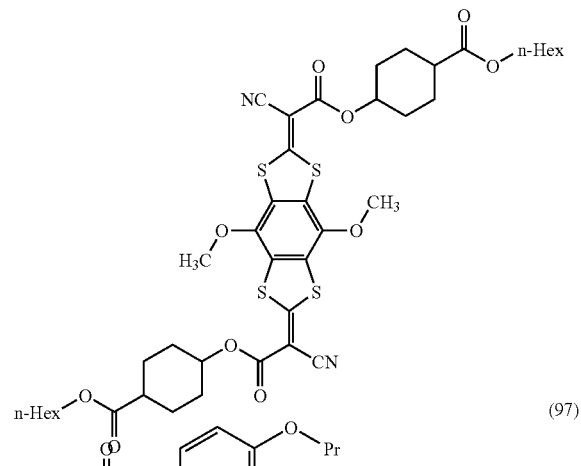
(96)
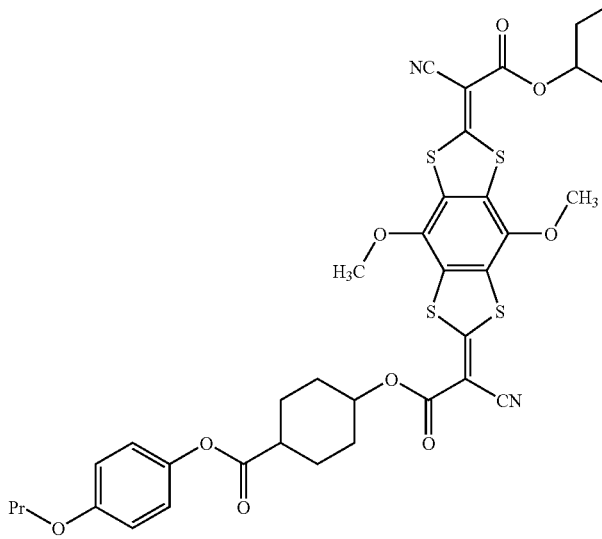
(97)
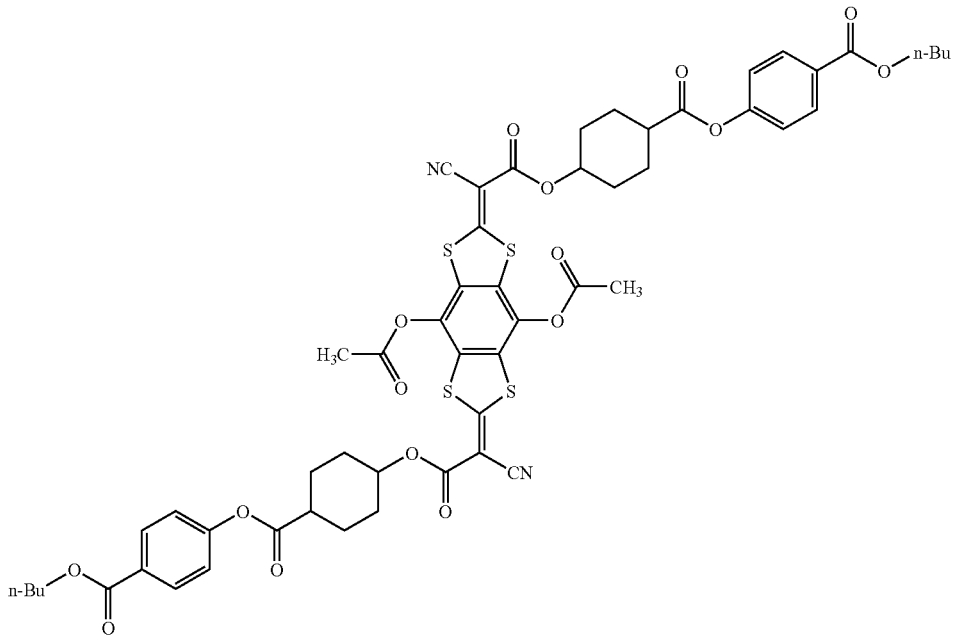
(98)

(99)
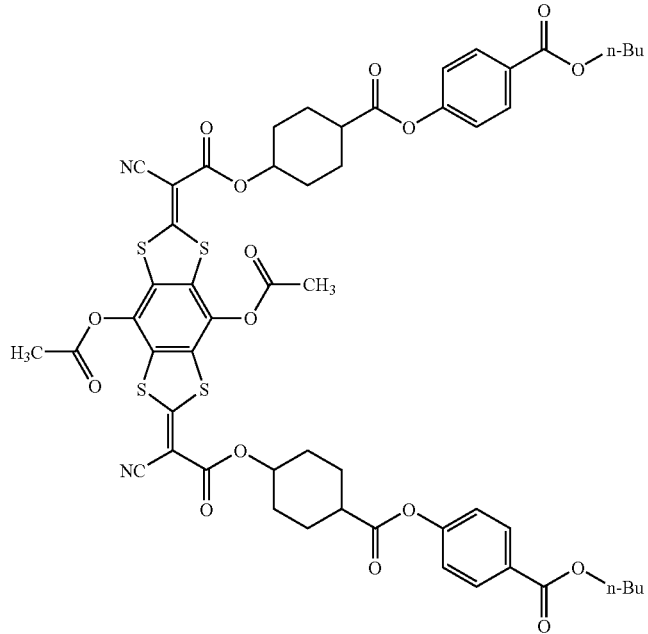
(100)
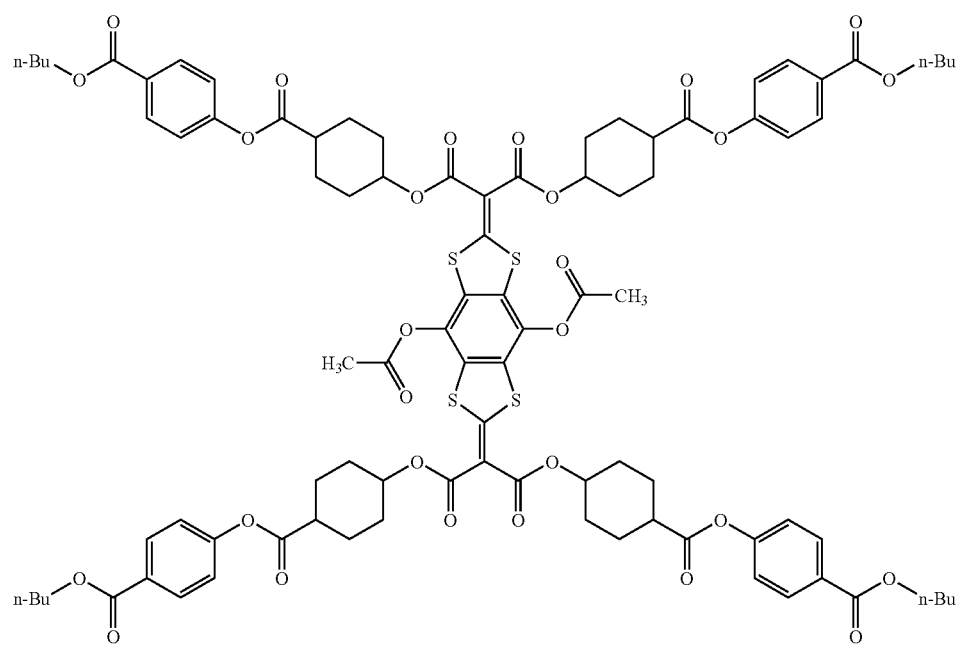

(101)
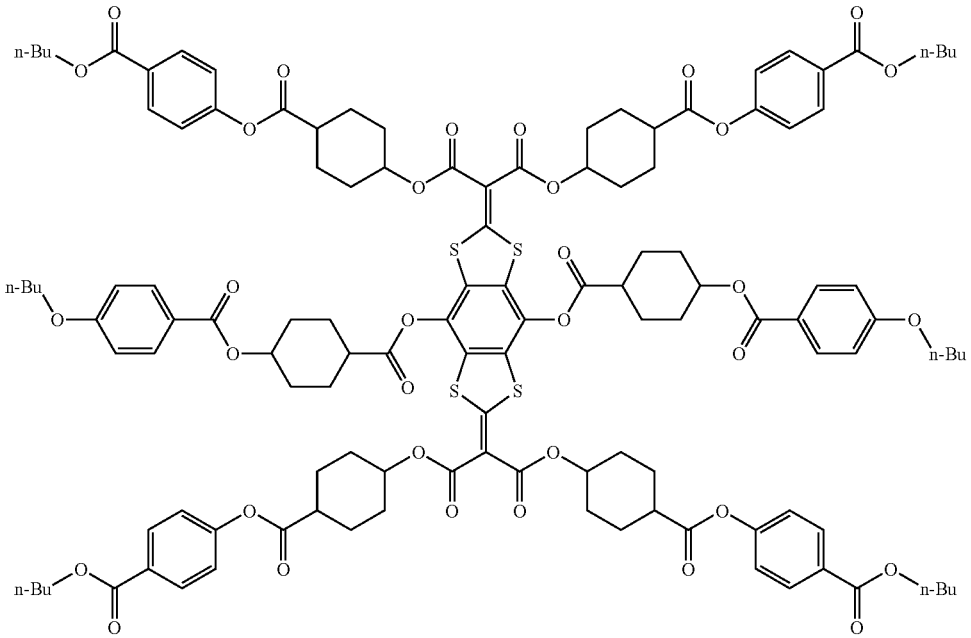
(102)
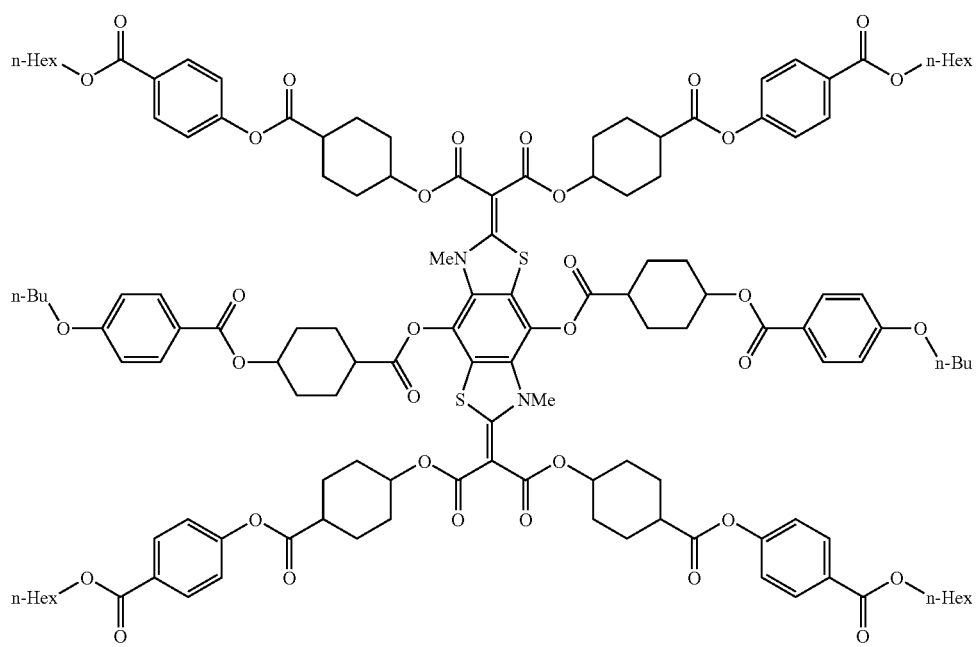
(103)
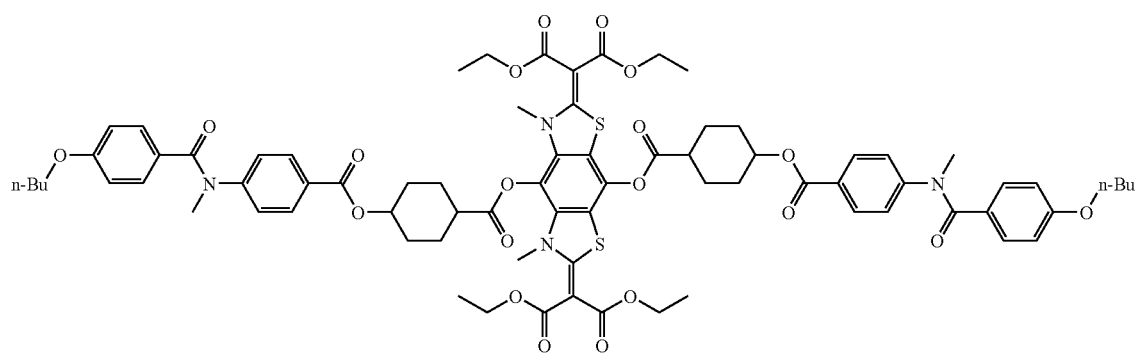

-continued
(104)
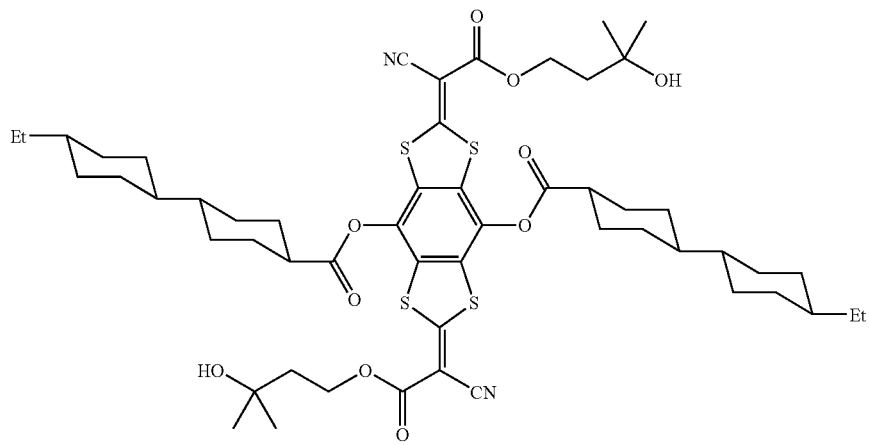
(105)
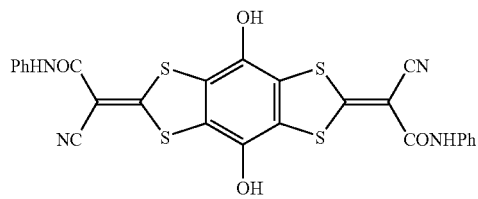
(106)
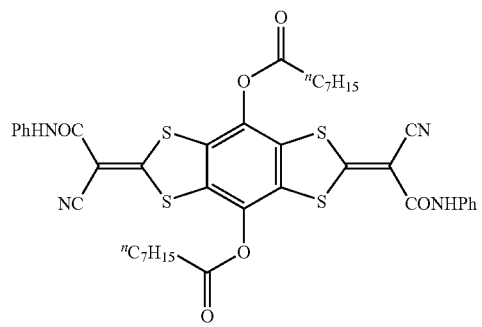
(107)
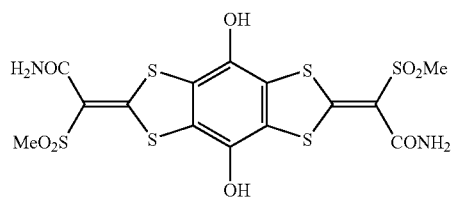
(108)
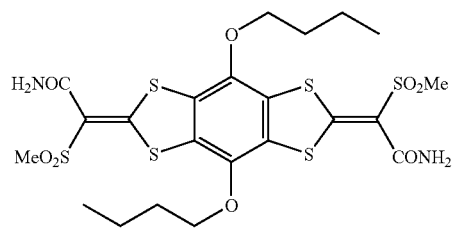
(109)
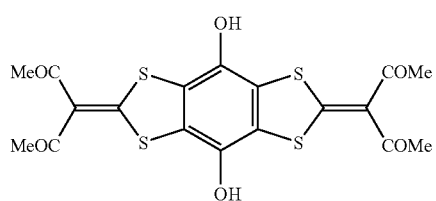
(110)
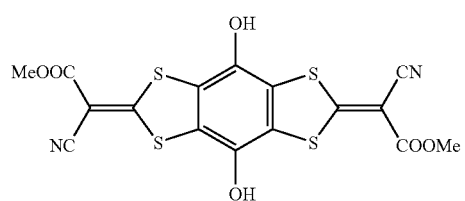
(111)
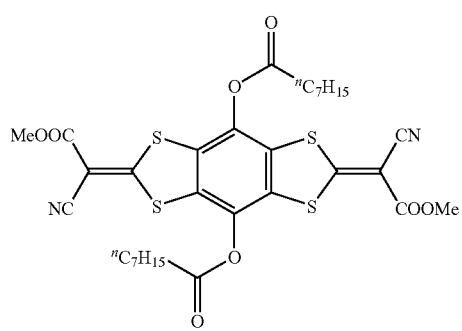
(112)
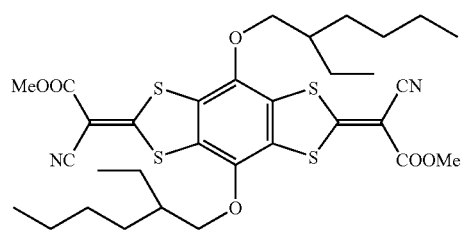

-continued
(113)
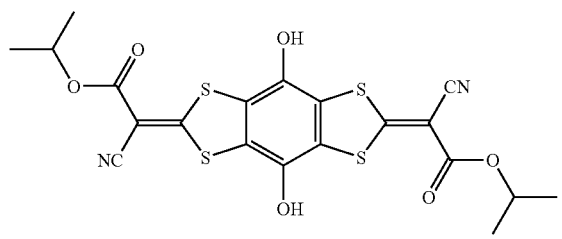
(114)
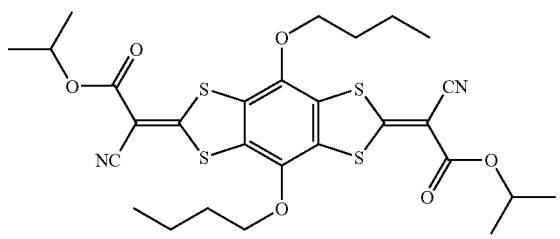
(115)
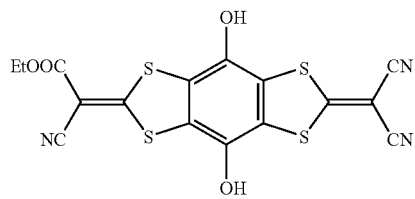
(116)
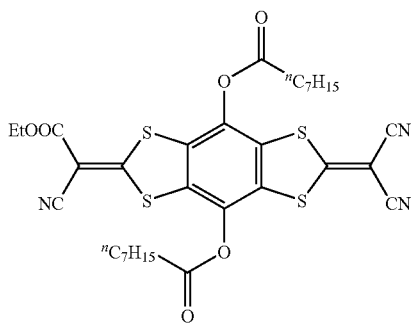
(117)
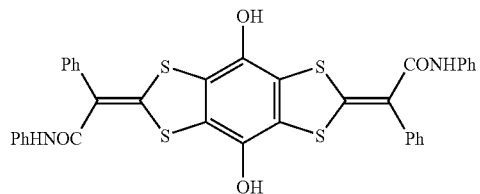
(118)
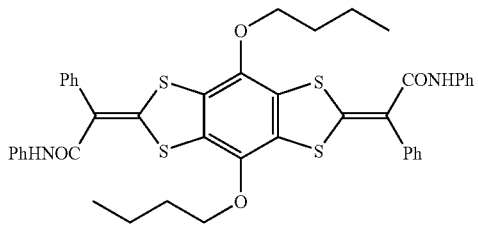
(119)
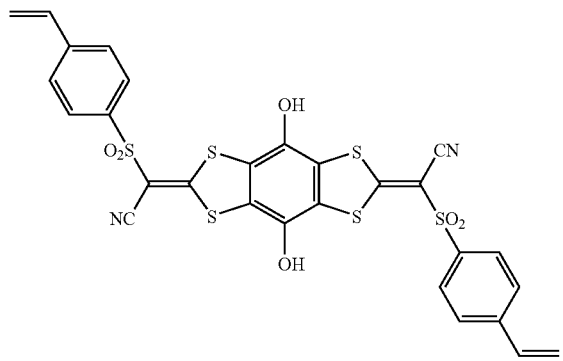
(120)
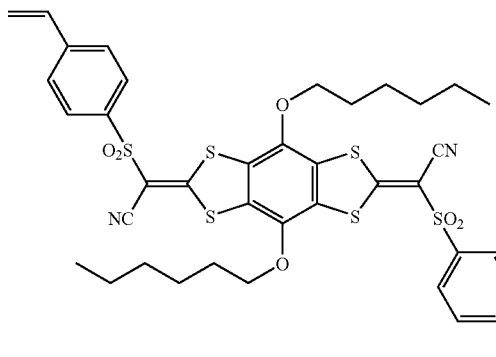
(121)
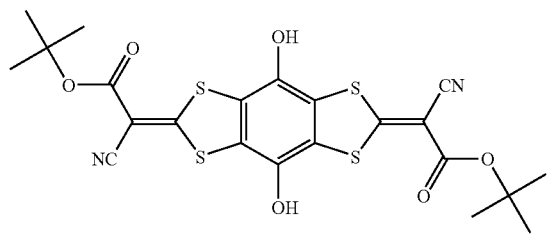
(122)
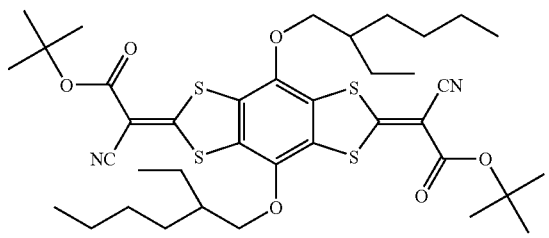

-continued
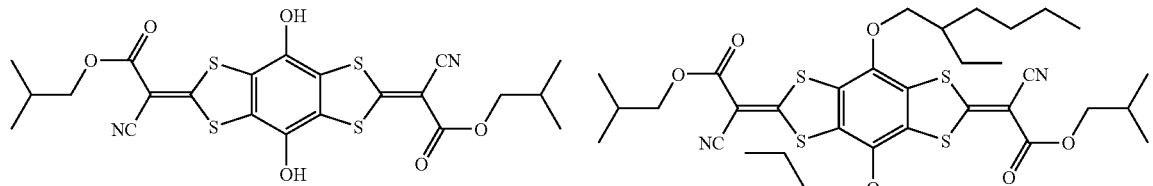
(123) (124)
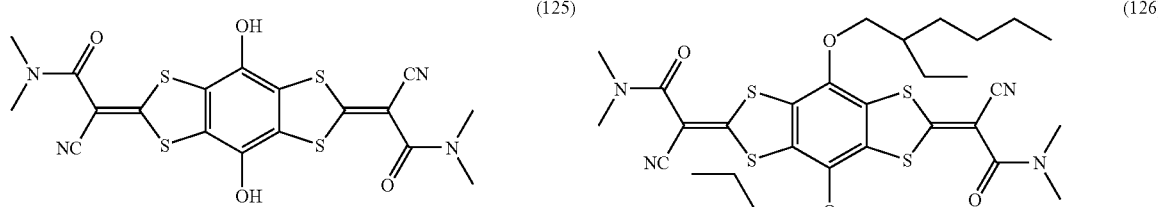
(125) (126)
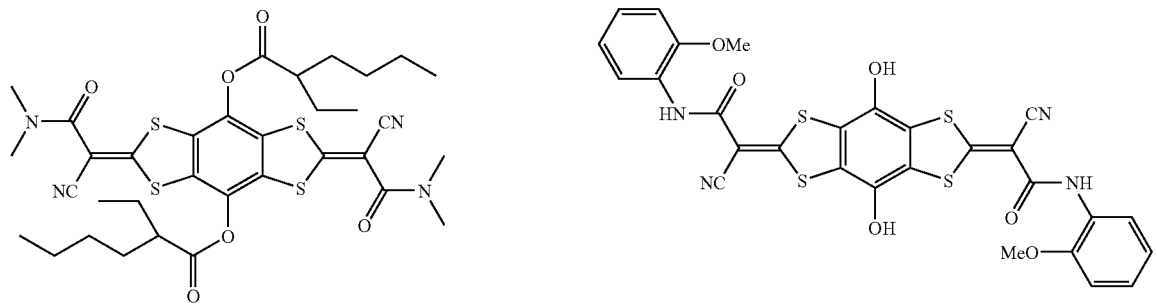
(127) (128)
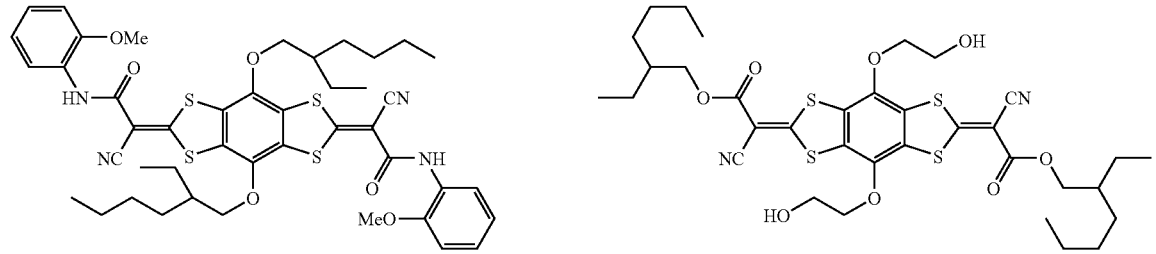
(129) (130)
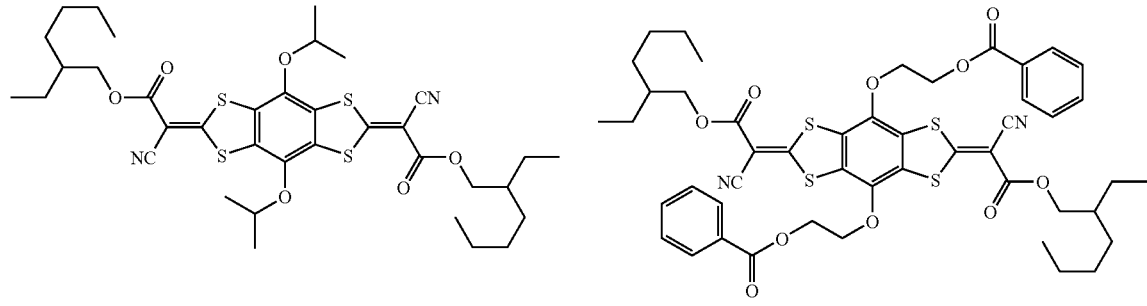
(131) (132)
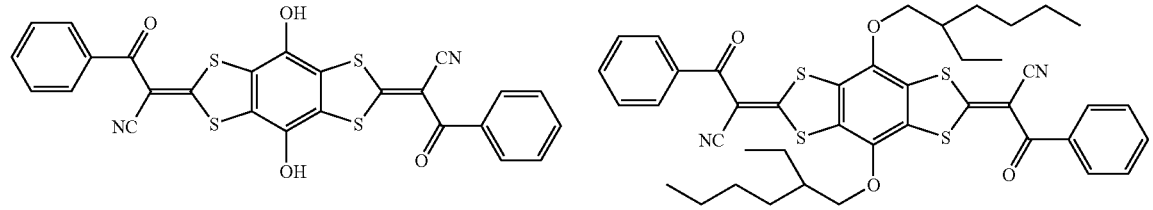
(133) (134)

-continued
| 73 | 74 |
|---|---|
| (135) 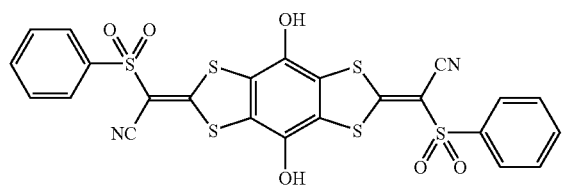 | (136) 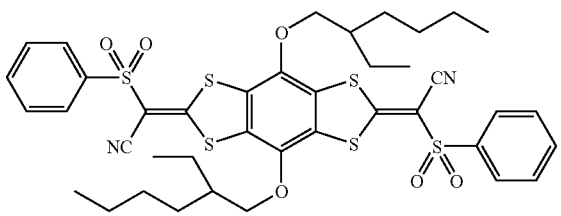 |
| (137) 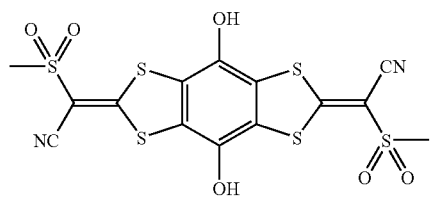 | (138) 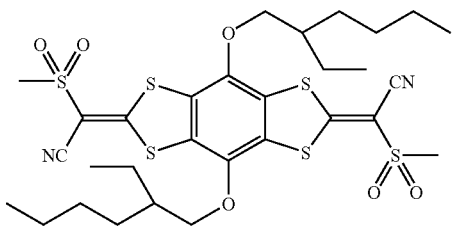 |
| (139) 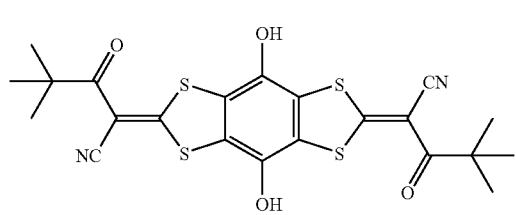 | (140) 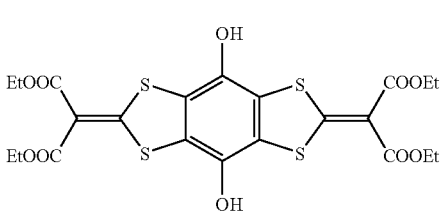 |
| (141) 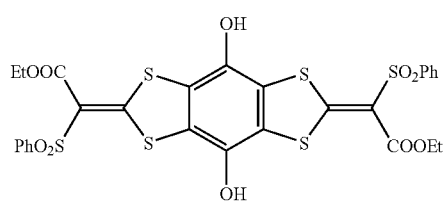 | (142) 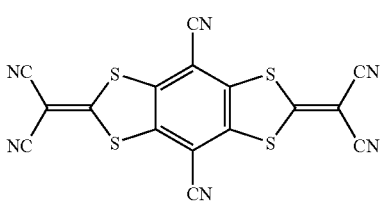 |
| (143) 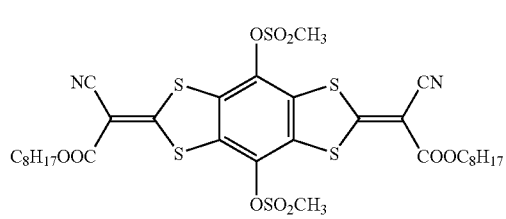 | (144) 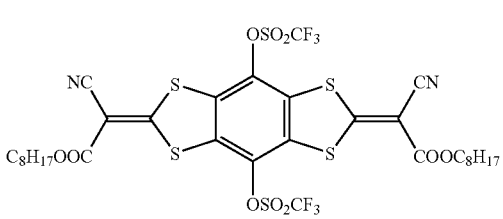 |
| (145) 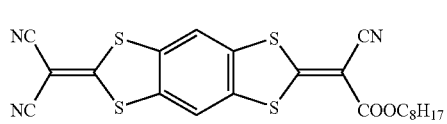 | (146) 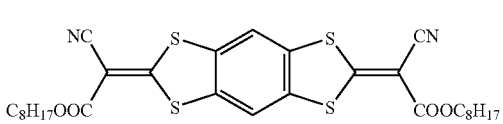 |
| (147) 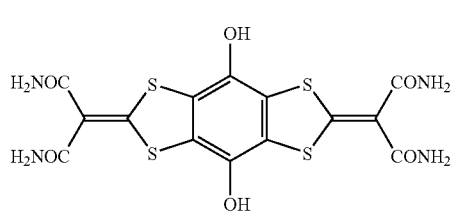 | (148) 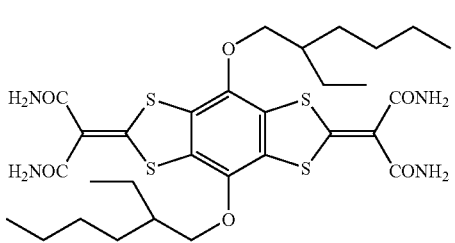 |

-continued
(149)
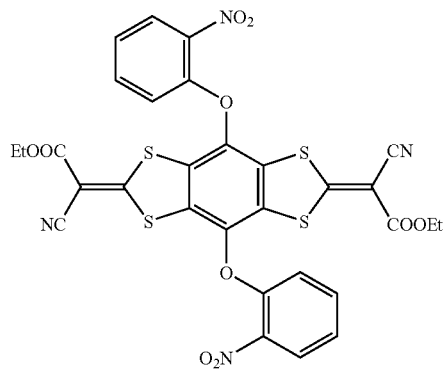
(150)
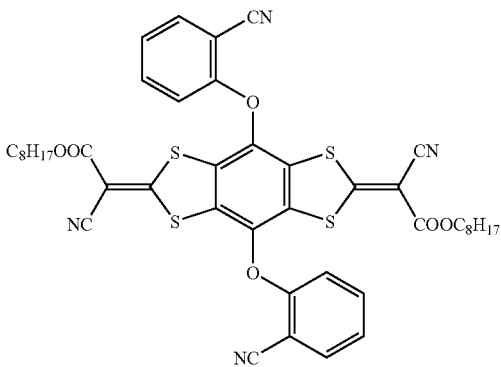
(151)
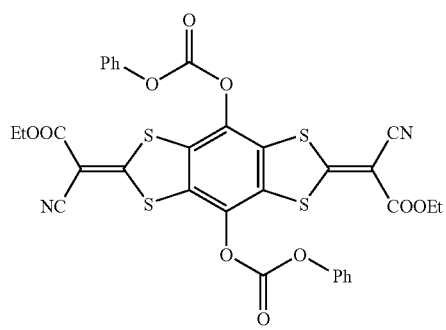
(152)
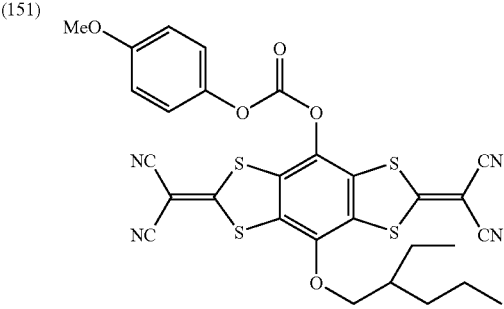
(153)
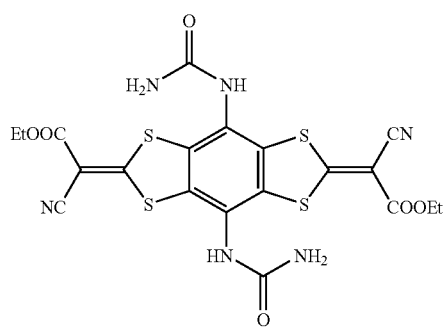
(154)
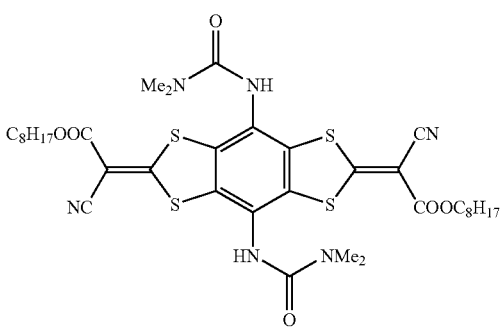
(155)
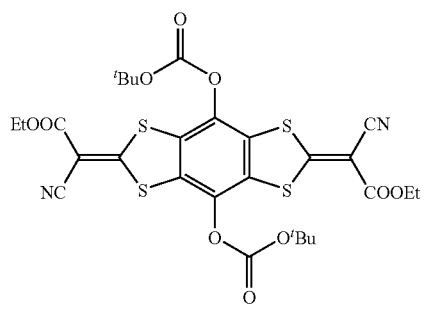
(156)
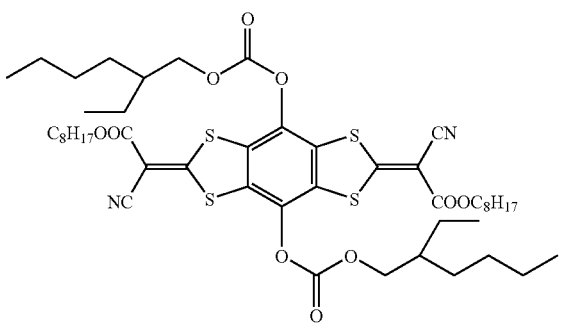

-continued
(157)
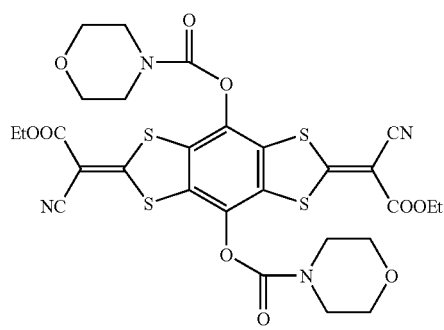
(158)
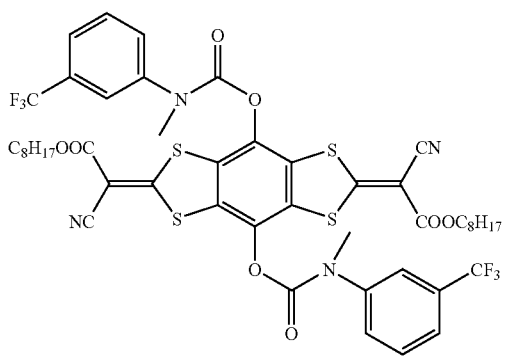
(159)
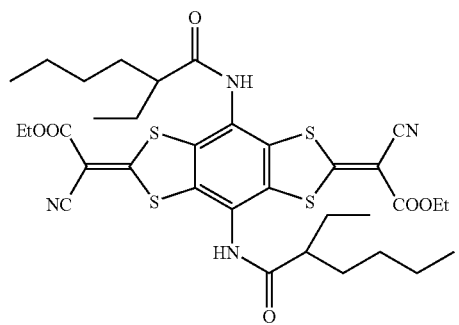
(160)
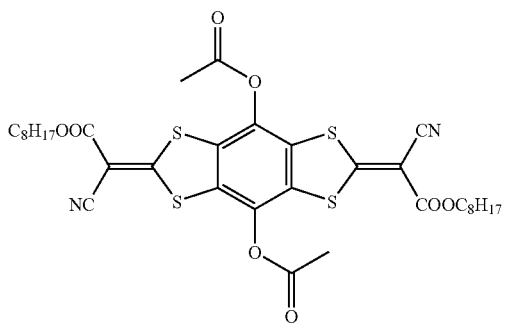
(B101)
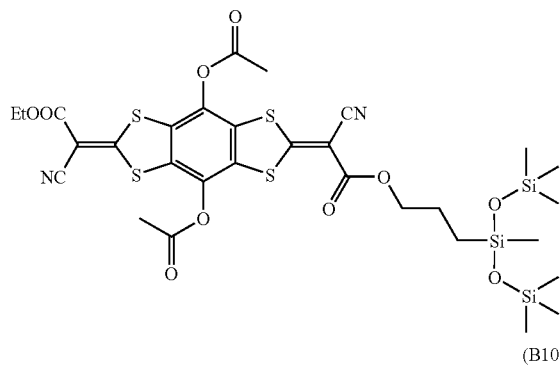
(B102)
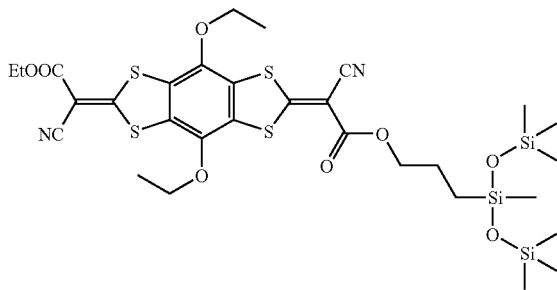
(B103)
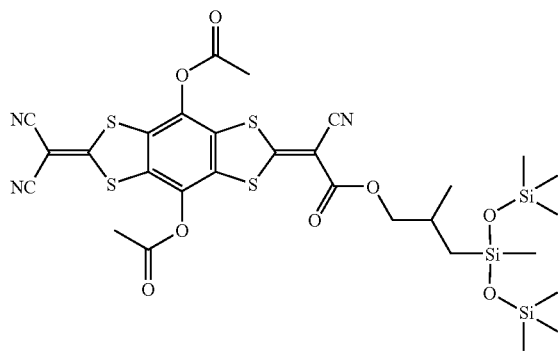
(B104)
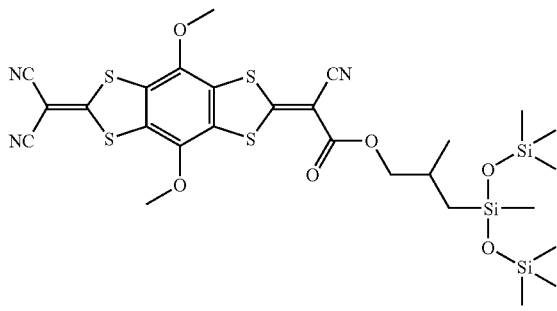

-continued
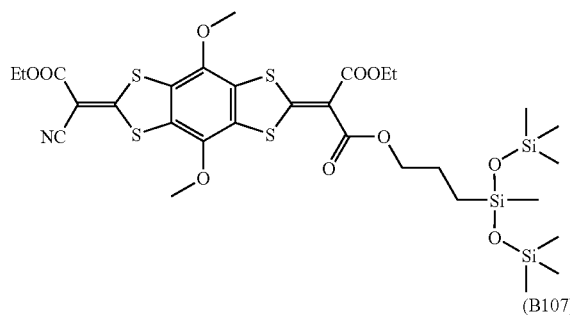
(B105)
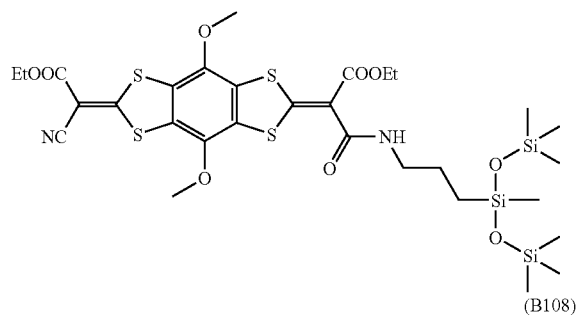
(B106)
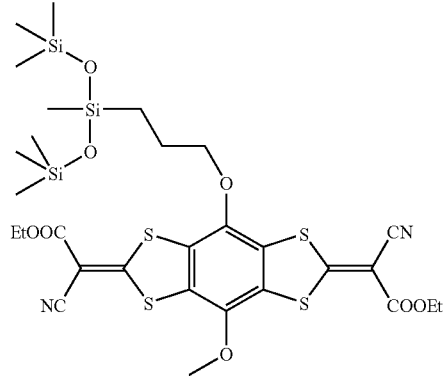
(B107)
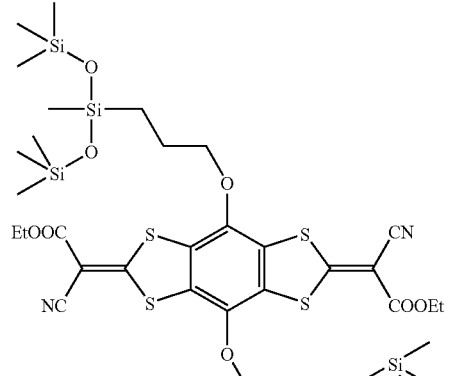
(B108)
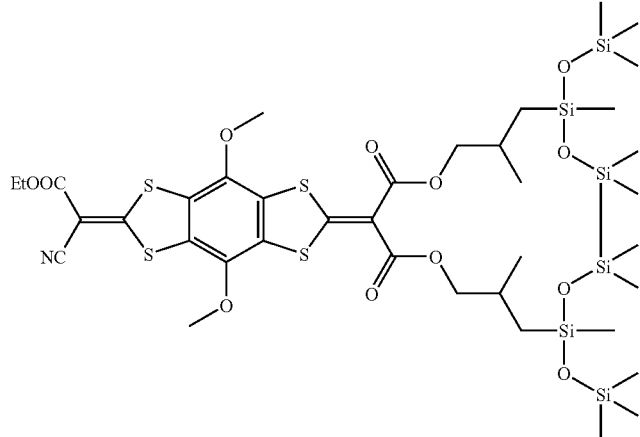
(B109)
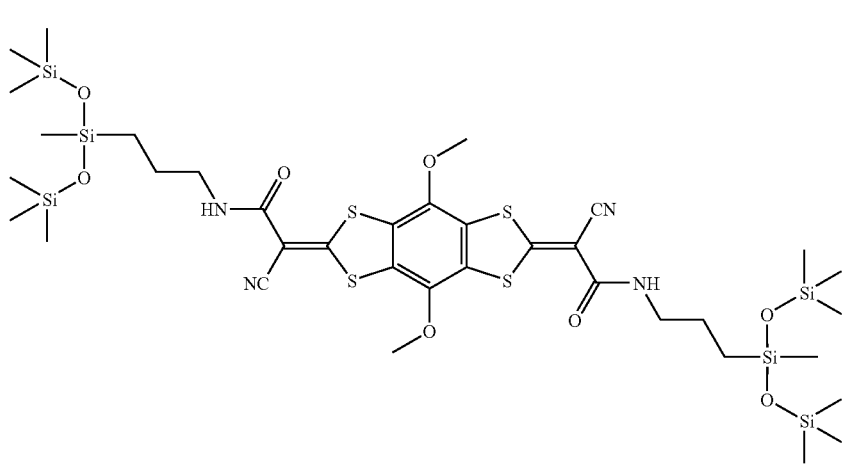
(B110)

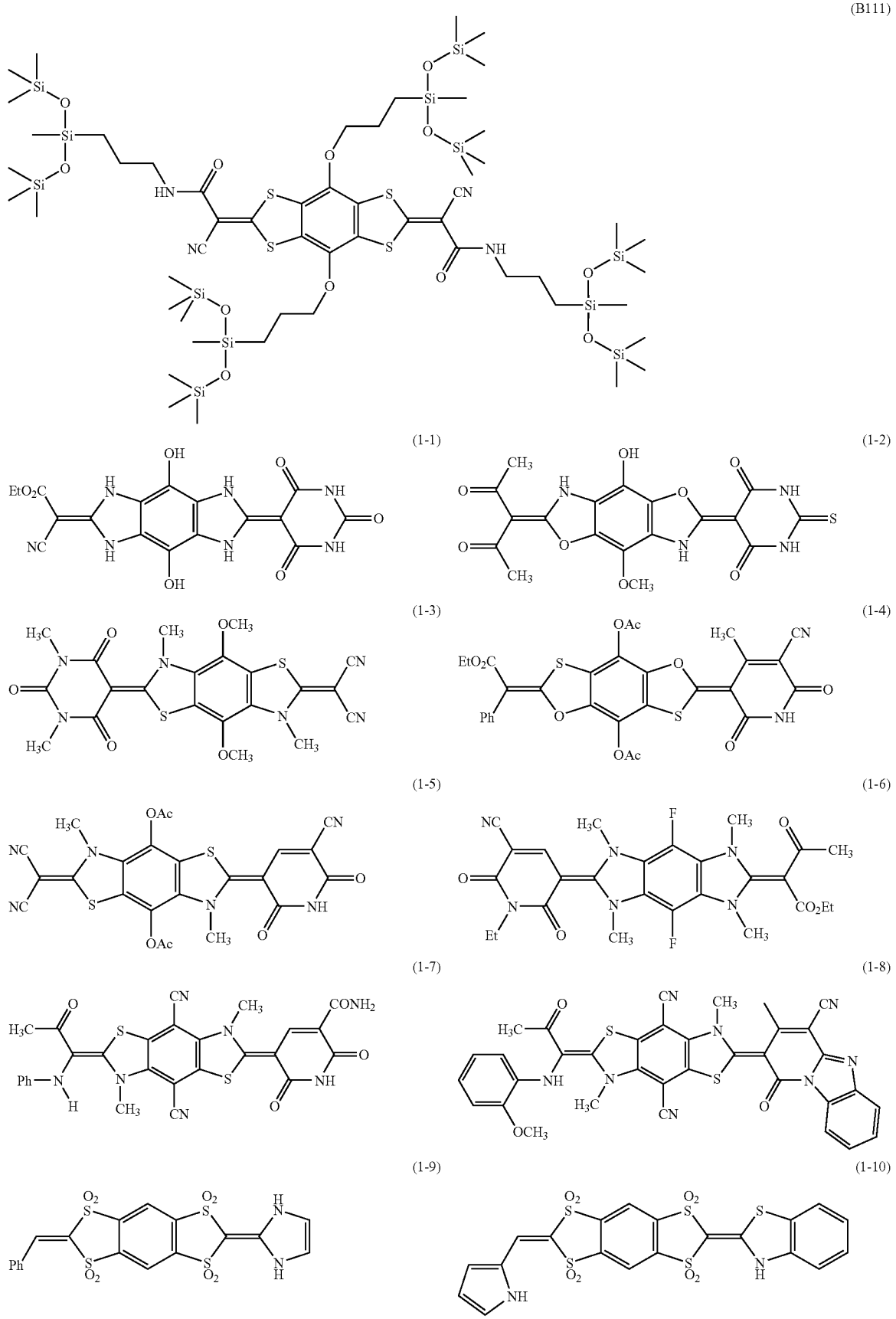

-continued
(1-11)
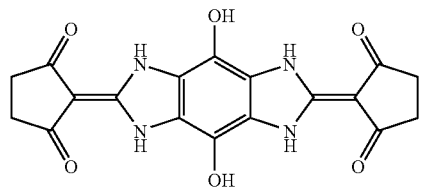
(1-12)
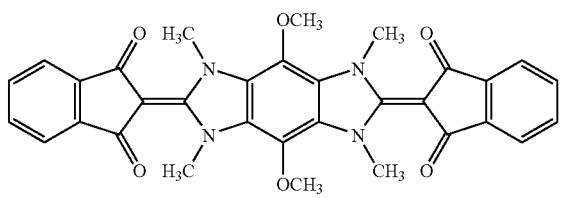
(1-13)
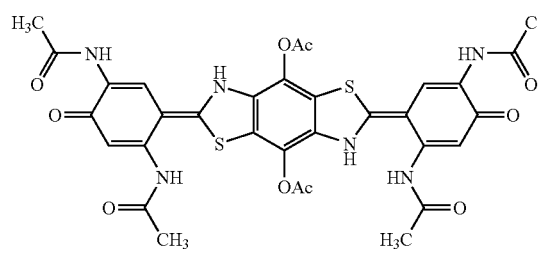
(1-14)
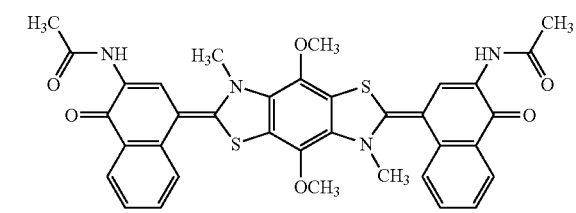
(1-15)
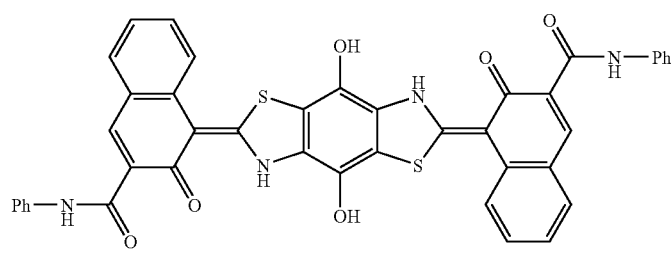
(1-16)
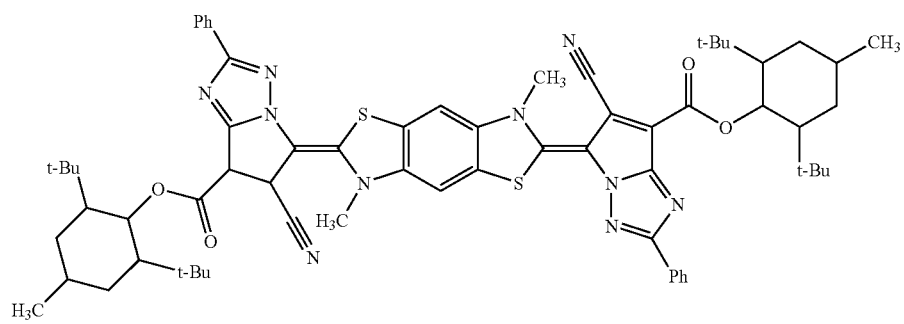
(1-17)
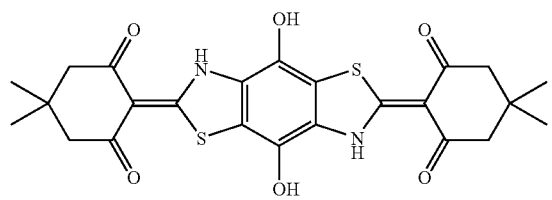
(1-18)
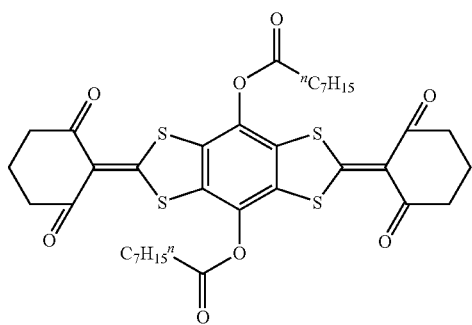

-continued
(1-19)
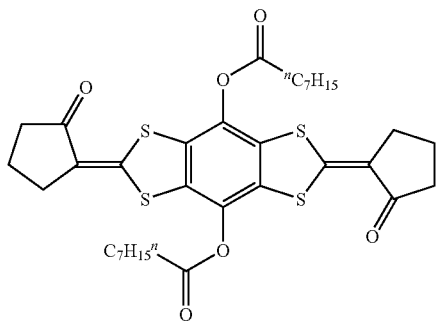
(1-20)
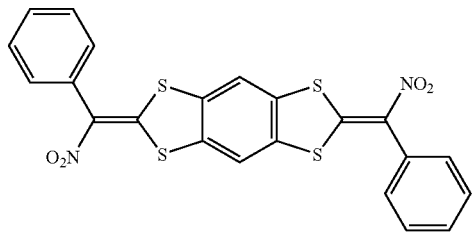
(1-21)
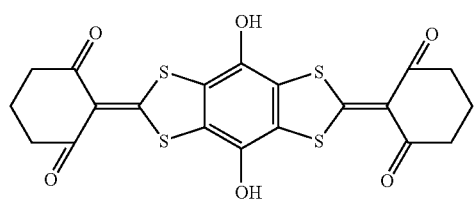
(1-22)
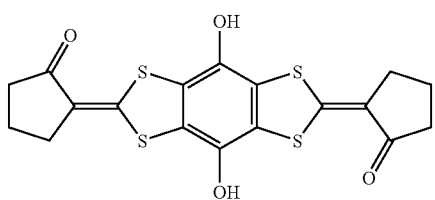
(2-1)
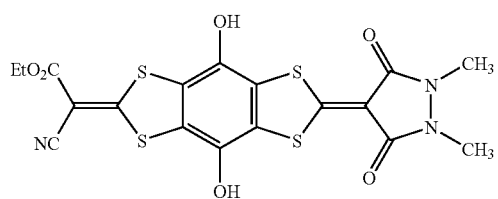
(2-2)
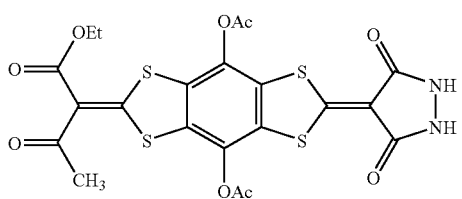
(2-3)
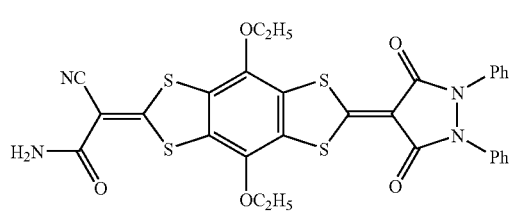
(2-4)
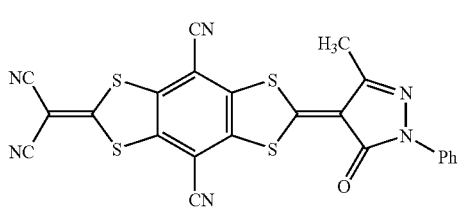
(2-5)
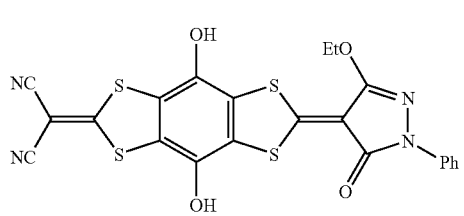
(2-6)
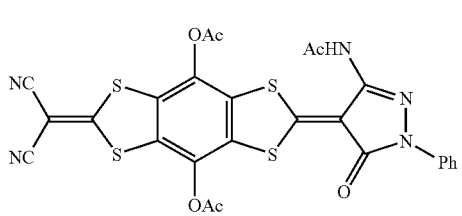
(2-7)
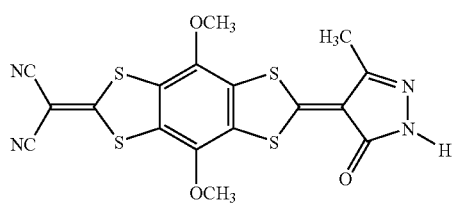
(2-8)
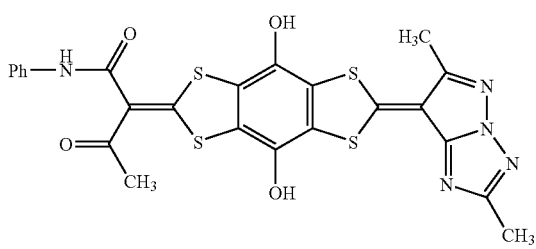

-continued
(2-9)
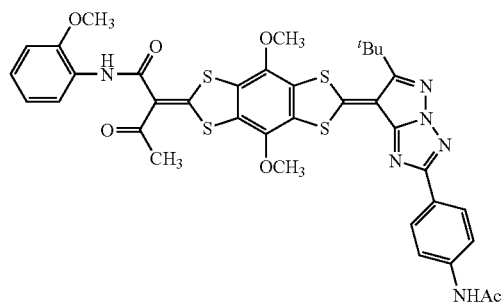
(2-10)
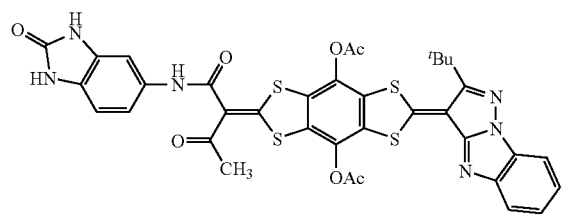
(2-11)
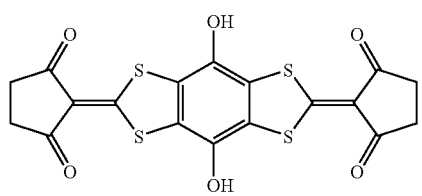
(2-12)
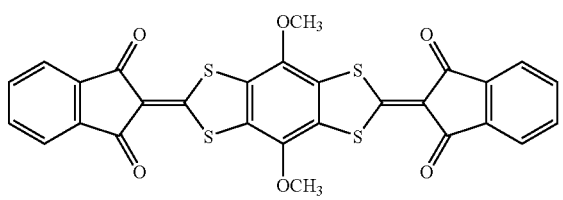
(2-13)
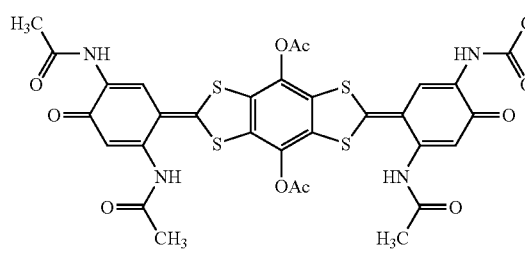
(2-14)
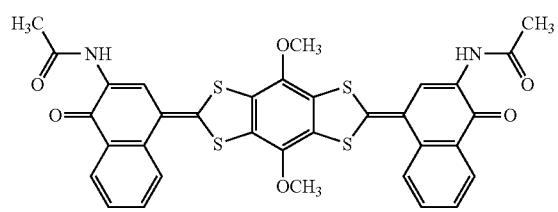
(2-15)
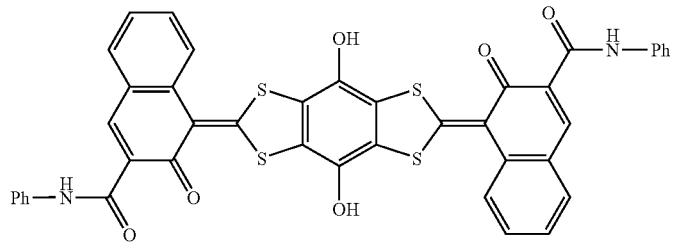
(2-16)
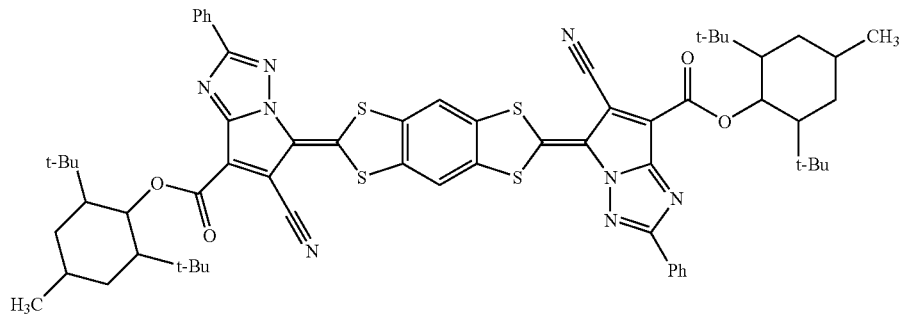

-continued
(2-17)
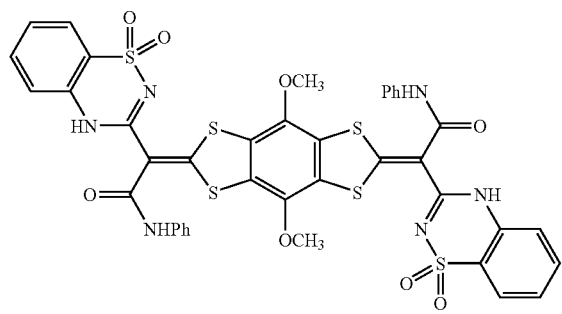
(2-18)
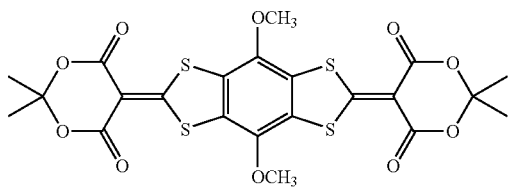
(2-19)
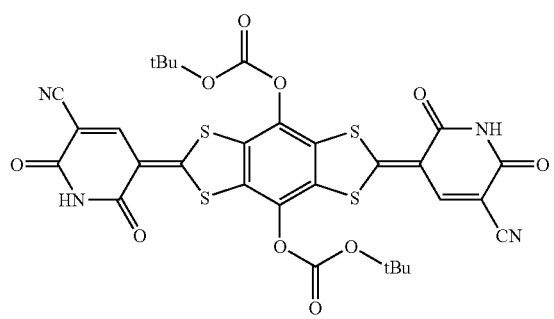
(2-20)
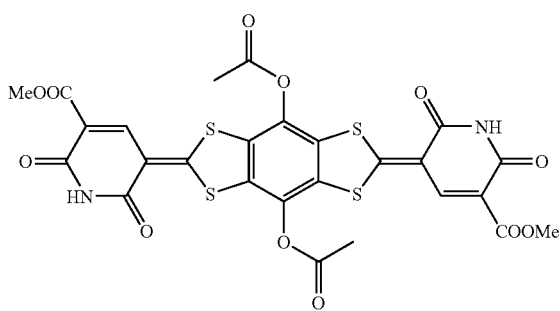
(3-1)
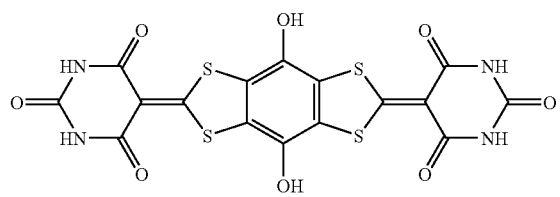
(3-2)
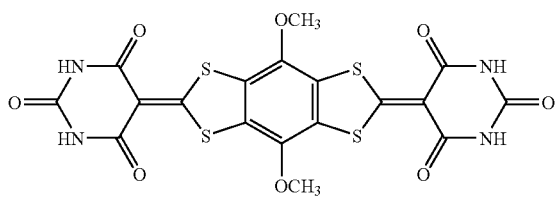
(3-3)
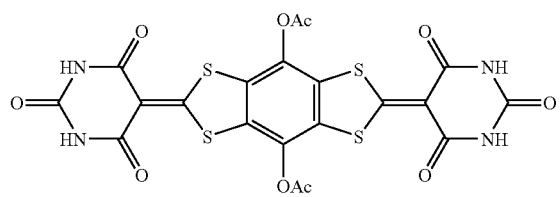
(3-4)
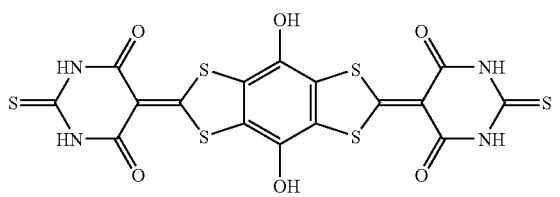
(3-5)
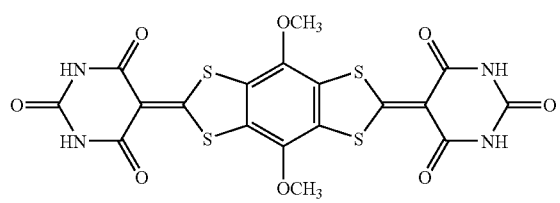
(3-6)
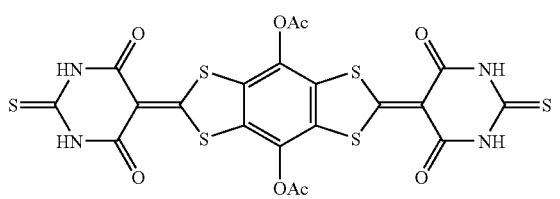

-continued
(3-7)
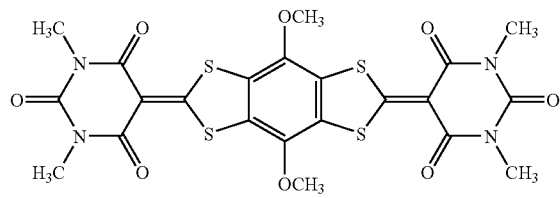
(3-8)
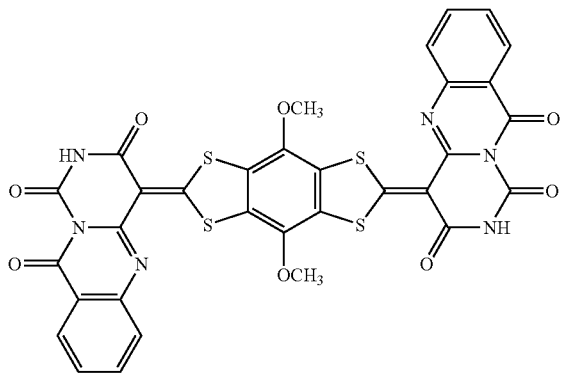
(3-9)
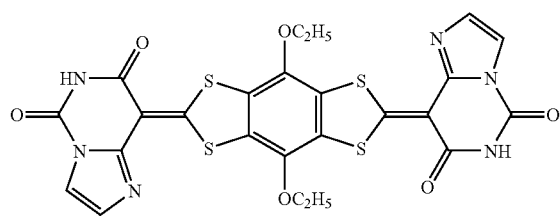
(3-10)
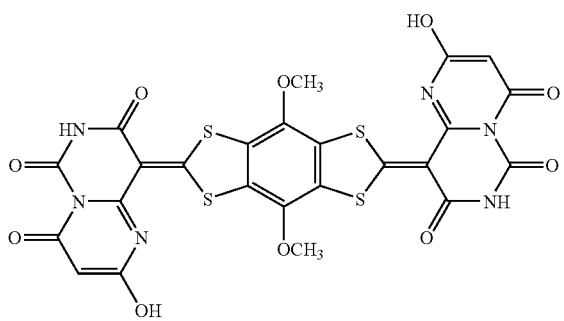
(3-11)
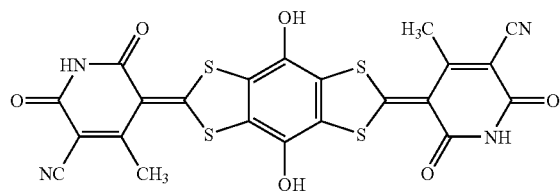
(3-12)
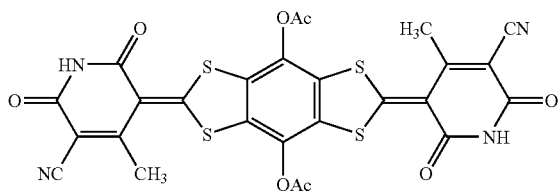
(3-13)
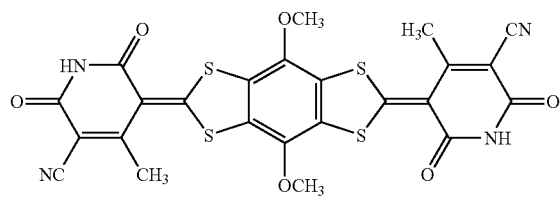
(3-14)
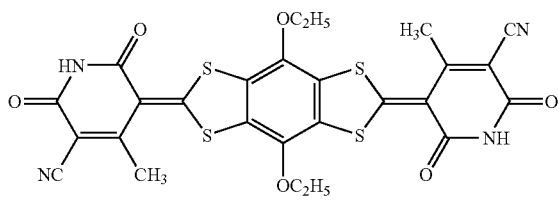
(3-15)
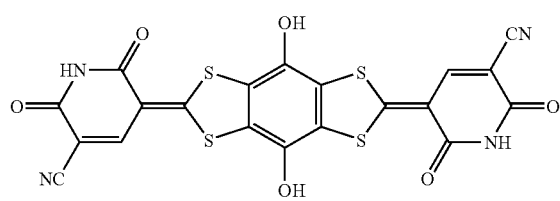
(3-16)
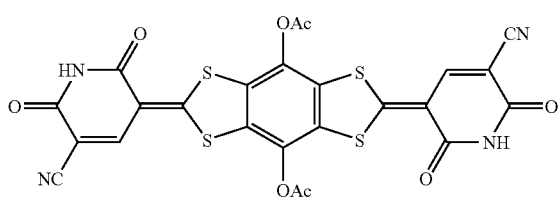
(3-17)
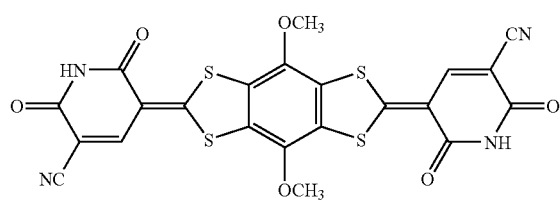
(3-18)
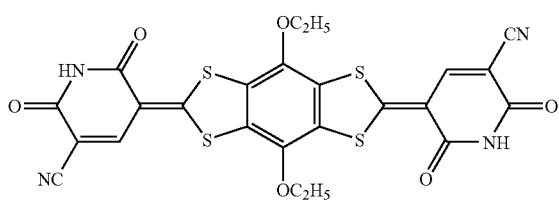

-continued
(3-19)
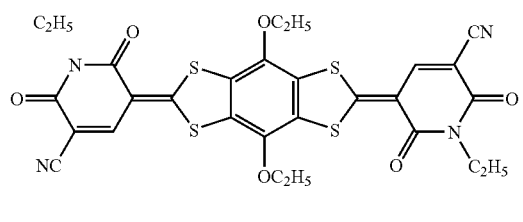
(3-20)
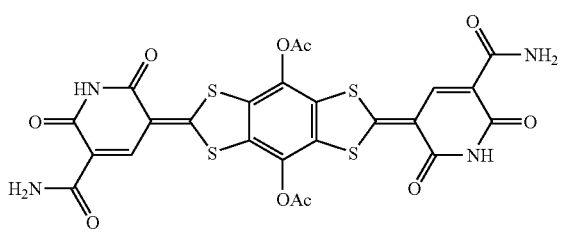
(3-21)
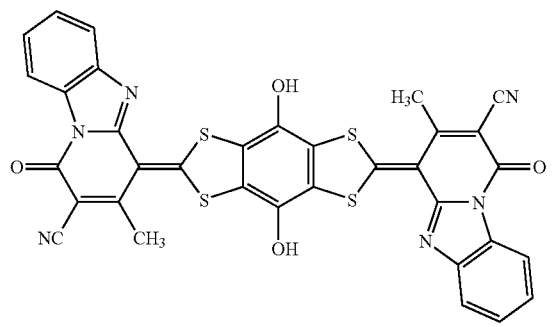
(3-22)
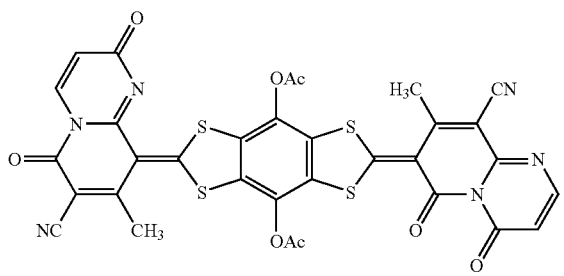
(3-23)
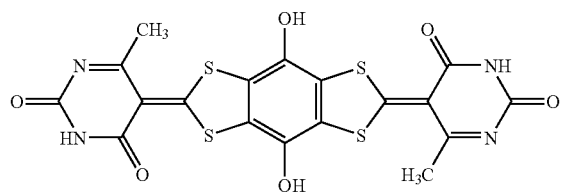
(3-24)
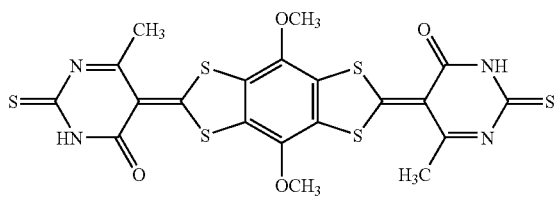
(3-25)
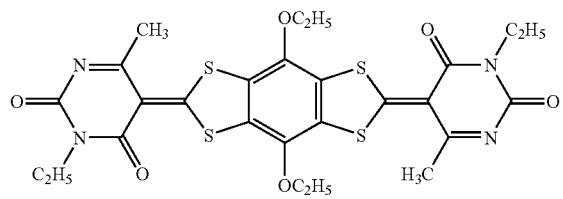
(3-26)
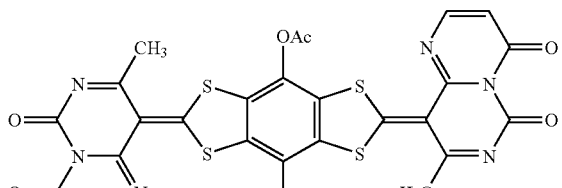
(3-27)
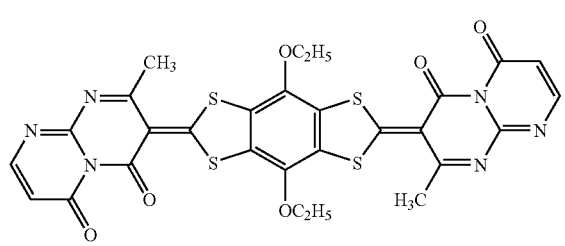
(3-28)
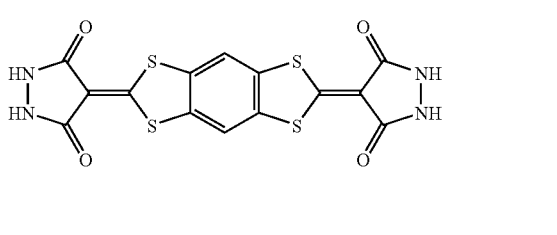
(3-29)
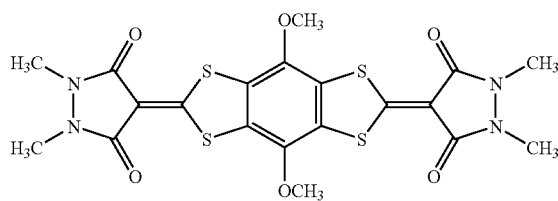
(3-30)
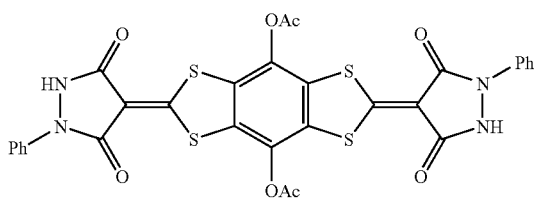

-continued
(3-31)
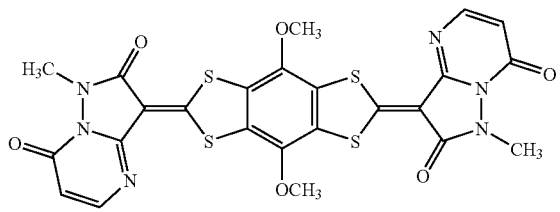
(3-32)
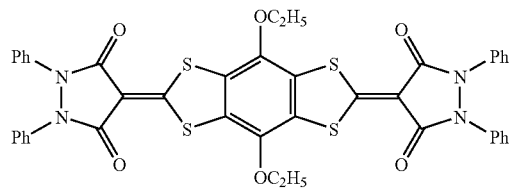
(3-33)
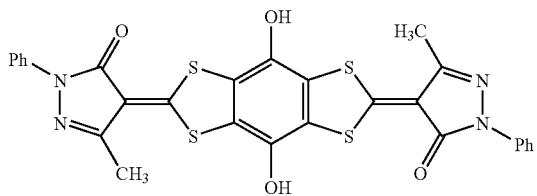
(3-34)
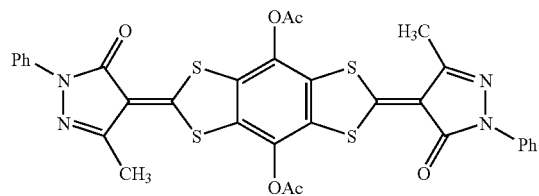
(3-35)
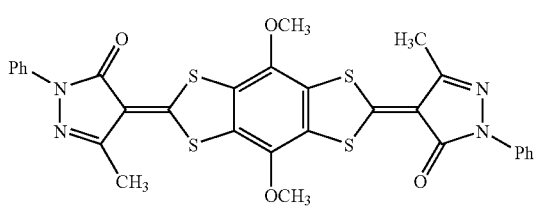
(3-36)
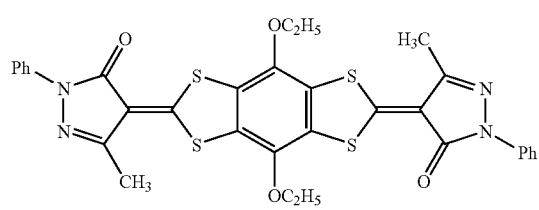
(3-37)
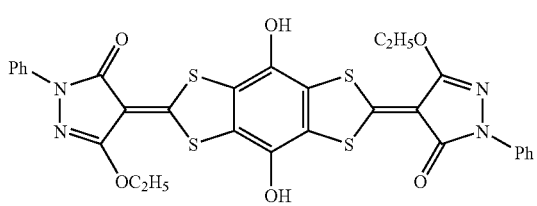
(3-38)
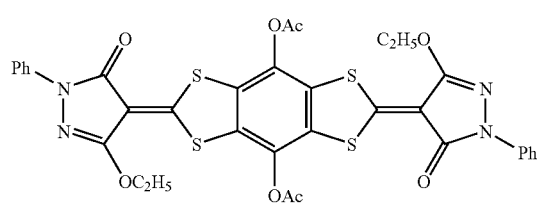
(3-39)
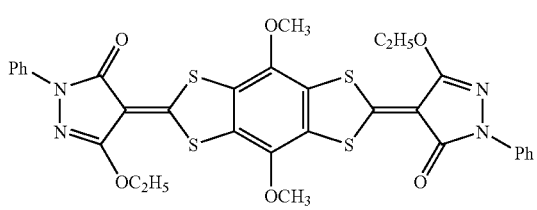
(3-40)
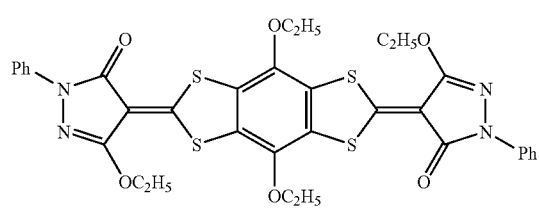
(3-41)
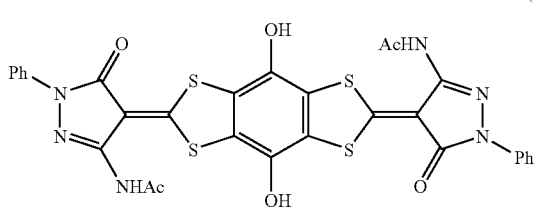
(3-42)
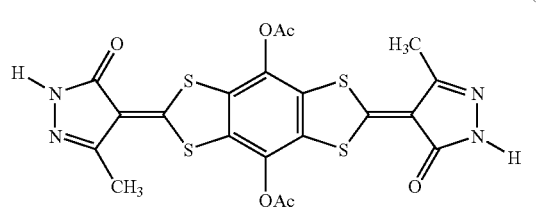
(3-43)
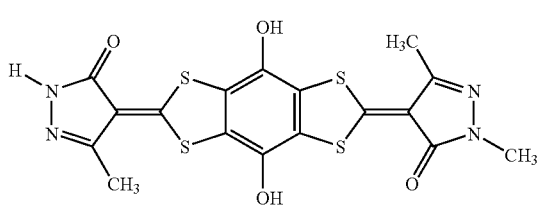
(3-44)

-continued
(3-45)
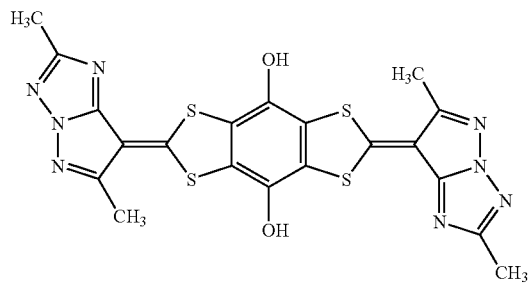
(3-46)
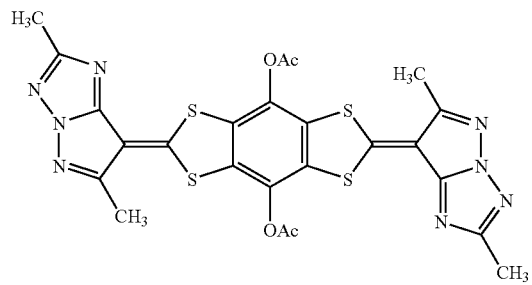
(3-47)
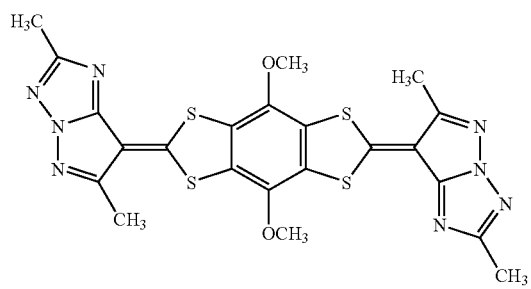
(3-48)
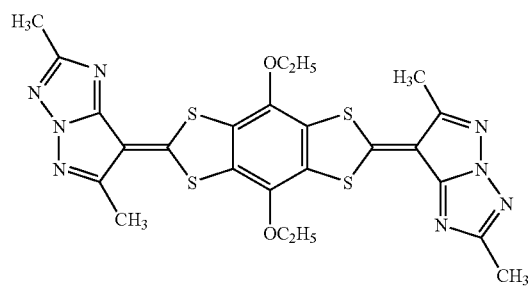
(3-49)
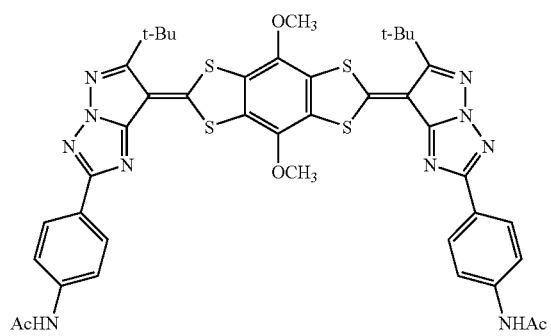
(3-50)
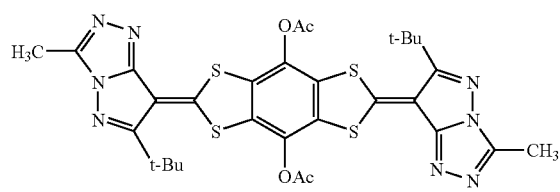
(3-51)
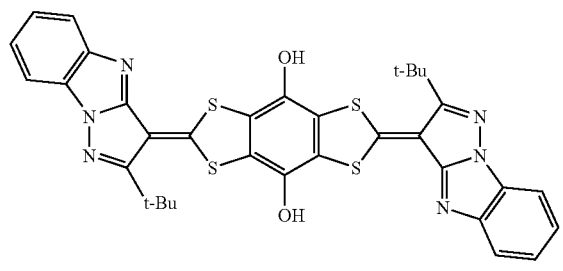
(3-52)
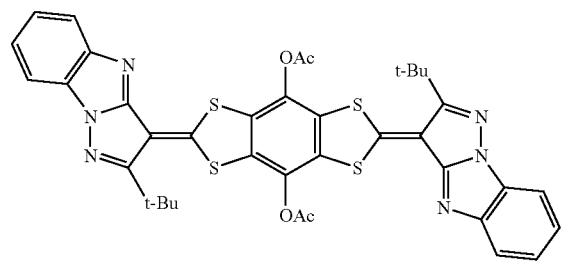
(3-53)
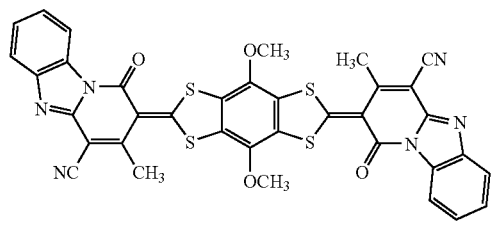
(3-54)
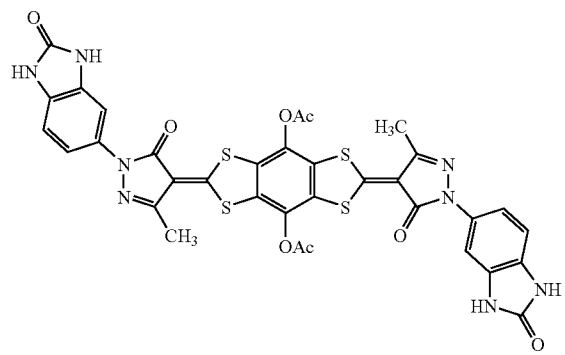

-continued
(3-55)
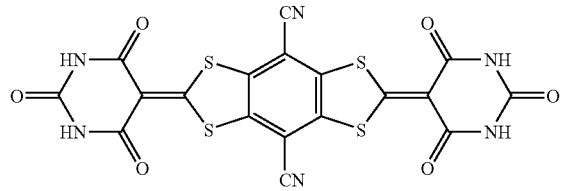
(3-56)
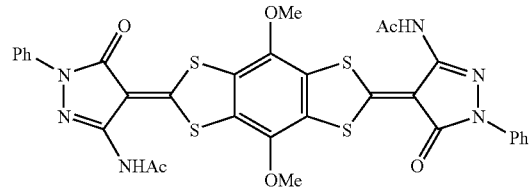
(3-57)
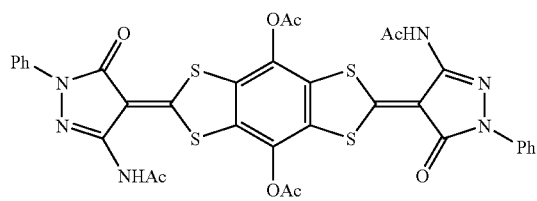
(3-58)
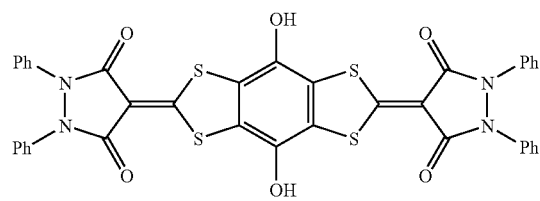
(3-59)
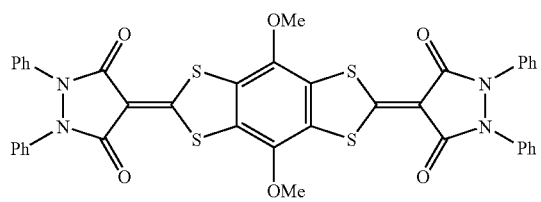
(3-60)
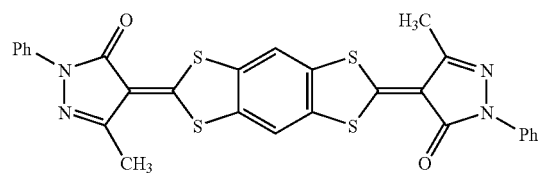
(3-61)
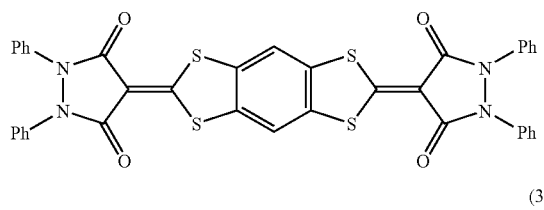
(3-62)
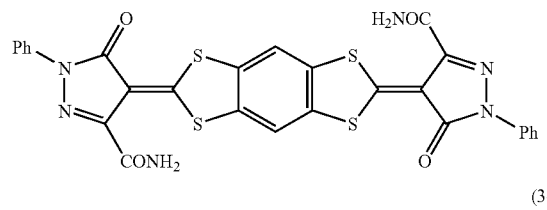
(3-63)
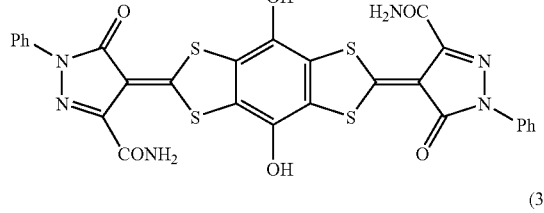
(3-64)
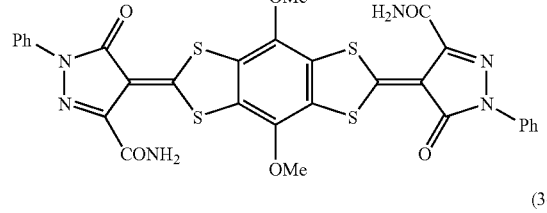
(3-65)
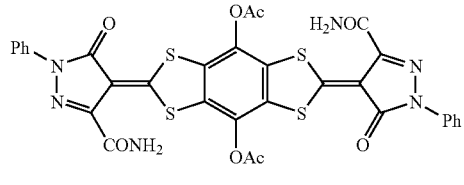
(3-66)
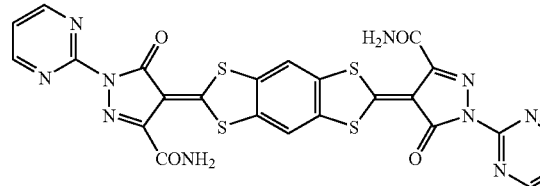
(3-67)
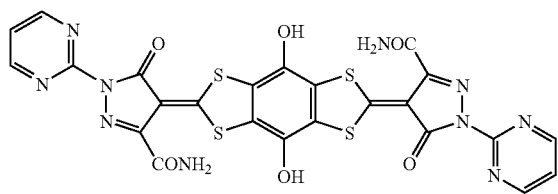
(3-68)
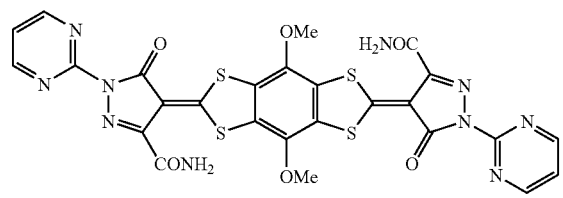

-continued
(3-69)
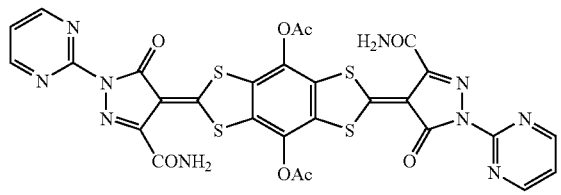
(3-70)
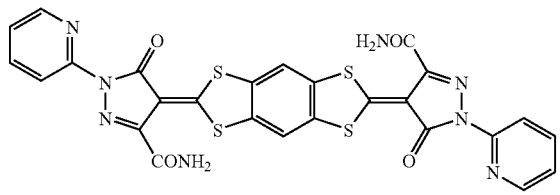
(3-71)
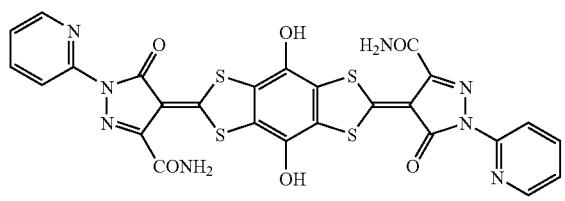
(3-72)
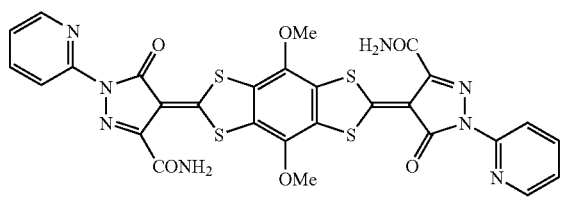
(3-73)
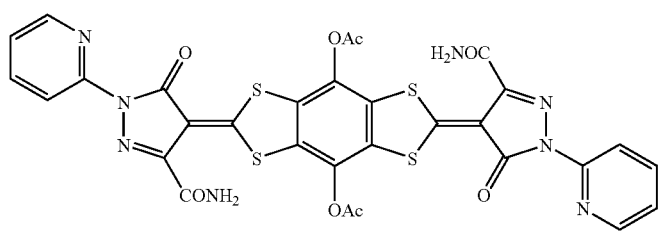
(3-74)
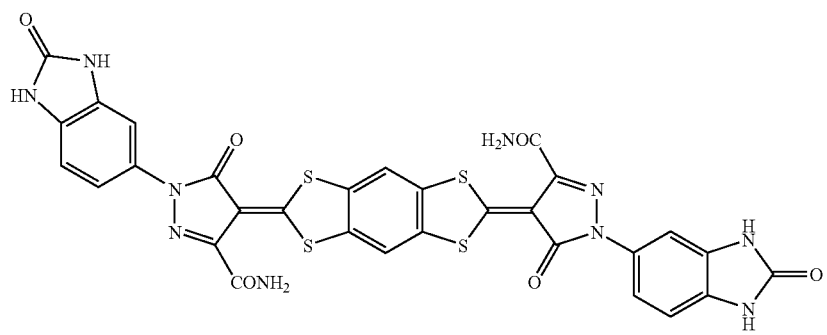
(3-75)
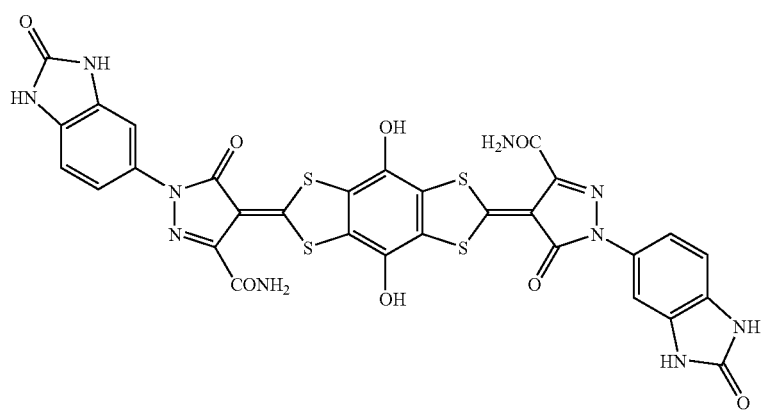

(3-76)
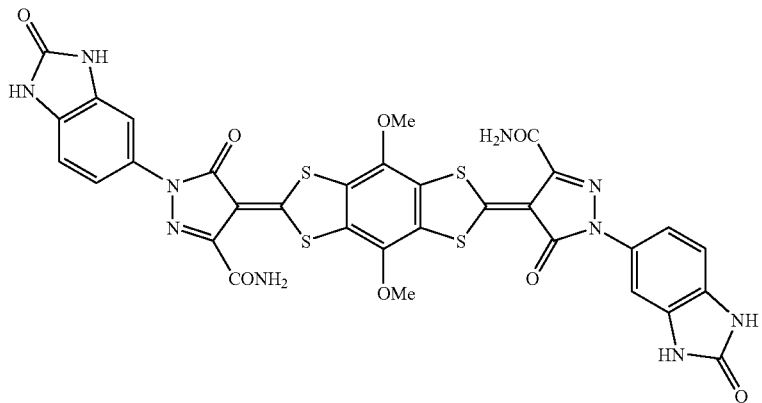
(3-77)
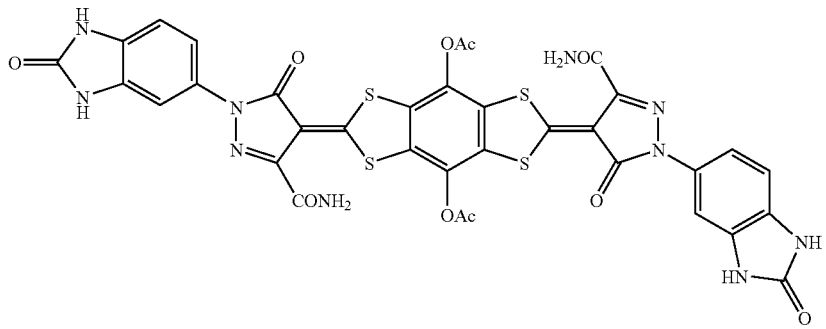
(3-78)
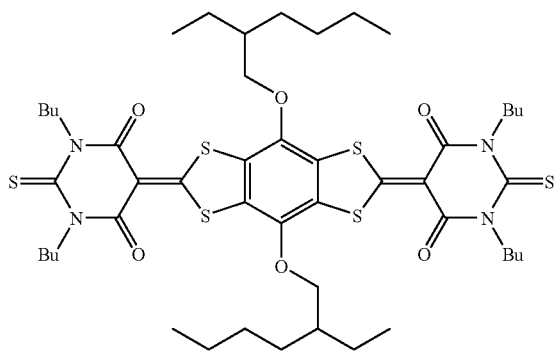
(3-79)
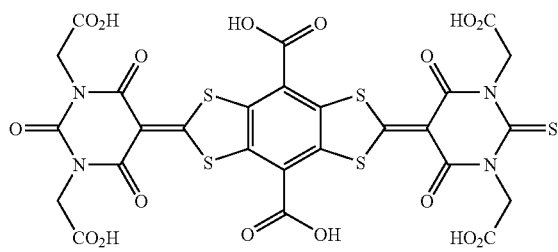
(4-1)
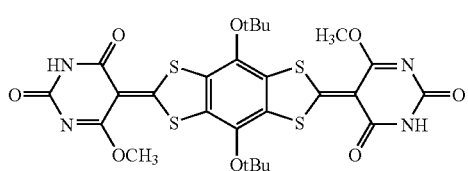
(4-2)
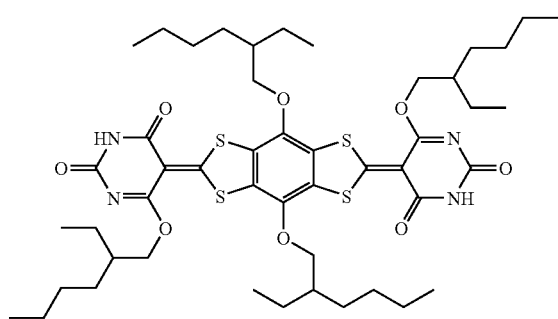

-continued
(4-3)
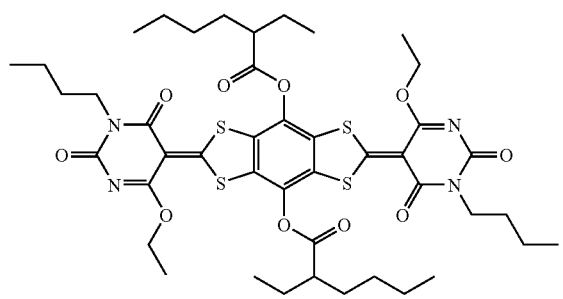
(4-4)
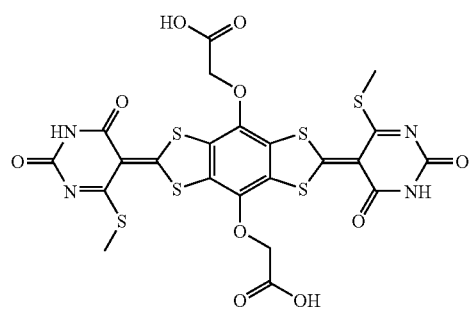
(4-5)
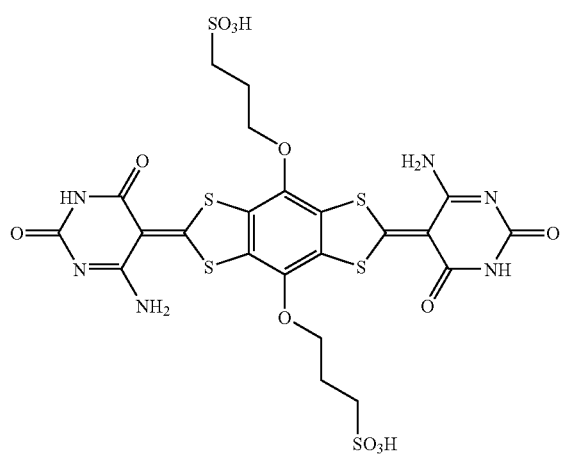
(4-6)
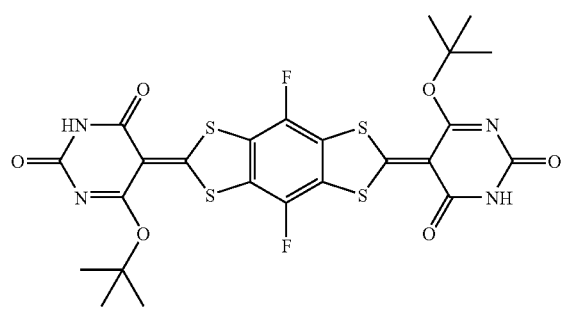
(4-7)
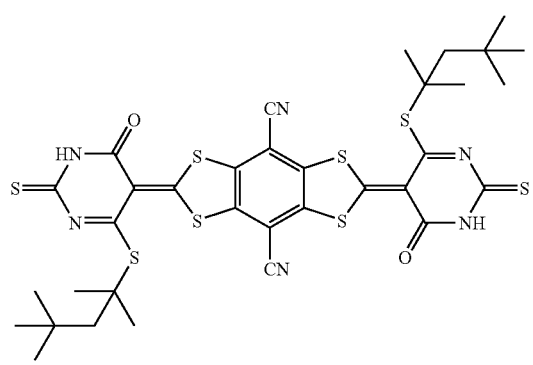
(4-8)
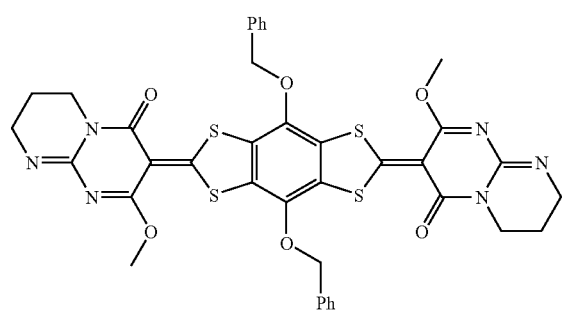
(4-9)
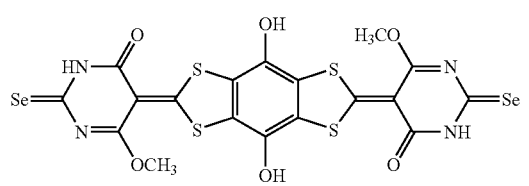
(4-10)
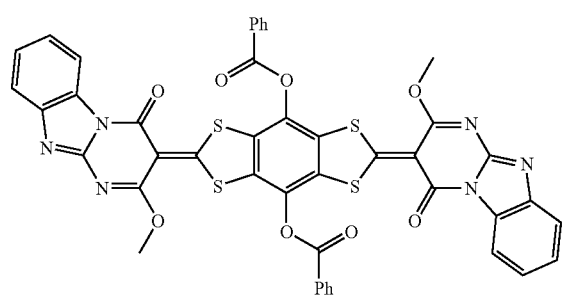

(4-11) 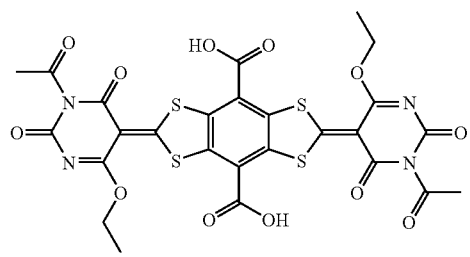
(4-12) 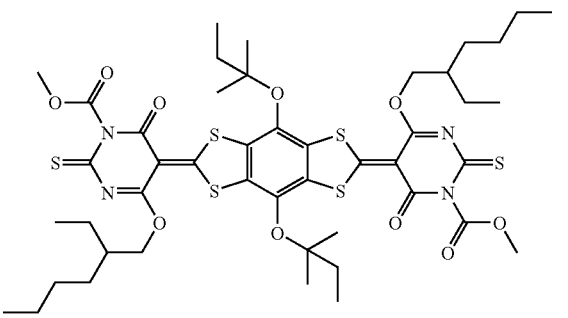
(4-13) 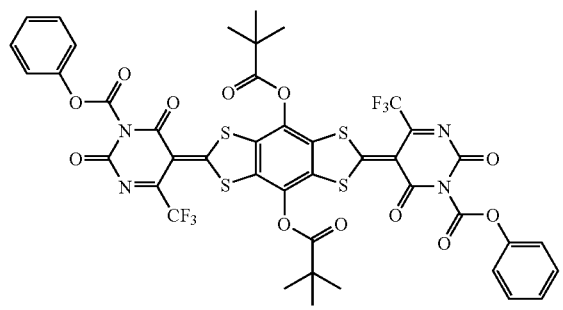
(4-14) 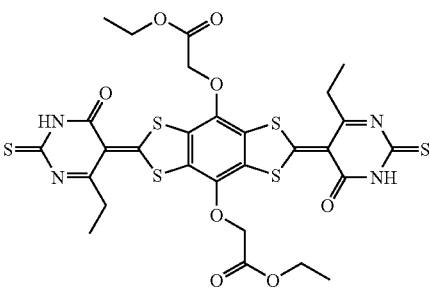
(4-15) 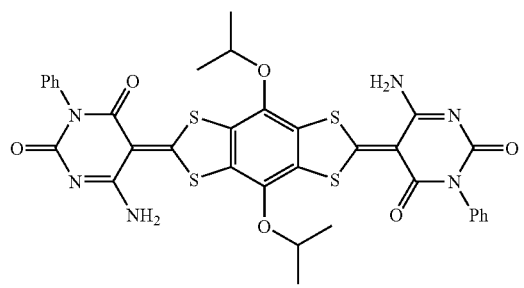
(4-16) 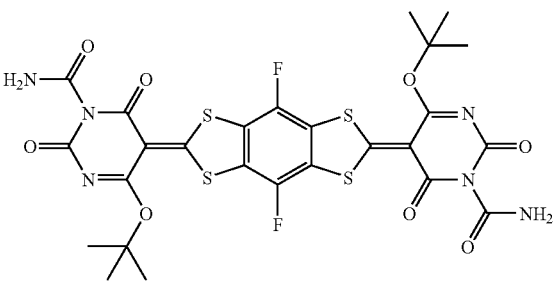
(4-17) 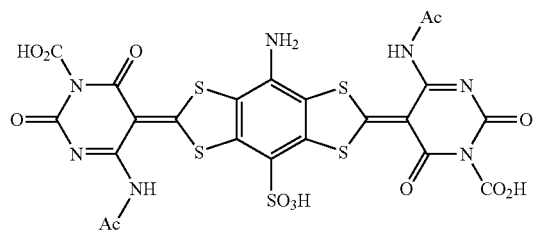
(4-18) 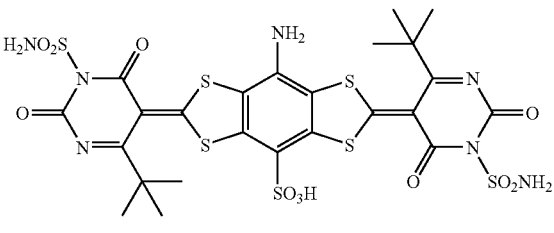
(4-19) 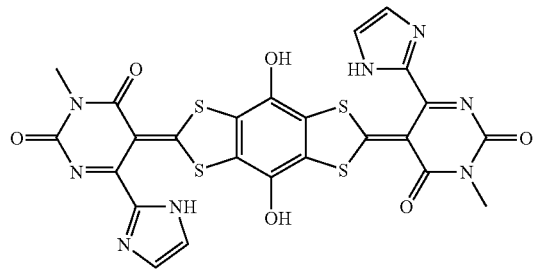
(4-20) 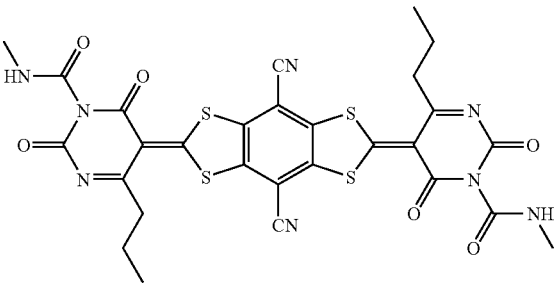

-continued
(4-21)
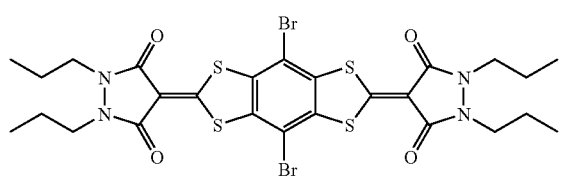
(4-22)
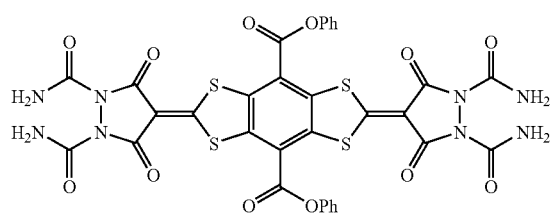
(4-23)
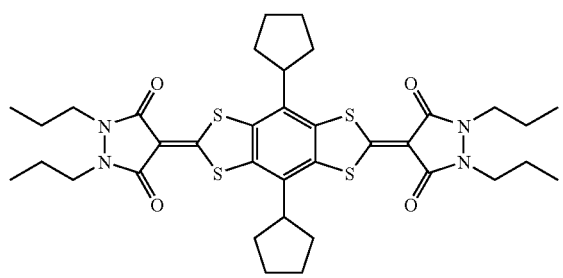
(4-24)
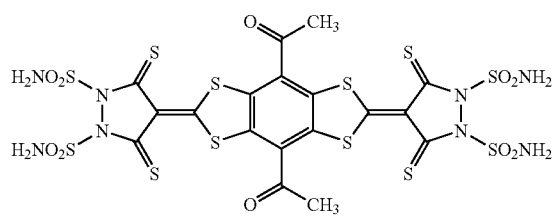
(4-25)
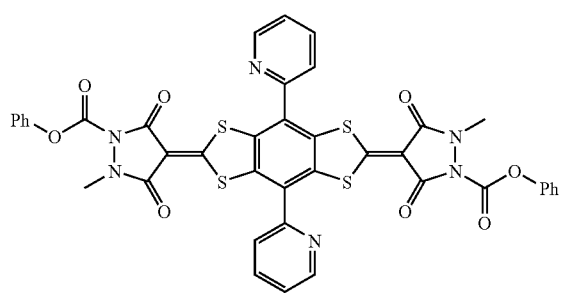
(4-26)
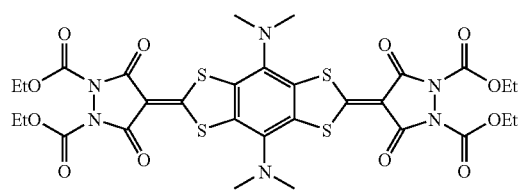
(4-27)
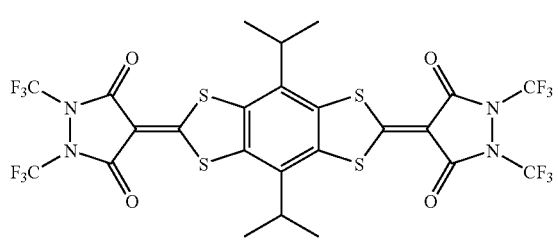
(4-28)
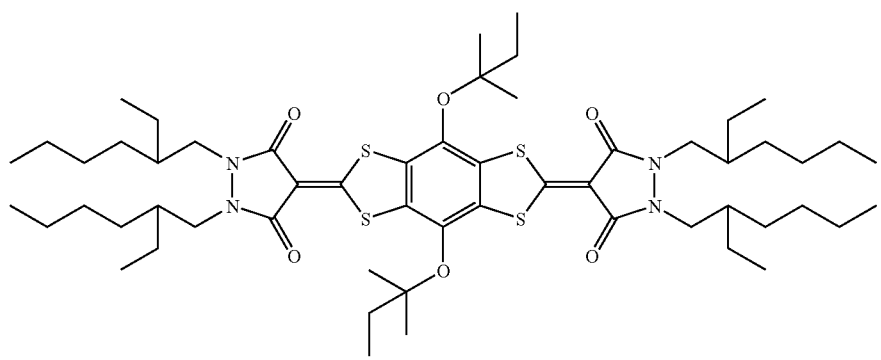

-continued
(4-29)
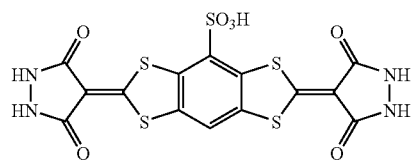
(4-30)
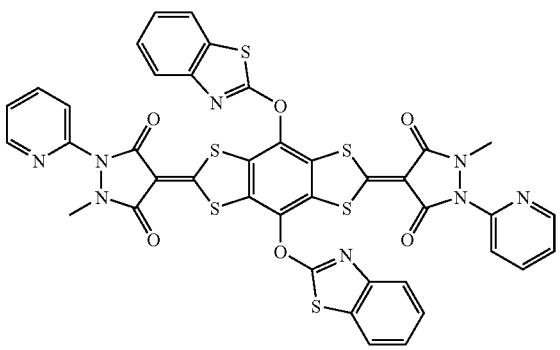
(4-31)
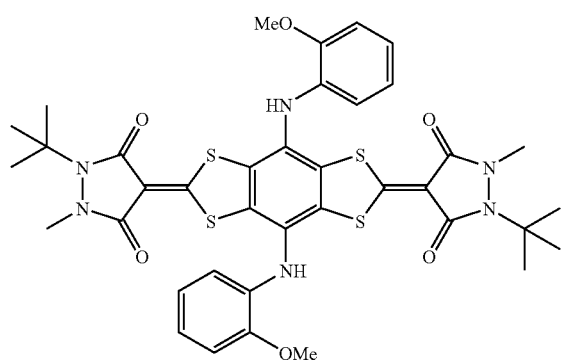
(4-32)
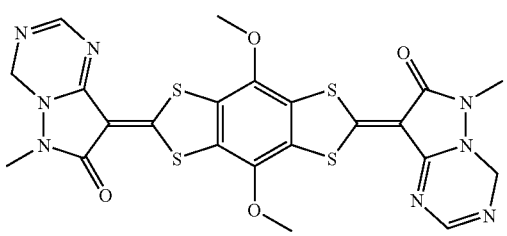
(4-33)
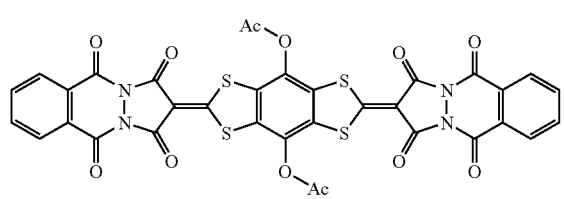
(4-34)
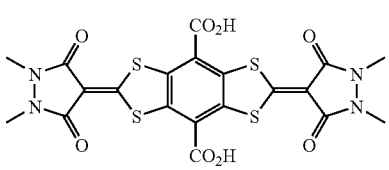
(4-35)
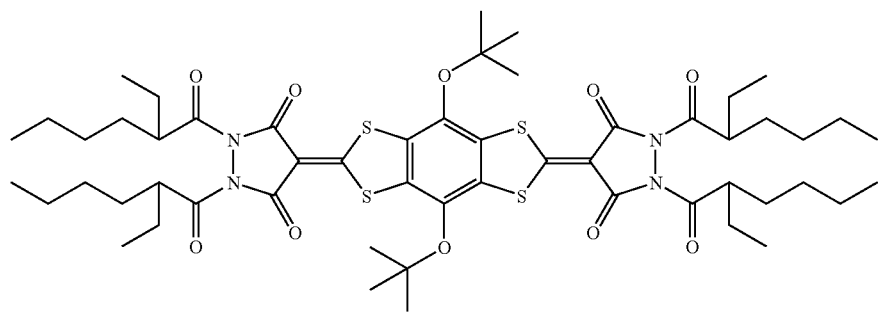
(5-1)
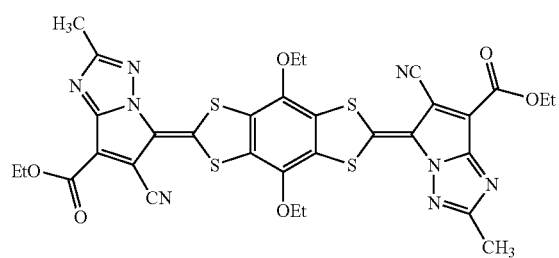
(5-2)
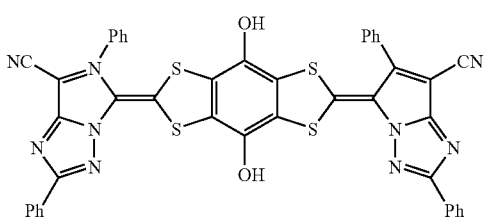

-continued
(5-3)
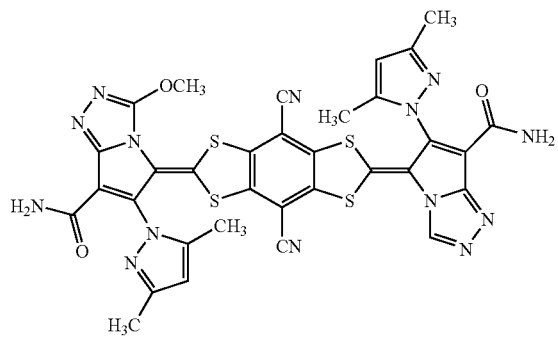
(5-4)
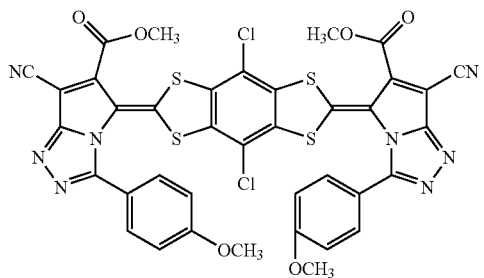
(5-5)
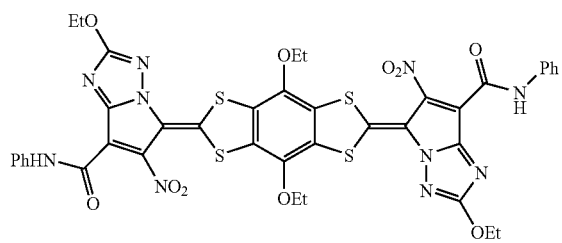
(5-6)
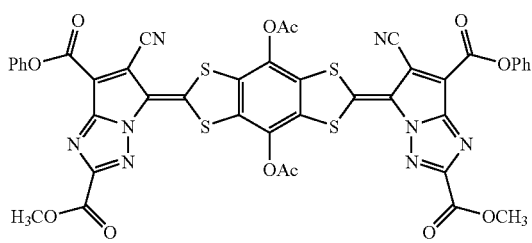
(5-7)
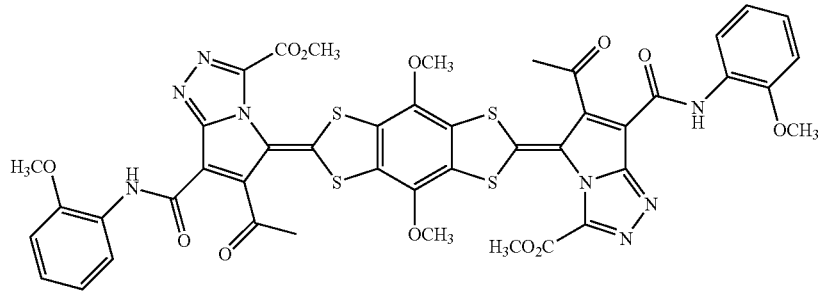
(5-8)
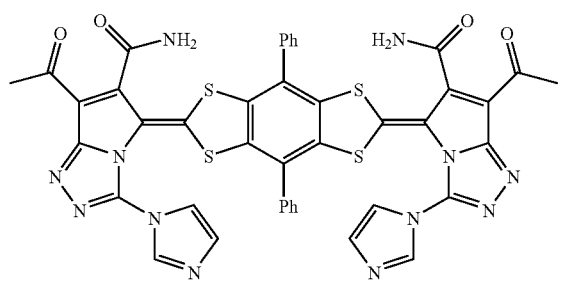
(5-9)
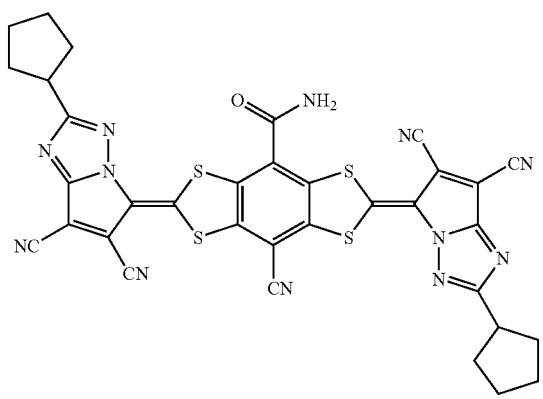
(5-10)
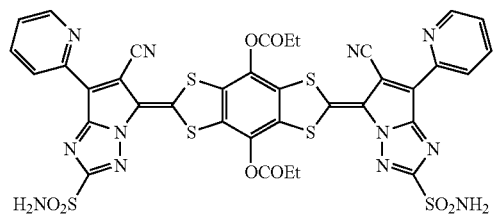
(5-11)
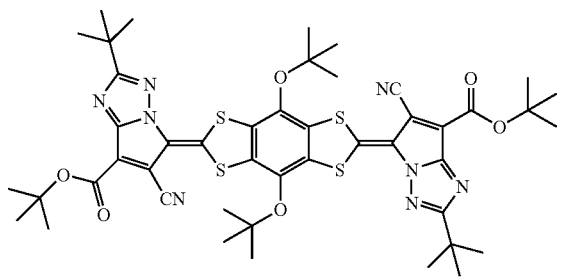

(5-12)
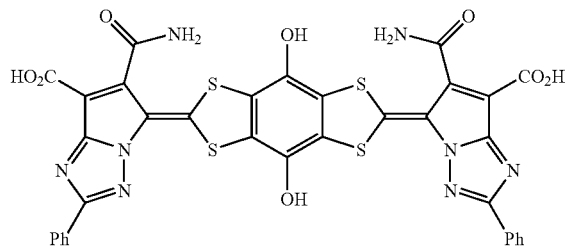
(5-13)
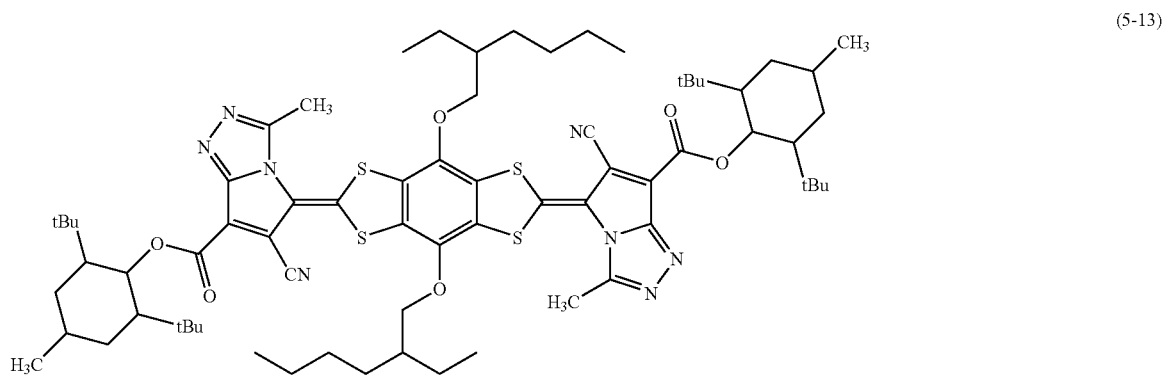
(5-14)
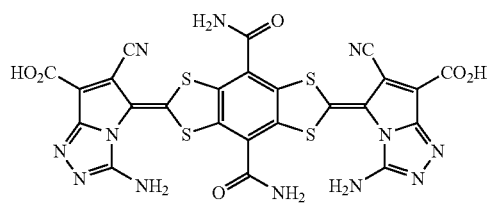
(5-15)
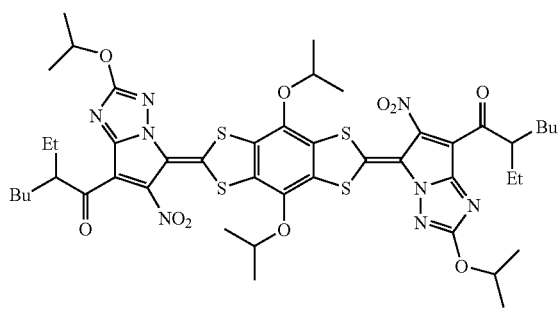
(5-16)
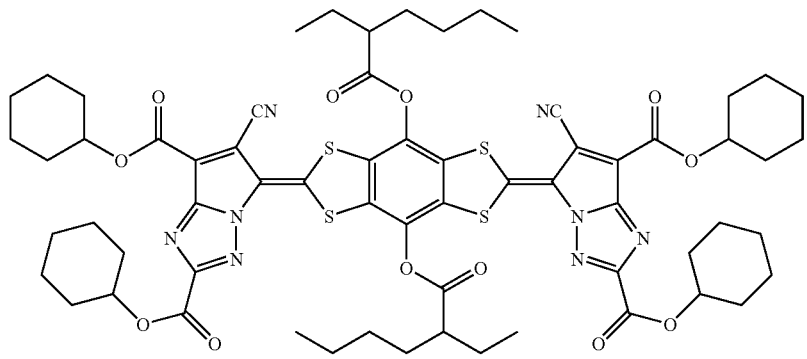

-continued
(5-17)
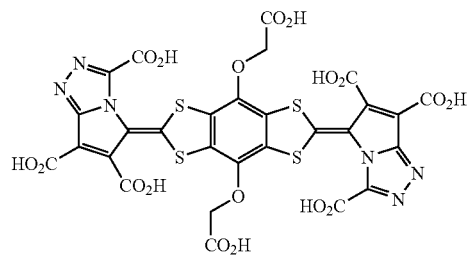
(5-18)
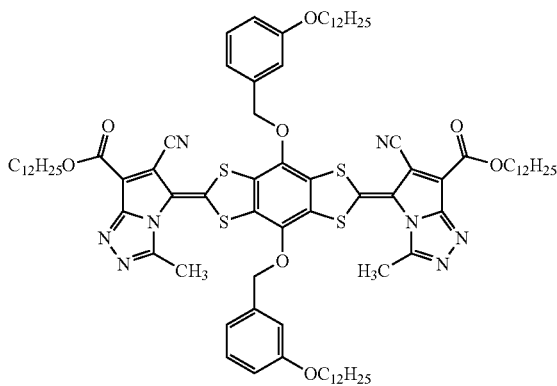
(6-1)
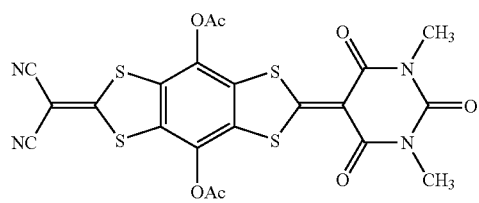
(6-2)
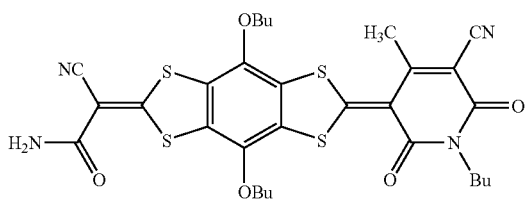
(6-3)
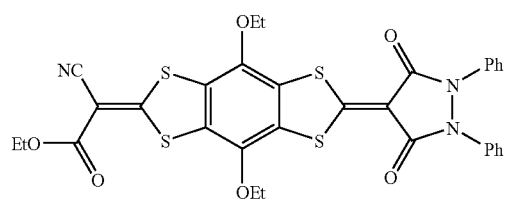
(6-4)
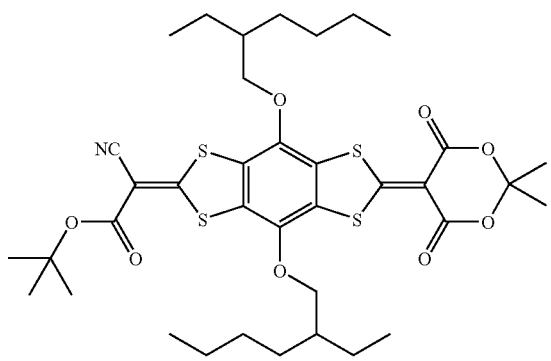
(6-5)
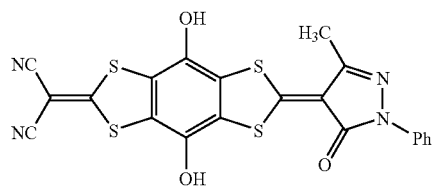
(6-6)
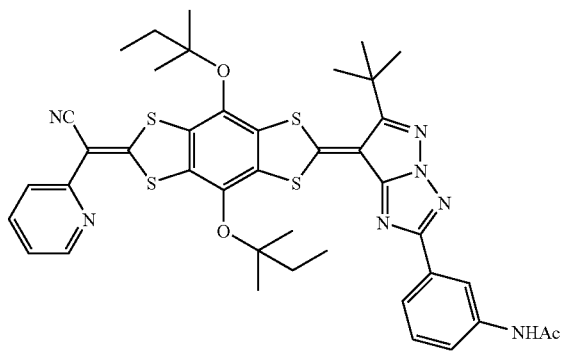
(6-7)
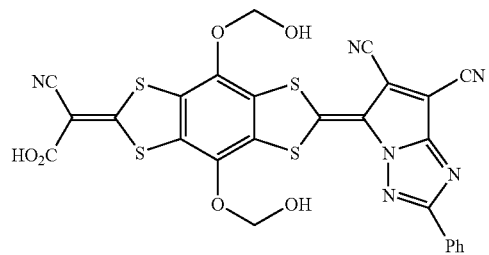
(6-8)

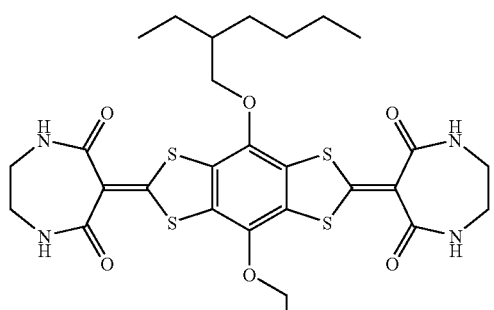

(6-9)

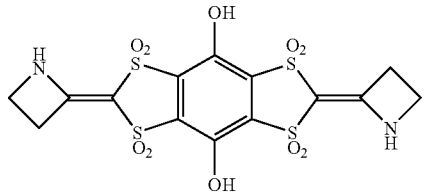

(6-10)

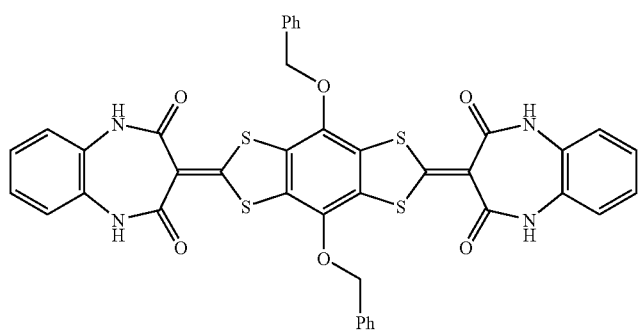

(6-11)

The compound represented by formula (I-1) or (Ia-1) above can be synthesized by any method. Examples of the synthetic method are described in detail below together with the description of the second embodiment of the present invention.

The compound in the first embodiment of the present invention may have a tautomer, depending on its structure and the environment to which the compound is exposed. In the present specification, only a typical tautomer is described, but the other tautomer different from that described in the present specification are also included in the compound in the first embodiment of the present invention.

The compound in the first embodiment of the present invention may be a cation or anion with an appropriate counter ion, depending on its structure and the environment to which the compound is exposed. In the present specification, a hydrogen ion is recited as a typical counter cation, while a hydroxide ion is recited as a typical counter anion. However, compounds with the other counter ion are also included in the compound in the present invention. The counter ion may be one ion or a variety of ions with an arbitrary proportion.

When $R^{21}$ and $R^{22}$, $R^{23}$ and $R^{24}$, $X^{21}$ and $X^{22}$, $X^{23}$ and $X^{24}$, or $R^{25}$ and $R^{26}$ are different from each other, the compound in the first embodiment of the present invention may have a geometrical isomer wherein the respective groups are exchanged. Such a geometrical isomer is also included in the compound in the present invention, even when only one geometrical isomer is described in the present specification. In addition, even if a mixture of the geometrical isomers is formed in the synthesis or purification process, only a typical isomeric structure is shown in the present specification. When the compound is a geometrical isomer mixture, the abundance ratio may be arbitrary between 0:1 to 1:0.

The compound in the first embodiment of the present invention may have an isotopic element (such as $^2H$, $^3H$, $^{13}C$, $^{15}N$, $^{17}O$, or $^{18}O$).

The intended use of the compound as an ultraviolet absorbent in the first embodiment of the present invention is described in detail below together with the description of the second embodiment of the present invention.

Next, the second embodiment of the present invention is described in detail.

The ultraviolet absorbent of the second embodiment of the present invention is characterized in that its molecular weight is 1,000 or less and its molar extinction coefficient at the maximum absorption wavelength is 75,000 or more. The ultraviolet absorbent satisfying these physical properties exhibits a performance in which molar extinction coefficient per molecular weight is large, so that a sufficient ultraviolet ray-shielding effect can be attained using only a small amount of the ultraviolet absorbent.

It is desirable that light absorption of the ultraviolet absorbent is large in order to obtain a large ultraviolet absorbing effect using only a small amount of the ultraviolet absorbent. As described in Sumio Tokita, "Chemistry Seminar 9. Color Chemistry", (Maruzen, 1982), p. 154 to 155, the light-absorption intensity, namely the oscillator intensity of light is proportional to the integral of the molar extinction coefficient. Besides, the molar extinction coefficient is a value that is proportional to a square of transition moment. The transition moment is represented by a function of distance vector as described on page 12 of "Kinosei sikiso (Functional Dyes)" by Shin Ohkawara, Ken Matsuoka, Tsuneaki Hirashima and Teijirou Kitao (Kodansha Scientific, 1992). Accordingly, the transition moment becomes small with respect to the short-wave absorbing compound that is composed of a short conjugated system. As a result, generally the shorter-wave absorbing compound, the smaller light absorption. In fact, with reference to a molar extinction coefficient at the maximum absorption wavelength of ordinary ultraviolet absorbents, the molar extinction coefficient of benzophenone-based or benzotriazole-based ultraviolet absorbents is not more than about 10,000 to 30,000.

Further, the molar extinction coefficient at the maximum absorption wavelength varies depending on a shape of absorption spectrum. Namely, even though light absorption is the same, there may be a difference in molar extinction coefficient between a sharp spectrum compound and a broad spectrum compound. For a large molar extinction coefficient, is desired a sharp spectrum, namely a spectrum with a small half width. An ultraviolet absorbent giving a broad spectrum has also absorption in the long-wavelength side from the maximum absorption wavelength. Accordingly, in order to shield the light in the long-wavelength ultraviolet range effectively without yellowing, an ultraviolet absorbent showing a spectrum having a small half width is preferable.

The molar extinction coefficient in the second embodiment of the present invention is a desirable value as a physical property of the ultraviolet absorbent. However, the value of molar extinction coefficient that has been attained by the present invention is a range to which the conventional ultraviolet absorbent could not reach in the past.

The molar extinction coefficient at the maximum absorption wavelength is preferably in the range of from 78,000 to 150,000, more preferably from 85,000 to 120,000, and especially preferably from 90,000 to 110,000.

The half width is preferably 60 nm or less, more preferably 50 nm or less, and furthermore preferably 45 nm or less.

The absorption maximum wavelength and the half width specified in the present invention can be determined easily by a skilled person in the art. The measuring methods are described, for example, in Chemical Society of Japan Ed., "Experimental Chemistry Lecture, Chapter 7, Spectroscopy II", 4th Ed., (Maruzen, 1992), p. 180 to 186. Specifically, they are determined by dissolving a sample in a suitable solvent and measuring the spectrum in a spectrophotometer by using two quartz or glass cells for the sample and control. For example, the solvent for use is required to be capable of dissolving the sample, have no absorption in the measurement wavelength range, have smaller interaction with the solute molecule, and have relatively low volatility. Any solvent may be used, as long as it satisfies the conditions above. In the present invention, the measurement is made by using ethyl acetate (EtOAc) as the solvent.

The molar extinction coefficient is defined, for example, in Chemical Society of Japan Ed., "New Experimental Chemistry Lecture, Chapter 9 Analytical Chemistry [II]", (Maruzen, 1977), p. 244, and can be determined, together with the absorption maximum wavelength above.

The absorption maximum wavelength and the half width of the dyes in the present invention are determined by preparing a solution in ethyl acetate as the solvent at a concentration of approximately $5 \times 10^{-5}$ mol·dm$^{-3}$ and by measurement while using a quartz cell having an optical path length of 10 mm.

The spectral half width is described, for example, in Chemical Society of Japan Ed., "Experimental Chemistry Lecture, Chapter 3 Basic Operation III", 4th Ed., (Maruzen, 1991), p. 154. The half width is described in the literature above by using wave number as abscissa, but the half width is plotted against wavelength in the present invention and thus, the unit of the half value width is nm. Specifically, it is defined as the width of the absorption band at an absorbance of ½ of that at the absorption maximum wavelength and used as an indicator of the absorption spectral shape.

As the ultraviolet absorbents with a large molar extinction coefficient, there are compounds having a plurality of ultraviolet absorbing structures in one molecule, such as a polymerized ultraviolet absorbent described in, for example, JP-T-2006-526671 and JP-T-2007-507567. The molar extinction coefficient of the compound such as a polymerized ultraviolet absorbent apparently becomes large. However, coincidentally a molecular weight of the compound also becomes large, so that there is no change in the molar extinction coefficient per the ultraviolet absorbing structure. Although low-volatility effect owing to polymerization can be expected, a problem that is caused by increase in amount of use has not been dissolved yet.

The ultraviolet absorbent with a small molecular weight is preferred. However, a minimum molecular structure is necessary for the ultraviolet absorbent to have a desired capacity. Taking account of a molecular weight necessary to give preferable properties with reference to molecular weights of the existing ultraviolet absorbents, it was found in the present invention that the molecular weight of 1000 or less is enough. The molecular weight is more preferably in the range of from 350 to 950, furthermore preferably from 400 to 930, and especially preferably from 500 to 910.

For reference, molecular weights of the benzotriazole-based compounds that are widely used ultraviolet absorbents are about 300, and their molar extinction coefficients are about 20,000. Besides, molecular weights of the triazine-based compounds are about 600, and their molar extinction coefficients are about 60,000. The relation between molecular weight and molar extinction coefficient at the maximum absorption wavelength that is defined by the present invention cannot be attained by a combination of hitherto known ultraviolet absorbents, and it could not be accomplished until a novel skeleton of the ultraviolet absorbent is found by the present inventors.

The ultraviolet absorbent in the second embodiment of the present invention comprises the compound represented by the aforementioned formula (I).

In formula (I), $R^1$, $R^2$, $R^3$ and $R^4$ each have the same meaning as those of $R^{21}$, $R^{22}$, $R^{23}$ and $R^{24}$ in formula (I-1), respectively, and preferable substituents are also the same. However, unlike in the case of Formula (I-1), the compounds wherein $R^1$, $R^2$, $R^3$ and $R^4$ each represent an alkylthio group are also included.

Like in the case of Formula (I-1), it is preferable that at least one of $R^1$, $R^2$, $R^3$ and $R^4$ represents a substituent having a Hammett substituent constant ρ value of 0.2 or more.

At least one of $R^1$, $R^2$, $R^3$ and $R^4$ is still more preferably an alkoxycarbonyl group having 6 or more carbon atoms, still more preferably an alkoxycarbonyl group having 6 to 20 carbon atoms, still more preferably an alkoxycarbonyl group having 6 to 12 carbon atoms. The alkoxy moiety may have any substituent on any position. Examples of the substituent include those described above. The alkoxy group in the alkoxycarbonyl group is, for example, a hexyloxy group, a 2-ethylhexyloxy group, an octyloxy group, a decyloxy group, or a dodecyloxy group.

Preferable examples of the pair of $R^1$ and $R^2$ and the pair of $R^3$ and $R^4$ include those recited in the above-described Table 1 as preferable specific examples of the pair of $R^{21}$ and $R^{22}$ and the pair of $R^{23}$ and $R^{24}$ in Formula (I-1). However, the present invention is not limited to these specific examples. The wavy line in the above Table indicates the binding site on the heterocycle shown in formula (I).

$R^5$ and $R^6$ each have the same meaning as those of $R^{25}$ and $R^{26}$ in formula (I-1), respectively, and preferable substituents are also the same.

Preferable examples of $R^5$ or $R^6$ include those recited in the above-described Table 2 as preferable specific examples of $R^{25}$ or $R^{26}$. However, the present invention is not limited to these specific examples. The wavy line in the above Table indicates the binding site on the benzene ring shown in formula (I).

$X^1$, $X^2$, $X^3$ and $X^4$ each have the same meaning as those of $X^{21}$, $X^{22}$, $X^{23}$ and $X^{24}$ in formula (I-1), respectively, and preferable substituents are also the same.

Preferable examples of the pair of $X^1$ and $X^2$ and the pair of $X^3$ and $X^4$ include those recited in the above-described Table 3 as preferable specific examples of the pair of $X^{21}$ and $X^{22}$ and the pair of $X^{23}$ and $X^{24}$ in Formula (I-1). However, the present invention is not limited to these specific examples. The wavy line in the above Table indicates the binding site on the carbon atoms in formula (I) to which $R^1$ and $R^2$ or $R^3$ and $R^4$ bound.

The compound represented by Formula (I) is preferably a compound represented by the following Formula (Ia).

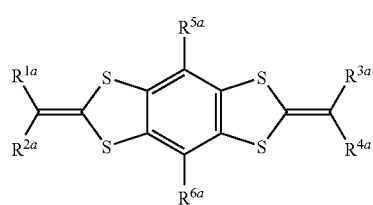

Formula (Ia)

In formula (Ia), $R^{1a}$, $R^{2a}$, $R^{3a}$ and $R^{4a}$ each represent a monovalent substituent. However, at least one of $R^{1a}$, $R^{2a}$, $R^{3a}$ and $R^{4a}$ represents a cyano group, an alkoxycarbonyl group having 1 to 20 carbon atoms (preferably 1 to 10 carbon atoms), an aryloxycarbonyl group having 6 to 20 carbon atoms (preferably 6 to 10 carbon atoms), a carbamoyl group having 1 to 20 carbon atoms (preferably 1 to 10 carbon atoms), an alkylcarbonyl group having 1 to 20 carbon atoms (preferably 1 to 10 carbon atoms), an arylcarbonyl group having 6 to 20 carbon atoms (preferably 6 to 10 carbon atoms), an alkylsulfonyl group having 1 to 20 carbon atoms (preferably 1 to 10 carbon atoms) or an arylsulfonyl group having 6 to 20 carbon atoms (preferably 6 to 10 carbon atoms).

It is preferable that each of $R^{1a}$, $R^{2a}$, $R^{3a}$ and $R^{4a}$ is a monovalent substituent by which at least one of the combination of ($R^{1a}$, $R^{2a}$) and the combination of ($R^{3a}$, $R^{4a}$) form no ring. It is especially preferable that each of $R^{1a}$, $R^{2a}$, $R^{3a}$ and $R^{4a}$ is a monovalent substituent by which neither the combination of ($R^{1a}$, $R^{2a}$) nor the combination of ($R^{3a}$, $R^{4a}$) forms a ring. Absence of ring formation provides such advantages that the ultraviolet absorbent is able to exhibit an excellent long-wavelength ultraviolet absorption performance, and also a self-yellow color development of the ultraviolet absorbent can be prevented.

In the present specification, examples of the monovalent substituent that does not form any ring include a straight-chain or branched alkyl group having 1 to 20 carbon atoms (preferably 1 to 10 carbon atoms) (e.g., methyl, ethyl), an aryl group having 6 to 20 carbon atoms (preferably 6 to 10 carbon atoms) (e.g., phenyl, naphthyl), a cyano group, an alkoxycarbonyl group having 1 to 20 carbon atoms (preferably 1 to 10 carbon atoms) (e.g., methoxycarbonyl), an aryloxycarbonyl group having 6 to 20 carbon atoms (preferably 6 to 10 carbon atoms) (e.g., phenoxycarbonyl), a substituted or unsubstituted carbamoyl group having 1 to 20 carbon atoms (preferably 1 to 10 carbon atoms) (e.g., carbamoyl, N-phenylcarbamoyl, N,N-dimethylcarbamoyl), an alkylcarbonyl group having 1 to 20 carbon atoms (preferably 1 to 10 carbon atoms) (e.g., acetyl), an arylcarbonyl group having 6 to 20 carbon atoms (preferably 6 to 10 carbon atoms) (e.g., benzoyl), a nitro group, a substituted or unsubstituted sulfamoyl group having 0 to 20 carbon atoms (preferably 0 to 10 carbon atoms) (e.g., sulfamoyl, N-phenylsulfamoyl), an alkylsulfonyl group having 1 to 20 carbon atoms (preferably 1 to 10 carbon atoms) (e.g., methanesulfonyl), an arylsulfonyl group having 6 to 20 carbon atoms (preferably 6 to 10 carbon atoms) (e.g., benzenesulfonyl), and a four- to seven-membered (preferably five- to six-membered) heterocyclic group (e.g., pyridyl, morpholino). The substituent may be further substituted, and multiple substituents, if present, may be the same as or different from each other.

Herein, at least one of the monovalent substituents $R^{1a}$, $R^{2a}$, $R^{3a}$ and $R^{4a}$ is a cyano group, an alkoxycarbonyl group having 1 to 20 carbon atoms (preferably 1 to 10 carbon atoms), an aryloxycarbonyl group having 6 to 20 carbon atoms (preferably 6 to 10 carbon atoms), a carbamoyl group having 1 to 20 carbon atoms (preferably 1 to 10 carbon atoms), an alkylcarbonyl group having 1 to 20 carbon atoms (preferably 1 to 10 carbon atoms), an arylcarbonyl group having 6 to 20 carbon atoms (preferably 6 to 10 carbon atoms), an alkylsulfonyl group having 1 to 20 carbon atoms (preferably 1 to 10 carbon atoms) or an arylsulfonyl group having 6 to 20 carbon atoms (preferably 6 to 10 carbon atoms).

$R^{1a}$, $R^{2a}$, $R^{3a}$ and $R^{4a}$ each are particularly preferably selected from a cyano group, an alkoxycarbonyl group having 1 to 20 carbon atoms (preferably 1 to 10 carbon atoms), an aryloxycarbonyl group having 6 to 20 carbon atoms (preferably 6 to 10 carbon atoms), a carbamoyl group having 1 to 20 carbon atoms (preferably 1 to 10 carbon atoms), an alkylcarbonyl group having 1 to 20 carbon atoms (preferably 1 to 10 carbon atoms), an arylcarbonyl group having 6 to 20 carbon atoms (preferably 6 to 10 carbon atoms), an alkylsulfonyl group having 1 to 20 carbon atoms (preferably 1 to 10 carbon atoms) or an arylsulfonyl group having 6 to 20 carbon atoms (preferably 6 to 10 carbon atoms). It is more preferable that a pair of $R^{1a}$ and $R^{2a}$, and a pair of $R^{3a}$ and $R^{4a}$ are the same in terms of combination of the members in each pair.

$R^{5a}$ and $R^{6a}$ each represent an alkoxy group having 1 to 20 carbon atoms (preferably 1 to 10 carbon atoms), an aryloxy group having 6 to 20 carbon atoms (preferably 6 to 10 carbon atoms), an acyloxy group having 1 to 20 carbon atoms (preferably 1 to 10 carbon atoms), an alkoxycarbonyloxy group having 1 to 20 carbon atoms (preferably 1 to 10 carbon atoms), an aryloxycarbonyloxy group having 6 to 20 carbon atoms (preferably 6 to 10 carbon atoms), a carbamoyloxy group having 1 to 20 carbon atoms (preferably 1 to 10 carbon atoms), an amino group having 0 to 20 carbon atoms (preferably 0 to 10 carbon atoms), an acylamino group having 1 to 20 carbon atoms (preferably 1 to 10 carbon atoms), or a carbamoylamino group having 1 to 20 carbon atoms (preferably 1 to 10 carbon atoms).

$R^{5a}$ and $R^{6a}$ may further have a substituent. Examples of the substituent include the monovalent substituents described above. Examples of a divalent substituent include a carbonyl group and an imino group. Multiple substituents, when present, may be the same as or different from each other. The substituents may bind to each other, forming a fused ring or a spiro ring.

Specific examples of the compound represented by the aforementioned Formula (I) or (Ia) include the specific examples of the compound represented by Formula (I-1) or (Ia-1). However, the present invention is not limited to these specific examples. In addition to these specific examples, the following (161) is listed as one of the specific examples of the compound represented by Formula (I) or (Ia).

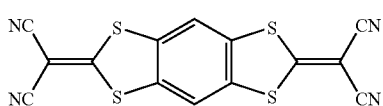

(161)

The compound represented by formula (I) or (Ia) above (Hereinafter, formula (I-1) or (Ia-1) and formula (I) or (Ia) in combination are collectively designated as formula (I) or the like in some cases.) can be synthesized by any method. For example, such a compound can be synthesized by introducing desirable substituents into a synthetic intermediate, a compound represented by formula (I) wherein $R^5$ and $R^6$ each are a hydroxy group, and alkylation or acylation.

For example, when $X^1$, $X^2$, $X^3$ and $X^4$ each are all a sulfur atom, the synthetic intermediate represented by formula (I) wherein $R^5$ and $R^6$ each are a hydroxy group can be synthesized according to the method in any one of known patents and literatures, for example, JP-A-63-225382, p. 3, right upper column, line 1 to left lower column, line 1 Reference Examples; and lines 5 to 12 on page 109 of Liebigs Ann. Chem., 1969, vol. 726, p. 103-109.

In addition, the compound represented by formula (I) above and the like can be synthesized according to the synthetic routes for preparation of similar compounds described, for example, in Journal of Organic Chemistry, 1990, vol. 55, p. 5347-5350, experimental section on p. 5349, right column, line 27; ibid., 1994, vol. 59, p. 3077-3081, p. 3081, lines 11 to 16; Tetrahedron Letters, 1991, vol. 32, p. 4897-4900, p. 4897, line 9 to p. 4899, line 3; ibid., 1977, vol. 26, p. 2225, Table 1; Tetrahedron, 1993, vol. 49, p. 3035-3042, p. 3037, lines 11 to 20 and p. 3040, lines 22 to 38; Journal of the American Chemical Society, 1958, vol. 80, p. 1662-1664, p. 1664, right column, lines 6 to 15; ibid., 1995, vol. 117, p. 9995-10002, p. 9996, right column, line 12 to p. 9997, left column, line 46; JP-A-6-80672, p. 4, left column, line 43 to right column, line 45; Phosphorus, Sulfur, and Silicon, 1997, vol. 120 & 121, p. 121-143, p. 123, line 18 to p. 124, line 3; Chem. Commun., 2004, p. 1758-1759, p. 1758, left column, lines 44 to 54; German Patent No. 3728452, p. 4, line 46 to p. 5, line 16; JP-A-51-100097, p. 3, left upper column, line 3 to p. 4, left lower column, line 4; and JP-T-5-506428, p. 12, right lower column, line 1 to p. 35, right lower column, line 1.

Besides, the compound represented by Formula (I) above can also be synthesized by reacting a bis-(N,N-dialkyliminium) compound (e.g., the synthetic intermediate M-2 in EXAMPLES to be described below) with an active methylene compound or heterocyclic compound, where the iminium compound is preliminarily prepared by reacting quinones and salt of N,N-dialkyldithiocarbamate.

For example, the exemplified compound (1) can be synthesized by reacting a hydroquinone compound (the synthetic intermediate B in EXAMPLES to be described below) and 2-ethylhexanoyl chloride in the presence of base, where the hydroquinone compound is preliminarily prepared by reacting chloranil with the disodium salt obtained by the reaction of carbon disulfide and malononitrile in the presence of sodium hydroxide. The exemplified compound (2) can be synthesized in reaction of the hydroquinone compound (the synthetic intermediate B in EXAMPLES to be described below) with 2-ethylhexyl bromide in the presence of base.

The hydroquinone compound (the synthetic intermediate B in EXAMPLES to be described below) can be also prepared by reacting bis-(N,N-diethyliminium) compound (the synthetic intermediate M-2 in EXAMPLES to be described below) and malononitrile, where the iminium compound is preliminarily prepared by reacting 1,4-benzoquinone and potassium N,N-diethyldithiocarbamate.

The exemplified compound (11) can be synthesized by allowing carbon disulfide and ethyl cyanoacetate to react with each other in the presence of potassium hydroxide to obtain a dipotassium salt, and allowing the dipotassium salt to react with chloranil to obtain the exemplified compound (72), and allowing the exemplified compound (72) to react with 2-ethylhexanoyl chloride in the presence of base. The exemplified compound (12) can be synthesized by allowing the exemplified compound (72) to react with 2-ethylhexyl bromide in the presence of base.

Further, the exemplified compound (72) can be also synthesized by reacting the synthetic intermediate M-2 in EXAMPLES with ethyl cyanoacetate.

The exemplified compound (59) can be synthesized by allowing carbon disulfide and ethyl cyanoacetate to react with each other in the presence of potassium hydroxide to obtain a dipotassium salt, and allowing the dipotassium salt to react with hexafluorobenzene.

The exemplified compound (51) can be synthesized by allowing the exemplified compound (59) to react with sodium dodecanethiolate.

The compound represented by formula (I) or (Ia) above may have a tautomer, depending on its structure and the environment to which the compound is exposed. In the present specification, only a typical tautomer is described, but the other tautomer different from that described in the present specification is also included in the compound represented by formula (I) or (Ia) that can be used in the present invention.

The compound represented by formula (I) or (Ia) above may be a cation or anion with an appropriate counter ion depending on the structure and the environment where the compound is located. In the present specification, a hydrogen ion is recited as a typical counter cation, while a hydroxide ion as a typical counter anion. However, compounds with other counter ions are also included in the compound represented by formula (I) or (Ia) above. The counter ion may be one ion or a variety of ions with an arbitrary proportion.

When $R^1$ and $R^2$, $R^3$ and $R^4$, $X^1$ and $X^2$, $X^3$ and $X^4$, or $R^5$ and $R^6$ are different from each other, the compound represented by formula (I) or (Ia) may have a geometrical isomer wherein the respective groups are exchanged. Such a geometrical isomer is also included in the compound represented by formula (I) or (Ia) that can be used in the present invention, even when only one geometrical isomer is described in the present specification. In addition, even if a mixture of the geometrical isomers is formed in the synthesis or purification process, only a typical isomeric structure is shown in the present specification. When the compound is a geometrical isomer mixture, the abundance ratio may be arbitrary between 0:1 to 1:0.

The compound represented by formula (I) or (Ia) may have an isotopic element (such as $^2H$, $^3H$, $^{13}C$, $^{15}N$, $^{17}O$, or $^{18}O$).

A polymer having the structure of the compound represented by formula (I) or (Ia) above in its recurring unit as the ultraviolet absorptive group can also be used favorably in the present invention. Hereinafter, examples of the recurring unit containing the structure of the compound represented by formula (I) or (Ia) above will be shown.

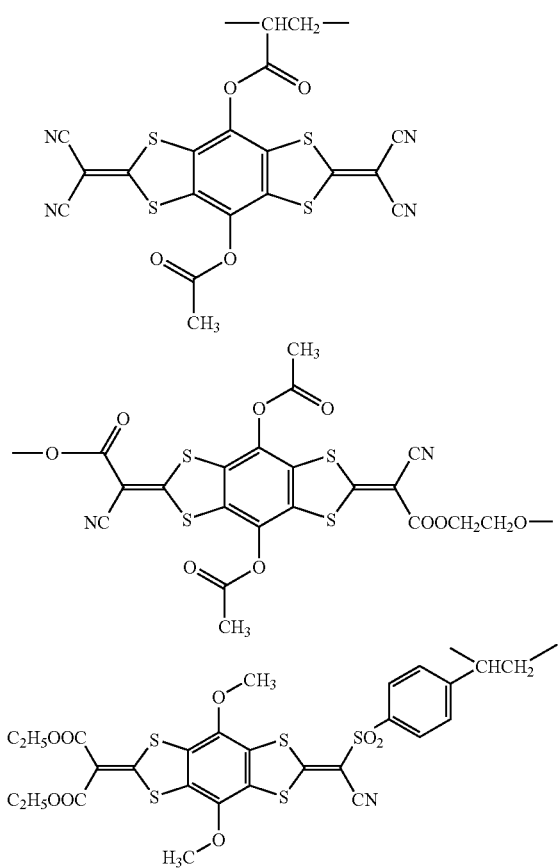

The polymer may be a homopolymer having one kind of recurring unit or a copolymer having two or more kinds of recurring units. It may be a copolymer having another recurring unit additionally. Hereinafter, examples of the other recurring unit are shown.

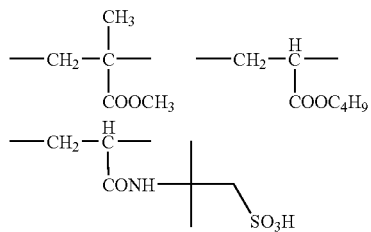

Examples of the polymer having the structure of the ultraviolet absorbent in the recurring unit are described, for example, in JP-B-1-53455 p. 4, left lower column, line 12 to p. 13, left upper column, line 38; JP-A-61-189530, p. 3, right upper column, line 13 to p. 6 lower column, line 12; and EP Patent No. 27242, p. 3, line 40 to p. 8, line 13. The polymer can be prepared with reference to the methods described in these Patent Documents.

The maximum absorption wavelength of the ultraviolet absorbent of the present invention (Hereinafter, the ultraviolet absorbent according to the first embodiment of the present invention and the ultraviolet absorbent according to the second embodiment of the present invention in combination are collectively designated as the ultraviolet absorbent of the present invention in some cases.) is not particularly limited, but with a preferable range of from 280 nm to 400 nm and a more preferable range of from 320 nm to 380 nm.

The ultraviolet absorbent of the present invention is suitably used as a composition containing the same. Examples of the composition include a dispersion, a solution, a mixture and a coated material.

The ultraviolet absorbent of the present invention may be used in the state of dispersion in which the ultraviolet absorbent is dispersed in a dispersing medium. Hereinafter, the dispersion containing the ultraviolet absorbent according to the present invention will be described.

The medium for dispersing the ultraviolet absorbent according to the present invention is arbitrary. Examples thereof include water, organic solvents, resins, resin solutions, and the like. These media may be used alone or in combination of two or more.

Examples of the organic solvents as the dispersing medium that can be used for the ultraviolet absorbent of the present invention include hydrocarbon-based solvents such as pentane, hexane and octane; aromatic solvents such as benzene, toluene and xylene; ether-based solvents such as diethylether and methyl-t-butylether; alcoholic solvents such as methanol, ethanol and isopropanol; ester-based solvents such as acetone, ethyl acetate and butyl acetate; ketone-based solvents such as methyl ethyl ketone; nitrile-based solvents such as acetonitrile and propionitrile; amide-based solvents such as N,N-dimethylformamide, N,N-dimethylacetamide and N-methylpyrrolidone; sulfoxide-based solvents such as dimethylsulfoxide; amine-based solvents such as triethylamine and tributylamine; carboxylic acid-based solvents such as acetic acid and propionic acid; halogen-based solvents such as methylene chloride and chloroform; and heterocycle-based solvents such as tetrahydrofuran and pyridine. These solvents may be used as a mixture at any rate.

Examples of the resins as the dispersing medium that can be used for the ultraviolet absorbent of the present invention include various known thermoplastic and thermosetting resins commonly used for production of molded article, sheet, film and others. Examples of the thermoplastic resins include polyethylene series resins, polypropylene series resins, poly(meth)acrylic ester series resins, polystyrene series resins, styrene-acrylonitrile series resins, acrylonitrile-butadiene-styrene series resins, polyvinyl chloride series resins, polyvinylidene chloride series resins, polyvinyl acetate series resins, polyvinylbutyral series resins, ethylene-vinyl acetate series copolymers, ethylene-vinylalcohol series resins, polyethylene terephthalate resins (PET), polybutylene terephthalate resins (PBT), liquid crystal polyester resins (LCP), polyacetal resins (POM), polyamide resins (PA), polycarbonate resins, polyurethane resins, and polyphenylene sulfide resins (PPS), and these resins may be used alone or as polymer blend or alloy of two or more. The resin may be used as a thermoplastic molding material containing a natural resin and additionally a filler such as glass fiber, carbon fiber, semi-carbonized fiber, cellulosic fiber or glass bead, a flame retardant, and the like. As needed, resin additives commonly used, such as polyolefin series resin fine powder, polyolefin series wax, ethylene bisamide wax, and metal soap, may be used alone or in combination.

Examples of the thermosetting resins include epoxy resins, melamine resins, and unsaturated polyester resins, and the resin may be used as a thermosetting molding material containing a natural resin and additionally a filler, such as glass fiber, carbon fiber, semi-carbonized fiber, cellulosic fiber or glass bead, and a flame retardant.

The ultraviolet absorbent compound of the first embodiment of the present invention and the dispersion containing the ultraviolet absorbent of the second embodiment of the present invention may contain other additives such as dispersant, antifoam, preservative, antifreezing agent, surfactant, and others. The dispersion may contain any other compounds additionally. Examples of the other additives include dye, pigment, ultraviolet absorbent, infrared absorbent, flavoring agent, polymerizable compound, polymer, inorganic material, metal and the like.

For example, a high-speed-agitation dispersing machine providing a high-sharing force or a dispersing machine imparting a high-strength ultrasonic may be used as the apparatus for preparation of the ultraviolet absorbent compound of the first embodiment of the present invention and the dispersion containing the ultraviolet absorbent of the second embodiment of the present invention. Specific examples thereof include colloid mill, homogenizer, capillary emulsifier, liquid siren, electromagnetic-distortion ultrasonic wave generator, emulsifier having a Pallmann whistle, and the like. The high-speed-agitation dispersing machine favorably used in the present invention is a dispersing machine in which a dispersing part is revolving in liquid at high speed (500 to 15,000 rpm, preferably 2,000 to 4,000 rpm) such as dissolver, polytron, homomixer, homoblender, keddy mill, or jet agitator. The high-speed-agitation dispersing machine that can be used in the present invention is also called a dissolver or a high-speed impeller dispersing machine, and, as described in JP-A-55-129136, a dispersing machine having impellers of saw-teeth shaped plate alternately bent in the vertical direction that are connected to the shaft revolving at high speed is also a favorable example.

Various methods may be used in preparation of an emulsified dispersion containing a hydrophobic compound. For example, in dissolving a hydrophobic compound in an organic solvent, the hydrophobic compound is dissolved in a solvent or a mixture of two or more arbitrarily selected from high-boiling point organic materials, water-immiscible low boiling point organic solvents and water-miscible organic solvents, and the solution is then dispersed in water or an aqueous hydrophilic colloid solution in the presence of a surfactant compound. The water-insoluble phase containing the hydrophobic compound and the aqueous phase may be mixed by the so-called normal mixing method of adding the water-insoluble phase into the agitated aqueous phase or by the reverse mixing method of adding the phases reversely.

The content of the ultraviolet absorbent in the dispersion containing the ultraviolet absorbent according to the present invention may not be determined specifically, because it varies according to application and type of usage, and is thus arbitrary according to application. Preferably, the content is 0.001 to 80 mass %, more preferably 0.01 to 50 mass %, with respect to the total amount of the dispersion.

The ultraviolet absorbent according to the present invention can be used in the state of a solution dissolved in a liquid medium. Hereinafter, the solution containing the ultraviolet absorbent according to the present invention will be described.

The liquid dissolving the ultraviolet absorbent according to the present invention is arbitrary. It is, for example, water, an organic solvent, a resin, a resin solution, or the like. Examples of the organic solvent, the resin, and the resin solution include those described above as the dispersing medium. These may be used alone or in combination.

The solution of the ultraviolet absorbent according to the present invention may contain any other compounds additionally. Examples of the other additives include dye, pigment, ultraviolet absorbent, infrared absorbent, flavoring agent, polymerizable compound, polymer, inorganic material, metal and the like. Components other than the ultraviolet absorbent according to the present invention may not necessarily be dissolved.

The content of the ultraviolet absorbent in the solution containing the ultraviolet absorbent according to the present invention may not be determined specifically, because it varies according to application and type of usage, and thus the concentration is arbitrary according to application. The concentration in the entire solution is preferably 0.001 to 30 mass %, more preferably 0.01 to 10 mass %. A solution at higher concentration may be prepared in advance and diluted at a desired time before use. The dilution solvent is selected arbitrarily from the solvents described above.

Further, the ultraviolet absorbent of the present invention may be used in the state of a mixture with any other compounds. The following is an explanation of a mixture containing the ultraviolet absorbent of the present invention.

The mixture containing the ultraviolet absorbent of the present invention is not limited in both a form and a state thereof. Examples of the mixture include a liquid, a solid and a liquid crystal. With respect to the solid, there are various states as exemplified by flat membrane-like, powder-like, spherical particle-like, granular particle-like, non-individual body-like, fiber-like, tube-like, hollow fiber type, plate-like, and porous type states. The solid may be exemplified by one having a multi-layer structure and another having a composition with lack of uniformity. It is particularly preferred that the solid is a polymer material containing the ultraviolet absorbent of the present invention.

The polymer composition is used in preparation of the polymer material. The polymer composition contains a polymer substance described below and the ultraviolet absorbent according to the present invention.

The ultraviolet absorbent according to the present invention can be contained in the polymer substance in various methods. When the ultraviolet absorbent according to the present invention is compatible with the polymer substance, the ultraviolet absorbent according to the present invention may be added to the polymer substance directly. The ultraviolet absorbent according to the present invention may be dissolved in an auxiliary solvent compatible with the polymer substance, and then the obtained solution be added to the polymer substance. The ultraviolet absorbent according to the present invention may be dispersed in a high-boiling point organic solvent or a polymer, and the obtained dispersion be added to the polymer substance. Alternatively, the dispersion may be coated on the surface of the polymer material.

The boiling point of the high-boiling point organic solvent is preferably 180° C. or higher, more preferably 200° C. or higher. The melting point of the high-boiling point organic solvent is preferably 150° C. or lower, more preferably 100° C. or lower. Examples of the high-boiling point organic solvents include phosphoric esters, phosphonic esters, benzoic esters, phthalic esters, fatty acid esters, carbonate esters, amides, ethers, halogenated hydrocarbons, alcohols and paraffins. Phosphoric esters, phosphonic esters, phthalic ester, benzoic esters and fatty acid esters are preferable.

The method of adding the ultraviolet absorbent according to the present invention is determined, by reference to the description in JP-A-58-209735, JP-A-63-264748, JP-A-4-191851, JP-A-8-272058, and British Patent No. 2016017A.

Hereinafter, the polymer substance that can be used in the polymer composition will be described. The polymer substance is a natural or synthetic polymer or copolymer. Examples thereof include the followings:

<1> Monoolefinic and diolefinic polymers such as polypropylene, polyisobutylene, polybut-1-ene, poly-4-methyl pent- 1-ene, polyvinylcyclohexane, polyisoprene and polybutadiene; cycloolefin polymers such as of cyclopentene or norbornene; polyethylenes (crosslinkable as needed) such as high-density polyethylene (HDPE), high-density and high-molecular weight polyethylene (HDPE-HMW), high-density and ultrahigh molecular weight polyethylene (HDPE-UHMW), medium-density polyethylene (MDPE), low-density polyethylene (LDPE), and linear low-density polyethylene (LLDPE), (VLDPE) and (ULDPE).

Polyolefins (that is, polymers of the monoolefins exemplified in the paragraph above), preferably polyethylene and polypropylene, may be prepared by various methods, particularly by the following methods:
a) Radical polymerization (normally under high pressure and elevated temperature), and
b) Catalytic polymerization normally by using one or more metals in the groups IVb, Vb, VIb and VIII of the Periodic Table.

The metal is normally bound to one or more ligands, typically π- or σ-coordinating groups such as oxide, halide, alcoholate, ester, ether, amine, alkyl, alkenyl and/or aryl. The metal complex is in the free state or immobilized on a base material such as activated magnesium chloride, titanium (III) chloride, alumina or silicon oxide. The catalyst may be soluble or insoluble in the polymerization medium. The catalyst may be used as it is in polymerization or in combination with another activating agent, such as metal alkyl, metal hydride, metal alkyl halide, metal alkyl oxide or metal alkyloxane, the metal being an element in the groups Ia, IIa and/or IIIa of the Periodic Table. The activating agent may be modified properly with an other ester, ether, amine or silylether group. Such a catalyst system is normally called Philips, Standard Oil-Indiana, Ziegler (Natta), TNZ (Du Pont), metallocene or single site catalyst (SSC).

<2> Mixture of the polymers described in <1> above such as polypropylene/polyisobutylene, polypropylene/polyethylene mixture (such as PP/HDPE and PP/LDPE), and mixture of different type of polyethylenes (such as LDPE/HDPE).

<3> Copolymers of a monoolefin and a diolefin or a monoolefin or diolefin with another vinyl monomer such as ethylene/propylene copolymer, mixture of linear low-density polyethylene (LLDPE) and its low-density polyethylene (LDPE), propylene/but-1-ene copolymer, propylene/isobutylene copolymer, ethylene/but-1-ene copolymer, ethylene/hexene copolymer, ethylene/methylpentene copolymer, ethylene/heptene copolymer, ethylene/octene copolymer, ethylene/vinylcyclohexane copolymer, ethylene/cycloolefin copolymer (such as COC (Cyclo-Olefin Copolymer) of ethylene/norbornene), ethylene/1-olefin copolymer producing 1-olefin in situ, propylene/butadiene copolymer, isobutylene/isoprene copolymer, ethylene/vinylcyclohexene copolymer, ethylene/alkyl acrylate copolymer, ethylene/alkyl methacrylate copolymer, ethylene/vinyl acetate copolymer or ethylene/acrylic acid copolymer and the salts thereof (ionomers); and terpolymers of ethylene and propyrene with diene such as hexadiene, dicyclopentadiene or ethylidene-norbornene; and mixtures of such copolymers and the polymer described in the above 1) such as polypropylene/ethylene-propylene copolymer, LDPE/ethylene-vinyl acetate copolymer (EVA), LDPE/ethylene-acrylic acid copolymer (EAA), LLDPE/EVA, LLDPE/EAA and alternating or random polyalkylene/carbon monooxide copolymer and the mixture thereof with other polymer such as polyamide.

<4> Mixtures of hydrocarbon resins (for example, having 5 to 9 carbon atoms) containing hydrogenated derivatives (such as tackifier) and polyalkylene and starch.

The homopolymers and copolymers described in <1> to <4> above may have any steric structure, syndiotactic, isotactic, hemiisotactic or atactic; and atactic polymers are preferable. Stereoblock polymers are also included.

<5> Polystyrene, poly(p-methylstyrene), and poly(α-methylstyrene).

<6> Aromatic homopolymer and copolymers prepared from aromatic vinyl monomers including all isomers of styrene, α-methylstyrene, and vinyltoluene, in particular all isomers of p-vinyltoluene, ethylstyrene, propylstyrene, vinyl biphenyl, vinylnaphthalene, and vinylanthracene, and the mixture thereof. The homopolymers and copolymers may have any steric structure, syndiotactic, isotactic, hemiisotactic or atactic; and atactic polymers are preferable. Stereoblock polymers are also included.

<6a> Copolymers of the aromatic vinyl monomers or comonomers selected from ethylene, propylene, dienes, nitriles, acids, maleic anhydride, maleimide, vinyl acetate and vinyl chloride or its acryl derivative and the mixture thereof, such as styrene/butadiene, styrene/acrylonitrile, styrene/ethylene (copolymer), styrene/alkyl methacrylate, styrene/butadiene/alkyl acrylate, styrene/butadiene/alkyl methacrylate, styrene/maleic anhydride, and styrene/acrylonitrile/methyl acrylate; styrene copolymers and other polymers including high shock-resistant mixtures such as polyacrylate, diene polymer, and ethylene/propylene/diene terpolymer; and styrene block copolymers such as styrene/butadiene/styrene, styrene/isoprene/styrene, styrene/ethylene/butylene/styrene and styrene/ethylene/propylene/styrene.

<6b> Hydrogenated aromatic polymers prepared from the hydrogenated polymers described in <6>, in particular polycyclohexylethylene (PCHE), often called polyvinylcyclohexane (PVCH), prepared by hydrogenation of atactic polystyrene.

<6c> Hydrogenated aromatic polymers prepared by hydrogenation of the polymers described in <6a> above.

The homopolymers and copolymers may have any steric structure, syndiotactic, isotactic, hemiisotactic or atactic, and atactic polymers are preferable. Stereoblock polymers are also included.

<7> Graft copolymers of an aromatic vinyl monomer such as styrene or α-methylstyrene, including graft copolymers of polybutadiene/styrene; polybutadiene-styrene or polybutadiene-acrylonitrile copolymer/styrene; polybutadiene/styrene and acrylonitrile (or methacrylonitrile); polybutadiene/styrene, acrylonitrile and methyl methacrylate; polybutadiene/styrene and maleic anhydride; polybutadiene/styrene, acrylonitrile and maleic anhydride or maleimide; polybutadiene/styrene and maleimide; polybutadiene/styrene and alkyl acrylate or methacrylate; ethylene/propylene/diene terpolymer/styrene and acrylonitrile; polyalkyl acrylate or polyalkyl methacrylate/styrene and acrylonitrile; acrylate/butadiene copolymer/styrene and acrylonitrile; and mixtures thereof with the copolymers described in <6> above such as known copolymer mixtures of ABS, SAN, MBS, ASA and AES polymer.

<8> Halogen-containing polymers such as polychloroprene, chlorinated rubber, chlorinated or brominated copolymers of isobutylene-isoprene (halobutyl rubbers), chlorinated or sulfochlorinated polyethylene, ethylene-chlorinated ethylene copolymer, and epichlorohydrin homopolymer and copolymers; in particular, polymers of a halogen-containing vinyl compound such as polyvinyl chloride, polyvinylidene chloride, polyvinyl fluoride, polyvinylidene fluoride, and copolymers thereof such as polyvinyl chloride/vinylidene chloride, polyvinyl chloride/vinyl acetate or vinylidene chloride/vinyl acetate copolymer.

<9> Polymers derived from α,β-unsaturated acid and the derivatives thereof such as polyacrylates and polymethacrylates; and high-impact polymethyl methacrylate, polyacrylamide and polyacrylonitrile modified with butyl acrylate.

<10> Copolymers of the monomers described in <9> above or with another unsaturated monomer such as acrylonitrile/butadiene copolymer, acrylonitrile/alkyl acrylate copolymer, acrylonitrile/alkoxyalkyl acrylate or acrylonitrile/vinyl halide copolymer and acrylonitrile/alkyl methacrylate/butadiene terpolymer.

<11> Polymers derived from an unsaturated alcohol and an amine, and acyl derivatives or acetals thereof such as polyvinylalcohol, polyvinyl acetate, polyvinyl stearate, polyvinyl benzoate, polyvinyl maleate, polyvinylbutyral, polyallyl phthalate and polyallylmelamine; and copolymers thereof with the olefin described in <1> above.

<12> Homopolymers and copolymers of cyclic ether such as polyalkylene glycols, polyethyleneoxide, polypropyleneoxide or bisglycidylether, and the copolymers thereof.

<13> Polyacetals such as polyoxymethylene and polyoxymethylene containing ethyleneoxide as the comonomer; polyacetals modified with a thermoplastic polyurethane, acrylate or MBS.

<14> Mixtures of polyphenyleneoxide and sulfide, and those of polyphenyleneoxide and styrene polymer or polyamide.

<15> Polyurethanes derived from a polyether, polyester or polybutadiene having a hydroxyl group terminal and an aliphatic or aromatic polyisocyanate, and the precursors thereof.

<16> Polyamides and copolyamides derived from a diamine and a dicarboxylic acid and/or aminocarboxylic acid or the corresponding lactam, such as polyamide 4, polyamide 6, polyamides 6/6, 6/10, 6/9, 6/12, 4/6 and 12/12, polyamide 11, polyamide 12, and an aromatic polyamide from m-xylenediamine and adipic acid; polyamides prepared from hexamethylenediamine and isophthalic and/or terephthalic acid, in the presence or absence of a modifying agent elastomer such as poly-2,4,4-trimethylhexamethylene terephthalamide and poly-m-phenylene isophthalamide; block copolymers of the polyamides above with polyolefin, olefin copolymer, ionomer or chemically bonded or grafted elastomer; block copolymers of the polyamides above with polyether such as polyethylene glycol, polypropylene glycol or polytetramethylene glycol; polyamides or copolyamides modified with EPDM or ABS; and polyamides condensed during processing (RIM polyamides).

<17> Polyurea, polyimide, polyamide-imide, polyether imide, polyester-imide, polyhydantoin and polybenzimidazole.

<18> Polyesters derived from a dicarboxylic acid and a diol and/or a hydroxycarboxylic acid or the corresponding lactone such as polyethylene terephthalate, polybutylene terephthalate, poly-1,4-dimethylolcyclohexane terephthalate, polyalkylene naphthalate (PAN) and polyhydroxybenzoate; block copolyether esters derived from hydroxyl terminal polyethers; and polyesters modified with polycarbonate or MBS; the polyesters and polyester copolymers specified in U.S. Pat. No. 5,807,932 (2nd column, line 53) are also incorporated herein by reference.

<19> Polycarbonates and polyester carbonates.
<20> Polyketones.
<21> Polysulfones, polyether sulfones and polyether ketones.
<22> Crosslinked polymers derived from an aldehyde component and another phenol component and also from urea and melamine such as phenol/formaldehyde resin, urea/formaldehyde resin and melamine/formaldehyde resin.

<23> Dry and non-dry alkyd resins.
<24> Unsaturated polyester resins derived from saturated and unsaturated dicarboxylic acids, a polyvalent alcohol, and a crosslinking agent vinyl compound, and less flammable halogen-containing derivatives thereof.
<25> Substituted acrylates, for example, crosslinkable acrylic resins derived from epoxy acrylate, urethane acrylate or polyester acrylate.
<26> Crosslinked alkyd, polyester and acrylate resins crosslinked with a melamine resin, urea resin, isocyanate, isocyanurate, polyisocyanate or epoxy resin.
<27> Crosslinked epoxy resins derived from an aliphatic, alicyclic, heterocyclic or aromatic glycidyl compound, for example, glycidyl ether products of bisphenol A or bisphenol F crosslinked with a common curing agent such as anhydride or amine in the presence or absence of an accelerator.
<28> Natural polymers such as cellulose, rubber, gelatin and chemically modified derivatives of their homologous series such as cellulose acetate, cellulose propionate and cellulose butyrate, and cellulose ethers such as methylcellulose; and rosins and the derivatives thereof.
<29> Polymer blends (polyblends) of the polymers described above such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic PUR, POM/acrylate, POM/MBS, PPO/HIPS, PPO/PA6.6 and copolymer, PA/HDPE, PA/PP, PA/PPO, PBT/PC/ABS and PBT/PET/PC.
<30> Natural and synthetic organic materials of a pure monomeric compound or a mixture of the compounds such as mineral oils, animal and vegetable fats, oils and waxes, or synthetic ester (such as phthalate, adipate, phosphate or trimellitate)-based oils, fats and waxes, and mixtures thereof with a synthetic ester and mineral oil at any rate, mixtures typically used as a fiber-spinning composition, and the aqueous emulsions thereof.
<31> Aqueous emulsions of natural or synthetic rubber, for example, a natural latex or latexes of a carboxylated styrene/butadiene copolymer.
<32> Polysiloxanes, for example, the soft hydrophilic polysiloxane described in U.S. Pat. No. 4,259,467 and the hard polyorganosiloxane described in U.S. Pat. No. 4,355,147.
<33> Polyketimines in combination with an unsaturated acrylpolyacetoacetate resin or an unsaturated acrylic resin including urethane acrylate, polyester acrylate, vinyl or acrylic copolymers having a pendant unsaturated group, and acrylated melamines. The polyketimine is prepared from a polyamine and a ketone in the presence of an acid catalyst.
<34> Radiant ray-hardening compositions containing an ethylenically unsaturated monomer or oligomer and a polyunsaturated aliphatic oligomer.
<35> Epoxy melamine resins such as photostabilized epoxy resins crosslinked with a coetherified high-solid content melamine resin sensitive to epoxy groups, such as LSE-4103 (trade name, manufactured by Monsanto).

The polymer substance for use in the present invention, for example, in the second embodiment of the present invention, is preferably a synthetic polymer, more preferably a polyolefin, an acrylic polymer, polyester, polycarbonate, or a cellulose ester. Among them, polyethylene, polypropylene, poly (4-methylpentene), polymethyl methacrylate, polycarbonate, polyethylene terephthalate, polyethylene naphthalate, polybutylene terephthalate, and triacetylcellulose are particularly preferable.

The polymer substance for use in the present invention is preferably a thermoplastic resin.

The polymer material containing the ultraviolet absorbent according to the present invention may contain any additives such as antioxidant, photostabilizer, processing stabilizer, antidegradant, and compatibilizer, as needed in addition to the polymer substance above and the ultraviolet absorbent according to the present invention.

The compound according to the present invention is particularly suitable for use in stabilizing an organic material against damage by light, oxygen or heat. In particular, the compound according to the present invention is most suitable for use as a photostabilizer, particularly an ultraviolet absorbent. Hereinafter, application of the compound according to the present invention as an ultraviolet absorbent will be described.

Examples of the materials stabilized by the ultraviolet absorbent according to the present invention include dyes, pigments, foods, beverages, body-care products, vitamins, pharmaceuticals, inks, oils, fats, waxes, surface coating agents, cosmetics, photographic materials, fabrics and the dyes thereof, plastic materials, rubbers, paints, polymer materials, polymer additives and the like.

The ultraviolet absorbent according to the present invention may be used by any method when used. The ultraviolet absorbents according to the present invention may be used alone, or used as a composition, but are preferably used as a composition. In particular, polymer materials containing the ultraviolet absorbent according to the present invention are favorable. Hereinafter, the polymer materials containing the ultraviolet absorbent according to the present invention will be described.

The polymer material containing the ultraviolet absorbent according to the present invention contains the polymer substance above. The polymer material containing the ultraviolet absorbent according to the present invention may be made only of the polymer substance, or may be formed by using the polymer substance dissolved in an arbitrary solvent.

The polymer material including the ultraviolet absorbent according to the present invention is applicable to any application where synthetic resin is used, and particularly favorable to applications where there is possibility of exposure to light such as sunlight or ultraviolet light. Specific examples thereof include glass alternatives and their surface-coating agent; coating agents for the window glass, lighting glass and light-source-protecting glass such as of house, facility, and vehicle; window films such as of house, facility and vehicle; interior and exterior materials such as of house, facility and vehicle, paints for the interior and exterior materials, and the paint films formed by the paints; alkyd resin lacquer paints and the paint films formed by the paints; acrylic lacquer paints and the paint films formed by the paints; materials for ultraviolet-emission sources such as fluorescent lamp and mercury lamp; materials for precision machines and electric and electronic devices; materials for shielding electromagnetic and other waves emitted from various displays; containers or packaging materials for foods, chemicals and drugs; special packages such as bottle, box, blister, and cup; discoloration inhibitors for compact disk coating, agricultural and industrial sheet or film, print, colored products, dyes and pigments; protective film for polymer supports (e.g., plastic parts such as mechanical and automotive parts); print over-coating, ink-jet medium film, delustered laminate film, optical light film, safety glass/front glass intermediate layer, electrochromic/photochromic film, over-lamination film, solar-heat-controlling film, cosmetics such as anti-sunburn cream, shampoo, rinse, and hair dressing; apparel fiber products such as sport wear, stockings and cap and the fibers; home interior products such as curtain, carpet and wall paper; medical devices such as plastic lens, contact lens and artificial eye; optical materials such as optical filter, backlight display film, prism, mirror, and photographic material; mold film, transfer-type sticker, anti-graffiti film, stationery products such as tape and ink; indicator display plates and devices and the surface-coating agents thereof, and the like.

The shape of the polymer material containing the ultraviolet absorbent according to the present invention may be flat film, powder, spherical particle, crushed particle, bulky continuous particle, fiber, tube, hollow fiber, granule, plate, porous particle, or the other.

In the present invention, two or more kinds of compounds in the present invention different in structure may be used in combination. Alternatively, the compound in the present invention and one or more kinds of ultraviolet absorbents different in structure may be used in combination. Two kinds (preferably three kinds) of ultraviolet absorbents when used in combination absorb ultraviolet ray in a wider wavelength range. In addition, the use of two or more kinds of ultraviolet absorbents in combination has a function to stabilize the dispersion state of the ultraviolet absorbents. Any ultraviolet absorbent having a structure other than that of ultraviolet absorbent in the present invention may be used. Examples thereof include those described, for example, in Yasuichi Okatsu Ed., "Development of Polymer Additives and Environmental Measures" (CMC Publishing, 2003), Chapter 2; and Toray Research Center Inc., Technical Survey Dept., Ed., "New Trend of Functional Polymer Additives" (Toray Research Center Inc., 1999), Chapter 2.3.1. Examples thereof include ultraviolet absorbing structures such as triazine-based, benzotriazole-based, benzophenone-based, merocyanine-based, cyanine-based, dibenzoylmethane-based, cinnamic acid-based, acrylate-based, benzoic ester-based, and oxalic diamide-based compounds. Specific examples thereof are described, for example, in Fine Chemicals, 2004, May, p. 28 to 38; Toray Research Center Inc., Technical Survey Dept., Ed., "New Trend of Functional Polymer Additives" (Toray Research Center Inc., 1999), p. 96 to 140; and Yasuichi Okatsu Ed., "Development of Polymer Additives and Environmental Measures" (CMC Publishing, 2003), p. 54 to 64.

Among these, preferable are benzotriazole-based, benzophenone-based, salicylic acid-based, acrylate-based, and triazine-based compounds. More preferable are benzotriazole-based, benzophenone-based, and triazine-based compounds. Particularly preferable are benzotriazole-based and triazine-based compounds.

The benzotriazole-based compound is preferably a compound having an effective absorption wavelength of approximately 270 to 380 nm that is represented by formula (IIa), (IIb) or (IIc).

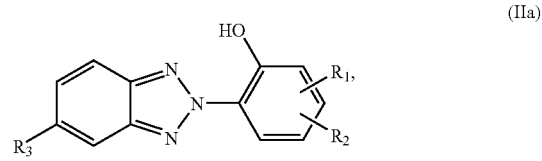

(IIa)

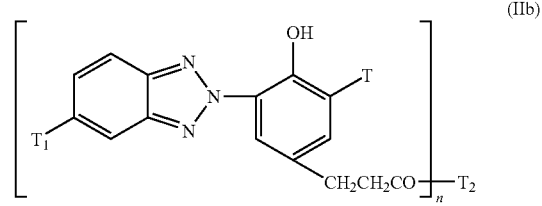

(IIb)

-continued

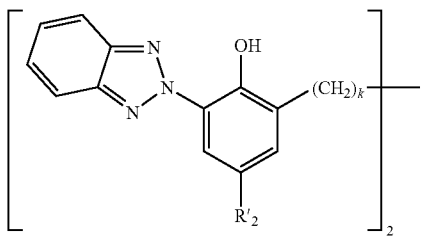
(IIc)

[In formula (IIa),

R₁ represents a hydrogen atom, an alkyl group having 1 to 24 carbon atoms, a phenylalkyl group wherein the alkyl moiety has 1 to 4 carbon atoms, a cycloalkyl group having 5 to 8 carbon atoms, or a group represented by the following formula:

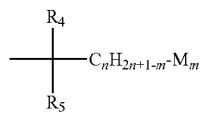

(In the formula, R₄ and R₅ each independently represent an alkyl group having 1 to 5 carbon atoms; R₄ may bond together with a —C$_n$H$_{2n+1-m}$ group to form a cycloalkyl group having 5 to 12 carbon atoms; m represents 1 or 2. n represents an integer of 2 to 20; and M represents a —COOR₆ group wherein R₆ represents a hydrogen atom, an alkyl group having 1 to 12 carbon atoms, an alkoxyalkyl group wherein each of the alkyl moiety and the alkoxy moiety has 1 to 20 carbon atoms, or a phenylalkyl group wherein the alkyl moiety has 1 to 4 carbon atoms.);

R₂ represents a hydrogen atom, a halogen atom, an alkyl group having 1 to 18 carbon atoms, a phenylalkyl group wherein the alkyl moiety has 1 to 4 carbon atoms, with the proviso that a hydrogen atom is excluded from at least one of R₁ and R₂; and R₃ represents a hydrogen atom, a chlorine atom, an alkyl group having 1 to 4 carbon atoms, an alkoxy group having 1 to 4 carbon atoms, or a —COOR₆ group (wherein R₆ has the same meaning as described above).]

[In formula (IIb),

T represents a hydrogen atom or an alkyl group having 1 to 6 carbon atoms;

T₁ represents a hydrogen atom, a chlorine atom, an alkyl group having 1 to 4 carbon atoms, or an alkoxy group having 1 to 4 carbon atoms, n represents 1 or 2;

when n is 1, T₂ is a chlorine atom, —OT₃ or the group represented by the following formula;

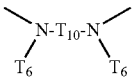

when n is 2, T₂ is a group represented by the following formula:

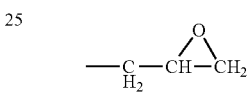

or —O-T₉-O;

(Herein, T₃ represents a hydrogen atom; an alkyl group having 1 to 18 carbon atoms, which is unsubstituted or substituted with 1 to 3 hydroxyl groups or —OCOT₆; an alkyl group having 1 to 18 carbon atoms wherein a continuous C—C bond is once or several times interrupted with —O— or —NT₆-, and the alkyl moiety is unsubstituted or substituted with a hydroxyl group or —OCOT₆; a cycloalkyl group having 5 to 12 carbon atoms, which is unsubstituted or substituted with a hydroxyl group and/or an alkyl group having 1 to 4 carbon atoms; an alkenyl group having 2 to 18 carbon atoms, which is unsubstituted or substituted with a hydroxyl group; a phenyl alkyl group wherein the alkyl moiety has 1 to 4 carbon atoms; —CH₂CH(OH)-T₇, or the group represented by following formula;

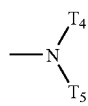

T₄ and T₅ each independently represent a hydrogen atom, an alkyl group having 1 to 18 carbon atoms, an alkyl group having 3 to 18 carbon atoms wherein a continuous C—C bond is once or several times interrupted with —O— or —NT₆-, a cycloalkyl group having 5 to 12 carbon atoms, a phenyl group, a phenyl group substituted with an alkyl group having 1 to 4 carbon atoms, an alkenyl group having 3 to 8 carbon atoms, a phenylalkyl group wherein the alkyl moiety has 1 to 4 carbon atoms, or a hydroxyalkyl having 2 to 4 carbon atoms;

T₆ represents a hydrogen atom, an alkyl group having 1 to 18 carbon atoms, a cycloalkyl group having 5 to 12 carbon atoms, an alkenyl group having 3 to 8 carbon atoms, a phenyl group, a phenyl group substituted with an alkyl group having 1 to 4 carbon atoms, or a phenylalkyl group wherein the alkyl moiety has 1 to 4 carbon atoms;

T₇ represents a hydrogen atom, an alkyl group having 1 to 18 carbon atoms, a phenyl group which is unsubstituted or substituted with a hydroxyl group, a phenylalkyl group wherein the alkyl moiety has 1 to 4 carbon atoms, or —CH₂OT₈;

T₈ represents an alkyl group having 1 to 18 carbon atoms, an alkenyl group having 3 to 8 carbon atoms, a cycloalkyl group having 5 to 10 carbon atoms, a phenyl group, a phenyl group substituted with an alkyl group having 1 to 4 carbon atoms, or a phenylalkyl group wherein the alkyl moiety has 1 to 4 carbon atoms;

T₉ represents an alkylene group having 2 to 8 carbon atoms, an alkenylene group having 4 to 8 carbon atoms, an alkynylene group having 4 carbon atoms, a cyclohexylene group, an alkenylene group having 2 to 8 carbon atoms wherein a continuous C—C bond is once or several times interrupted with —O—, —CH₂CH(OH)CH₂O-T₁₁-OCH₂CH(OH)CH₂—, or —CH₂—C(CH₂OH)₂—CH₂—;

T₁₀ represents an alkylene group having 2 to 20 carbon atoms wherein a continuous C—C bond is once or several times interrupted with —O—, or a cyclohexylene group;

T₁₁ represents an alkylene group having 2 to 8 carbon atoms, an alkylene group having 2 to 18 carbon atoms wherein a continuous C—C bond is once or several times interrupted with —O—, a 1,3-cyclohexylene group, a 1,4-cyclohexylene group, a 1,3-phenylene group, or 1,4-phenylene group; and alternatively, $T_{10}$ and $T_6$ may bond together with two nitrogen atoms to form a piperazine ring.]

[In formula (IIc), $R'_2$ represents an alkyl group having 1 to 12 carbon atoms; and k is a number of 1 to 4.]

Typical examples of the compound represented by any one of formulae (IIa) to (IIc) include 2-(2'-hydroxy-5'-methylphenyl)benzotriazole, 2-(2'-hydroxy-5'-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3'-dodecyl-5'-methylphenyl)-5-chlorobenzotriazole, 2-(2'-hydroxy-3',5'-di-t-amylphenyl)benzotriazole, 2-(2'-hydroxy-5'-(1,1,3,3-tetramethylbutyl)phenyl)benzotriazole, 2-(2'-hydroxy-4'-octyloxyphenyl)benzotriazole, 2-(2'-hydroxy-3'-(3,4,5,6-tetrahydrophthalimidylmethyl)-5'-methylbenzyl)phenyl)benzotriazole, 2-(3'-sec-butyl-5'-t-butyl-2'-hydroxyphenyl)benzotriazole, 2-(3',5'-bis-(α,α-dimethylbenzyl)-2'-hydroxyphenyl)benzotriazole, 2-(3'-t-butyl-2'-hydroxy-5'-(2-octyloxycarbonylethyl)phenyl)-5-chloro-benzotriazole, 2-(3'-t-butyl-5'-[2-(2-ethylhexyloxy)-carbonylethyl]-2'-hydroxyphenyl)-5-chloro-benzotriazole, 2-(3'-t-butyl-2'-hydroxy-5'-(2-methoxycarbonylethyl)phenyl)-5-chloro-benzotriazole, 2-(3'-t-butyl-2'-hydroxy-5'-(2-methoxycarbonylethyl)phenyl)benzotriazole, 2-(3'-t-butyl-2'-hydroxy-5'-(2-octyloxycarbonylethyl)phenyl)benzotriazole, 2-(3'-t-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-t-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol], ester exchange products of 2-[3'-t-butyl-5'-(2-methoxycarbonylethyl)-2'-hydroxyphenyl]-2H-benzotriazole and polyethylene glycol 300; and the compound represented by the following formula:

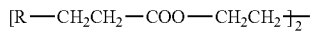

(wherein, R represents 3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole or the like).

The triazine-based compound is preferably a compound having an effective absorption wavelength of approximately 270 to 380 nm that is represented by formula (III).

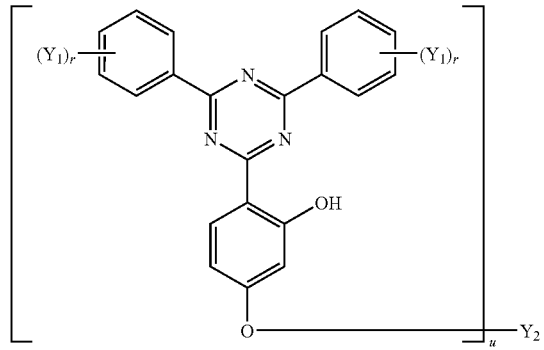

[In Formula (III),
u is 1 or 2, and r is an integer of 1 to 3,
substituent groups $Y_1$'s each independently represent a hydrogen atom, a hydroxyl group, a phenyl group, a halogen atom, a halogenomethyl group, an alkyl group having 1 to 12 carbon atoms, an alkoxy group having 1 to 18 carbon atoms, or an alkoxy group having 1 to 18 carbon atoms substituted with —COO—($C_1$ to $C_{18}$ alkyl).

When u is 1, $Y_2$ represents an alkyl group having 1 to 18 carbon atoms, a phenyl group unsubstituted or substituted with a hydroxyl group, a halogen atom or an alkyl or alkoxy group having 1 to 18 carbon atoms;
an alkyl group having 1 to 12 carbon atoms substituted with —COOH, —COO$Y_8$, —CON$H_2$, —CONH$Y_9$, —CON$Y_9Y_{10}$, —N$H_2$, —NH$Y_9$, —N$Y_9Y_{10}$, —NHCO$Y_{11}$, —CN and/or —OCO$Y_{11}$;
an alkyl group having 4 to 20 carbon atoms wherein a continuous carbon-carbon bond is interrupted with one or more oxygen atoms, in which the alkyl moiety is unsubstituted or substituted with a hydroxyl group or an alkoxy group having 1 to 12 carbon atoms;
an alkenyl group having 3 to 6 carbon atoms, a glycidyl group, a cyclohexyl group unsubstituted or substituted with a hydroxyl group, an alkyl group having 1 to 4 carbon atoms and/or —OCO$Y_{11}$; a phenylalkyl group with its alkyl group having 1 to 5 carbon atoms, unsubstituted or substituted with a hydroxyl group, a chlorine atom and/or a methyl group; —CO$Y_{12}$ or —SO$_2Y_{13}$.

Alternatively, when u is 2, $Y_2$ represents an alkylene group having 2 to 16 carbon atoms, an alkenylene group having 4 to 12 carbon atoms, a xylylene group, an alkylene group having 3 to 20 carbon atoms wherein a continuous carbon-carbon bond is interrupted with one or more —O— atoms and/or the alkylene moiety is substituted with a hydroxyl group; —$CH_2CH(OH)CH_2$—O—$Y_{15}$—OCH$_2$CH(OH)CH$_2$, —CO—$Y_{16}$—CO—, —CO—NH—$Y_{17}$—NH—CO—, or —(CH$_2$)$_m$—CO$_2$—$Y_{18}$—OCO—(CH$_2$)$_m$.

(Herein,
m is 1, 2 or 3;
$Y_8$ represents an alkyl group having 1 to 18 carbon atoms, an alkenyl group having 3 to 18 carbon atoms, an alkyl group having 3 to 20 carbon atoms wherein a continuous carbon-carbon bond is interrupted with one or more oxygen or sulfur atoms or —NT$_6$-, and/or the alkyl group is substituted with a hydroxyl group, an alkyl group having 1 to 4 carbon atoms substituted with —P(O)(O$Y_{14}$)$_2$, —N$Y_9Y_{10}$, or —OCO$Y_{11}$ and/or a hydroxyl group, an alkenyl group having 3 to 18 carbon atoms, a glycidyl group, or an phenylalkyl group with its alkyl moiety having 1 to 5 carbon atoms;
$Y_9$ and $Y_{10}$ each independently represent an alkyl group having 1 to 12 carbon atoms, an alkoxyalkyl group having 3 to 12 carbon atoms, a dialkylaminoalkyl group having 4 to 16 carbon atoms, or a cyclohexyl group having 5 to 12 carbon atoms, or alternatively, $Y_9$ and $Y_{10}$ may be an alkylene, oxaalkylene or azaalkylene group having 3 to 9 carbon atoms in combination;
$Y_{11}$ represents an alkyl group having 1 to 18 carbon atoms, an alkenyl group having 2 to 18 carbon atoms, or a phenyl group;
$Y_{12}$ represents an alkyl group having 1 to 18 carbon atoms, an alkenyl group having 2 to 18 carbon atoms, a phenyl group, an alkoxy group having 1 to 12 carbon atoms, a phenoxy group, an alkylamino group having 1 to 12 carbon atoms, or a phenylamino group;
$Y_{13}$ represents an alkyl group having 1 to 18 carbon atoms, a phenyl group, or an alkylphenyl group with its alkyl group having 1 to 8 carbon atoms;
$Y_{14}$ represents an alkyl group having 1 to 12 carbon atoms or a phenyl group;

$Y_{15}$ represents an alkylene group having 2 to 10 carbon atoms, a phenylene group, or -phenylene-M-phenylene- (wherein, M represents —O—, —S—, —SO$_2$—, —CH$_2$— or —C(CH$_3$)$_2$—);

$Y_{16}$ represents an alkylene group having 2 to 10 carbon atoms, an oxaalkylene or thiaalkylene group, a phenylene group, or an alkenylene group having 2 to 6 carbon atoms;

$Y_{17}$ represents an alkylene group having 2 to 10 carbon atoms, a phenylene group, or an alkylphenylene group with its alkyl group having 1 to 11 carbon atoms; and $Y_{18}$ represents an alkylene group having 2 to 10 carbon atoms, or an alkylene group having 4 to 20 carbon atoms wherein a continuous carbon-carbon bond is interrupted once or several times with oxygen)].

Typical examples of the compound represented by formula (III) include 2-(4-butoxy-2-hydroxyphenyl)-4,6-di(4-butoxyphenyl)-1,3,5-triazine, 2-(4-butoxy-2-hydroxyphenyl)-4,6-di(2,4-dibutoxyphenyl)-1,3,5-triazine, 2,4-di(4-butoxy-2-hydroxyphenyl)-6-(4-butoxyphenyl)-1,3,5-triazine, 2,4-di(4-butoxy-2-hydroxyphenyl)-6-(2,4-dibutoxyphenyl)-1,3,5-triazine, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris(2-hydroxy-4-(3-butoxy-2-hydroxypropoxy)phenyl)-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxy-propyloxy]phenyl}-4,6-bis(2,4-dimethylphenyl)-1,3,5-triazine and 2-(2-hydroxy-4-(2-ethylhexyl)oxy)phenyl-4,6-di(4-phenyl)phenyl-1,3,5-triazine.

The benzophenone-based compound is preferably a compound having an effective absorption wavelength of approximately 270 to 380 nm. Typical examples of the benzophenone-based compound include 2,4-dihydroxybenzophenone, 2-hydroxy-4-methoxybenzophenone, 2-hydroxy-4-octyloxybenzophenone, 2-hydroxy-4-decyloxybenzophenone, 2-hydroxy-4-dodecyloxybenzophenone, 2-hydroxy-4-benzyloxybenzophenone, 2-hydroxy-4-(2-hydroxy-3-methacryloxypropoxy)benzophenone, 2-hydroxy-4-methoxy-5-sulfobenzophenone, 2-hydroxy-4-methoxy-5-sulfobenzophenone trihydrate, 2-hydroxy-4-methoxy-2'-carboxybenzophenone, 2-hydroxy-4-octadecyloxybenzophenone, 2-hydroxy-4-diethylamino-2'-hexyloxycarbonylbenzophenone, 2,2'-dihydroxy-4-methoxybenzophenone, 2,2',4,4'-tetrahydroxybenzophenone, 2,2'-dihydroxy-4,4'-dimethoxybenzophenone, and 1,4-bis(4-benzyloxy-3-hydroxyphenoxy)butane.

The salicylic acid-based compound above is preferably a compound having an effective absorption wavelength of approximately 290 to 330 nm, and typical examples thereof include phenyl salicylate, 4-t-butylphenyl salicylate, 4-octylphenyl salicylate, dibenzoylresorcinol, bis(4-t-butylbenzoyl)resorcinol, benzoylresorcinol, 2,4-di-t-butylphenyl 3,5-di-t-butyl-4-hydroxysalicylate, and hexadecyl 3,5-di-t-butyl-4-hydroxysalicylate.

The acrylate-based compound above is preferably a compound having an effective absorption wavelength of approximately 270 to 350 nm, and typical examples thereof include 2-ethylhexyl 2-cyano-3,3-diphenylacrylate, ethyl 2-cyano-3,3-diphenylacrylate, isooctyl 2-cyano-3,3-diphenylacrylate, hexadecyl 2-cyano-3-(4-methylphenyl)acrylate, methyl 2-cyano-3-methyl-3-(4-methoxyphenyl)cinnamate, butyl 2-cyano-3-methyl-3-(4-methoxyphenyl)cinnamate, methyl 2-carbomethoxy-3-(4-methoxyphenyl)cinnamate 2-cyano-3-(4-methylphenyl)acrylate salt, 1,3-bis(2'-cyano-3,3'-diphenylacryloyl)oxy)-2,2-bis(((2'-cyano-3,3'-diphenylacryloyl)oxy)methyl)propane, and N-(2-carbomethoxy-2-cyanovinyl)-2-methylindoline.

The oxalic diamide-based compound above is preferably a compound having an effective absorption wavelength of approximately 250 to 350 nm, and typical examples thereof include 4,4'-dioctyloxyoxanilide, 2,2'-dioctyloxy-5,5'-di-t-butyloxanilide, 2,2'-didodecyloxy-5,5'-di-t-butyloxanilide, 2-ethoxy-2'-ethyloxanilide, N,N'-bis(3-dimethylaminopropyl)oxamide, 2-ethoxy-5-t-butyl-2'-ethyloxanilide, and 2-ethoxy-2'-ethyl-5,4'-di-t-butyloxanilide.

The content of the ultraviolet absorbent in the polymer material is not determined specifically, because it varies according to application and type of usage, and the concentration is arbitrary according to desirable application. It is preferably 0.001 to 10 mass %, more preferably 0.01 to 5 mass %, in the polymer material.

Although practically sufficient ultraviolet-shielding effect is obtained only with the ultraviolet absorbent according to the present invention in the present invention, a white pigment which has higher hiding power such as titanium oxide may be used in the case where further strictness is demanded. In addition, a trace (0.05 mass % or less) amount of colorant may be used additionally, if the appearance or the color tone is of a problem or as needed. Alternatively, a fluorescent brightener may be used additionally for applications demanding transparency or whiteness. Examples of the fluorescent brighteners include commercialized products, the compounds represented by Formula [1] and typical exemplary compounds 1 to 35 described in JP-A-2002-53824, and the like.

Since the polymer material containing the ultraviolet absorbent according to the present invention contains the ultraviolet made of the compound represented by formula (I), the polymer material is superior in light resistance (ultraviolet fastness), causing no precipitation or bleed out of the ultraviolet absorbent during long-term use. In addition, the polymer material according to the present invention, which has superior long-wavelength ultraviolet absorption capacity, can be used as an ultraviolet-absorbing filter or container, for protection, for example, of an ultraviolet-sensitive compound therein. It is possible to obtain a molded article (such as container) of the polymer material according to the present invention, for example, by molding the polymer substance by any molding method such as extrusion molding or injection molding. It is also possible to prepare a molded article coated with an ultraviolet-absorbing film made of the polymer material according to the present invention, by coating and drying a solution of the polymer substance on a separately prepared molded article.

When the polymer material containing the ultraviolet absorbent according to the present invention is used as an ultraviolet-absorbing filter or film, the polymer substance is preferably transparent. Examples of the transparent polymer materials include cellulose esters (such as diacetylcellulose, triacetylcellulose (TAC), propionylcellulose, butyrylcellulose, acetyl propionyl cellulose, and nitrocellulose), polyamides, polycarbonates, polyesters (such as polyethylene terephthalate, polyethylene naphthalate, polybutylene terephthalate, poly-1,4-cyclohexane dimethylene terephthalate, polyethylene-1,2-diphenoxyethane-4,4'-dicarboxylate, and polybutylene terephthalate), polystyrenes (such as syndiotactic polystyrene), polyolefins (such as polyethylene, polypropylene, and polymethylpentene), polymethyl methacrylate, syndiotactic polystyrene, polysulfones, polyether sulfones, polyether ketones, polyether imides, polyoxyethylene, and the like. Preferable are cellulose esters, polycarbonates, polyesters, polyolefins, and acrylic resins; more preferable are polycarbonates and polyesters; further preferable are polyesters; and particularly preferable is polyethylene terephthalate. The polymer material containing the ultraviolet absorbent according to the present invention may be used as a transparent support, and the transmittance of the transparent support is preferably 80% or more, more preferably 86% or more.

Hereinafter, the packaging material containing the ultraviolet absorbent according to the present invention will be described. The packaging material containing the ultraviolet absorbent according to the present invention may be a packaging material of any kind of polymer, as long as it contains the compound represented by formula (I). Examples thereof include the thermoplastic resins described in JP-A-8-208765; the polyvinylalcohols described in JP-A-8-151455; the polyvinyl chlorides described in JP-A-8-245849; the polyesters described in JP-A-10-168292 and JP-A-2004-285189; the heat-shrinkable polyesters described in JP-A-2001-323082; the styrene-based resins described in JP-A-10-298397; the polyolefins described in JP-A-11-315175, JP-A-2001-26081, and JP-A-2005-305745; the ROMP's described in JP-T-2003-524019; and the like. It may be, for example, the resin having a vapor-deposition thin film of an inorganic compound described in JP-A-2004-50460 or JP-A-2004-243674. It may be, for example, the paper coated with a resin containing an ultraviolet absorbent described in JP-A-2006-240734.

The packaging material containing the ultraviolet absorbent according to the present invention may be that for packaging anything such as food, beverage, medicine, cosmetics, or individual health care product. Examples thereof include the food packaging materials described in JP-A-11-34261 and JP-A-2003-237825; the colored liquid packaging materials described in JP-A-8-80928; the liquid preparation-packaging materials described in JP-A-2004-51174; the medicine container packaging materials described in JP-A-8-301363 and JP-A-11-276550; the medical sterilization packaging materials described in JP-A-2006-271781; the photographic photosensitive material packaging materials described in JP-A-7-287353; the photograph film packaging materials described in JP-A-2000-56433; the UV-hardening ink packaging materials described in JP-A-2005-178832; the shrink labels described in JP-A-2003-200966 and JP-A-2006-323339; and the like.

The packaging material containing the ultraviolet absorbent according to the present invention may be the transparent packaging material described, for example, in JP-A-2004-51174 or the light-shielding packaging material described, for example, in JP-A-2006-224317.

The packaging material containing the ultraviolet absorbent according to the present invention may have ultraviolet light-shielding property as well as other properties, as described, for example, in JP-A-2001-26081 and JP-A-2005-305745. Examples thereof include the packaging materials having gas-barrier property described, for example, in JP-A-2002-160321; those containing an oxygen indicator as described, for example, in JP-A-2005-156220; those containing both an ultraviolet absorbent and a fluorescent brightener described, for example, in JP-A-2005-146278; and the like.

The packaging material containing the ultraviolet absorbent according to the present invention may be prepared by any method. Examples of the method include the method of forming an ink layer described, for example, in JP-A-2006-130807; the method of melt-extruding and laminating a resin containing an ultraviolet absorbent described, for example, in JP-A-2001-323082 and JP-A-2005-305745; the method of coating on a base film described, for example, in JP-A-9-142539; the method of dispersing an ultraviolet absorbent in an adhesive described, for example, in JP-A-9-157626; and the like.

Hereinafter, the container containing the ultraviolet absorbent according to the present invention will be described. The container containing the ultraviolet absorbent according to the present invention may be a container of any kind of polymer, as long as it contains the compound represented by formula (I). Examples thereof include the thermoplastic resin containers described in JP-A-8-324572; the polyester containers described in JP-A-2001-48153, JP-A-2005-105004, and JP-A-2006-1568; the polyethylene naphthalate containers described in JP-A-2000-238857; the polyethylene containers described in JP-A-2001-88815; the cyclic olefin-based resin composition containers described in JP-A-7-216152; the plastic containers described in JP-A-2001-270531; the transparent polyamide containers described in JP-A-2004-83858; and the like. It may be the paper container containing a resin described, for example, in JP-A-2001-114262 or JP-A-2001-213427. It may be, alternatively, the glass container having an ultraviolet-absorbing layer described, for example, in JP-A-7-242444, JP-A-8-133787, or JP-A-2005-320408.

The container containing the ultraviolet absorbent according to the present invention is used as containers in various applications including food, beverage, medicine, cosmetics, individual health care product, shampoo and the like. Examples thereof include the liquid fuel-storing containers described in JP-A-5-139434; the golf ball containers described in JP-A-7-289665; the food containers described in JP-A-9-295664 and JP-A-2003-237825; the liquor containers described in JP-A-9-58687; the medicine-filling containers described in JP-A-8-155007; the beverage containers described in JP-A-8-324572 and JP-A-2006-298456; the oily food containers described in JP-A-9-86570; the analytical reagent solution containers described in JP-A-9-113494; the instant noodle containers described in JP-A-9-239910; the light-resistant cosmetic preparation containers described in JP-A-11-180474, JP-A-2002-68322, and JP-A-2005-278678; the medicine containers described in JP-A-11-276550; the high-purity chemical solution containers described in JP-A-11-290420; the liquid agent containers described in JP-A-2001-106218; the UV-hardening ink containers described in JP-A-2005-178832; the plastic ampoules described in WO 04/93775 pamphlet; and the like.

The container containing the ultraviolet absorbent according to the present invention may have ultraviolet-shielding property as well as other properties, as described, for example, in JP-A-5-305975 and JP-A-7-40954. Examples of such containers include the antimicrobial containers described in JP-A-10-237312; the flexible containers described in JP-A-2000-152974; the dispenser containers described in JP-A-2002-264979; the biodegradable containers described in, for example, JP-A-2005-255736; and the like.

The container containing the ultraviolet absorbent according to the present invention may be prepared by any method. Examples of the method include the two-layer stretching blow-molding method described in JP-A-2002-370723; the multilayer coextrusion blow-molding method described in JP-A-2001-88815; the method of forming an ultraviolet-absorbing layer on the external surface of an container described in JP-A-9-241407; the methods of using a shrinkable film described in JP-A-8-91385, JP-A-9-48935, JP-T-11-514387, JP-A-2000-66603, JP-A-2001-323082, JP-A-2005-105032, and WO 99/29490 pamphlet; the method of using a supercritical fluid described in JP-A-11-255925; and the like.

Hereinafter, the paint and the coated film containing the ultraviolet absorbent according to the present invention will be described. The paint containing the ultraviolet absorbent according to the present invention may be a paint of any composition, as long as it contains the compound represented by formula (I). Examples thereof include those of acrylic resin-base, urethane resin-base, aminoalkyd resin-base, epoxy resin-base, silicone resin-base, and fluororesin-base. To these resins, a base compound, curing agent, diluent, leveling agent, cissing inhibitor or the like may be added.

For example, when an acrylic urethane resin or a silicon acrylic resin is selected as the transparent resin component, the curing agent is preferably polyisocyanate; and the diluent is preferably a hydrocarbon-based solvent such as toluene or xylene, an ester-based solvent such as isobutyl acetate, butyl acetate and amyl acetate, or an alcohol-based solvent such as isopropyl alcohol or butyl alcohol. The acrylic urethane resin is an acrylic urethane resin obtained by reaction of a methacrylate (typically, methyl methacrylate), hydroxyethyl methacrylate copolymer and a polyisocyanate. In such a case, the polyisocyanate is, for example, tolylene diisocyanate, diphenylmethane diisocyanate, polymethylene polyphenylene polyisocyanate, tolidine diisocyanate, naphthalene diisocyanate, hexamethylene diisocyanate, isophorone diisocyanate, xylylene diisocyanate, dicyclohexylmethane diisocyanate, hexamethylene diisocyanate or the like. Examples of other transparent resin components include polymethyl methacrylate, polymethyl methacrylate/styrene copolymer, polyvinyl chloride, polyvinyl acetate, and the like. In addition to these components, a leveling agent such as an acrylic or silicone resin, a silicone-based or acrylic cissing inhibitor, and others may be added as needed.

The paint containing the ultraviolet absorbent according to the present invention may be used in any application. Examples thereof include the ultraviolet-shielding paints described in JP-A-7-26177, JP-A-9-169950, JP-A-9-221631, and JP-A-2002-80788; the ultraviolet- and near infrared-shielding paints described in JP-A-10-88039; the electromagnetic wave-shielding paints described in JP-A-2001-55541; the clear paints described in JP-A-8-81643; the metallic paint compositions described in JP-A-2000-186234; the cationic electrodeposition paints described in JP-A-7-166112; the antimicrobial and lead-free cationic electrodeposition paints described in JP-A-2002-294165; the powder paints described in JP-A-2000-273362, JP-A-2001-279189, and JP-A-2002-271227; the aqueous intermediate-layer paints, aqueous metallic paints, and aqueous clear paints described in JP-A-2001-9357; the topcoat paints for automobile, construction, and civil work described in JP-A-2001-316630; the hardening paints described in JP-A-2002-356655; the coat-film forming compositions for use on plastic materials such as automobile bumper described in JP-A-2004-937; the paints for a metal plate described in JP-A-2004-2700; the hardening gradient coat films described in JP-A-2004-169182; the coating materials for an electric wire described in JP-A-2004-107700; the paints for automobile repair described in JP-A-6-49368; the anionic electrodeposition paints described in JP-A-2002-38084 and JP-A-2005-307161; the paints for an automobile described in JP-A-5-78606, JP-A-5-185031, JP-A-10-140089, JP-T-2000-509082, JP-T-2004-520284, and WO 2006/097201 pamphlet; the paints for a coated steel plate described in JP-A-6-1945; the paints for a stainless steel described in JP-A-6-313148; the lamp moth-repellent paints described in JP-A-7-3189; the UV-hardening paints described in JP-A-7-82454; the antimicrobial paints described in JP-A-7-118576; the eyestrain protection paints described in JP-A-2004-217727; the anti-fog paints described in JP-A-2005-314495; the ultra-weather-resistance paints described in JP-A-10-298493; the gradient paints described in JP-A-9-241534; the photocatalyst paints described in JP-A-2002-235028; the strippable paints described in JP-A-2000-345109; the concrete separation paints described in JP-A-6-346022; the anti-corrosion paints described in JP-A-2002-167545; the protective paints described in JP-A-8-324576; the water-repellent protective paints described in JP-A-9-12924; the anti-plate glass scattering paints described in JP-A-9-157581; the alkali-soluble protective paints described in JP-A-9-59539; the aqueous temporary protective paint compositions described in JP-A-2001-181558; the flooring paints described in JP-A-10-183057; the emulsion paints described in JP-A-2001-115080; the two-liquid aqueous paints described in JP-A-2001-262056; the one-liquid paints described in JP-A-9-263729; the UV-hardening paints described in JP-A-2001-288410; the electron beam-hardening paint compositions described in JP-A-2002-69331; the thermosetting paint compositions described in JP-A-2002-80781; the aqueous paints for baking lacquer described in JP-T-2003-525325; the powder paints and the slurry paints described in JP-A-2004-162021; the repair paints described in JP-A-2006-233010; the powder-paint aqueous dispersions described in JP-T-11-514689; the paints for a plastic article described in JP-A-2001-59068 and JP-A-2006-160847; the electron beam-hardening paints described in JP-A-2002-69331; and the like.

The paint containing the ultraviolet absorbent according to the present invention generally contains a paint (containing a transparent resin component as the principal component) and an ultraviolet absorbent. The paint contains the ultraviolet absorbent preferably in an amount of 0 to 20 mass % with respect to the resin. The thickness of the film coated is preferably 2 to 1,000 μm, more preferably 5 to 200 μm. The method of coating the paint is arbitrary, and examples of the method include a spray method, a dipping method, a roller coating method, a flow coater method, a blow coating method, and the like. The drying after coating is preferably carried out at a temperature of approximately room temperature to 120° C. for 10 to 90 minutes, although the condition may vary according to the paint composition.

The coated film containing the ultraviolet absorbent according to the present invention is a coated film formed by using the paint containing the ultraviolet absorbent according to the present invention that contains the ultraviolet absorbent containing the compound represented by formula (I) above.

Hereinafter, the ink containing the ultraviolet absorbent according to the present invention will be described. The ink containing the ultraviolet absorbent according to the present invention may be any ink in any form, as long as it contains the compound represented by formula (I) above. For example, it may be dye ink, pigment ink, aqueous ink, solvent ink, or the like. It may be used in any application. Examples of the applications include the screen printing ink described in JP-A-8-3502; the flexographic printing ink described in JP-T-2006-521941; the gravure printing ink described in JP-T-2005-533915; the lithographic offset printing ink described in JP-T-11-504954; the letterpress printing ink described in JP-T-2005-533915; the UV ink described in JP-A-5-254277; the EB ink described in JP-A-2006-30596; and the like. Other examples thereof include the inkjet inks described in JP-A-11-199808, WO 99/67337 pamphlet, JP-A-2005-325150, JP-A-2005-350559, JP-A-2006-8811, and JP-T-2006-514130; the photochromic ink described in JP-A-2006-257165; the thermal transfer ink described in JP-A-8-108650; the masking ink described in JP-A-2005-23111; the fluorescence ink described in JP-A-2004-75888; the security ink described in JP-A-7-164729; the DNA ink described in JP-A-2006-22300; and the like.

Any product obtained by using the ink containing the ultraviolet absorbent according to the present invention is also included in the present invention. Examples thereof include the print laminated films obtained by laminating the print, and the packaging materials and containers prepared by using the laminated film described in JP-A-2006-70190; the ink-receiving layer described in JP-A-2002-127596; and the like.

Hereinafter, the fiber containing the ultraviolet absorbent according to the present invention will be described. The fiber containing the ultraviolet absorbent according to the present invention may be a fiber of any kind of polymer, as long as it contains the compound represented by formula (I) above. Examples thereof include the polyester fibers described in JP-A-5-117508, JP-A-7-119036, JP-A-7-196631, JP-A-8-188921, JP-A-10-237760, JP-A-2000-54287, JP-A-2006-299428, and JP-A-2006-299438; the polyphenylene sulfide fibers described in JP-A-2002-322360 and JP-A-2006-265770; the polyamide fibers described in JP-A-7-76580, JP-A-2001-348785, JP-A-2003-41434, and JP-A-2003-239136; the epoxy fibers described in WO 03/2661 pamphlet; the aramide fibers described in JP-A-10-251981; the polyurethane fibers described in JP-A-6-228816; the cellulosic fibers described in JP-T-2005-517822; and the like.

The fiber containing the ultraviolet absorbent according to the present invention may be prepared by any method. Examples of the method include the method, as described in JP-A-6-228818, of processing a polymer previously containing the compound represented by formula (I) above into fiber, and the methods, as described, for example, in JP-A-5-9870, JP-A-8-188921, and JP-A-10-1587, of processing a material processed in a fiber form with a solution containing the compound represented by formula (I) above. As described in JP-A-2002-212884 and JP-A-2006-16710, the fiber may be processed by using a supercritical fluid.

The fiber containing the ultraviolet absorbent according to the present invention can be used in various applications. Examples thereof include the clothing described in JP-A-5-148703; the backing cloth described in JP-A-2004-285516; the underwear described in JP-A-2004-285517; the blanket described in JP-A-2003-339503; the hosiery described in JP-A-2004-11062; the synthetic leather described in JP-A-11-302982; the moth-repellent mesh sheet described in JP-A-7-289097; the mesh sheet for construction described in JP-A-10-1868; the carpet described in JP-A-5-256464; the moisture-permeable water-repellent sheet described in JP-A-5-193037; the nonwoven fabric described in JP-A-6-114991; the ultrafine fiber described in JP-A-11-247028; the fibrous sheet described in JP-A-2000-144583; the refreshing clothing described in JP-A-5-148703; the moisture-permeable water-repellent sheet described in JP-A-5-193037; the flame-resistant synthetic suede cloth structure described in JP-A-7-18584; the resin tarpaulin described in JP-A-8-41785; the filming agent, external wall material, and agricultural greenhouse described in JP-A-8-193136; the net and mesh for construction described in JP-A-8-269850; the filter substrate described in JP-A-8-284063; the stainproof filming agent described in JP-A-9-57889; the mesh fabric and land net described in JP-A-9-137335; the underwater net described in JP-A-10-165045; the ultrafine fibers described in JP-A-11-247027 and 11-247028; the textile fiber described in JP-A-7-310283 and JP-T-2003-528974; the air-bag base cloth described in JP-A-2001-30861; the ultraviolet-absorbing fiber products described in JP-A-7-324283, JP-A-8-20579, and JP-A-2003-147617; and the like.

Hereinafter, the construction material containing the ultraviolet absorbent according to the present invention will be described. The construction material containing the ultraviolet absorbent according to the present invention may be a construction material of any kind of polymer, as long as it contains the compound represented by formula (I) above. Examples thereof include the vinyl chloride-based material described in JP-A-10-6451; the olefin-based material described in JP-A-10-16152; the polyester-based material described in JP-A-2002-161158; the polyphenylene ether-based material described in JP-A-2003-49065; the polycarbonate-based material described in JP-A-2003-160724; and the like.

The construction material containing the ultraviolet absorbent according to the present invention may be prepared by any method. Examples of the method include the method, as described in JP-A-8-269850, of forming a material containing the compound represented by formula (I) above into a desired shape; the methods, as described, for example, in JP-A-10-205056, of forming a laminate of a material containing the compound represented by formula (I) above; the methods, as described, for example, in JP-A-8-151457, of forming a coated layer containing the compound represented by formula (I) above; and the methods, as described, for example, in JP-A-2001-172531, of forming it by coating a paint containing the compound represented by formula (I) above.

The construction material containing the ultraviolet absorbent according to the present invention can be used in various applications. Examples thereof include the external construction materials described in JP-A-7-3955, JP-A-8-151457, and JP-A-2006-266042; the wood structure for construction described in JP-A-8-197511; the roofing material for construction described in JP-A-9-183159; the antimicrobial construction material described in JP-A-11-236734; the base construction material described in JP-A-10-205056; the antifouling construction material described in JP-A-11-300880; the flame-resistant material described in JP-A-2001-9811; the ceramic construction material described in JP-A-2001-172531; the decorative construction material described in JP-A-2003-328523; the painted articles for construction described in JP-A-2002-226764; the facing materials described in JP-A-10-6451, JP-A-10-16152, and JP-A-2006-306020; the construction net described in JP-A-8-269850; the moisture-permeable water-repellent sheet for construction described in JP-A-9-277414; the mesh sheet for construction described in JP-A-10-1868; the construction film described in JP-A-7-269016; the decorative film described in JP-A-2003-211538; the coating materials for construction described in JP-A-9-239921, JP-A-9-254345, and JP-A-10-44352; the adhesive composition for construction described in JP-A-8-73825; the civil work construction structure described in JP-A-8-207218; the pathway coating material described in JP-A-2003-82608; the sheet-shaped photocuring resin described in JP-A-2001-139700; the wood-protecting paint described in JP-A-5-253559; the push-switch cover described in JP-A-2005-2941780; the bond-sheeting agent described in JP-A-9-183159; the base construction material described in JP-A-10-44352; the wall paper described in JP-A-2000-226778; the decorative polyester film described in JP-A-2003-211538; the decorative polyester film for molded material described in JP-A-2003-211606; the flooring material described in JP-A-2004-3191; and the like.

Hereinafter, the recording medium containing the ultraviolet absorbent according to the present invention will be described. The recording medium containing the ultraviolet absorbent according to the present invention may be any medium, as long as it contains the compound represented by formula (I) above. Examples thereof include the inkjet recording media described in JP-A-9-309260, JP-A-2002-178625, JP-A-2002-212237, JP-A-2003-266926, JP-A-2003-266927, and JP-A-2004-181813; the image-receiving medium for thermal transfer ink described in JP-A-8-108650; the image-receiving sheet for sublimation transfer described in JP-A-10-203033; the image-recording medium described in JP-A-2001-249430; the heat-sensitive recording medium described in JP-A-8-258415; the reversible heat-sensitive recording media described in JP-A-9-95055, JP-A-2003-145949, and JP-A-2006-167996; the information-photorecording medium described in JP-A-2002-367227; and the like.

Hereinafter, the image display device containing the ultraviolet absorbent according to the present invention will be described. The image display device containing the ultraviolet absorbent according to the present invention may be any device, as long as it contains the compound represented by formula (I) above. Examples thereof include the image display device employing an electrochromic element described in JP-A-2006-301268; the image display device of so-called electronic paper described in JP-A-2006-293155; the plasma display described in JP-A-9-306344; the image display device employing an organic EL element described in JP-A-2000-223271; and the like. The ultraviolet absorbent according to the present invention may be contained, for example, in the ultraviolet-absorbing layer formed in the laminated structure described in JP-A-2000-223271 or in a necessary part such as the circularly polarizing plate described, for example, in JP-A-2005-189645.

Hereinafter, the solar cell cover containing the ultraviolet absorbent according to the present invention will be described. The solar cell according to the present invention may be made of any kind of element. Examples thereof include a crystalline silicon solar cell, an amorphous silicon solar cell, and a dye-sensitized solar cell. As described in JP-A-2000-174296, a cover material has been used as a protective part for providing a crystalline silicon solar cell or an amorphous silicon solar cell with antifouling property, impact resistance, and durability. As described in JP-A-2006-282970, dye-sensitized solar batteries, which employ a metal oxide-based semiconductor that is activated by excitation of light (in particular, ultraviolet light) as its electrode material, have a problem of the photosensitizer colorant adsorbed being decomposed and thus the photovoltaic efficiency gradually declining, and for that reason, installation of an additional ultraviolet-absorbing layer was proposed.

The solar cell cover containing the ultraviolet absorbent according to the present invention may be a cover of any kind of polymer. Examples of the polymer include the polyester described in JP-A-2006-310461; the thermosetting transparent resin described in JP-A-2006-257144; the α-olefin polymer described in JP-A-2006-210906; the polypropylene described in JP-A-2003-168814; the polyether sulfone described in JP-A-2005-129713; the acrylic resin described in JP-A-2004-227843; the transparent fluorine resin described in JP-A-2004-168057; and the like.

The solar cell cover containing the ultraviolet absorbent according to the present invention may be prepared by any method. For example, the ultraviolet-absorbing layer described in JP-A-11-40833 may be formed; the layers respectively containing the ultraviolet absorbent may be laminated, as described in JP-A-2005-129926; it may be contained in the filler layer resin, as described in JP-A-2000-91611; or a film may be formed, together with the ultraviolet absorbent-containing polymer described in JP-A-2005-346999.

The solar cell cover containing the ultraviolet absorbent according to the present invention may be in any form. Examples thereof include the film and sheet described in JP-A-2000-91610 and JP-A-11-261085; the laminate film described, for example, in JP-A-11-40833; the cover glass structure described in JP-A-11-214736; and the like. The ultraviolet absorbent may be contained in the sealer described in JP-A-2001-261904.

The glass and the glass-coating film containing the ultraviolet absorbent according to the present invention will be described. The glass and the glass-coating film containing the ultraviolet absorbent according to the present invention may be any one in any form, so long as they contain the compound represented by formula (I). Further, they may be used for any purposes. Examples thereof include the heat ray-blocking (barrier) glass described in JP-A-5-58670 and JP-A-9-52738; the window glass described in JP-A-7-48145; the colored glass described in JP-A-8-157232, JP-A-10-45425 and JP-A-11-217234; the ultraviolet sharp-cut glass for high intensity light sources such as mercury lamp and metal halide lamp described in JP-A-8-59289; the frit glass described in JP-A-5-43266; the ultraviolet-blocking (barrier) glass for vehicles described in JP-A-5-163174; the colored heat ray-absorbing glass described in JP-A-5-270855; the fluorescent brightening agent-containing ultraviolet-absorbing heat-insulation glass described in JP-A-6-316443; the ultraviolet and heat ray-blocking (barrier) glass for automobiles described in JP-A-7-237936; the exterior stained glass described in JP-A-7-267682; the water repellent ultraviolet and infrared ray-blocking (barrier) glass described in JP-A-7-291667; the glass for head up display of vehicles described in JP-A-7-257227; the dimming heat barrier multilayer window described in JP-A-7-232938; the ultraviolet and infrared rays cut glass described in JP-A-5-78147, JP-A-7-61835 and JP-A-8-217486; the ultraviolet ray cut glass described in JP-A-6-127974 and JP-A-7-53241; the ultraviolet and infrared rays-absorbing window glass described in JP-A-8-165146; the ultraviolet cut-off antifouling window film described in JP-A-10-17336; the light transmission panel for plantation house described in JP-A-9-67148; the ultraviolet and infrared rays-absorbing and low transmission glass described in JP-A-10-114540; the low reflectance and low transmission glass described in JP-A-11-302037; the edge-light apparatus described in JP-A-2000-16171; the rough surface-formed plate glass described in JP-A-2000-44286; the laminated display glass described in JP-A-2000-103655; the conductive film glass described in JP-A-2000-133987; the anti-glare glass described in JP-A-2000-191346; the ultraviolet and infrared rays-absorbing and middle transmission glass described in JP-A-2000-7371; the privacy-protected window glass for vehicles described in JP-A-2000-143288; the antifogged glass for vehicles described in JP-A-2000-239045; the glass for paving materials described in JP-A-2001-287977; the drain anti-adhesion and heat ray-blocking glass plate described in JP-A-2002-127310; the ultraviolet and infrared rays-absorbing bronze glass described in JP-A-2003-342040; the laminated glass described in WO 01/019748; a glass with ID identification function described in JP-A-2004-43212; the PDP optical filter described in JP-A-2005-70724; and the skylight window described in JP-A-2005-105751. The glass containing the ultraviolet absorbent according to the present invention may be produced according to any method.

Other examples of applications include the illuminating device light source covers described in JP-A-8-102296, 2000-67629, and JP-A-2005-353554; the synthetic leathers described in JP-A-5-272076 and JP-A-2003-239181; the sport goggle described in JP-A-2006-63162; the deflection lens described in JP-A-2007-93649; the hardcoat for various plastic products described in JP-A-2001-214121, JP-A-2001-214122, JP-A-2001-315263, JP-A-2003-206422, JP-A-2003-25478, JP-A-2004-137457, and JP-A-2005-132999; the hardcoat for bonding on external window described in JP-A-2002-36441; the window film described in JP-A-10-250004; the high-definition antiglare hard-coat film described in JP-A-2002-36452; the antistatic hard-coat film described in JP-A-2003-39607; the permeable hard-coat film described in JP-A-2004-114355; the antiforgery ledger sheet described in JP-A-2002-113937; the turf purpura-preventing agent described in JP-A-2002-293706; the sealant for bonding resin film sheet described in JP-A-2006-274179; the optical guiding parts described in JP-A-2005-326761; the rubber-coating agent described in JP-A-2006-335855; the agricultural covering materials described in JP-A-10-34841 and JP-A-2002-114879; the color candles described in JP-T-2004-532306 and JP-T-2004-530024; the cloth-rinsing agent composition described in JP-T-2004-525273; the prism sheet described in JP-A-10-287804; the protective layer transfer sheet described in JP-A-2000-71626; the photocuring resin product described in JP-A-2001-139700; the flooring sheet described in JP-A-2001-159228; the light-blocking printing label described in JP-A-2002-189415; the fuel cup described in JP-A-2002-130591; the articles with hard-coat film described in JP-A-2002-307619; the intermediate transfer recording medium described in JP-A-2002-307845; the synthetic hair described in JP-A-2006-316395; the low-temperature heat-shrinkable films for label described in WO 99/29490 pamphlet and JP-A-2004-352847; the fishing goods described in JP-A-2000-224942; the micro beads described in JP-A-8-208976; the precoated metal plate described in JP-A-8-318592; the thin film described in JP-A-2005-504735; the heat-shrinkable film described in JP-A-2005-105032; the in-mold molding label described in JP-A-2005-37642; the projection screen described in JP-A-2005-55615; the decorative sheets described in JP-A-9-300537, JP-A-2000-25180, JP-A-2003-19776, and JP-A-2005-74735; the hot-melt adhesive described in JP-A-2001-207144; the adhesives described in JP-T-2002-543265, JP-T-2002-543266 and U.S. Pat. No. 6,225,384; the electrodeposited coat and the basecoat described in JP-A-2004-352783; the wood surface-protecting agent described in JP-A-7-268253; the light-controlling materials, light-controlling films, and light-controlling glasses described in JP-A-2003-253265, JP-A-2005-105131, JP-A-2005-300962, and Japanese Patent No. 3915339; the moth-repellent lamp described in JP-A-2005-304340; the touch panel described in JP-A-2005-44154; the sealant for bonding resin film sheet described in JP-A-2006-274197; the polycarbonate film coating material described in JP-A-2006-89697; the optical fiber tape described in JP-A-2000-231044; the solid wax described in JP-T-2002-527559; and the like.

Hereinafter, the method of evaluating the light stability of the polymer material will be described. Preferable methods of evaluating the light stability of the polymer material are described, for example, in "Methods for Improving the Photostability of Polymers" (CMC Publishing, 2000) p. 85 to 107; "Basis and Physical Properties of High Functional Coatings" (CMC Publishing, 2003), p. 314 to 359; "Durability of Polymer Materials and Composite Material Products" (CMC Publishing, 2005); "Elongation of Lifetime of Polymer Materials and Environmental Measures" (CMC Publishing, 2000); H. Zweifel Ed., "Plastics Additives Handbook, 5th Edition" (Hanser Publishers), p. 238 to 244; and Tadahiko Kutsura, "Basic Seminar 2. Science of Plastic Packaging Container" (Society of packaging Science & Technology, Japan, 2003), Chapter 8.

In addition, the light stability in each application can be evaluated by the following known evaluation methods.

The photodegradation of polymer materials can be determined by the method described in JIS-K7105:1981, JIS-K7101:1981, JIS-K7102:1981, JIS-K7219:1998, JIS-K7350-1:1995, JIS-K7350-2:1995, JIS-K7350-3:1996, JIS-K7350-4:1996 or a method referring to those.

The light stability in the packaging or container application can be determined by the method of JIS-K7105 and a method referring to that. Typical examples thereof include the light transmittance and transparency evaluation of the bottle body and the functional test of the bottle content after ultraviolet irradiation by using a xenon light source described in JP-A-2006-298456; the haze value evaluation after xenon lamp irradiation described in JP-A-2000-238857; the haze value evaluation by using a halogen lamp as the light source described in JP-A-2006-224317; the yellowing evaluation after mercury lamp irradiation by using a blue wool scale described in JP-A-2006-240734; the haze value evaluation by using Sunshine Weather Meter and the visual observation of color development described in JP-A-2005-105004 and JP-A-2006-1568; the ultraviolet light transmittance evaluation described in JP-A-7-40954, JP-A-8-151455, JP-A-10-168292, JP-A-2001-323082, and JP-A-2005-146278; the ultraviolet-blocking evaluation described in JP-A-9-48935 and 9-142539; the light transmittance evaluation described in JP-A-9-241407, JP-A-2004-243674, JP-A-2005-320408, JP-A-2005-305745, and JP-A-2005-156220; the evaluation of the viscosity of the ink in ink container described in JP-A-2005-178832; the light transmittance evaluation, the visual observation of the container sample and the color difference ΔE evaluation after sunlight irradiation described in JP-A-2005-278678; the ultraviolet light transmittance evaluation, the light transmittance evaluation, and the color difference evaluation after white fluorescent lamp irradiation described in JP-A-2004-51174; the light transmittance evaluation, the haze value evaluation, and the color tone evaluation described in JP-A-2004-285189; the yellowness index evaluation described in JP-A-2003-237825; the light-blocking evaluation and the brightness evaluation by using the color difference Formula of the L*a*b* color system described in JP-A-2003-20966; the yellowing evaluation by using the color difference ΔEa*b* of a sample after irradiation of xenon lights of different in wavelength described in JP-A-2002-68322; the ultraviolet absorbance evaluation after ultraviolet light irradiation described in JP-A-2001-26081; the film tensile elongation test after photoirradiation by using Sunshine Weather Meter described in JP-A-10-298397; the antimicrobial evaluation after photoirradiation in a xenon weather meter described in JP-A-10-237312; the evaluation of discoloration of a package content after fluorescent lamp irradiation described in JP-A-9-239910; the evaluation of oil peroxide value and color tone after fluorescent lamp irradiation of a salad oil-filled bottle described in JP-A-9-86570; the evaluation of the difference in absorbance after chemical lamp irradiation described in JP-A-8-301363; the evaluation of surface glossiness retention rate and appearance after photoirradiation by using Sunshine Weather Meter described in JP-A-8-208765; the evaluation of color difference and bending strength after photoirradiation by using Sunshine Weather-O-meter described in JP-A-7-216152; the light-blocking rate evaluation and the evaluation of the peroxide generated in kerosene described in JP-A-5-139434; and the like.

The long-term durability thereof when the polymer material is used in the coating and coated film applications can be evaluated according to the method of JIS-K5400, JIS-K5600-7-5:1999, JIS-K5600-7-6:2002, JIS-K5600-7-7:1999, JIS-K5600-7-8:1999, or JIS-K8741 or a method referring to those. Typical examples thereof include the evaluation of the color density, the color difference $\Delta Ea^*b^*$ in the CIE $L^*a^*b^*$ color coordinates, and the residual brilliance after photoirradiation in an xenon light-endurance test machine and an UVCON apparatus described in JP-T-2000-509082; the absorbance evaluation after photoirradiation on a film placed on a quartz slide in an xenon arc light-endurance test machine and the evaluation of the color density and the color difference $\Delta Ea^*b^*$ in the CIE $L^*a^*b^*$ color coordinates after fluorescent or UV lamp irradiation on wax described in JP-T-2004-520284; the color tone evaluation after photoirradiation in a Metalweather weather-resistance test machine described in JP-A-2006-160847; the evaluation of brilliance retention rate and the evaluation by using color difference $\Delta Ea^*b^*$ after photoirradiation test by using a metal HID lamp, and the evaluation of glossiness after photoirradiation by a sunshine carbon arc light source described in JP-A-2005-307161; the evaluation by using color difference $\Delta Ea^*b^*$, the brilliance retention rate evaluation and the appearance evaluation after photoirradiation in a Metalweather weather-resistance test machine described in JP-A-2002-69331; the brilliance retention rate evaluation after photoirradiation by using Sunshine Weather-O-Meter described in JP-A-2002-38084; the evaluation by using the color difference $\Delta Ea^*b^*$ and the brilliance retention rate evaluation after photoirradiation in a QUV weather-resistance test machine described in JP-A-2001-59068; the brilliance retention rate evaluation after photoirradiation by using Sunshine Weather-O-Meter described in JP-A-2001-115080, JP-A-6-49368, and JP-A-2001-262056; the evaluation of post-irradiation appearance after photoirradiation on a coated plate by using Sunshine Weather-O-Meter described in JP-A-8-324576, JP-A-9-12924, JP-A-9-169950, JP-A-9-241534, and JP-A-2001-181558; the evaluation of the brilliance retention rate and the change in brightness after photoirradiation by using Sunshine Weather-O-Meter described in JP-A-2000-186234; the evaluation of the appearance of the deteriorated coated film after dew cycle WOM photoirradiation on coated film described in JP-A-10-298493; the evaluation of the ultraviolet light transmittance of coated film described in JP-A-7-26177; the evaluation of the ultraviolet-blocking rate of coated film described in JP-A-7-3189 and JP-A-9-263729; the comparative evaluation of the period until the brilliance retention rate of the coated film declines to 80% by using Sunshine Weather-O-Meter as described in JP-A-6-1945; the evaluation of rusting after photoirradiation by using a Dewpanel Light Control Weather Meter described in JP-A-6-313148; the evaluation of the strength of a concrete to the coated formwork after external exposure described in JP-A-6-346022; the evaluation by using the color difference $\Delta Ea^*b^*$, the lattice adhesion test and the surface appearance evaluation after external photoirradiation described in JP-A-5-185031; the brilliance retention rate evaluation after external photoirradiation described in JP-A-5-78606; the evaluation of post-irradiation yellowing ($\Delta YI$) by using a carbon arc light source described in JP-A-2006-63162; and the like.

The light stability when the polymer material is used in the ink application is determined by the method of JIS-K5701-1:2000, JIS-K7360-2, or ISO105-B02 or a method referring to those. Specific examples thereof include the evaluation of the color density and the measurement by the CIE $L^*a^*b^*$ color coordinates after photoirradiation by using an office fluorescent lamp or a discoloration tester described in JP-T-2006-514130; the electrophoretic evaluation after ultraviolet light irradiation by using an xenon arc light source described in JP-A-2006-22300; the print concentration evaluation with a xenon fade meter described in JP-A-2006-8811; the ink blurring evaluation by using a 100 W chemical lamp described in JP-A-2005-23111; the evaluation of the dye residual ratio in the image-forming range by using a weather meter described in JP-A-2005-325150; the evaluation of print chalking and discoloration by using an Eye Super UV Tester described in JP-A-2002-127596; the evaluation of print by using the color difference $\Delta Ea^*b^*$ in the CIE $L^*a^*b^*$ color coordinates after photoirradiation by a xenon fade meter described in JP-A-11-199808 and JP-A-8-108650; the reflectance evaluation after photoirradiation by using a carbon arc light source described in JP-A-7-164729; and the like.

The light stability of the solar cell module can be determined according to the method of JIS-C8917:1998 or JIS-C8938:1995 or a method referring to those. Specific examples thereof include the I-V-measuring photovoltaic efficiency evaluation after photoirradiation by a xenon lamp light source having a sunlight-simulating compensation filter described in JP-A-2006-282970; and the evaluation of discoloration gray scale degree, color, and apparent adhesiveness after photoirradiation by using Sunshine Weather Meter or a fade mater described in JP-A-11-261085 and JP-A-2000-144583.

The light stability of fibers and fiber products can be evaluated according to the method of JIS-L1096:1999, JIS-A5905:2003, JIS-L0842, JIS-K6730, JIS-K7107, DIN75.202, SAEJ1885, SN-ISO-105-B02, or AS/NZS4399 or a method referring to those. Examples thereof include the ultraviolet light transmittance evaluation described in JP-A-10-1587, JP-A-2006-299428, and JP-A-2006-299438; the blue scale discoloration evaluation after photoirradiation by using a xenon light source or a carbon arc light source described in JP-A-6-228816, JP-A-7-76580, JP-A-8-188921, JP-A-11-247028, JP-A-11-247027, JP-A-2000-144583, JP-A-2002-322360, JP-A-2003-339503, and JP-A-2004-11062; the UV-blocking rate evaluation described in JP-A-2003-147617; the ultraviolet-blocking property evaluation described in JP-A-2003-41434; the blue scale discoloration evaluation after dry cleaning and after irradiation by using a carbon arc light source described in JP-A-11-302982; the evaluation of lightness index and color difference $\Delta E^*$ according to chromaticness index after irradiation by using a Fade-O-meter described in JP-A-7-119036 and JP-A-10-251981; the tensile strength evaluation after photoirradiation by using a UV tester or Sunshine Weather Meter described in JP-A-9-57889, JP-A-9-137335, JP-A-10-1868, and JP-A-10-237760; the total transmission and strength retention evaluation described in JP-A-8-41785 and JP-A-8-193136; the ultraviolet protection factor (UPF) evaluation described in JP-T-2003-528974, JP-T-2005-517822, and JP-A-8-20579; the discoloration gray scale evaluation after irradiation by using a high-temperature fade meter described in JP-A-6-228818, JP-A-7-324283, JP-A-7-196631, and JP-A-7-18584; the appearance evaluation after external photoirradiation described in JP-A-7-289097; the evaluation of yellowness index (YI) and yellowing degree (ΔYI) after ultraviolet irradiation described in JP-A-7-289665; the reflectance evaluation described in JP-T-2003-528974; and the like.

The light stability of the construction material can be evaluated according to the method of JIS-A1415:1999 or a method referring to that. Specific examples thereof include the surface color tone evaluation after photoirradiation by using Sunshine Weather-O-Meter described in JP-A-2006-266402; the appearance evaluation after irradiation by using a carbon arc light source, the post-irradiation appearance evaluation by using an Eye Super UV Tester, the post-irradiation absorbance evaluation, the post-irradiation chromaticity, the color difference evaluation, and the evaluation by using the color difference ΔEa*b* of CIE L*a*b* color coordinates after photoirradiation by using a metal HID lamp light source, and brilliance retention rate evaluation described in JP-A-2004-3191 and JP-A-2006-306020; the evaluation of the change in haze value after photoirradiation by using Sunshine Weather Meter and the elongation retention rate after photoirradiation by using a tensile test machine described in JP-A-10-44352, JP-A-2003-211538, JP-A-9-239921, JP-A-9-254345, and JP-A-2003-211606; the evaluation of ultraviolet transmittance after solvent dip-coating and the visual evaluation of post-irradiation appearance by using an Eye Super UV Tester described in JP-A-2002-161158; the evaluation of brilliance change after a QUV test described in JP-A-2002-226764; the brilliance retention rate evaluation after irradiation by using Sunshine Weather-O-Meter described in JP-A-2001-172531; the evaluation by using the color difference ΔEa*b* after ultraviolet irradiation by using a black light blue fluorescent lamp described in JP-A-11-300880; the evaluation of post-irradiation adhesion retention rate and ultraviolet-blocking property by using a UVCON acceleration test machine described in JP-A-10-205056; the appearance evaluation, the total light transmittance evaluation, the haze change evaluation, and tensile shear adhesive strength evaluation after external exposure (JIS-A1410) described in JP-A-8-207218 and JP-A-9-183159; the evaluation of total light transmittance of the light in the entire wavelength range, the haze evaluation, and the yellowing degree evaluation after irradiation by using a xenon weather meter described in JP-A-8-151457; the evaluation of yellowing degree (ΔYI) and ultraviolet absorbent residual ratio after irradiation by using Sunshine Weather-O-Meter described in JP-A-7-3955; and the like.

The light stability when the polymer material is used in the recording medium application can be evaluated according to the method of JIS-K7350 or a method referring to that. Specific examples thereof include the evaluation of the difference in base color in the printing unit after fluorescent lamp irradiation described in JP-A-2006-167996; the evaluation of image density residual rate after irradiation by using a xenon weather meter described in JP-A-10-203033 and JP-A-2004-181813; the evaluation of the change in optical reflection density after irradiation by using a xenon weather meter described in JP-A-2002-207845; the yellowing degree evaluation based on the L*a*b* evaluation system after irradiation by using a Suntest CPS photodiscoloration tester described in JP-A-2003-266926; the post-irradiation discoloration evaluation by using a fade meter described in JP-A-2003-145949; the visual evaluation of post-irradiation discoloration by using a xenon fade meter described in JP-A-2002-212237; the color density retention rate evaluation after indoor sunlight irradiation and the post-irradiation color density retention rate evaluation by using a xenon weather meter described in JP-A-2002-178625; the evaluation of post-exposure C/N by using a fade meter described in JP-A-2002-367227; the fog density evaluation after fluorescent lamp irradiation described in JP-A-2001-249430; the optical reflection density evaluation and the erasability evaluation after irradiation by using a fluorescent lamp described in JP-A-9-95055; the evaluation of post-irradiation color difference ΔE* by using an Atlas fade meter described in JP-A-9-309260; the visual evaluation of post-irradiation discoloration by using a carbon arc fade meter described in JP-A-8-258415; the evaluation of the retention rate of organic EL element color-changing property described in JP-A-2000-223271; the measurement and evaluation of organic EL display brightness after photoirradiation by a xenon discoloration tester described in JP-A-2005-189645; and the like.

Other evaluation methods include those of JIS-K7103 and ISO/DIS9050 or a method referring to those. Specific examples thereof include the appearance evaluation of a polycarbonate coating film after irradiation by a UV tester described in JP-A-2006-89697; the blue scale evaluation of a synthetic hair after irradiation with ultraviolet light described in JP-A-2006-316395; the evaluation of water contact angle on a processing cloth for evaluation after irradiation by using an accelerated weather-resistance test machine described in JP-A-2006-335855; the visual evaluation of an image projected on a projection screen after irradiation by using a weather-resistance test machine described in JP-A-2005-55615; the evaluation of the deterioration of sample surface and visual evaluation of appearance after irradiation by using a Sunshine Weather Meter or a metal weather meter described in JP-A-2005-74735; the visual evaluation of appearance after photoirradiation by using a metal lamp reflector described in JP-A-2005-326761; the evaluation of the light transmittance of bottle label described in JP-A-2002-189415 and JP-A-2004-352847; the evaluation of polypropylene deterioration after irradiation by using a xenon weather meter under humid condition described in JP-A-2003-19776; the evaluation of the deterioration of a hard-coat film, the deterioration evaluation, the hydrophilicity evaluation and the abrasion resistance evaluation of the base material by using Sunshine Weather-O-Meter described in JP-A-2002-36441 and JP-A-2003-25478; the evaluation of the gray scale color difference of synthetic leather after irradiation by using a xenon lamp light described in JP-A-2003-239181; the evaluation of liquid crystal device characteristics after irradiation by using a mercury lamp described in JP-A-2003-253265; the post-irradiation adhesiveness evaluation by using Sunshine Weather-O-Meter described in JP-A-2002-307619; the evaluation of the degree of turf purpura described in JP-A-2002-293706; the evaluation of ultraviolet light transmittance and tensile strength after irradiation by using a xenon arc light source described in JP-A-2002-114879; the concrete adhesion velocity evaluation described in JP-A-2001-139700; the appearance evaluation and the coated-film adhesiveness evaluation after irradiation by using Sunshine Weather-O-Meter described in JP-A-2001-315263; the evaluation of post-irradiation yellowing degree and adhesiveness by using a carbon arc light source described in JP-A-2001-214121 and JP-A-2001-214122; the adhesiveness evaluation by using an ultraviolet fade meter described in JP-A-2001-207144; the evaluation of insect-repellency when illumination is turned on described in JP-A-2000-67629; the evaluation of the laminated glass yellowing degree (ΔYI) by using Eye Super UV Tester described in JP-A-10-194796; the evaluation of the surface appearance and brilliance retention rate after QUV irradiation and humidity-resistance tests described in JP-A-8-318592; the evaluation of color difference over time by using a dew panel light control weather meter described in JP-A-8-208976; the evaluation of the glossiness (DI) and the yellowness index (YI) in the wood base-coated state after irradiation by using a xenon Weather-O-meter described in JP-A-7-268253; the ultraviolet absorbance evaluation after repeated processing of UV irradiation and storage in dark described in JP-T-2002-5443265 and JP-T-2002-543266; the evaluation of dye discoloration color difference ΔE after ultraviolet irradiation described in JP-T-2004-532306; and the like.

The ultraviolet absorbent of the present invention may be used as a cosmetic preparation. Next, the usage of the ultraviolet absorbent of the present invention as a cosmetic preparation is explained in detail.

As the cosmetic preparation containing the ultraviolet absorbent of the present invention, there are embodiments such as a cream, a gel, a lotion, an alcoholic solution, an aqueous/alcoholic solution, an emulsion, a wax/aliphatic composition, a stick preparation, a powder and an ointment. The aforementioned cosmetic preparation may additionally contains aids and additives such as a moderate surfactant, a superfatting agent, a pearl essence wax, a consistency controlling agent, a thickener, a polymer, a silicone compound, a fat, a wax, a stabilizer, a biologically (biogenic) active component, a odor eliminating active component, a dandruff remover, a coating-forming agent, a swelling agent, an additional UV light-protecting factor, an antioxidant, a hydrotropic agent, a preservative, an insecticide, a self-tanning agent, a solubilizer, perfume oil, a colorant, and a antibacterial agent.

Examples of the materials that are suitably used as the aforementioned superfatting agent include lanolin, lecithin, polyoxyethylene-modified or acrylated lanolin and lecithin derivatives, a polyol-fatty acid ester, monoglyceride and a fatty acid alkanolamide. The foregoing fatty acid alkanolamide is also able to act as a foam stabilizer.

Suitable compounds of the aforementioned moderate surfactants are more specifically surfactants especially excellently accepted by a skin. Examples of such suitable compounds include a fatty alcohol polyglycolether sulfate, monoglyceride sulfate, a mono and/or di-alkylsulfosuccinate, fatty acid isethionate, fatty acid sarcosinate, fatty acid tauride, fatty acid glutamate, α-olefin sulfonic acid, ether carbonic acid, alkyloligoglycoside, fatty acid glucamide, alkylamide betaine, and/or a protein-fatty acid condensate. The foregoing protein-fatty acid condensate is preferably derived from a wheat protein.

As examples of the aforementioned pearl essence wax, preferred are alkyleneglycol esters, especially distearic acid ethyleneglycol; a fatty acid alkanolamide, especially coco fatty acid diethanolamide; partial glyceride, especially stearic acid monoglyceride; esters of unsubstituted or hydroxyl-substituted polyvalent carboxylic acid and aliphatic alcohol having 6 to 22 carbon atoms, especially a long-chain ester of tartaric acid; fatty materials such as a fatty alcohol, fatty ketone, fatty aldehyde, fatty ether and fatty carbonate each having at least 24 carbon atoms in total, especially laurone and distearyl ether; ring-opening products that are formed by fatty acids such as stearic acid, hydroxystearic acid and behenic acid, olefin epoxide having 12 to 22 carbon atoms, a fatty alcohol having 12 to 22 carbon atoms, or a polyol having 2 to 15 carbon atoms and 2 to 10 hydroxyl groups; and a mixture of these materials.

Examples of the aforementioned consistency controlling agent include not only a fatty alcohol or hydroxy fatty alcohol having 12 to 22 carbon atoms, preferably 16 to 18 carbon atoms, but also partial glyceride, a fatty acid and a hydroxy-fatty acid. Preferred are mixtures of the foregoing materials and alkyloligoglucoside having the same chain length and/or fatty acid N-methyl glucamide, or polyglycerol poly-12-hydroxystearate. Suitable examples of the aforementioned thickener include Aerosil type compounds (hydrophilic silicic acid); polysaccharides, especially xanthan gum, guar gum, agar, arginate, Tyloses, carboxymethyl cellulose, and hydroxymethyl cellulose, or fatty acid mono- and di-ester of relatively high molecular polyethyleneglycol, polyacrylic acids (Carbopol (registered trademark) manufactured by Goodrich and Synthalen (registered trademark) manufactured by Sigma), polyacrylamide, polyvinyl alcohol and polyvinyl pyrrolidone; surfactants such as polyoxyethylene fatty acid glyceride, esters of fatty acid and polyol such as pentaerythritol and trimethylol propane; polyoxyethylene fatty alcohol ether having a limited homolog distribution; alkyloligoglucosides; and electrolytes such as sodium chloride and ammonium chloride.

As to the aforementioned polymers, examples of suitable cationic polymers include cationic cellulose derivatives such as a quarternary hydroxymethyl cellulose available by a trade name of polymer JR400 (registered trademark) manufactured by Amerchol, a cationic starch, a copolymer of diallyl ammonium salt and acrylamide, quarternary vinylpyrrolidone/vinylimidazole polymer such as Lubicat (registered trademark) that is a product of BASF, a condensate of polyglycol and amine, a quarternary collagen polypeptide such as lauryldimonium hydroxypropyl hydrolysed collagen (Lamequat (registered trademark) L/Gruenau), a quarternary wheat polypeptide, polyethylene imine, a cationic silicone polymer such as amide meticone, a copolymer of adipic acid and dimethylaminohydroxypropyldiethylenetriamine (Cartaretin (registered trademark)/Sandoz), a copolymer of acrylic acid and dimethyldiallylammonium chloride (Merquat (registered trademark) 550/Chemviron) such as polyaminopolyamide and its cross-linked water-soluble polymer as described in FR-A-2252840, a cationic chitin derivative such as a quarternary chitosan, that is dispersed in the form of fine crystals in case of necessity, a condensate of dihaloalkane (e.g., dibromobutane) and bisdialkylamine (e.g., bisdimethylamino-1,3-propane), a cationic guar gum, such as Jaguar (registered trademark) C-17 and Jaguar (registered trademark) C-16, each of which is a product of Celanese, a quarternary ammonium salt polymer such as Mirapol (registered trademark) A-15, Mirapol (registered trademark) AD-1, Mirapol (registered trademark) AZ-1, each of which is a product of Miranol.

Preferred examples of the anionic, dipolar ionic, amphoteric ionic, or nonionic polymer are vinyl acetate/crotonic acid copolymer, vinylpyrrolidone/vinylacrylate copolymer, vinyl acetate/butyl maleate/isobornyl acrylate copolymer, methylvinyl ether/maleic acid anhydride copolymer and ester thereof, non-cross linked polyacrylic acid and polyacrylic acid that is cross linked with a polyol, acrylamide propyltrimethylammonium chloride/acrylate copolymer, octylacrylamide/methylmethacrylate/tert-butylaminoethyl methacrylate/2-hydroxy propylmethacrylate copolymer, polyvinylpyrrolidone, vinylpyrrolidone/vinylacetate copolymer, vinylpyrrolidone/dimethylaminoethyl methacrylate/vinylcaprolactam terpolymer, and cellulose ethers and silicones each derived from these compounds in case of necessity.

Suitable examples of the aforementioned silicone compounds include dimethylpolysiloxane, methylphenylpolysiloxane, cyclic silicone, and amino-, fatty acid-, alcohol-, polyether-, epoxy-, fluorine-, glycocide-, and/or alkyl-modified silicone compounds. They may be in the form of liquid or resin at room temperature. Simethicone, namely, a mixture of silicate hydride and dimethicone having an average chain length of 200 to 300 dimethylsiloxane units is also suitable. It is also suitable to use a volatile silicone compound described in Cosm. Toil., 91, 27 (1976).

As the aforementioned fats, there is exemplified glyceride. As the aforementioned wax, especially preferred are bees wax, carnauba wax, candelilla wax, montan wax, paraffin wax, a hydrogenated castor oil, and in case of necessity, a hydrophilic wax, for example, a fatty acid ester and a micro wax each of which is a solid at room temperature, and is mixed with cetylstearyl alcohol or partial glyceride. It is also possible to use metal salts of fatty acid as the aforementioned stabilizer, for example, magnesium, aluminum or zinc salt of stearic acid or ricinolic acid.

As the aforementioned biologically (biogenic) active component, preferred are materials such as tocopherol, tocopherol acetate, tocopherol palmitate, ascorbic acid, deoxyribonucleic acid, retinol, bisabolol, allantoin, phytantriol, pantenol, AHA acid, amino acid, ceramide, pseudo-ceramide, essential oil, an extracted vegetable solution, and vitamin complex.

As the aforementioned odor eliminating active component, especially preferred are materials such as antihidrotics, for example, aluminum chlorohydrate (see J. Soc. Cosm. Chem., 24, 281 (1973)). For example, aluminum chlorohydrate in accordance to formula $Al_2(OH)_5Cl.2.5\ H_2O$ is available by Locron (registered trademark) of Hoechst AG, Frankfurt (FRG) on the market. The usage of this article on the market is especially preferred (see J. Pharm. Pharmacol. 26, 531 (1975)). In addition to the chlorohydrate, it is also possible to use aluminum hydroxyacetate and acidic aluminum/zirconium salt. An esterase inhibitor may be additionally used as another odor eliminating effective component. As the inhibitor, preferred are trialkyl citrate such as trimethyl citrate, tripropyl citrate, triisopropyl citrate, and tributyl citrate, with especially preferred trialkyl citrate being ethyl citrate (Hydagen (registered trademark) Cat, Henkel KGaA, Duesseldorf/FRG). The foregoing inhibitor inhibits enzyme activity, thereby to inhibit formation of a bad odor. Other materials that are considered as an esterase inhibitor are sterol sulfate or phosphate such as lanosterol, cholesterol, campesterol, stigmasterol, and sitosterol sulfate or phosphate; dicarboxylic acid and its ester such as glutaric acid, monoethyl gultarate, diethyl gultarate, adipic acid, monoethyl adipate, diethyl adipate, malonic acid, diethyl malonate, and hydroxycarboxylic acid and its ester such as diethyl citrate, diethyl malate, tartaric acid and diethyl tartarate. It is possible to incorporate in a preparation (especially a stick preparation) antibacterial active components that are able to affect bacteria flora, to kill sweat-decomposing bacteria, and to inhibit their growth. Examples of the antibacterial active components include chitosan, phenoxyethanol and gluconic acid chlorhexidine. It has been proved that 5-chloro-2-(2,4-dichlorophenoxy)phenol (Irgasan (registered trademark), Ciba Specialty Chemicals) is also especially effective to the antibacterial activities.

As the aforementioned antihidrotics, there can be used materials such as climbazole, octopirox and zinc pyrithione. Examples of the conventional film-forming agent include chitosan, microcrystalline chitosan, a quaternary chitosan, polyvinyl pyrrolidone, vinylpyrrolidine/vinylacetate copolymer, a polymer of quaternary cellulose derivative containing acrylic acid with a high content, collagen, hyaluronic acid and its salt, and similar compounds. As the swelling agent for a aqueous phase, there can be used montmorillonite, clay mineral, Pemulen (BF Goodrich), alkyl-modified type Carbopol (BF Goodrich). Further suitable polymers and swelling agents can be found in the review of R. Lochhead, Cosm. Toil., 108, 95 (1993).

In the cosmetic formulations containing the ultraviolet absorbent of the present invention, it is possible to use, in addition to a primary light-protecting material, a secondary light-protecting material of antioxidants capable of prohibiting photochemical chain reaction that is induced in the time when ultraviolet rays penetrate skin or hair. Typical examples of the antioxidants include amino acids (e.g., glycine, histidine, tyrosine, tryptophan) and derivatives thereof, imidazole (e.g., urocanic acid) and derivatives thereof, peptides such as D,L-carnosine, D-carnosine, L-carnosine, and derivatives thereof (e.g., anserine), carotenoid, carotenes (e.g., α-carotene, β-carotene, lycopene) and derivatives thereof, chlorogenic acid and derivatives thereof, lipoic acid and derivatives thereof (e.g., dihydrolipoic acid), gold thioglucose, propylthiouracil, and other thiols (e.g., thioredoxin, glutathione, cysteine, cystine, cystamine and glycosyl, N-acetyl, methyl, ethyl, propyl, amyl, butyl, lauryl, palmitoyl, oleyl, γ-linoleyl, cholesteryl and glyceryl esters of these thiols) and these salts, dilauryl thiodipropionate, distearyl thiodipropionate, thiodipropionic acid and derivatives thereof (esters, ethers, peptides, lipids, nucleotides, nucleosides, and these salts), and sulfoxyimine compounds with a very small acceptable dose (for example, pmole to μmole/kg) (e.g., buthionine sulfoxiimine, homocysteine sulfoxiimine, buthionine sulfones, penta-, hexa- or hepta-thionine sulfoxiimine), and (metal) chelating agents (e.g., α-hydroxy fatty acid, palmitic acid, phytic acid, lactoferrin), α-hydroxy acid (e.g., citric acid, lactic acid, malic acid), humic acid, bile acid, a bile extract, bilirubin, biliverdin, EDTA, EGTA and derivatives thereof, unsaturated fatty acids and derivatives thereof (e.g., γ-linolenic acid, linolic acid, oleic acid), folic acid and derivatives thereof, ubiquinone and ubiquinol and derivatives thereof, vitamin C and derivatives thereof (e.g., ascorbyl palmitate, magnesium ascorbyl phosphate, ascorbyl acetate), tocopherol and derivatives thereof (e.g., vitamin E actate), vitamin A and derivatives thereof (e.g., vitamin A palmitate), and coniferyl benzoate in benzoin resin, luteic acid and derivatives thereof, α-glucosyl lutein, ferulic acid, furfurylidene glucitol, carnosine, butylhydroxytoluene, butylhydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and its salt, e.g., di-sodium salt), zinc and derivatives thereof (e.g., ZnO, $ZnSO_4$), selenium and derivatives thereof (e.g., selenium methionine), stilbene and derivatives thereof (e.g., stilbeneoxide, trans-stilbeneoxide), and suitable derivatives of the above-described active components (salts, esters, ethers, sugars, nucleotides, nucleosides, peptides and lipids). HALS compounds (hindered amine-series light stabilizer) may be added to the above-mentioned examples of the antioxidants. An amount of the antioxidant present in the cosmetic preparation ranges from 0.001 to 30% by mass, preferably from 0.01 to 3% by mass, based on mass of the UV absorbent.

In order to improve flowability, it is possible to use a hydrotropic agent such as ethanol, isopropyl alcohol and polyol. The polyol that is considered to use for this purpose has preferably 2 to 15 carbon atoms and at least two hydroxyl groups.

The above-mentioned polyol may have an additional functional group, especially an amino group, and/or may be modified with nitrogen. Typical examples of the polyol are set forth below:

Glycerol;

Alkylene glycol, for example, ethylene glycol, diethylene glycol, propylene glycol, butylene glycol, hexylene glycol, and polyethylene glycol having average molecular weight of 100 to 1,000 Da;

Technical Oligoglycerol mixtures having 1.5 to 10 of characteristic (intrinsic) condensation degree, for example, technical diglycerol mixture with a glycerol content of 40 to 50% by mass;

Methylol compounds, for example, especially trimethylol ethane, trimethylol propane, trimethylol butane, pentaerythritol, dipentaerythritol;

Lower alkyl glycoxides, especially those compounds having 1 to 8 carbon atoms in the alkyl moiety, for example, methyl glycoxide and butyl glycoxide;

Sugar alcohol having 5 to 12 carbon atoms, for example, sorbitol and mannitol;

Sugar having 5 to 12 carbon atoms, for example, glucose and saccharose;

Amino sugar, for example, glucamine: and

Dialcohol amine, for example, diethanol amine, or 2-amino-1,3-propanediol.

Examples of the afore-mentioned suitable preservatives include phenoxyethanol, a formaldehyde solution, paraben, pentanediol, sorbic acid and preservatives recited in Schedule 6, Parts A and B of the cosmetics Regulations.

Examples of the afore-mentioned perfume oil include a mixture of natural and/or synthetic aromatic materials. Examples of the natural aromatic materials include extracts from flowers (e.g., lily, lavender, rose, jasmine, neroli, ylang-ylang), stems and leaves (geranium, patchouli, petitgrain), fruits (aniseed, coriander, fennel, needle juniper), fruit skin (bergamot, lemon, orange), roots (mace, angelica, celery, cardamom, costus, iris, sweet flag), woods (pine tree, sandalwood, guaiacum wood, cedar, rosewood), herbs and grasses (tarragon, lemongrass, sage, thyme), needles and twigs (spruce, pine, European red pine, stone pine), and resins and balsam (galbanum, elemi, benzoin, myrrh, frankincense, opopanax). Examples of the animal-origin materials include civet and castoreum. Typical examples of the synthetic aromatic materials include articles of esters, ethers, aldehydes, ketones, alcohols and hydrocarbons.

Examples of the ester series aromatic materials include benzyl acetate, phenoxyethyl isobutylate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styralyl propionate, and benzyl salicylate. Examples of the ethers include benzylethyl ether. Examples of the aldehydes include straight chain alkanal having 8 to 18 carbon atoms, citral, citronellal, citronellyloxyaldehyde, cyclamen aldehyde, hydroxycitronellal, lilial, and bougeonal. Examples of the ketones include ionone compounds, α-isomethyl ionone, and methyl cedryl ketone. Examples of the alcohols include anethole, citronellol, eugenol, isoeugenol, geraniol, linalool, phenylethyl alcohol, and terpineol. Examples of the hydrocarbons include mainly terpenes and balsams. It is preferred to use a mixture of various aromatic materials that produce attractive perfume in combination. As aromatic oil, it is also suitable to use, as primary aromatic components, relatively low volatile ethers such as sage oils, chamomile oils, clove oils, Melissa oils, cinnamon leaf oils, lime oils, juniper nut oil, vetiver oils, frankincense oil, galbanum oils, labolanum oils, and lavandin oil. It is preferred to use alone or in combination bergamot oil, dihydromyrcenol, lilial, citronellol, phenylethyl alcohol, α-hexylcinnamaldehyde, geraniol, benzyl acetone, cyclamen aldehyde, linalool, boisambrene forte, ambroxan, indole, hedione, sandelice, lemon oil, tangerine oil, orange oil, allylamyl glycolate, cyclovertal, lavandin oil, Clary Sage oil, β-damascone, Bourbon geranium oil, cyclohexyl salicylate, vertofix Coeur, iso-E-super, Fixolide NP, evernyl, iraldein gamma, phenyl acetate, geranyl acetate, benzyl acetate, rose oxide, romillat, irotyl, and floramat.

Materials that has been authorized to use for cosmetics may be used as a colorant. Examples of those materials are compiled by, for example, "Kosmetische Farbenittel" Verlag Chemie, Weinheim, 1984, p. 81 to 106, that is a publication of Farbstoffkomission der Deutchen Forschunggemeinschaft. Usually, the colorant may be used in a concentration of from 0.001 to 0.1% by mass based on the total amount of the mixture.

Examples of the afore-mentioned antibacterial agent include preservatives having a specific function against Gram-positive bacteria such as 2,4,4'-trichloro-2'-hydroxy-diphenyl ether, chlorohexidine (1,6-di(4-chlorophenyl biguanide)hexane), and TTC (3,4,4'-trichlorocarbanilide). Many aromatic materials and ether oils also have antibacterial activities.

Typical examples thereof include eugenol, menthol, and thymol that are contained as an effective component in clove oils, mint oils and thyme oils. A typical example of the natural deodorant is terpene alcohol farnesol (3,7,11-trimethyl-2,6,10-dodecatriene-1-ol) that is present in lime oils. It has been proved that glycerol monolaurate also acts as a antibacterial agent. An additional amount of the antibacterial agent is usually in the range of 0.1 to 2% by mass based on the solid content of the preparation.

A cosmetic preparation containing the ultraviolet absorbent of the present invention may contain, as an aid, antifoaming agents such as silicone; structural materials such as maleic acid; solubilizing agents such as ethylene glycol, propylene glycol, glycerol and diethylene glycol; opacifier such as latex, styrene/PVP or styrene/acrylamide copolymers; chlating agents such as EDTA, NTA, and β-alanine di-acetate or phosphonate; propellants such as propane/butane mixture, $N_2O$, dimethyl ether, $CO_2$, $N_2$, and air; so-called couplers such as oxidative dye precursors, or developer components; reducing agents such as thioglycolic acid and derivatives thereof, thiolactic acid, cysteamine, thiomalic acid, α-mercaptoethane sulfonic acid; or oxidants such as hydrogen peroxide, potassium bromide, and sodium bromide.

Examples of the afore-mentioned insecticide include N,N-diethyl-m-toluamide, 1,2-pentane diol and Insecticide 3535. Suitable examples of the afore-mentioned self-tanning agent include dihydroxyacetone, erythrulose, and a mixture of dihydroxyacetone and erythrulose.

A cosmetic composition containing the ultraviolet absorbent of the present invention may be incorporated in various cosmetic preparations. For example, the following preparations are especially preferred.

Skin care preparations: for example, skin-washing and cleansing preparations with a tablet type or liquid soap form, synthetic detergents, or pastes for cleaning;

Bathing preparations: for example, bathing preparations in the form of liquid (preparations for foam bath, milk and shower) or solid such as bath cube and bath salt;

Skin care preparations: for example skin emulsion, multi emulsion, or skin oil;

Cosmetic personal care preparations: for example facial make-up in the form of day cream or powder cream; facial powder (powder or solid), cheek rouge or cream make-up; eye care preparations, for example, eye shadow preparations, mascara, eye liner, eye cream, or eye fix cream; lip care preparations such as lip stick, lip gloss, and lip outline pencil; nail care preparations such as nail lacquer, nail lacquer remover, nail hardener, and cuticle remover;

Foot care preparations: for example, foot bath, foot powder, foot cream or foot balsam, special deodorant, antiperspirant, foot corn-removing preparations;

Light-protecting preparations: for example, sun milk, lotion, cream or oil, sun block or tropical, pre-tanning preparations, after sun preparations;

Skin-tanning preparations: for example, self-tanning cream;

Bleaching preparations: for example, preparations for bleaching skin, or whitening preparations Insecticides: for example, insecticide oil, lotion, spray or stick;

Deodorants: for example, deodorant spray, pump-type spray, deodorant gel, stick or roll-on;

Antiperspirants: for example, antiperspirant stick, cream or lotion;

Preparations for cleansing and caring an injured skin: for example, synthetic detergents (solid or liquid), peeling or scrubbing preparations, or peeling mask;

Depilating preparations as a chemical (hair removing): for example, depilating powder, depilating preparations with liquid, cream, paste, gel, or aerosol form;

Shaving preparations: for example shaving soap, foaming shaving cream, non-foaming shaving cream, pre-shaving preparations for foam, gel or dry-shaving, after shave or after-shave lotion;

Fragrance preparations: for example, fragrances (eau de cologne, eau de toilette, eau de parfum, parfum de toilette, parfum), perfume oil or cream;

Cosmetic hair treatment preparations: for example, hair washing preparations in the form of shampoo and conditioner; hair care preparations such as pretreatment preparations, hair tonic, styling cream, styling gel, pomade, hair rinse, treatment pack, and intensive hair treatment; hair structuring preparations such as hair waving preparations for permanent wave (hot wave, mild wave and cold wave), hair straightening preparations, liquid hair setting preparations, hair foam, hair spray, bleaching preparations such as a hydrogen peroxide solution, a lightening shampoo, a bleaching cream, a bleaching powder, a bleaching paste or oil, a temporary semi-permanent hair color or permanent hair color, preparations containing a self-oxidising dye, or natural hair colorant such as henna and chamomile.

Each of the above-recited preparations may be present in various forms as exemplified below.

A form of liquid preparation such as W/O, O/W, O/W/O, W/O/W, or PIT emulsion and all kinds of micro emulsions;

A form of gel;

A form of oil, cream, milk, or lotion;

A form of powder, lacquer, tablet, or make-up

A form of stick;

A form of spray (spray containing an injection gas, or a pump-type soray), or aerosol;

A form of foam; or

A form of paste.

It is also preferred that cosmetic preparations containing the ultraviolet absorbent of the present invention may be contained in cosmetics in the form such that the ultraviolet absorbent of the present invention is encapsulated in microcapsules. A method of encapsulating a functional component is sometimes used to reduce an effect to a human body and/or to enhance stability of the compound. Especially, this method has been used in order to ensure the usage of a light-sensitive component like ultraviolet absorbents. For example, it is possible to use SILASOMA (trade name, a product of Seiwa kasei) that is available on the market. As the material for micro capsulation (membrane material) in the foregoing goods on the market, there is used a silicone-resinified polypeptide that is composed of a silicone part and a polypeptide part. The polypeptide part is obtained by hydrolysis of collagen, silk protein and the like (see the publication of JP-A-2001-106612). As a material for capsulation, it is possible to use any materials such as natural polymers and synthetic polymers. Of these materials, it is preferred to use naturally-derived polymers such as collagen, gelatin, dextrin and DNA. Further, imparting of optical responsivity to the capsule material (membrane material) enables to discharge the ultraviolet absorbent of the present invention from the portion to which light is exposed. This method is preferable because the ultraviolet absorbent contacts with a skin only in case of necessity, so that stimulation to skin can be reduced as much as possible, and stability of the ultraviolet absorbent can be maintained.

In the cosmetic formulations containing the ultraviolet absorbent of the present invention, especially favorable embodiments of the cosmetic preparation for skin are light-protecting preparations such as milk, lotion, cream, oil, sun block or tropical, pre-tanning preparations or after-sun preparations, and skin tanning preparations (e.g., self-tanning cream). Particularly interesting embodiments are sun-protect creams, sun-protect lotions, sun-protect oils, sun-protect milks and spray-type sun-protect preparations.

In the cosmetic formulations containing the ultraviolet absorbent of the present invention, especially favorable embodiments of the cosmetic preparation for hair are the aforementioned preparations for hair treatment, especially hair wash preparations of shampoo and hair conditioner; hair care preparations such as pretreatment preparations, hair tonic, styling cream, styling gel, pomade, hair rinse, treatment pack, intensive hair dressing, hair straightening preparations, liquid hair setting preparations, hair foam, hair spray. Especially preferred are shampoo-type hair wash preparations.

The following is a preferable exemplary composition of the shampoo:

| | |
|---|---|
| Ultraviolet absorbent of the present invention | 0.01 to 5% by mass |
| Sodium laureth-2-sulfate | 12.0% by mass |
| Cocamidopropyl betaine | 4.0% by mass |
| Sodium chloride | 3.0% by mass |
| Water to make | 100% by mass |

In the cosmetic formulations containing the ultraviolet absorbent of the present invention, the following cosmetic preparation may especially favorably be used in embodiments of the cosmetic formulations for hair:

$a_1$) A self-emulsifiable raw composition that is composed of the ultraviolet absorbent of the present invention, PEG-6-$C_{10}$ oxo alcohol and sorbitan sesquioleate, and further contains water, and if desired, any quaternary ammonium compound such as 4% minkamidopropyldimethyl-2-hydroxylethyl ammonium chloride and Quaternium 80.

a₂) A self-emulsifiable raw composition that is composed of the ultraviolet absorbent of the present invention, tributyl citrate, and PEG-20-solbitan monooleate, and further contains water, and if desired, any quaternary ammonium compound such as 4% minkamidopropyldimethyl-2-hydroxylethyl ammonium chloride and Quaternium 80.

b) Quat-doped solutions (four times concentrated solution) of the ultraviolet absorbent of the present invention in butyl triglycol and tributyl citrate, c) A mixture or solution of the ultraviolet absorbent of the present invention with n-alkyl pyrrolidone.

In the case where the ultraviolet absorbent of the present invention is used for cosmetic formulations, they may be used by containing them in a cream, gel, lotion, alcoholic or aqueous/alcoholic solution, water-containing emulsion, oil-containing emulsion, wax/fat composition, stick formulations, powder and paste. Usage of the ultraviolet absorbent of the present invention enables to provide cosmetic formulations that are excellent in long-wave ultraviolet ray absorbing capacity and that are able to maintain the capacity for a long term. Examples of the ultraviolet absorbents of the present invention include the compound represented by formula (I) or (Ia). However, the ultraviolet absorbent of the present invention may be a silicone derivative represented by formula (Ib) in order to enhance both extension to skin and solubility to a silicone oil that is an oil component. Formula (Ib) is explained in detail below.

and $X^{4b}$ in the structures of the formula (Ib). The residue bonds with the linking group W.

$R^{b1}$ to $R^{b9}$, which may be the same or different, represent an alkyl group having 1 to 20 carbon atoms, more preferably 1 to 10 carbon atoms, an alkoxy group, an aryl group having 6 to 20 carbon atoms, more preferably 6 to 10 carbon atoms, a hydroxyl group or a hydrogen atom.

W represents a divalent linking group. The linking group is composed of an atom or a group of atoms of a carbon atom and a hetero atom such as a nitrogen atom, a sulfur atom and an oxygen atom. The divalent linking group represents one having 1 to 20 carbon atoms composed of one or more groups selected from, for example, an alkylene group (e.g., methylene, ethylene, propylene, butylene, pentylene), an arylene group (e.g., phenylene, naphthylene), an alkenylene group (e.g., ethenylene, propenylene), an alkynylene group (e.g., ethinylene, propinylene), an amido group, an ester group, a sulfonamide group, a sulfonic acid ester group, an ureido group, a sulfonyl group, a sulfinyl group, a thioether group, an ether group, a carbonyl group, —N(Va)-(Va represents a hydrogen atom or an monovalent substituent. Examples of the monosubstituent are those exemplified in the aforementioned E.), and a divalent heterocyclic group (e.g., 6-chloro-1,3,5-triazine-2,4-diyl, pyrimidine-2,4-diyl, quinoxaline-2,3-diyl). Further, the linking group may have a monovalent substituent E. Further, the linking group may contain a ring (aromatic or non-aromatic hydrocarbon rings or heterocycles).

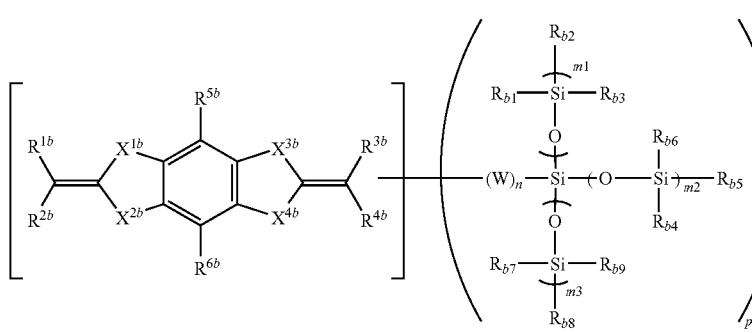

Formula (Ib)

In formula (Ib), $R^{1b}$, $R^{2b}$, $R^{3b}$, $R^{4b}$, $R^{5b}$, and $R^{6b}$ each have the same meanings as the forgoing $R^1$, $R^2$, $R^3$, $R^4$, $R^5$, and $R^6$ and preferable cases are also the same. $X^{1b}$, $X^{2b}$, $X^{3b}$, and $X^{4b}$ each have the same meanings as the forgoing $X^1$, $X^2$, $X^3$, and $X^4$, respectively, and preferable cases are also the same.

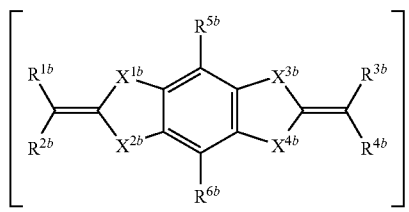

The chemical unit represents a residue (monovalent substituent) that is formed by eliminating one or plural numbers of hydrogen atoms or monovalent substituents from an arbitrary position of $R^{1b}$, $R^{2b}$, $R^{3b}$, $R^{4b}$, $R^{5b}$, $R^{6b}$, $X^{1b}$, $X^{2b}$, $X^{3b}$, W is preferably an alkylene group having 10 carbon atoms or less, an arylene group having 15 carbon atoms or less, a divalent linking group containing an ether group having 10 carbon atoms or less, and a divalent linking group containing an amino group having 10 carbon atoms or less. More preferred are an alkylene group having 5 carbon atoms or less, an arylene group having 10 carbon atoms or less, and a divalent linking group containing an ether group having 5 carbon atoms or less. Especially preferred is an alkylene group having 4 carbon atoms or less.

Each of m1, m2, and m3 represents a number of the bond [—O—Si—] and is an integer of 0 or more. m1, m2, and m3 are preferably an integer of 0 to 10, more preferably an integer of 0 to 6. n represents an integer of 0 to 5. When n is an integer of 2 or more, W's may be the same or different. n is preferably an integer of 0 to 3, more preferably 0 or 1. p represents a number of substitution to the aforementioned residue, specifically an integer of 1 to 5. p is preferably an integer of 1 to 3, more preferably 1 or 2.

Of the residues bonding to the linking group W, preferred are groups that are formed by eliminating one hydrogen atom or monovalent substituent from $R^{1b}$, $R^{2b}$, $R^{3b}$, $R^{4b}$, $R^{5b}$ or $R^{6b}$, each of which represents an ester group, an amido group, a carbonyl group, a sulfonamido group, a sulfonic acid ester group, an ureido group, a sulfonyl group, or a sulfinyl group, more preferably an ester group, an amido group, a sulfonamido group, or a sulfonic acid ester group, and especially preferably an ester group, or an amido group.

Preferable examples of the compound represented by the aforementioned formula (Ib) include (B101) to (B111) listed above as specific examples of the compound represented by formula (I-1) or (Ia-1). However, the present invention is not limited to these specific examples.

The heterocyclic compound of the present invention is useful for functional materials such as medicines, agricultural chemicals, dyes, pigments, ultraviolet absorbents, liquid crystals, organic semiconductors, organic electric conductors, organic electronic materials, or medical diagnostic materials, and synthetic intermediates thereof.

Especially, the compound of the present invention is useful for dyes, pigments, or ultraviolet absorbents each having high fastness to light, high molar extinction coefficient $\epsilon$, and further providing a sharp absorption. Among them, the compound of the present invention has an extremely excellent long-wave ultraviolet absorbing capacity and therefore can be preferably used as an ultraviolet absorbent. By incorporating the compound of the present invention having absorption in an ultraviolet range in polymer molded articles such as plastics or fibers, light stability of the molded articles can be increased. Further, the polymer materials containing the compound of the present invention having absorption in an ultraviolet range can be used as a filter or a container that protects contents that are vulnerable to ultraviolet rays, using excellent ultraviolet absorbing capacity of the compound.

The ultraviolet absorbent of the present invention satisfying the aforementioned physical properties exhibits a performance in which molar absorption coefficient per molecular weight is large. Therefore, a sufficient ultraviolet ray-shielding effect can be attained using only a small amount of the compound. This is a great merit when compared to the molar absorption coefficient of both widely used benzotriazole-based ultraviolet absorbents and triazine-based ultraviolet absorbents being around 20,000 and around 60,000 respectively.

Further, the ultraviolet absorbent of the present invention containing the compound represented by the aforementioned formula (I) exhibits excellent effects such that the ultraviolet absorbent has both a high light fastness and a high molar absorption coefficient $\epsilon$ and provides a sharp absorption. The ultraviolet absorbent of the present invention may be used as a composition. Specifically, the ultraviolet absorbent of the present invention may be contained in a polymer molded article such as plastics and fibers, thereby to enhance light stability of the polymer molded article.

Further, the polymer materials containing the ultraviolet absorbent of the present invention can be used as a filter or a container for protecting their contents whose ultraviolet fastness is vulnerable to ultraviolet rays, using excellent ultraviolet absorbing capacity of the compound.

The present invention will be described in more detail based on the following examples, but the invention is not intended to be limited thereby.

EXAMPLES

Example 1

Preparation of Exemplified Compound (1)

To a solution of 80 g of sodium hydroxide dissolved in 800 ml of ethanol, 100 mL of ethanol solution of 66 g of malononitrile was added while cooling with ice, and subsequently 76 g of carbon disulfide was added. After reaction at room temperature for 1 hour, the obtained solid was filtrated and then washed with ethanol, to give 166 g of the following synthetic intermediate A (yield: 89%).

To a dispersion of 12.3 g of chloranil dispersed in 100 mL of N,N-dimethylacetamide, 50 ml of solution of the following synthetic intermediate A was added while cooling with ice, and allowed to react at room temperature for 6 hours. After adding water to the reaction solution, the obtained solid was filtrated and then washed with water, to give 15 g of the following synthetic intermediate B (yield: 78%).

To a dispersion of 1.16 g of the synthetic intermediate B in 5 mL of N,N-dimethylacetamide, 0.84 mL of 2,6-lutidine was added, and subsequently 1.1 mL of 2-ethylhexanoyl chloride was added and allowed to react at room temperature for 5 hours. Water was added to the reaction solution, and the obtained solid was filtrated, washed with water, purified and recrystallized, to give 0.6 g of the exemplified compound (1) (yield: 31%).

MS: m/z 638 (M+)

$^1$H NMR (CDCl$_3$) δ 0.98 (t, 6H), 1.09 (t, 6H), 1.35-1.90 (m, 16H), 2.68 (m, 2H)

$^{13}$C NMR (CDCl$_3$) δ 11.96, 13.96, 22.61, 25.21, 29.75, 31.36, 47.14, 68.79, 111.54, 130.41, 136.51, 171.32, 175.38

λmax=380 nm (EtOAc), $\epsilon$=77600

The synthetic intermediate B could also be prepared by the following preparation method.

N-methylpyrrolidone was added to a mixture of the synthetic intermediate M-2 and malononitrile, and the solution was stirred in the nitrogen atmosphere at inner temperature of 80° C. for 4 hours. After cooling the solution to room temperature, 1N hydrochloric acid was added with stirring. The precipitated crystals were filtrated and washed with water, to give the synthetic intermediate B.

The exemplified compound (1) could also be prepared in the same manner as the above expect that the thus-obtained synthesis intermediate B was used.

The synthetic intermediate M-2 was prepared by the following preparation method.

N-methylpyrrolidone (100 ml) was added to 40 g (0.113 mol) of potassium diethyldithiocarbamate (53 mass % aqueous solution). Then, 60 mL of acetic acid was added to the solution with stirring while cooling with ice. While cooling with ice, 24.5 g (0.226 mol) of 1,4-benzoquinone was added bit by bit to the solution. After stirring the solution at room temperature for 2 hours, 150 mL of acetone was added to the solution. The precipitated crystals were filtrated and washed with acetone, to give 23.9 g of the exemplified compound M-2 (yield: 68.0%).

The synthetic intermediate M-2 could also be synthesized by the following preparation method.

Sodium diethyldithiocarbamate trihydrate 38.4 g (0.17 mol) was dissolved in a mixture of 19 ml of water and 180 ml of N-methylpyrrolidone, and subsequently 90 ml of acetic acid was added to the solution with stirring while cooling with ice. While cooling with ice, 18.4 g (0.17 mol) of 1,4-benzoquinone was added at inner temperature of 25° C. or lower over 30 minutes. After stirring the solution at room temperature for 2 hours, 9.2 g (0.085 mol) of 1,4-benzoquinone was added, then the solution was stirred at room temperature for 2 hours. After acetone (60 ml) was added to the solution, the precipitated crystals were filtrated and washed with acetone, to give 35 g of the synthetic intermediate M-2 (yield: 63%).
MS: m/z 402 (M+)
$^1$H NMR (CD$_3$COOD) δ 1.51 (t, 12H), 3.99 (s, 8H), 6.70 (s, 8H)

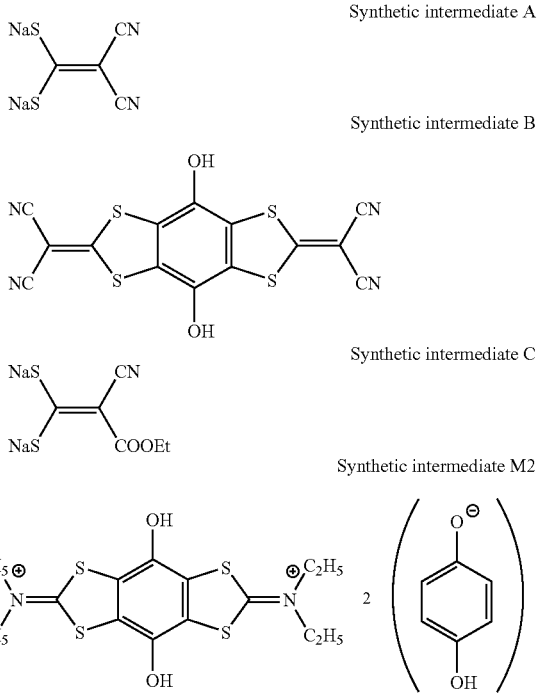

Example 2

Preparation of Exemplified Compound (2)

To a dispersion of 1.16 g of the synthesis intermediate B above in 5 mL of N,N-dimethylacetamide, 1.24 mL of 2-ethylhexylbromide was added, and subsequently 1 g of potassium carbonate was added and allowed to react at 60° C. for 5 hours. Water was added to the reaction solution, and the obtained solid was filtrated, washed with water and purified, to give 0.5 g of the exemplified compound (2) (yield: 27%).
MS: m/z 610 (M+)
λmax=381 nm (EtOAc), ε=78000

Example 3

Preparation of Exemplified Compound (72)

To a solution of 22.4 g of potassium hydroxide dissolved in 250 mL of ethanol, 21.3 mL of ethyl cyanoacetate was added while cooling with ice, and subsequently 15.2 g of carbon disulfide was added, and allowed to react at room temperature for 1 hour. The obtained solid was filtrated, washed with ethanol, to give 36.5 g of the synthetic intermediate C above (yield: 69%).

To a dispersion of 6.1. g of chloranil dispersed in 50 mL of N,N-dimethylacetamide, 25 ml of solution of the synthetic intermediate C above was added while cooling with ice, and allowed to react at room temperature for 5 hours. Water was added to the reaction solution, the obtained solid was filtrated and then washed with water, to give 15 g of the exemplified compound (72) (yield: 78%).
MS: m/z 480 (M+)

The exemplified compound (72) could also be prepared by the following preparation method.

N-methylpyrrolidone was added to a mixture of the synthetic intermediate M-2 and ethyl cyanoacetate, and the solution was allowed to react in the nitrogen atmosphere at inner temperature of 70° C. for 3 hours. After cooling to room temperature, methanol and acetic acid was added in this order with stirring. The thus-obtained precipitated crystals were filtrated and washed with methanol, to give the exemplified compound (72).

Example 4

Preparation of Exemplified Compound (11)

To a dispersion of 1.44 g of the exemplified compound (72) dispersed in 5 mL of N,N-dimethylacetamide, 0.84 mL of 2,6-lutidine was added, and subsequently 1.11 mL of 2-ethylhexanoly chloride was added and allowed to react at room temperature for 5 hours. Water was added to the reaction solution, the obtained solid was filtrated, washed with water and purified, to give 0.16 g of the exemplified compound (11) (yield: 8%).
MS: m/z 720 (M+)
$^1$H NMR (CDCl$_3$) δ 0.98 (t, 6H), 1.09 (t, 6H), 1.35-1.90 (m, 16H), 2.61-2.72 (m, 2H)
$^{13}$C NMR (CDCl$_3$) δ 11.96, 13.96, 22.61, 25.21, 29.75, 31.36, 47.14, 68.79, 111.54, 130.41, 136.51, 171.32, 175.38
λmax=381 nm (EtOAc), ε=92900

Example 5

Preparation of Exemplified Compound (12)

To a dispersion of 1.44 g of the exemplified compound (72) dispersed in 5 mL of N,N-dimethylacetamide, 1.24 mL of 2-ethylhexylbromide was added, and subsequently 1.0 g of potassium carbonate was added and allowed to react at 60° C. for 5 hours. Water was added to the reaction solution, the obtained solid was filtrated, washed with water and purified, to give 0.5 g of the exemplified compound (12) (yield: 24%).
MS: m/z 704 (M+)
$^1$H NMR (CDCl$_3$) δ 0.90-1.05 (m, 12H), 1.38 (t, 6H), 1.40-1.85 (m, 18H), 4.02-4.10 (m, 4H), 4.30-4.42 (m, 4H)
$^{13}$C NMR (CDCl$_3$) δ 11.98, 13.91, 12.25, 14.25, 22.70, 25.25, 29.71, 31.43, 47.16, 62.55, 111.54, 130.41, 136.51, 171.73
λmax=382 nm (EtOAc), ε=87600

Example 6

Preparation of Exemplified Compound (24)

In the same manner as Examples 3 and 5 except that pivaloyl acetonitrile was used in place of ethyl cyanoacetate, the exemplified compound (24) was obtained in yield of 4%.
MS: m/z 729 (M+)
$^1$H NMR (CDCl$_3$) δ 0.91-1.05 (m, 12H), 1.34-1.48 (m, 26H), 1.50-1.69 (m, 8H), 1.81-1.91 (m, 2H), 4.10-4.18 (m, 4H)
λmax=399 nm (EtOAc), ε=96000

The exemplified compound (24) could also be prepared by the following preparation method.

The exemplified compound (24) was obtained in yield of 4% in the same manner as Example 5 except that the exemplified compound (139) was used in place of the exemplified compound (72). The exemplified compound (139) was prepared in the following manner.

N-methylpyrrolidone (100 ml) was added to a mixture of 12.4 g (0.02 mol) of the synthetic intermediate M-2 and 6.0 g (0.048 mol) pivaloyl acetonitrile, and the solution was allowed to react in the nitrogen atmosphere at inner temperature of 80° C. for 4 hours. After cooling to room temperature, 30 ml of 1N hydrochloric acid was added with stirring. The precipitated crystals were filtrated and washed with water, to give 9.4 g of the exemplified compound (139) (yield: 98.0%).
$^1$H NMR (DMSO-$d_6$) δ 1.32 (s, 18H)

Example 7

Preparation of Exemplified Compound (74)

The exemplified compound (74) was synthesized in the same manner as Example 3 except that 3-hydroxyl-3-methylbutyl cyanoacetate was used in place of the ethyl cyanoacetate.
MS: m/z 596 (M+)
$^1$H NMR (DMSO-$d_6$) δ 1.16 (s, 12H), 1.79 (t, 4H), 4.30 (t, 4H), 3.70-4.90 (br, 2H), 10.0-11.5 (br, 2H)
The exemplified compound (74) could also be prepared by the following preparation method.
N-methylpyrrolidone (50 ml) was added to a mixture of 8.0 g (0.0128 mol) of the synthetic intermediate M-2 and 4.8 g (0.028 mol) 3-hydroxyl-3-methylbutyl cyanoacetate, and the solution was allowed to react in the nitrogen atmosphere at inner temperature of 80° C. for 3 hours. After cooling to room temperature, 30 ml of ethyl acetate and 50 ml of water were added to the solution. With stirring, 2.5 ml of concentrated hydrochloric acid was added. The precipitated crystals were filtrated and washed with ethyl acetate and water, to give 7.3 g of the exemplified compound (74) (yield: 95.5%).

Example 8

Preparation of Exemplified Compound (104)

To a dispersion of 3.0 g of the exemplified compound (74) dispersed in 10 mL of tetrahydrofuran (THF), 2.6 g of 4-(4-ethylcyclohexyl)cyclohexanecarbonyl chloride and 0.8 g of pyridine were added, and the solution was allowed to react at 60° C. for 5 hours. After water was added to the reaction solution, the obtained solid was filtrated, washed with water, and purified, to give 1.8 g of the exemplified compound (104) (yield: 35%).
MS: m/z 1046 (M+)
λmax=386 nm ($CH_2Cl_2$), ε=99900

Example 9

Preparation of Exemplified Compound (86)

The exemplified compound (86) was obtained in yield of 52% in the same manner as Example 3 except that 2-ethylhexyl cyanoacetate was used in place of the ethyl cyanoacetate.
MS: m/z 649 (M+)
$^1$H NMR (DMSO-$d_6$) δ 0.78-0.97 (m, 12H), 1.20-1.45 (m, 16H), 1.54-1.70 (m, 2H), 4.05-4.20 (m, 4H)
The exemplified compound (86) could also be prepared by the following preparation method.
N-methylpyrrolidone (30 ml) was added to a mixture of 8.0 g (0.02 mol) of the synthetic intermediate M-2 and 5.7 g (0.029 mol) 2-ethylhexyl cyanoacetate, and the solution was allowed to react in the nitrogen atmosphere at inner temperature of 70° C. for 3 hours. After cooling to room temperature, 40 ml of ethyl acetate and 8 ml of acetic acid were added in this order. The precipitated crystals were filtrated, washed with methanol, to give 8.0 g of the exemplified compound (86) (yield: 96.0%).

Example 10

Preparation of Exemplified Compound (81)

The exemplified compound (81) was obtained in yield of 18% in the same manner as Example 4 except that the exemplified compound (86) was used in place of the exemplified compound (72).
MS: m/z 900 (M+)
$^1$H NMR ($CDCl_3$) δ 0.81-0.95 (m, 12H), 1.02 (t, 6H), 1.12 (t, 6H), 1.22-1.54 (m, 24H), 1.61-1.92 (m, 10H), 2.61-2.72 (m, 2H), 4.12-4.28 (m, 4H)
λmax=381 nm (EtOAc), ε=99000

Example 11

Preparation of Exemplified Compound (82)

The exemplified compound (82) was obtained in yield of 32% in the same manner as Example 5 except that the exemplified compound (86) was used in place of the exemplified compound (72).
MS: m/z 873 (M+)
$^1$H NMR ($CDCl_3$) δ 0.82-1.06 (m, 24H), 1.25-1.61 (m, 32H), 1.62-1.81 (m, 4H), 4.01-4.08 (m, 4H), 4.12-4.23 (m, 4H)
λmax=383 nm (EtOAc), ε=92000

Example 12

Preparation of Exemplified Compound (87)

The exemplified compound (87) was obtained in yield of 18% in the same manner as Example 5 except that the exemplified compound (74) was used in place of the exemplified compound (72).
MS: m/z 821 (M+)
$^1$H NMR ($CDCl_3$) δ 0.81-1.08 (m, 12H), 1.32 (s, 14H), 1.34-1.45 (m, 8H), 1.46-1.72 (m, 8H), 1.73-1.85 (m, 2H), 1.98 (t, 4H), 4.04-4.09 (m, 4H), 4.48 (t, 4H)
λmax=383 nm (EtOAc), ε=92000

Example 13

Preparation of Exemplified Compound (88)

The exemplified compound (88) was obtained in yield of 19% in the same manner as Example 5 except that the exemplified compound (86) was used in place of the exemplified compound (72), and dimethyl sulfate was used in place of the 2-ethylhexylbromide.
MS: m/z 677 (M+)
$^1$H NMR ($CDCl_3$) δ 0.83-0.92 (dt, 12H), 1.25-1.50 (m, 16H), 1.62-1.74 (m, 2H), 4.02 (s, 6H), 4.15-4.27 (m, 4H)
λmax=383 nm (EtOAc), ε=92000

Example 14

Preparation of Exemplified Compound (121)

The exemplified compound (121) was obtained in yield of 55% in the same manner as Example 3 except that t-butyl cyanoacetate was used in place of the ethyl cyanoacetate.

MS: m/z 537 (M+)

The exemplified compound (121) could also be prepared by the following preparation method.

To a dispersion of 3.1 g of the synthetic intermediate M-2 in 20 mL of N-methylpyrrolidone, 1.69 g of t-butyl cyanoacetate was added, and the solution was subsequently allowed to react at 80° C. for 6 hours. After cooling the solution to room temperature, and adding 5 ml of acetic acid and 20 ml of methanol thereto, yellowish powder was obtained. The obtained powder was recrystallized from methanol, to give the exemplified compound (121) in yield of 55%.

Example 15

Preparation of Exemplified Compound (122)

The exemplified compound (122) was obtained in yield of 15% in the same manner as Example 5 except that the exemplified compound (121) was used in place of the exemplified compound (72).

MS: m/z 760 (M+)

$^1$H NMR (CDCl$_3$) δ 0.93-1.08 (m, 12H), 1.42 (s, 18H), 1.51-1.67 (m, 16H), 1.79-1.88 (m, 2H), 4.08-4.15 (m, 4H)

Example 16

Preparation of Exemplified Compound (130)

To a dispersion of 1.06 g of the exemplified compound (86) dispersed in 10 mL of N,N-dimethylacetamide, 0.44 g of 2-bromoethanol was added, and subsequently 0.66 g of potassium carbonate was added and allowed to react at 80° C. for 4 hours. After adding an aqueous solution of hydrochloric acid to the reaction solution, the produced solid was filtrated and then washed with water, recrystallized from ethanol, to give 0.65 g of the exemplified compound (130) (yield: 55%).

MS: m/z 736 (M+)

$^1$H NMR (CDCl$_3$) δ 0.87-0.99 (m, 12H), 1.25-1.48 (m, 16H), 1.61-1.78 (m, 2H), 4.01-4.06 (m, 4H), 4.16-4.22 (m, 4H), 4.25-4.32 (m, 4H)

Example 17

Preparation of Exemplified Compound (131)

The exemplified compound (131) was obtained in yield of 18% in the same manner as Example 16 except that 2-iodopropane was used in place of the 2-bromoethanol.

MS: m/z 734 (M+)

$^1$H NMR (CDCl$_3$) δ 0.85-0.97 (m, 12H), 1.25-1.50 (m, 16H), 1.62-1.73 (m, 2H), 4.17-4.25 (m, 4H), 4.65-4.77 (m, 2H)

Example 18

Preparation of Exemplified Compound (132)

The exemplified compound (132) was obtained in yield of 45% in the same manner as Example 16 except that 2-bromomethyl benzoate was used in place of the 2-bromoethanol.

MS: m/z 945 (M+)

$^1$H NMR (CDCl$_3$) δ 0.85-0.99 (m, 12H), 1.27-1.50 (m, 16H), 1.65-1.76 (m, 2H), 4.17-4.24 (m, 4H), 4.45-4.52 (m, 4H), 4.63-4.70 (m, 4H), 7.42-4.60 (m, 6H), 8.05-8.12 (m, 4H)

Example 19

Preparation of Exemplified Compound (123)

The exemplified compound (123) was obtained in yield of 72% in the same manner as Example 3 except that iso-butyl cyanoacetate was used in place of the ethyl cyanoacetate.

MS: m/z 536 (M+)

The exemplified compound (123) could also be prepared by the following preparation method.

The exemplified compound (123) was obtained in yield of 49% in the same manner as the reaction using the synthetic intermediate M-2 in Example 14 except that iso-butyl cyanoacetate was used in place of the t-butyl cyanoacetate.

Example 20

Preparation of Exemplified Compound (124)

The exemplified compound (124) was synthesized in yield of 24% in the same manner as Example 5 except that the exemplified compound (123) was used in place of the exemplified compound (72).

MS: m/z 760 (M+)

$^1$H NMR (CDCl$_3$) δ 0.90-1.10 (m, 24H), 1.30-1.68 (m, 16H), 1.70-1.84 (m, 2H), 1.99-2.14 (m, 2H), 4.00-4.12 (m, 8H)

Example 21

Preparation of Exemplified Compound (125)

The exemplified compound (125) was obtained in yield of 63% in the same manner as Example 3 except that 2-cyano-N,N'-dimethylacetamide was used in place of the ethyl cyanoacetate.

MS: m/z 478 (M+)

The exemplified compound (125) could also be prepared by the following preparation method.

The exemplified compound (125) was obtained in yield of 59% in the same manner as the reaction using the synthetic intermediate M-2 in Example 14 except that 2-cyano-N,N'-dimethylacetamide was used in place of the t-butyl cyanoacetate.

Example 22

Preparation of Exemplified Compound (126)

The exemplified compound (126) was obtained in yield of 1% in the same manner as Example 5 except that the exemplified compound (125) was used in place of the exemplified compound (72).

MS: m/z 703 (M+)

$^1$H NMR (CDCl$_3$) δ 0.90-1.14 (m, 12H), 1.28-1.70 (m, 16H), 1.71-1.85 (m, 2H), 3.01-3.32 (s, 12H), 3.95-4.08 (m, 4H)

Example 23

Preparation of Exemplified Compound (127)

The exemplified compound (127) was obtained in yield of 6% in the same manner as Example 4 except that the exemplified compound (125) was used in place of the exemplified compound (72), and triethylamine was used in place of the 2,6-lutidine.

MS: m/z 731 (M+)

$^1$H NMR (CDCl$_3$) δ 0.95-1.02 (t, 6H), 1.10-1.14 (t, 6H), 1.40-1.55 (m, 8H), 1.75-1.93 (m, 8H), 2.60-2.69 (s, 2H), 3.01-3.30 (s, 12H)

Example 24

Preparation of Exemplified Compound (128)

The exemplified compound (128) was obtained in yield of 88% in the same manner as Example 3 except that 2-cyano-N-(2-methoxyphenyl)acetamide was used in place of the ethyl cyanoacetate.

MS: m/z 634 (M+)

The exemplified compound (128) could also be prepared by the following preparation method.

The exemplified compound (128) was obtained in yield of 89% in the same manner as the reaction using the synthetic intermediate M-2 in Example 14 except that 2-cyano-N-(2-methoxyphenyl)acetamide was used in place of the t-butyl cyanoacetate.

Example 25

Preparation of Exemplified Compound (129)

The exemplified compound (129) was obtained in yield of 1% in the same manner as Example 5 except that the exemplified compound (128) was used in place of the exemplified compound (72).

MS: m/z 859 (M+)

$^1$H NMR (CDCl$_3$) δ 0.90-1.14 (m, 12H), 1.28-1.70 (m, 16H), 1.71-1.89 (m, 2H), 3.90 (s, 6H), 4.01-4.11 (m, 4H), 6.82-6.90 (m, 2H), 6.91-7.00 (m, 2H), 7.02-7.09 (m, 2H), 8.30-8.35 (m, 2H), 8.41 (s, 2H)

Example 26

Preparation of Exemplified Compound (133)

The exemplified compound (133) was obtained in yield of 84% in the same manner as Example 3 except that benzoylacetonitrile was used in place of the ethyl cyanoacetate.

MS: m/z 544 (M+)

The exemplified compound (133) could also be prepared by the following preparation method.

The exemplified compound (133) was obtained in yield of 85% in the same manner as the reaction using the synthetic intermediate M-2 in Example 14 except that benzoylacetonitrile was used in place of the t-butyl cyanoacetate.

Example 27

Preparation of Exemplified Compound (134)

The exemplified compound (134) was obtained in yield of 5% in the same manner as Example 5 except that the exemplified compound (133) was used in place of the exemplified compound (72).

MS: m/z 770 (M+)

$^1$H NMR (CDCl$_3$) δ 0.95-1.01 (t, 6H), 1.04-1.12 (t, 6H), 1.51-1.69 (m, 16H), 1.82-1.92 (m, 2H), 4.15-4.21 (m, 4H), 7.49-7.62 (m, 6H), 7.98-8.03 (m, 4H)

Example 28

Preparation of Exemplified Compound (135)

The exemplified compound (135) was obtained in yield of 46% in the same manner as Example 3 except that phenylsulfonylacetonitrile was used in place of the ethyl cyanoacetate.

MS: m/z 616 (M+)

The exemplified compound (135) could also be prepared by the following preparation method.

The exemplified compound (135) was obtained in yield of 44% in the same manner as the reaction using the synthetic intermediate M-2 in Example 14 except that phenylsulfonylacetonitrile was used in place of the t-butyl cyanoacetate.

Example 29

Preparation of Exemplified Compound (136)

The exemplified compound (136) was obtained in yield of 6% in the same manner as Example 5 except that the exemplified compound (135) was used in place of the exemplified compound (72).

MS: m/z 842 (M+)

$^1$H NMR (CDCl$_3$) δ 0.85-1.13 (m, 12H), 1.40-1.70 (m, 16H), 1.75-1.86 (m, 2H), 3.92-4.12 (td, 4H), 7.54-7.64 (m, 4H), 7.66-7.73 (m, 2H), 7.98-8.03 (m, 4H)

Example 30

Preparation of Exemplified Compound (137)

The exemplified compound (137) was obtained in yield of 49% in the same manner as Example 3 except that methylsulfonylacetonitrile was used in place of the t-butyl cyanoacetate.

MS: m/z 492 (M+)

The exemplified compound (137) could also be prepared by the following preparation method.

The exemplified compound (137) was obtained in yield of 53% in the same manner as the reaction using the synthetic intermediate M-2 in Example 14 except that methylsulfonylacetonitrile was used in place of the t-butyl cyanoacetate.

Example 31

Preparation of Exemplified Compound (138)

The exemplified compound (138) was obtained in yield of 4% in the same manner as Example 5 except that the exemplified compound (137) was used in place of the exemplified compound (72).

MS: m/z 928 (M+)

$^1$H NMR (CDCl$_3$) δ 0.84-1.04 (m, 12H), 1.32-1.61 (m, 16H), 1.72-1.83 (m, 2H), 3.21 (s, 6H), 4.01-4.025 (m, 4H)

Example 32

Preparation of Exemplified Compound (7)

To a suspension of 1.93 g of the synthetic intermediate B suspended in 20 mL of tetrahydrofuran, 1.1 g of acetic anhydride was added, followed by addition of 2.1 mL of triethylamine. Thereafter, the mixture was refluxed for 3 hours. The precipitates produced in the reaction mixture were filtrated and washed with tetrahydrofuran, followed by drying. Thus, 0.84 g of the exemplified compound (7) (pale yellow crystal) was obtained.

Infrared absorption spectrum (cm$^{-1}$): 2216 (s), 1795 (s), 1479 (s), 1423 (m), 1369 (m), 1144 (s)

$^1$H NMR (CDCl$_3$) δ 0.84-1.04 (m, 12H), 1.32-1.61 (m, 16H), 1.72-1.83 (m, 2H), 3.21 (s, 6H), 4.01-4.025 (m, 4H)

Example 33

Preparation of Exemplified Compound (140)

The exemplified compound (140) was obtained in yield of 53% in the same manner as Example 6 except that diethyl malonate was used in place of the pivaloylacetonitrile.

MS: m/z 574 (M+)

Example 34

Preparation of Exemplified Compound (141)

The exemplified compound (141) was obtained in the same manner as the reaction using the synthetic intermediate M-2 in Example 7 except that ethyl phenylsulfonylacetate was used in place of the 3-hydroxyl-3-methylbutyl cyanoacetate.

MS: m/z 710 (M+)

Example 35

Preparation of Exemplified Compound (142)

To a solution of 20 g of the synthetic intermediate A dissolved in 5 mL of N,N-dimethylacetamide and 0.5 g of water, 1 g of tetrafluoroterephthalonitrile was added, and subsequently was allowed to react at room temperature for 6 hours. After water was added to the reaction solution, the obtained solid was filtrated, washed with water, purified, and recrystallized, to give 1.2 g of the exemplified compound (142) (yield: 59%).

MS: m/z 404 (M−)

$^{13}$C NMR (CDCl$_3$) δ 69.42, 103.99, 111.75, 112.47, 139.19, 173.47

Example 36

Preparation of Exemplified Compound (143)

To a solution of 13 g of the exemplified compound (86) dissolved in 50 mL of N,N-dimethylacetamide, 6.7 ml of triethylamine was added in the nitrogen atmosphere, subsequently 3.7 mL of methanesulfonylchloride was added bit by bit. The obtained reaction solution was allowed to react at room temperature overnight. After the reaction solution was added to iced water, the obtained mixture was adjusted to acidic by adding concentrated hydrochloric acid. The obtained solid was filtrated and washed with water, to give the exemplified compound (143).

MS: m/z 805 (M+)

Example 37

Preparation of Exemplified Compound (144)

To a solution of 1.95 g of the exemplified compound (86) dissolved in 30 mL of methylenechloride, 1.25 mL of triethylamine was added in the nitrogen atmosphere while cooling with ice bath, subsequently 1.48 mL of trifluoromethanesulfonic acid anhydride was dropped bit by bit. The obtained reaction solution was allowed to react at room temperature for 6 hours. After water was added to the reaction solution, the mixture was extracted by ethyl acetate. After being dried with sodium sulfate, the extract was concentrated, to give the exemplified compound (144).

MS: m/z 913 (M+)

Example 38

One mg of the Exemplified Compound (1) was dissolved in 100 ml of ethyl acetate, to give a sample solution. Similarly, sample solutions of Exemplified Compounds (2), (11), (12), (24), (81), (82), (87) and (88), respectively, were prepared. In addition, two mg of the comparative compound 1 was dissolved in 100 ml of ethyl acetate, to give a sample solution. Similarly, sample solutions of the comparative compounds 2 (the exemplified compound VIII described in JP-B-49-11155), 11 and 12, respectively, were also prepared. The UV spectrum of each sample solution was determined in a 1 cm quartz cell by using Spectrophotometer UV-3600 (product name) manufactured by Shimadzu Corporation. Based on the thus-obtained spectrum chart, were calculated the maximum absorption wavelength, the molar extinction coefficient (ε) at the maximum absorption wavelength and the half width (a width of absorption band corresponding to a half extinction at the maximum absorption wavelength). The results are shown in Table 4 set forth below.

TABLE 4

| Sample No. | Ultraviolet absorbent | Molecular weight | λmax (nm) | ε | Half width (nm) | Remarks |
|---|---|---|---|---|---|---|
| 101 | Exemplified compound (1) | 639 | 380 | 78000 | 27 | This invention |
| 102 | Exemplified compound (2) | 611 | 381 | 78000 | 28 | This invention |
| 103 | Exemplified compound (11) | 733 | 381 | 93000 | 26 | This invention |
| 104 | Exemplified compound (12) | 705 | 382 | 88000 | 28 | This invention |
| 105 | Exemplified compound (24) | 729 | 399 | 96000 | 18 | This invention |
| 106 | Exemplified compound (81) | 901 | 381 | 99000 | 27 | This invention |
| 107 | Exemplified compound (82) | 873 | 383 | 92000 | 28 | This invention |
| 108 | Exemplified compound (87) | 821 | 383 | 92000 | 27 | This invention |
| 109 | Exemplified compound (88) | 677 | 383 | 92000 | 26 | This invention |
| 110 | Comparative compound 1 | 501 | 369 | 24000 | 45 | Comparative example |
| 111 | Comparative compound 2 | 585 | 363 | 23000 | 46 | Comparative example |
| 112 | Comparative compound 1 | 548 | 366 | 27000 | 38 | Comparative example |
| 113 | Comparative compound 12 | 520 | 360 | 28000 | 39 | Comparative example |

Comparative compound 1

TABLE 4-continued

| Sample No. | Ultraviolet absorbent | Molecular weight | λmax (nm) | ε | Half width (nm) | Remarks |
|---|---|---|---|---|---|---|

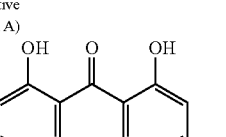

Comparative compound 2

Comparative compound 11

Comparative compound 12

The results shown in Table 4 demonstrate that when compared to comparative compounds in which one heterocycle is fused to the benzene ring, the compounds represented by formula (I), in which two heterocycles are fused to the benzene ring, have properties such that λmax shifts to a longer wavelength side, a molar extinction coefficient ε is enhanced twice or more, and a half width is decreased from about 40 nm to about 27 nm, and give an intensive and sharp absorption at the around the border between the ultraviolet region and the visible region. From the results, it is understood that the compounds represented by formula (I) have an excellent ultraviolet absorbing properties exceeding a double ultraviolet-absorbing effect that is simply expected by a compound having two heterocycles. Accordingly, it is understood that the ultraviolet absorbents of the present invention that are composed of the compound represented by formula (I) have an excellent absorbing properties.

Spectra of the exemplified compound (12) and the comparative compound 12 are shown in FIG. 1.

Example 39

Was dissolved 5 mg of the exemplified compound (1) in 100 mL of ethyl acetate and then the resulting solution was diluted with ethyl acetate so that absorbance became the range of from 0.95 to 1.05. Similarly, sample solutions of Exemplified Compounds (2), (11), (12), (24), (81) and (82) and comparative compounds A and B, respectively, were prepared. The absorbance of each sample solution was determined in a 1 cm quartz cell by using Spectrophotometer UV-3600 (product name) manufactured by Shimadzu Corporation. The cell containing the sample solution was photoirradiated by a xenon lamp with its UV filter removed at an illuminance of 170,000 lux, and the amount of each ultraviolet absorbent remaining after irradiation for one week was determined. The residual amount was calculated according to the following Formula:

Residual amount (%)=100×(100−Transmittance after irradiation)/(100−Transmittance before irradiation)

The transmittance is a value determined at the maximum absorption wavelength of each compound. The result is shown in Table 5.

TABLE 5

| Sample No. | Ultraviolet absorbent | Residual amount (%) | Remarks |
|---|---|---|---|
| 201 | Exemplified compound (1) | 93 | This invention |
| 202 | Exemplified compound (2) | 92 | This invention |
| 203 | Exemplified compound (11) | 92 | This invention |
| 204 | Exemplified compound (12) | 94 | This invention |
| 205 | Exemplified compound (24) | 92 | This invention |
| 206 | Exemplified compound (81) | 92 | This invention |
| 207 | Exemplified compound (82) | 94 | This invention |
| 208 | Comparative compound A | 76 | Comparative example |
| 209 | Comparative compound B | 38 | Comparative example |

(Comparative compound A)

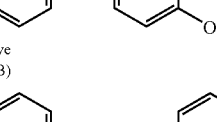

(Comparative compound B)

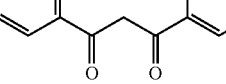

As shown in Table 5, it is understood that the ultraviolet absorbents of the present invention are more resistant to decompose by light irradiation compared to the existing ultraviolet absorbent having an absorption area in the UV-A region, which results in high fastness to light.

Example 40

With respect to the exemplified compounds (11), (12), (81), (82), (83) and (85), 100 mg of each compound was weighed. Each of them was mixed with MEK (2-butanone) and 900 mg of ethyl acetate, to examine its solubility. Judgment of solubility was performed according to the following two criteria for evaluation.

<1> Existence or non-existence of insoluble materials is observed visually.
<2> A sample is filtrated through a micro filter having 0.25 μm size. Thereafter, the filtrate is diluted as much as 1000 times more than the original amount, to measure absorbance. The thus-obtained absorbance is compared to the molar extinction coefficient that is obtained by a separate measurement of the about $5 \times 10^{-5}$ mol·dm$^{-3}$ standard solution. In the case where the absorbance is 95% or less of the standard solution, it is judged that insoluble materials exist.

The thus-obtained results are shown in Table 6. The result is indicated as "○" when the sample dissolves, and as "x" when insoluble materials exist.

TABLE 6

|  | MEK | Ethyl acetate |
|---|---|---|
| Exemplified compound (11) | X | X |
| Exemplified compound (12) | X | X |
| Exemplified compound (81) | ○ | ○ |
| Exemplified compound (82) | ○ | ○ |
| Exemplified compound (83) | ○ | ○ |
| Exemplified compound (85) | ○ | ○ |

As shown in Table 6, it is understood that the exemplified compounds (81), (82), (83) and (85), in which $R^1$, $R^2$, $R^3$ and $R^4$ in formula (I) each independently represent an alkoxycarbonyl group having 6 or more carbon atoms, are excellent in solubility, compared to the exemplified compounds (11) and (12), in which $R^1$, $R^2$, $R^3$ and $R^4$ in formula (I) each independently represent an alkoxycarbonyl group having less than 6 carbon atoms. The difference in solubility is remarkable between the exemplified compounds (12) and (83) that have the same molecular weight, but are only different in position of each of the 2-ethylhexyl group and the ethyl group, which demonstrates that solubility is greatly affected by $R^1$, $R^2$, $R^3$ and $R^4$.

Example 41

With respect to the exemplified compounds (11), (12), (81) and (82), 3 mg of each compound was weighed in an aluminum plate of 2 mm in diameter and 2 mm in height. They were heated and left in an oven at 280° C. for 30 minutes, and then allowed to cool to room temperature. Based on a change in mass before and after heating, a mass reduction rate owing to heating was examined with respect to each compound. The mass reduction rate was calculated according to the following equation:

Mass reduction rate (%)=(Mass before heating−Mass after heating)/(Mass before heating)×100

The results are shown in Table 7.

TABLE 7

|  | Mass reduction rate (%) |
|---|---|
| Exemplified compound (11) | 10 |
| Exemplified compound (12) | 7 |
| Exemplified compound (81) | 6 |
| Exemplified compound (82) | 3 |

As shown in Table 7, it is understood that the exemplified compounds (12) and (82), in which $R^5$ and $R^6$ in formula (I) each independently represent an alkoxy group, provide less mass reduction than do the exemplified compounds (11) and (81), in which $R^5$ and $R^6$ in formula (I) each independently represent an acyloxy group, which demonstrates that mass reduction by heating is greatly affected by both $R^5$ and $R^6$ with a preferable group being an alkoxy group.

Example 42

Preparation of Sun-Screen Cream (301 to 308)

1. Composition of Sun-Screen Cream

| [A] | |
|---|---|
|  | Numerical value (% by mass) |
| A mixture of polyglycerol/sodium stearoyl lactate | 2.5 |
| Behenyl alcohol | 2.5 |
| SQUALANE | 4.0 |
| Tri-2-ethylhexanoic acid glyceryl | 3.0 |
| 2-Ethylhexyl p-methoxycinnamate | 6.0 |
| Ultraviolet absorbent Compound | 2.0 |

| [B] | |
|---|---|
|  | Numerical value (% by mass) |
| Preservatives | proper quantity |
| 1,3-Butyleneglycol | 5.0 |
| Xanthan gum (2% aqueous solution) | 15.0 |
| Purified water to make | 100.0 |

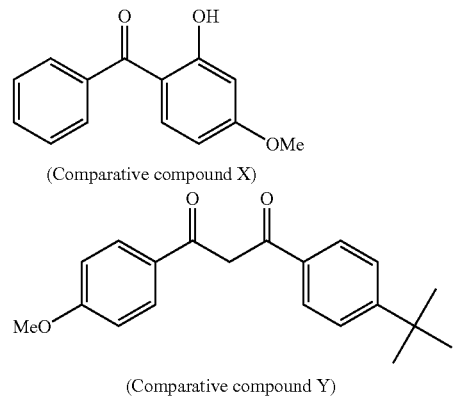

(Comparative compound X)

(Comparative compound Y)

<Preparation>
Each of the forgoing A and B was heated to temperatures of 70 to 80° C. to make a uniform solution respectively. Then, A was added to B, and the resultant mixture was stirred at 5,000 rpm for 7 minutes using a homo mixer while keeping at 80° C. Thereafter, the mixture was cooled with paddle stirring. At the time when the mixture cooled down to the range of 35 to 30° C., the stirring was stopped and the mixture was allowed to stand. In samples (301), (302), (303), (304), (305), (306), (307), and (308), were used the exemplified compounds (1), (11), (12), (24), (81) and (82) and the comparative compounds X and Y, respectively. Each of these compounds was mixed according to the above-described formula, respectively. The comparative compound Y is identical to the comparative compound B.

2. Evaluation of Sun-Screen Cream
<Evaluation Method>

With respect to the creams (samples 301 to 308) prepared above, evaluation was performed as follows.

The cream was coated on a slide glass so that a coated amount became 2 mg/cm$^2$, and then dried for 60 minutes. Light irradiation test was performed using a merry-go-round type xenon color-fastness test machine. Using a 500 W lamp as a xenon light source, light was irradiated from the coating side for 200 hours. After light irradiation, the cream was dissolved in DMSO, and a residual amount was measured using HPLC. For evaluation, a residual rate after irradiation was calculated, assuming that the residual rate (non-irradiation) was 100. The results are shown in Table 8.

TABLE 8

| Sample No. | Ultraviolet absorbent | Residual rate (%) | |
|---|---|---|---|
| 301 | Exemplified compound (1) | 94 | This invention |
| 302 | Exemplified compound (11) | 94 | This invention |
| 303 | Exemplified compound (12) | 95 | This invention |
| 304 | Exemplified compound (24) | 92 | This invention |
| 305 | Exemplified compound (81) | 93 | This invention |
| 306 | Exemplified compound (82) | 95 | This invention |
| 307 | Comparative compound X | 71 | Comparative example |
| 308 | Comparative compound Y | 31 | Comparative example |

As shown in Table 8, it is understood that the samples 307 and 308 containing the comparative compound X or Y have a low residual rate of the ultraviolet absorbent after 200 hours of irradiation and therefore are inferior in fastness to light. In contrast, the samples 301 to 306 each containing the compound represented by formula (I) have 90% or more residual rate of the ultraviolet absorbent after 200 hour of irradiation and therefore are superior in fastness to light. From these results, it is understood that cosmetic formulations containing the ultraviolet absorbent of the present invention are excellent in a long-wavelength ultraviolet absorbing capacity and are able to maintain the absorbing capacity.

Example 43

Preparation of Built-in Polymer Type UV Agent-Containing Polymer Films (401 to 404)

To 15 g of polyethylene terephthalate, the exemplified compounds (81) and (82) were added, respectively, in a quantity such that absorbance at 400 nm became 1% at the time of forming a film with a thickness of 50 µm. After fusion mixing at 265° C., UV agent-containing polymer films (401) and (402) were prepared by cooling and stretching. Further, UV agent-containing polymer films (403) and (404) were prepared by mixing and thin film-making in the same manner as the above films, except that a comparative compound Za and the abovementioned comparative compound 12 were used in place of the exemplified compounds.

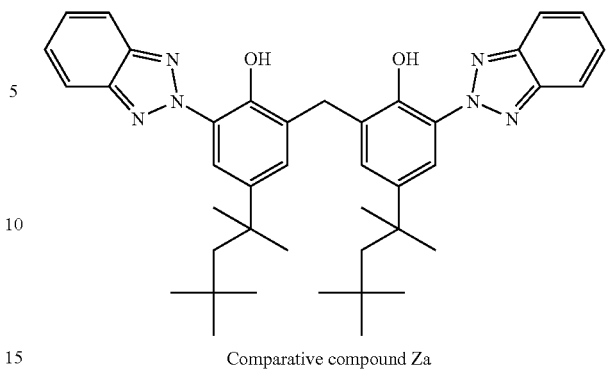

Comparative compound Za (Evaluation)

A degree of coloring in each of the prepared samples was evaluated by measuring absorbance of the sample at 420 nm 440 nm and 460 nm, and also by examining them visually. The results are shown in Table 9.

TABLE 9

| Sample No. | Ultraviolet absorbent | 400 nm | 420 nm | 440 nm | 460 nm | Colored |
|---|---|---|---|---|---|---|
| 401 | Exemplified compound 81 | 1% | 85% | 99% | 99% | ○ |
| 402 | Exemplified compound 82 | 1% | 89% | 99% | 99% | ○ |
| 403 | Comparative compound Za | 1% | 45% | 65% | 85% | x (yellow) |
| 404 | Comparative compound 12 | 1% | 65% | 72% | 78% | Δ to x |

○: Not colored
Δ: Slightly colored
x: Distinctly colored

As shown in Table 9, it is understood that the sample (403) containing the comparative compound Za is more colored yellow, compared to the samples (401) and (402) in which the exemplified compounds (81) and (82), respectively, are used. With respect to the sample (404) using the comparative compound 12 whose maximum absorption wavelength is shorter than that of the exemplified compounds (81) and (82), coloring was also observed owing to increase in amount necessary to prepare the sample. From these results, it is understood that the films using the ultraviolet absorbents of the present invention are free of coloring, and effectively absorb the light in the UV-A region.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-212318 filed in Japan on Aug. 16, 2007, Patent Application No. 2007-212319 filed in Japan on Aug. 16, 2007, Patent Application No. 2007-255732 filed in Japan on Sep. 28, 2007, Patent Application No. 2008-028229 filed in Japan on Feb. 7, 2008, and Patent Application No. 2008-028230 filed in Japan on Feb. 7, 2008, each of which is entirely herein incorporated by reference.

The invention claimed is:

1. A compound represented by formula (I-1):

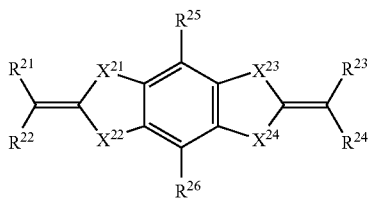

Formula (I-1)

wherein $R^{21}$, $R^{22}$, $R^{23}$ and $R^{24}$ each independently represent a hydrogen atom or a monovalent substituent, with the proviso that compounds, in which $R^{21}$, $R^{22}$, $R^{23}$ and $R^{24}$ each are an alkylthio group, are excluded; $R^{21}$ and $R^{22}$ and/or $R^{23}$ and $R^{24}$ may bond to each other to form a ring, with the proviso that compounds, in which the formed ring is a dithiol ring or a dithiolane ring, are excluded;

at least one of $R^{21}$, $R^{22}$, $R^{23}$ and $R^{24}$ represents —CN, —COOR$^{28}$, —CONR$^{29}$R$^{30}$, —COR$^{31}$ or —SO$_2$R$^{32}$ (in which $R^{28}$, $R^{29}$, $R^{30}$, $R^{31}$ and $R^{32}$ each represent a hydrogen atom or a monovalent substituent);

$R^{25}$ and $R^{26}$ each independently represent a hydrogen atom or a monovalent substituent;

$X^{21}$, $X^{22}$, $X^{23}$ and $X^{24}$ each independently represent a nitrogen atom, an oxygen atom or a sulfur atom;

compounds, wherein $R^{21}$, $R^{22}$, $R^{23}$ and $R^{24}$ each represent a cyan group; $X^{21}$, $X^{22}$, $X^{23}$ and $X^{24}$ each represent a sulfur atom; and $R^{25}$ and $R^{26}$ each represent a hydroxyl group or a hydrogen atom, are excluded; and compounds, wherein $R^{21}$ and $R^{23}$ each represent a hydrogen atom; $R^{22}$ and $R^{24}$ each represent an arylcarbonyl group; $X^{21}$, $X^{22}$, $X^{23}$ and $X^{24}$ each represent a sulfur atom; and $R^{25}$ and $R^{26}$ each represent a hydroxyl group, are excluded.

2. The compound according to claim 1, wherein, in formula (I-1), $R^{25}$ and $R^{26}$ each independently represent an alkoxy group, an aryloxy group, an acyloxy group, an alkoxycarbonyloxy group, an aryloxycarbonyloxy group, an acylamino group, a carbamoyloxy group, or a carbamoylamino group.

3. The compound according to claim 1, wherein, in formula (I-1), $X^{21}$, $X^{22}$, $X^{23}$ and $X^{24}$ each are a sulfur atom.

4. The compound according to claim 1, wherein the compound represented by formula (I-1) is a compound represented by formula (Ia-1) or formula (II-1):

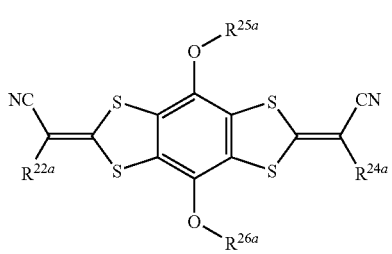

Formula (Ia-1)

wherein $R^{22a}$ and $R^{24a}$ each have the same meaning as those of $R^{22}$ and $R^{24}$ in formula (I-1), respectively; and $R^{25a}$ and $R^{26a}$ each represent an alkyl group having 1 to 20 carbon atoms, an aryl group having 6 to 20 carbon atoms, or a 4- to 7-membered heterocyclic group; and

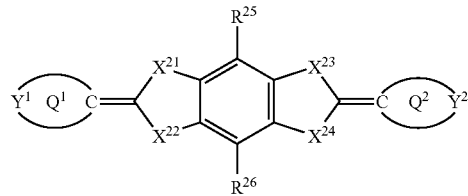

Formula (II-1)

wherein $R^{25}$, $R^{26}$, $X^{21}$, $X^{22}$, $X^{23}$ and $X^{24}$ each have the same meaning as those in formula (I-1), respectively; and $Y^1$ and $Y^2$ each represent a group of atoms necessary to form a 4- to 7-membered ring $Q^1$ or $Q^2$ together with the carbon atom to which $Y^1$ or $Y^2$ bonds.

5. An ultraviolet absorbent, comprising a compound represented by formula (I):

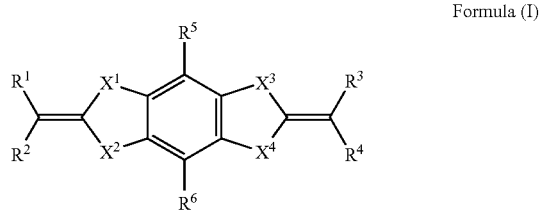

Formula (I)

wherein $R^1$, $R^2$, $R^3$ and $R^4$ each independently represent a hydrogen atom or a monovalent substituent; at least one of $R^1$, $R^2$, $R^3$ and $R^4$ represents a substituent having a Hammett substituent constant σp of 0.2 or more; $R^5$ and $R^6$ each independently represent a hydrogen atom or a monovalent substituent; and $X^1$, $X^2$, $X^3$ and $X^4$ each independently represent a nitrogen atom, an oxygen atom or a sulfur atom.

6. The ultraviolet absorbent according to claim 5, wherein, in formula (I), $R^5$ and $R^6$ each independently represent an alkoxy group, an aryloxy group, an acyloxy group, an alkoxycarbonyloxy group, an aryloxycarbonyloxy group, a carbamoyloxy group, an amino group, an acylamino group, or a carbamoylamino group.

7. The ultraviolet absorbent according to claim 5, wherein, in formula (I), at least one of $R^1$, $R^2$, $R^3$ and $R^4$ represents a cyano group, an alkoxycarbonyl group, an aryloxycarbonyl group, a carbamoyl group, an alkylcarbonyl group, an arylcarbonyl group, an alkylsulfonyl group, or an arylsulfonyl group.

8. The ultraviolet absorbent according to claim 5, wherein, in formula (I), $X^1$, $X^2$, $X^3$ and $X^4$ each are a sulfur atom.

9. The ultraviolet absorbent according to claim 5, wherein at least one of the pair of $R^1$ and $R^2$ and the pair of $R^3$ and $R^4$ does not form any ring.

10. The ultraviolet absorbent according to claim 5, wherein the pair of $R^1$ and $R^2$ and the pair of $R^3$ and $R^4$ do not form any ring.

11. The ultraviolet absorbent according to claim 5, wherein, in formula (I), at least one of $R^1$, $R^2$, $R^3$ and $R^4$ is an alkoxycarbonyl group having 6 or more carbon atoms.

12. The ultraviolet absorbent according to claim 5, wherein, in formula (I), $R^5$ and $R^6$ are an alkoxy group having 2 or more carbon atoms.

13. A composition, comprising the ultraviolet absorbent according to claim 5.

14. A polymer composition, comprising the ultraviolet absorbent according to claim 5 and a polymer substance.

* * * * *